(12) United States Patent
Ashworth et al.

(10) Patent No.: US 9,193,689 B2
(45) Date of Patent: Nov. 24, 2015

(54) 3-ARYL-5-SUBSTITUTED-ISOQUINOLIN-1-ONE COMPOUNDS AND THEIR THERAPEUTIC USE

(71) Applicant: INSTITUTE OF CANCER RESEARCH: ROYAL CANCER HOSPITAL (THE), London (GB)

(72) Inventors: Alan Ashworth, London (GB); Christopher James Lord, London (GB); Richard James Rowland Elliot, London (GB); Dan Niculescu-Duvaz, Sutton (GB); Roderick Porter, London (GB); Raymond John Boffey, Cambridge (GB); Melanie Jayne Bayford, Cambridge (GB); Stuart Firth-Clark, Cambridge (GB); Ashley Nicholas Jarvis, Cambridge (GB); Trevor Robert Perrior, Cambridge (GB); Rebekah Elisabeth Key, Cambridge (GB)

(73) Assignee: INSTITUTE OF CANCER RESEARCH: ROYAL CANCER HOSPITAL (THE), London (GB)

( * ) Notice: Subject to any disclaimer, the term of this patent is extended or adjusted under 35 U.S.C. 154(b) by 0 days.

(21) Appl. No.: 14/381,712

(22) PCT Filed: Mar. 7, 2013

(86) PCT No.: PCT/GB2013/050561
§ 371 (c)(1),
(2) Date: Aug. 28, 2014

(87) PCT Pub. No.: WO2013/132253
PCT Pub. Date: Sep. 12, 2013

(65) Prior Publication Data
US 2015/0099732 A1    Apr. 9, 2015

Related U.S. Application Data

(60) Provisional application No. 61/607,680, filed on Mar. 7, 2012.

(51) Int. Cl.
| C07D 401/04 | (2006.01) |
| A61K 31/4725 | (2006.01) |
| C07D 217/24 | (2006.01) |
| C07D 401/14 | (2006.01) |
| C07D 217/14 | (2006.01) |
| C07D 217/16 | (2006.01) |
| C07D 401/10 | (2006.01) |
| C07D 401/12 | (2006.01) |
| C07D 405/12 | (2006.01) |
| C07D 487/04 | (2006.01) |

(Continued)

(52) U.S. Cl.
CPC ............ *C07D 217/24* (2013.01); *C07D 217/14* (2013.01); *C07D 217/16* (2013.01); *C07D 401/04* (2013.01); *C07D 401/10* (2013.01); *C07D 401/12* (2013.01); *C07D 401/14* (2013.01); *C07D 405/12* (2013.01); *C07D 487/04* (2013.01); *C07D 487/08* (2013.01); *C07D 487/10* (2013.01)

(58) Field of Classification Search
None
See application file for complete search history.

(56) References Cited

U.S. PATENT DOCUMENTS

| 2,851,458 A | 9/1958 | Warner |
| 4,678,500 A | 7/1987 | Hay et al. |

(Continued)

FOREIGN PATENT DOCUMENTS

| EP | 1396488 A1 | 3/2004 |
| EP | 1544194 A1 | 6/2005 |

(Continued)

OTHER PUBLICATIONS

Adaimy et al., "Mutation in WNT10A is associated with an autosomal recessive ectodermal dysplasia: the odonto-onycho-dermal dysplasia." Am J Hum Genet. 81(4):821-8 (2007).

(Continued)

*Primary Examiner* — Zinna Northington Davi
(74) *Attorney, Agent, or Firm* — Clark & Elbing LLP

(57) ABSTRACT

The present invention pertains generally to the field of therapeutic compounds. More specifically the present invention pertains to certain 3-aryl-5-substituted-2H-isoquinolin-1-one compounds that, inter alia, inhibit PARP (e.g., PARP1, TNKS1, TNKS2, etc.) and/or Wnt signalling. The present invention also pertains to pharmaceutical compositions comprising such compounds, and the use of such compounds and compositions, both in vitro and in vivo, to inhibit PARP (e.g., PARP1, TNKS1, TNKS2, etc.); to inhibit Wnt signalling; to treat disorders that are ameliorated by the inhibition of PARP (e.g., PARP1, TNKS1, TNKS2, etc.); to treat disorders that are ameliorated by the inhibition of Wnt signalling; to treat proliferative conditions such as cancer, etc.

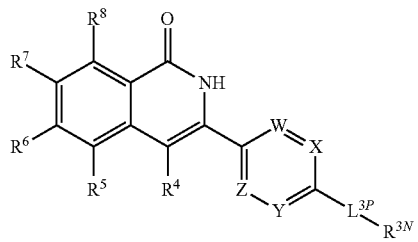

30 Claims, No Drawings

(51) Int. Cl.
*C07D 487/08* (2006.01)
*C07D 487/10* (2006.01)

(56) References Cited

U.S. PATENT DOCUMENTS

| | | | |
|---|---|---|---|
| 4,942,163 | A | 7/1990 | Behrens |
| 5,177,075 | A | 1/1993 | Suto et al. |
| 6,340,759 | B1 | 1/2002 | Ueno et al. |
| 2003/0225106 | A1 | 12/2003 | Askew et al. |
| 2004/0176361 | A1 | 9/2004 | Fujio et al. |
| 2007/0049555 | A1 | 3/2007 | Jagtap et al. |
| 2008/0188467 | A1 | 8/2008 | Wong et al. |
| 2009/0054392 | A1 | 2/2009 | Pelletier et al. |
| 2009/0076276 | A1 | 3/2009 | Fujio et al. |
| 2010/0197706 | A1 | 8/2010 | Evers et al. |
| 2010/0226879 | A1 | 9/2010 | Abbot et al. |
| 2013/0196967 | A1 | 8/2013 | Bartolozzi et al. |
| 2013/0281397 | A1 | 10/2013 | McLure et al. |
| 2013/0331375 | A1 | 12/2013 | Haynes et al. |
| 2013/0345215 | A1 | 12/2013 | Feng et al. |
| 2013/0345226 | A1 | 12/2013 | Hermann et al. |

FOREIGN PATENT DOCUMENTS

| | | |
|---|---|---|
| EP | 1557414 A1 | 7/2005 |
| EP | 1724262 A1 | 11/2006 |
| EP | 1854792 A1 | 11/2007 |
| EP | 1864976 A1 | 12/2007 |
| EP | 2090570 A1 | 8/2009 |
| GB | 1221971 | 6/2014 |
| WO | WO-99/18077 A1 | 4/1999 |
| WO | WO-02/094790 A1 | 11/2002 |
| WO | WO-03/026652 A1 | 4/2003 |
| WO | WO-03/099274 A1 | 12/2003 |
| WO | WO-2004/037805 A1 | 5/2004 |
| WO | WO-2004/058717 A1 | 7/2004 |
| WO | WO-2004/094452 A2 | 11/2004 |
| WO | WO-2005/075432 A1 | 8/2005 |
| WO | WO-2005/113540 A1 | 12/2005 |
| WO | WO-2006/045096 A2 | 4/2006 |
| WO | WO-2006/047277 A2 | 5/2006 |
| WO | WO-2006/063718 A1 | 6/2006 |
| WO | WO-2007/016525 A2 | 2/2007 |
| WO | WO-2008/060927 A2 | 5/2008 |
| WO | WO-2008/092231 A1 | 8/2008 |
| WO | WO-2009/027650 A1 | 3/2009 |
| WO | WO-2009/059994 A2 | 5/2009 |
| WO | WO-2009/127723 A1 | 10/2009 |
| WO | WO-2009/132000 A1 | 10/2009 |
| WO | WO-2010/059658 A1 | 5/2010 |
| WO | WO-2010/106436 A2 | 9/2010 |
| WO | WO-2010/123975 A1 | 10/2010 |
| WO | WO-2010/133647 A1 | 11/2010 |
| WO | WO-2011/045258 A1 | 4/2011 |
| WO | WO-2011/146882 A1 | 11/2011 |
| WO | WO-2011/157787 A1 | 12/2011 |
| WO | WO-2013/008217 A1 | 1/2013 |
| WO | WO-2013/010092 A1 | 1/2013 |
| WO | WO-2013/012723 A1 | 1/2013 |
| WO | WO-2013/076090 A1 | 5/2013 |
| WO | WO-2013/097225 A1 | 7/2013 |
| WO | WO-2013/097226 A1 | 7/2013 |
| WO | WO-2013/110433 A1 | 8/2013 |
| WO | WO-2013/117288 A1 | 8/2013 |
| WO | WO-2013/132253 A1 | 9/2013 |
| WO | WO-2013/134079 A1 | 9/2013 |
| WO | WO-2013/143663 A1 | 10/2013 |
| WO | WO-2013/164061 A1 | 11/2013 |
| WO | WO-2013/177349 A2 | 11/2013 |
| WO | WO-2013/182546 A1 | 12/2013 |
| WO | WO-2013/189904 A1 | 12/2013 |
| WO | WO-2014/023390 A2 | 2/2014 |
| WO | WO-2014/036022 A1 | 3/2014 |
| WO | WO-2014/044356 A1 | 3/2014 |
| WO | WO-2014/045101 A1 | 3/2014 |
| WO | WO-2014/048532 A1 | 4/2014 |
| WO | WO-2014/087165 A1 | 6/2014 |

OTHER PUBLICATIONS

Balemans et al.,"Identification of a 52 kb deletion downstream of the SOST gene in patients with van buchem disease", J Med Genet. 39(2):91-7 (2002).

Balemans et al.,"Increased bone density in sclerosteosis is due to the deficiency of a novel secreted protein (SOST)," Hum Mol Genet., 10(5):537-43 (2001).

Bao et al., "Inhibition of tankyrases induces axin stabilization and blocks wnt signalling in breast cancer cells," PLoS One. 7(11):e48670(9 pages) (2012).

Bergmann et al., "Mutations in the gene encoding the wnt-signaling component R-spondin 4 (RSPO4) cause autosomal recessive anonychia," Am J Hum Genet. 79(6):1105-9 (2006).

Beugelmans et al., "A common and general access to berberine and benzo[c]phenanthridine alkaloids," Tetrahedron, 48(38):8285-94 (1992).

Blaydon et al., "The gene encoding R-spondin 4 (RSPO4), a secreted protein implicated in wnt signaling, is mutated in inherited anonychia," Nat Genet. 38(11):1245-7 (2006).

Bregman et al., "Discovery of a class of novel tankyrase inhibitors that bind to both the nicotinamide pocket and the induced pocket," J Med Chem. 56(3):1341-5 (2013).

Cappelli et al., "Further studies on imidazo[4,5-b]pyridine AT1 angiotensin II receptor antagonists. effects of the transformation of the 4-phenylquinoline backbone into 4 phenylisoquinolinone or 1-phenylindene scaffolds," J Med Chem. 49(22):6451-64 (2006).

Caricasole et al., "The Wnt pathway, cell-cycle activation and beta-amyloid: novel therapeutic strategies in Alzheimer's disease?" Trends Pharmacol Sci. 24(5):233-8 (2003).

Casás-Selves et al., "Tankyrase and the canonical Wnt pathway protect lung cancer cells from EGFR inhibition," Cancer Res. 72(16):4154-64 (2012).

Chang et al., "Tankyrase-1 polymerization of poly(ADP-ribose) is required for spindle structure and function," Nat Cell Biol. 7(11):1133-9 (2005).

Cheon et al., "Structure-activity relationship studies of isoquinoline-one type anticancer agent," Arch Pharm Res. 24(4):276-80 (2001).

Cheon et al., "Synthesis and structure-activity relationship studies of 2,3-dihydroimidazo[2,1-a]isoquinoline analogs as antitumour agents," Arch Pharm Res. 20(2):138-43 (1997).

Cho et al., "Molecular modeling of 3-arylisoquinoline antitumor agents active against A-549. A comparative molecular field analysis study," Bioorg Med Chem. 10(9):2953-61 (2002).

Cho et al., "Synthesis and biological evaluation of 3-arylisoquinolines as antitumor agents," Bioorg Med Chem Lett. 8(1):41-6 (1998).

Cho et al., "Synthesis and comparative molecular field analysis (CoMFA) of antitumor 3-arylisoquinoline derivatives," Bioorg Med Chem. 6(12):2449-58 (1998).

Cho-Park et al., "Proteasome regulation by ADP-ribosylation," Cell. 153(3):614-27 (2013).

Christodoulides et al., "WNT10B mutations in human obesity," Diabetologia. 49(4):678-84 (2006).

Costantino et al., "Modeling of Poly(ADP-ribose)polymerase (PARP) Inhibitors. Docking of Ligands and Quantitative Structure—Activity Relationship Analysis," J Med Chem. 44:3786-94 (2001).

Couture et al., "A convenient synthesis of 3-aryl-2-methyl-3,4-dihydro-1(2H)-isoquinolones and—1,2,3,4-tetrahydroisoquinolines," Synth Commun. 30(15):2775-84 (2000).

Couture et al., "Intramolecular peterson olefination of ortho-trimethylsilylmethyl-N-acyl-N-alkylbenzamides. A new route to 2-alkyl-1(2H)isoquinolones," J Organomet Chem. 440:7-13 (1992).

Daniels, "Abnormal cytokinesis in cells deficient in the breast cancer susceptibility protein BRCA2," Science. 306(5697):876-9 (2004).

Deng et al., "Telomeric proteins regulate episomal maintenance of epstein-barr virus origin of plasmid replication," Mol Cell. 9(3):493-503 (2002).

(56) References Cited

OTHER PUBLICATIONS

Distler et al., "Inactivation of tankyrases reduces experimental fibrosis by inhibiting canonical Wnt signalling," Ann Rheum Dis. 72(9):1575-80 (2013).
Fancy et al., "Axin2 as regulatory and therapeutic target in newborn brain injury and remyelination," Nat Neurosci. 14(8):1009-16 (2011).
Gong et al., "LDL receptor-related protein 5 (LRP5) affects bone accrual and eye development," Cell. 107(4):513-23 (2001).
Grzeschik et al., "Deficiency of PORCN, a regulator of Wnt signaling, is associated with focal dermal hypoplasia," Nat Genet. 39(7):833-5 (2007).
Guimond et al., "Rhodium(III)-catalyzed isoquinolone synthesis: the N—O bond as a handle for C—N bond formation and catalyst turnover," J Am Chem Soc. 132(20):6908-9 (2010).
Haikarainen et al., "para-substituted 2-phenyl-3,4-dihydroquinazolin-4-ones as potent and selective tankyrase Inhibitors," ChemMedChem, 8(12):1978-85 (2013).
Harley, "Telomerase and cancer therapeutics," Nat Rev Cancer. 8(3):167-79 (2008).
Hsiao et al.,"Sister telomeres rendered dysfunctional by persistent cohesion are fused by NHEJ," J Cell Biol. 184(4):515-26 (2009).
Hsiao et al.,"Tankyrase function at telomeres, spindle poles, and beyond," Biochimie. (90)1:83-92 (2008).
Huang et al., "New ammonia equivalents for the Pd-catalyzed amination of aryl halides," Org Lett. 3(21):3417-9 (2001).
Huang et al., "Tankyrase inhibition stabilizes axin and antagonizes Wnt signalling," Nature. 461(7264):614-20 (2009).
International Preliminary Report and Written Opinion for International Patent Application No. PCT/GB2013/050561, mailed Sep. 18, 2014 (7 pages).
James et al., "WIKI4, a novel inhibitor of tankyrase and Wnt/β-catenin signaling," PLoS One 7(12):e50457 (10 pages) (2012).
Kaelin, "Synthetic lethality: a framework for the development of wiser cancer therapeutics," Genome Med. 1(10):99 (6 pages) (2009).
Khadka et al., "Synthesis of 12-oxobenzo[c]phenanthridinones and 4-substituted 3-arylisoquinolones via Vilsmeier-Haack reaction," Tetrahedron. 68(1):250-61 (2012).
Kim et al., "Hypothetical drug binding receptor site analysis using CoMFA method for 3-arylisoquinolines active against SK-OV-3 tumor cell line," Yakhak Hoechi. 46(4):219-25 (2002).
Kozlovsky et al., "GSK-3 and the neurodevelopmental hypothesis of schizophrenia," Eur Neuropsychopharmacol. 12(1):13-25 (2002).
Krishnakumar et al., "The PARP side of the nucleus: molecular actions, physiological outcomes, and clinical targets," Mol Cell. 39(1):8-24 (2010).
Lammi et al., "Mutations in AXIN2 cause familial tooth agenesis and predispose to colorectal cancer," Am J Hum Genet. 74(5):1043-50 (2004).
Le et al., "A versatile total synthesis of benzo[c]phenanthridine and protoberberine alkaloids using lithiated toluamide-benzonitrile cycloaddition," J Org Chem. 69(8): 2768-72 (2004).
Li et al., "Herpes simplex virus requires poly(ADP-ribose) polymerase activity for efficient replication and induces extracellular signal-related kinase-dependent phosphorylation and ICP0-dependent nuclear localization of tankyrase 1," J Virol., 86(1):492-503 (2011).
Li et al., "Platinum(II)-catalyzed intramolecular cyclization of alkynylbenzonitriles: synthesis of 1-alkoxyisoquinolines and isoquinolones," Tetrahedron Lett. 51(49):6422-5 (2010).
Li et al., "Synthesis and activity of 1-aryl-1'-imidazolyl methyl ethers as non-thiol farnesyltransferase inhibitors," Bioorg Med Chem Lett. 14(21):5371-6 (2004).
Lord et al., "Targeted therapy for cancer using PARP inhibitors," Curr Opin Pharmacol. 8(4):363-9 (2008).
Loughlin et al.,"Functional variants within the secreted frizzled-related protein 3 gene are associated with hip osteoarthritis in females," Proc Natl Acad Sci USA. 101(26):9757-62 (2004).
Marsili, "Conversion of indones to quinoline and isoquinoline derivatives. III. Schmidt reaction with 2,3-diphenylindone and similar compounds," Tetrahedron. 24(14):4981-91 (1968).
McCabe et al., "Targeting Tankyrase 1 as a therapeutic strategy for BRCA-associated cancer," Oncogene. 28(11):1465-70 (2009).
Merchant et al., "Synthesis of Heterocyclic Compounds involving Reactions of Indan-1-ones," Indian J Chem. 23B:863-5 (1984).
Mills et al., "Directed ortho metalation of N,N-diethylbenzamides. Silicon protection of ortho sites and the o-methyl group," J Org Chem. 54(18):4372-85 (1989).
Miyaoka et al., "Increased expression of Wnt-1 in schizophrenic brains," Schizophr Res. 38(1):1-6 (1999).
Moon et al., "WNT and beta-catenin signalling: diseases and therapies," Nat Rev Genet. 5(9):691-701 (2004).
Mudher et al., "Alzheimer's disease-do tauists and baptists finally shake hands?" Trends Neurosci. 25(1):22-6 (2002).
Musso et al., "Indanylidenes. 1. Design and synthesis of (E)-2-(4,6-difluoro-1-indanylidene)acetamide, a potent, centrally acting muscle relaxant with anti-inflammatory and analgesic activity," J Med Chem. 46(3):399-408 (2003).
Narwal et al., "Discovery of tankyrase inhibiting flavones with increased potency and isoenzyme selectivity," J Med Chem. 56(20):(33 pages) (2013).
Nathubhai et al., "Design and Discovery of 2-arylquinazolin-4-ones as Potent and Selective Inhibitors of Tankyrases," ACS Med Chem Lett. 4(12):(8 pages) (2013).
Oda et al., "2-Pyridone ring formation through the photo-reaction of arenecarbothioamides with unsaturated carboxylic acids," Heterocycles. 56:69-72 (2002).
Okano et al., "Synthesis of secondary arylamines through copper-mediated intermolecular aryl amination," Org Lett. 5(26):4987-90 (2003).
Olbrich et al., "CNDO/S-C1 Calculations of some Carbonyl-containing Organic Luminophores with a Stilbene Subchromophore," Z Naturforsch. 40a:859-63 (1985).
Oresmaa et al., "Synthesis, ocular effects, and nitric oxide donation of imidazole amidoximes," Eur J Med Chem. 41(9):1073-9 (2006).
Ouchi et al., "Regioselective aromatic substitution of 6,8-dihydroxy-4-ethoxycarbony1-2H-isoquinolin-1-one derivatives using the Stille coupling reaction," Heterocycles. 62:491-501 (2004).
Paine, "Towards Selective Inhibition of the Tankyrases," Biological & Medicinal Chemistry (BMCS) 6th Postgraduate Symposium, University of Cambridge, United Kingdom. 2 pages (2012).
Parma et al., "R-spondin1 is essential in sex determination, skin differentiation and malignancy," Nat Genet. 38(11):1304-9 (2006).
Riffell et al., "Tankyrase-targeted therapeutics: expanding opportunities in the PARP family," Nat Rev Drug Discov. 11(12):923-36 (2012).
Robitaille et al., "Mutant frizzled-4 disrupts retinal angiogenesis in familial exudative vitreoretinopathy," Nat Genet. 32(2):326-30 (2002).
Roy et al.,"Solution-phase synthesis of a diverse isocoumarin library," available in PMC Nov. 1, 2010, pubished in final edited form as: J Comb Chem. 11(6):1128-35 (2009).
Sarkhel et al., "Synthesis of some 3-aryl-5-methoxy-7-methylisocoumarins," Indian J Chem. 16B(11):1034-7 (1978).
Savarin et al., "Novel intramolecular reactivity of oximes: synthesis of cyclic and spiro-fused imines," Org Lett. 9(6):981-3 (2007).
Sharma et al., "Cytotoxicity and TOP1-targeting activity of 8- and 9-amino derivatives of 5-butyl-and 5-(2-N,N,dimethylamino)ethyl-5H-dibenzo[c,h][1,6]naphthyridin-6-ones," Eur J Med Chem 44(4):1471-6 (2009).
Shenglof et al., "Lanthanide assisted cross-coupling of aryl bromides with triethylaluminum," Tetrahedron Lett. 44:8593-5 (2003).
Shkreli et al., "Reversible cell-cycle entry in adult kidney podocytes through regulated control of telomerase and Wnt signaling," Nat Med. 18(1):111-9 (2011) (22 pages).
Shuler et al., "Preparation and X-Ray Crystal Structure of 3-(4-(Dimethylamino)phenyl)-2-(phenylamino)isoquinolin-1(2H)-one, 3-(4-Methoxyphenyl)-2-(phenylamino)isoquinolin-1(2H)-one, and 2-Methyl-N'-(4-methylbenzoyl)-N'-phenylbenzohydrazide from Polylithiated 2-methylbenzoic Acid Phenylhydrazide and Methyl

(56) References Cited

OTHER PUBLICATIONS 4-dimethylaminobenzoate, Methyl 4-methoxybenzoate, or Methyl 4-methylbenzoate," J Chem Crystallogr. 42(9):952-9 (2012).

Simchem and Krämer, 1969, "Reaktionen mit Halogenwasserstoffaddukten der Nitrile, I. Eine neue Isochinolinsynthese", Chemische Berichte., vol. 102, pp. 3656-3665.

Sinha et al., "Synthesis of some new 3-ethyl and 3-phenylisocoumarins," Indian J Heterocyclic Chem. 1(5):235-40 (1992).

Sunderland et al., "Synthesis of 4-alkyl, 4-aryl and 4-arylamino-5-aminoisoquinolin-1-ones and identification of a new PARP-2 selective inhibitor," Org Biomol Chem. 9(3):881-91 (2011).

Threadgill, "Design and discovery of potent inhibitors of the tankyrases, triple-function targets in the cancer cell," 19th ISCB International Conference (ISCBC-2013), Delhi, India, Book of Abstracts, p. 12 (2013).

Threadgill, "Potency and selectivity in the design and development of new tankyrase inhibitors," 20th ISCB International Conference (ISCBC-2014), Delhi, India, Book of Abstracts, p. 38 (2014).

Tocris Webpage for XAV939 (http://www.tocris.com/dispprod.php?ItemId=243282) retrieved on Jun. 6, 2011 (1 page).

Treus et al., "(Z)-Ethyl 2-phenyl-1-(2-vinylphenyl)vinylcarbamates. Part 1: Synthesis and preliminary studies on their divergent transformation into benzo[c]phenanthridines and 2-phenyl-1,4-naphthoquinones," Tetrahedron. 66(52):9986-95 (2010).

Tropsha et al., "Development of kNN QSAR models for 3-arylisoquinoline antitumor agents," Bull Korean Chem Soc. 32(7):2397-404 (2011).

Turner et al., "Hallmarks of 'BRCAness' in sporadic cancers," Nat Rev Cancer. 4(10):(6 pages) (2004).

Varallo et al., "Beta-catenin expression in Dupuytren's disease: potential role for cell-matrix interactions in modulating beta-catenin levels in vivo and in vitro," Oncogene. 22(24):3680-4 (2003).

Waaler et al., "A novel tankyrase inhibitor decreases canonical Wnt signaling in colon carcinoma cells and reduces tumor growth in conditional APC mutant mice," Cancer Res. 72(11):2822-32 (2012).

Wang et al., "Cardiac induction of embryonic stem cells by a small molecule inhibitor of Wnt/?catenin signaling," available in PMC Feb. 18, 2012, published in final edited form as: ACS Chem Biol. 6(2):192-7 (2011) (12 pages).

Woods et al., "Mutations in WNT7A cause a range of limb malformations, including Fuhrmann syndrome and Al-Awadi/Raas-Rothschild/Schinzel phocomelia syndrome," Am J Hum Genet. 79(2):402-8 (2006).

Xu et al., "Vascular development in the retina and inner ear: control by Norrin and Frizzled-4, a high-affinity ligand-receptor pair," Cell. 116(6):883-95 (2004).

Yeh et al., "Insulin-stimulated exocytosis of GLUT4 is enhanced by IRAP and its partner tankyrase," Biochem J. 402(2):279-90 (2007).

Zanon et al., "Copper-catalyzed domino halide exchange-cyanation of aryl bromides," J Am Chem Soc. 125(10):2890-1 (2003).

Zhou et al., "Short and Efficient Total Synthesis of Luotonin A and 22-Hydroxyacuminatine using a common cascade strategy," J Org Chem. 72(16):6270-2 (2007).

3-ARYL-5-SUBSTITUTED-ISOQUINOLIN-1-ONE COMPOUNDS AND THEIR THERAPEUTIC USE

This application is a 371 of PCT/GB2013/050561 filed Mar. 7, 2013 which claims benefit of 61/607,680 filed Mar. 7, 2012.

TECHNICAL FIELD

The present invention pertains generally to the field of therapeutic compounds. More specifically the present invention pertains to certain 3-aryl-5-substituted-2H-isoquinolin-1-one compounds that, inter alia, inhibit PARP (e.g., PARP1, TNKS1, TNKS2, etc.) and/or Wnt signalling. The present invention also pertains to pharmaceutical compositions comprising such compounds, and the use of such compounds and compositions, both in vitro and in vivo, to inhibit PARP (e.g., PARP1, TNKS1, TNKS2, etc.); to inhibit Wnt signalling; to treat disorders that are ameliorated by the inhibition of PARP (e.g., PARP1, TNKS1, TNKS2, etc.); to treat disorders that are ameliorated by the inhibition of Wnt signalling; to treat proliferative conditions such as cancer, etc.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Cancer

Cancer is the second largest cause of death worldwide. Cancer accounts for 13% of global mortality with more than 70% of cancer deaths occurring in low and middle-income countries where the prevalence of cancer is expected to increase as mortality from other diseases decreases. In the UK alone, a disease such as breast cancer kills over 12,000 women each year.

One approach to this problem has been to identify novel targets for cancer therapies and to use these to tailor the treatment of each patient according to the molecular make-up of their particular disease, rather than their overt clinical characteristics. While this has been in part successful, there are still a significant number of tumour types for which there are no targeted therapies and few treatment options other than surgery and cytotoxic chemotherapy.

PARP

There is now a significant body of evidence to suggest that inhibition of poly ADP ribose polymerase (PARP) superfamily proteins, such as PARP1, PARP2, Tankyrase 1 (also known as TNKS1, PARP5a) and Tankyrase 2 (also known as TNKS2, PARP5B) could have clinical utility. See, e.g., Krishnakumar et al., 2010. PARP superfamily members use beta-$NAD^+$ as a substrate to generate ADP-ribose polymers on amino acid residues of protein acceptors. The result is a dramatic post-translational modification that can significantly alter the properties of the protein acceptor. See, e.g., Krishnakumar et al., 2010.

Although much of the focus has been on PARP1, studies over the past decade have identified a family of as many as 17 proteins that share homology to the catalytic domain of PARP1. In addition to the PARP-like domain, the PARP family members are "functionalized" with a wide variety of other structural and functional domains (e.g., DBDs, RNA-binding domains, subcellular localization signals, macrodomains, BRCT motifs, ankyrin repeats, zinc fingers) that determine their overall biological activities. Recently, a unified nomenclature referring to this family of proteins as ADP-ribosyl transferases (ARTs) has been proposed to recognize that fact that (1) PARPs catalyze a transferase reaction, not a template-dependent polymerization reaction; and (2) not all family members have PARP activity; some are likely to function as mono(ADP-ribosyl) transferases (mARTs). This new nomenclature is reflected in a recent structure-based classification of PARP family members into three groups based on their catalytic domains: (1) PARPs 1-5, which are bona fide PARPs containing a conserved glutamate (Glu 988 in PARP1) that defines the PARP catalytic activity; (2) PARPs 6-8, 10-12, and 14-16, which are confirmed or putative mARTs; and (3) PARPs 9 and 13, which lack key NAD-binding residues and the catalytic glutamate, and are likely inactive. See, e.g., Krishnakumar et al., 2010.

PARP family members localize to various cellular compartments, including the nucleus, cytoplasm, mitochondria, and vault particles, although the subcellular localization and function of many of the PARPs are unknown. The known functions of the PARP family members span a wide range of cellular processes, including DNA repair, transcription, cellular signalling, cell-cycle regulation, and mitosis. This diverse array of processes plays key roles in a wide variety of biological outcomes, including differentiation, development, stress responses, inflammation, and cancer. See, e.g., Krishnakumar et al., 2010.

The primary nuclear PARPs are PARP1, PARP2 (the closest paralog to PARP1), PARP3, and tankyrases 1 and 2. PARP1 is a very well studied protein and has a well-established role in DNA repair. See, e.g., Lord et al., 2008. Tankyrase 1 encompasses four distinct domains; the N terminal HPS domain (homopolymeric stretches of His, Pro and Ser); the ankyrin domain, containing 24 ANK repeats; a SAM (sterile alpha module) domain; and a C terminal PARP catalytic domain. See, e.g., Hsiao et al., 2008.

The best characterised function of tankyrase 1 is in telomere maintenance. The cellular machinery that normally replicates genomic DNA is unable to synthesise DNA at the telomere, the structure that caps the end of each chromosome. DNA synthesis at the telomere is instead carried out by telomerase. This enzyme complex consists of a RNA template and a DNA polymerase catalytic subunit. However, the activity of telomerase in most human somatic cells is relatively low and as such, attrition of the DNA at the telomere gradually occurs. This attrition of telomeric DNA is one of the factors that can lead to replicative senescence in somatic cells and this shortening of telomeres is often referred to as a "mitotic clock" that predetermines the replicative capacity of most cells. However, the situation in cancer cells is considerably different from that in somatic cells; up to 90% of all human cancer cells have a high level of telomerase activity. This increased level of telomere maintenance is one of the factors that enables tumour cells to avoid senescence and perpetually replicate. See, e.g., Harley, 2008.

The length of telomeric DNA is determined by a "protein counting" mechanism in which a series of telomere-bound proteins negatively regulate the access of telomerase to the telomere. For example, longer telomeres bind a larger number of DNA double strand-binding Telomeric Repeat Binding Factor (TRF1) proteins. Together with the TIN2-TPP1-POT1 protein complex, TRF1 blocks the access of telomerase to the 3' DNA overhang at the end of chromosomes, thus limiting further extension of the telomere. Regulation of this process is controlled by tankyrase 1 which promotes telomeric extension by poly(ADP-ribosyl)ating TRF1, causing its release from the telomere and eventual proteasomal destruction. This release and degradation of TRF1 allows an enhanced level of telomerase access to the chromosome end and extension of the telomere. See, e.g., Harley, 2008.

Tankyrase 1 is also required after DNA replication in the $S/G_2$ phase of the cell cycle to resolve sister chromatid cohesion before mitosis ensues. Depletion of tankyrase 1 in HeLa cells results in mitotic arrest. Persistent sister chromatid cohesion in tankyrase 1 depleted cells results in sister chromatid fusion. See, e.g., Hsiao et al., 2009. The mitotic defect in tankyrase-depleted cells may, in part, be determined by the tankyrase 1-mediated poly(ADP ribosyl)ation of the protein NuMA, which plays an essential role in organising microtubules at spindle pores. See, e.g., Chang et al., 2005.

Recent work has also suggested a role for Tankyrase 1 in the control of oncogenic Wnt signalling, most likely via a mechanism that involves the stabilisation of the Wnt signalling component, Axin. See, e.g., Huang et al., 2009. In this latter work and subsequent work (see, e.g., James et al., 2012; Bao et al., 2012; Casás-Selves et al., 2012; Waaler et al., 2012; Riffell et al., 2012) a number of investigators have shown that toolbox, non-drug like small molecule inhibitors of tankyrase can inhibit oncogenic Wnt signalling and can inhibit tumour cells that are addicted to Wnt signalling.

Wnt Signalling

Wnt signalling is an intracellular protein signalling network that transduces signals from cell surface bound receptors to a series of gene transcription events. In canonical Wnt signalling, Wnt ligands bind to cell-surface receptors of the Frizzled family; Frizzled bound receptors activate Dishevelled family proteins. In turn, activated Dishevelled proteins inhibit the function of a complex of proteins including Axin 1 and 2, GSK-3, and the protein APC. This Axin/GSK-3/APC complex normally promotes the proteolytic degradation of the β-catenin intracellular signalling molecule. When Wnt signalling is stimulated and Dishevelled proteins are active, the "β-catenin destruction complex" is inhibited, β-catenin degradation is reduced and β-catenin is able to enter the nucleus and interact with TCF/LEF family transcription factors. This latter act drives a series of specific gene expression events that ultimately mediate Wnt signalling.

The association of dysregulated Wnt/β-catenin signalling with cancer has been well documented. Constitutively activated β-catenin signalling, caused either by APC deficiency or activating β-catenin mutations can lead to tumourigenesis. Furthermore, tankyrase is directly involved in the Wnt signalling cascade. Tankyrase PARylates both Axin 1 and Axin 2 and causes their degradation, driving β-catenin stabilisation/nuclear translocation and TCF/LEF mediated transcription. See, e.g., Huang et al., 2009. When tankyrase is inhibited, either genetically or with small molecules, Axin 1 and 2 levels are stabilized and β-catenin degradation is enhanced, ultimately suppressing Wnt signalling, even in situations where Wnt signalling is usually constitutively elevated, such as APC deficiency. See, e.g., Huang et al., 2009. These data suggest that tankyrase inhibition could be used in order to modulate Wnt signalling, both in cancer, but also in other, non-cancer, pathologies where Wnt signalling is aberrant.

In addition to its effects on Wnt signally, it has also recently been demonstrated that silencing of tankyrase 1 by RNA interference is lethal in tumour cells with deficiencies in either of the breast cancer susceptibility proteins, BRCA1 and BRCA2, but not in wild type cells. BRCA mutation carriers with cancer still retain functional BRCA protein function in their normal cells, whilst it is lacking in tumour cells, suggesting that a tankyrase 1 inhibitor could be used to selectively target tumour cells in BRCA patients. See, e.g., McCabe et al., 2009b. This approach of combining tumour-specific genetic deficiencies with inhibition of a drug target to elicit a therapeutic window is an example of a "synthetic lethal" approach to the design of cancer therapies. See, e.g., Kaelin, 2009. This BRCA selective effect of tankyrase 1 inhibition may be caused by telomere attrition (caused by tankyrase 1 inhibition) and stalled replication forks (caused by BRCA deficiency) acting in concert to cause a threshold of DNA damage that is inconsistent with cell viability. Alternatively, synergistic defects in cytokinesis and sister chromatid segregation caused by BRCA deficiency and tankyrase 1 inhibition may also underlie the BRCA selective effect. See, e.g., Daniels, 2004. The use of tankyrase 1 inhibition in this context is described in McCabe et al., 2009a and McCabe et al., 2009b.

It has been shown that a proportion of patients without BRCA mutations have clinical characteristics, tumour morphologies and tumour molecular profiles that are reminiscent of BRCA mutation-associated cancer, a property termed BRCAness. See, e.g., Turner et al., 2004. This BRCAness phenotype is most well described in a significant number of patients with triple negative breast tumours. See, e.g., Turner et al., 2004. It has been shown that BRCA1 deficient, triple-negative breast cancer cell lines such as HCC1937 are particularly sensitive to tankyrase 1 inhibition. See, e.g., McCabe et al., 2009a and McCabe et al., 2009b. Inhibiting tankyrase 1 therefore, may be very effective in patients with germ-line BRCA mutations as well as patients whose tumours exhibit a BRCAness phenotype.

Non-Tumourigenic Mechanisms Modulated by Tankyrase

In addition to tankyrase inhibitors having potential as cancer therapeutics, a number of other studies suggest tankyrase inhibitors could be used in a number of other non-cancer related pathologies, the majority of which are driven by aberrant Wnt signalling, of which tankyrase activity is a rate limiting step (see, e.g., Riffell et al., 2012).

For example:

Recent work has indicated that inhibition of tankyrase can stabilize Axin2 levels in immature oligodendrocyte progenitor cells (OLPs) (see, e.g., Fancy et al., 2011). On the basis that Axin2 function is essential for normal kinetics of remyelination, tankyrase inhibition has been shown to accelerate OLP myelination after hypoxic and demyelinating injury (see, e.g., Fancy et al., 2011). This data suggest that small molecule tankyrase inhibitors might serve as pharmacological agents that could aid remyelination in neuropathies such as multiple sclerosis, neonatal hypoxic ischemic encephalopathy (HIE), and neonatal periventricular leukomalacia (PVL) (see, e.g., Fancy et al., 2011).

Other studies have also shown that tankyrase is essential for Herpes Simplex Virus replication (HSV). Efficient HSV-1 replication requires tankyrase PARP activity (see, e.g., Li et al., 2011). Further support for this hypothesis comes from the observation that HSV did not replicate efficiently in cells depleted of tankyrase 1. Moreover, tankyrase and the tankyrase substrate TRF2 (telomeric repeat binding factor 2) control the degradation of Ebstein-Barr Virus (EBV) DNA (see, e.g., Deng et al., 2002), suggesting tankyrase inhibitors could have utility as antiviral agents.

In addition, tankyrase inhibition is known to modulate glucose uptake (see, e.g., Yeh et al., 2007), suggesting that a small molecule tankyrase inhibitor could have utility in the treatment of metabolic diseases such as type 2 diabetes. In this case, tankyrase inhibition is thought to modulate glucose uptake by altering the function and cellular localisation of the glucose transporter type 4 (GLUT4) and the aminopeptidase IRAP (insulin-responsive aminopeptidase).

In addition, tankyrase inhibition is known to induce cardiomyocyte differentiation (see, e.g., Wang et al., 2011), suggesting that small molecule tankyrase inhibitors could have some ability in the treatment of cardiac disorders, such as cardiac repair after cardiac infarction.

In addition, tankyrase inhibition is know to minimise the pathological effects of lung fibrosis and tankyrase inhibitors can improve the survival of mice with bleomycin induced lung fibrosis (see, e.g., Distler et al., 2012) suggesting that small molecule tankyrase inhibitors could have some usefuleness in the treatment of lung disorders and fibrotic disorders such as pulmonary fibrosis, cystic fibrosis, cirrhosis, endomyocardial fibrosis, mediastinal fibrosis, myelofibrosis, retroperitoneal fibrosis, progressive massive fibrosis, nephrogenic systemic fibrosis, Crohn's disease, keloid, scleroderma/systemic sclerosis and arthrofibrosis.

In addition to these pathologies, Wnt signalling and its modulation are also involved in a number of other pathogenic conditions suggesting that small molecules tankyrase inhibitors could have utility in these other Wnt related diseases, including:

Alzheimer's disease, where the Wnt mediator B-catenin activity is aberrant (see, e.g., Caricasole et al., 2003; Moon et al., 2004; Mudher and Lovestone, 2002);

Dupuytren skin disease, where the Wnt mediator B-catenin activity is also aberrant (see, e.g., Varallo et al., 2003);

tooth agenesis, where the Wnt mediator Axin2 activity is aberrant (see, e.g., Lammi et al., 2004);

osteoarthritis, where the Wnt mediator secreted frizzled-related protein 3 (FRP3) activity is aberrant (see, e.g., Loughlin et al., 2004);

exudative vitreoretinopathy, where the Wnt mediators frizzled family receptor 4 (FZD4) (see, e.g., Robitaille et al., 2002) and Norrie disease protein (see, e.g., Xu et al., 2004) activities are aberrant;

schizophrenia, where the Wnt mediators glycogen synthase kinase 3 beta (GSK3b) and wingless-type MMTV integration site family member 1 (Wnt1) are aberrant (see, e.g., Kozlovsky et al., 2002; Miyaoka et al., 1999);

osteoporosis, where the Wnt mediator low density lipoprotein receptor-related protein 5 (LRP5) activity is aberrant (see, e.g., Gong et al., 2001);

dermal hypoplasia, where the Wnt mediator porcupine homolog (PORCN) activity is aberrant (see, e.g., Grzeschik et al., 2007);

XX sex reversal, where the Wnt mediator R-spondin 1 (RSPO1) activity is aberrant (see, e.g., Parma et al., 2006);

anonychia and hyponychia, were the Wnt mediator R-spondin 4 (RSPO4) is aberrant (see, e.g., Bergmann et al., 2006; Blaydon et al., 2006);

sclerosteosis and Van Buchem disease, where the Wnt mediator sclerostin (SOST) activity is aberrant (see, e.g., Balemans et al., 2001; Balemans et al., 2002);

Fuhrmann syndrome, were the Wnt mediator wingless-related MMTV integration site 7A (Wnt7a) activity is aberrant (see, e.g., Woods et al., 2006);

Odonto-onchyo-dermal hypoplasia, where Wnt mediator wingless related MMTV integration site 10a (Wnt10a) activity is aberrant (see, e.g., Adaimy et al., 2007); and early onset obesity, where the Wnt mediator wingless related MMTV integration site 10b (Wnt10b) activity is aberrant (see, e.g., Christodoulides et al., 2006).

Moreover, aberrant telomerase protein component TERT expression and aberrant Wnt signalling are implicated in nephropathy, including HIV-associated nephropathy (see, e.g., Shkreli et al., 2011). Given the strong link between tankyrase inhibitors and modulation of both Wnt signalling and TERT function, it is likely that small molecule tankyrase inhibitors could be used in the treatment of these pathologies.

The inventors have identified a class of small molecule inhibitors of PARP superfamily members including PARP1 and Tankyrase 1 which are useful in the treatment of conditions, including proliferative conditions such as cancer. In some cases, these inhibitors are able to elicit biochemical inhibition of these targets as well as eliciting cellular activity including one or more or all of: (i) inhibition of Wnt signalling; (ii) inhibition of cell survival/proliferation; (iii) stabilisation of Axin and tankyrase levels; and (iv) formation of markers of DNA damage such as γH2AX foci.

It appears that the following 3-aryl-5-substituted-2H-isoquinolin-1-ones are known.

| # | Structure | Registry No. |
|---|---|---|
| P01 | 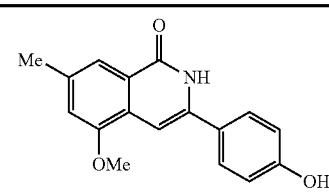 | 70351-69-8 |
| P02 | 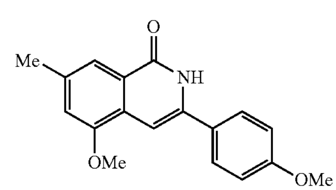 [SMILES: COc1ccc(-c2cc3c(OC)cc(C)cc3c(=O)[nH]2)cc1] | 70351-70-1 |

-continued

| # | Structure | Registry No. |
|---|---|---|
| P03 | 7-Me, 5-OMe isoquinolin-1(2H)-one with 3-(3-Me-4-OH-phenyl) | 70351-71-2 |
| P04 | 7-Me, 5-OMe isoquinolin-1(2H)-one with 3-(2-OH-4-Me-phenyl) | 70351-72-3 |
| P05 | 5-NMe₂ isoquinolin-1(2H)-one with 3-(4-Me-phenyl) | 203628-15-3 |
| P06 | 5-NMe₂ isoquinolin-1(2H)-one with 3-(4-Br-phenyl) | 203628-17-5 |
| P07 | 5-NMe₂ isoquinolin-1(2H)-one with 3-(4-OMe-phenyl) | 203628-19-7 |
| P08 | 5-NMe₂ isoquinolin-1(2H)-one with 3-(4-Cl-phenyl) | 220630-92-2 |
| P09 | 5-Me isoquinolin-1(2H)-one with 3-(4-OMe-phenyl) | 223553-35-3 |
| P10 | 5-OMe isoquinolin-1(2H)-one with 3-(3-F-4-OH-phenyl) | 884500-93-0 |
| P11 | 5-OMe isoquinolin-1(2H)-one with 3-(3-F-4-OTBDMS-phenyl) | 884501-99-9 |
| P12 | 7-F, 5-Me isoquinolin-1(2H)-one, 4-O-CH₂CH₂NH₂, 3-(4-OMe-phenyl) | 1256940-02-9 |
| P13 | 7-F, 5-Me isoquinolin-1(2H)-one, 4-O-(CH₂)₃-piperidinyl, 3-(4-OMe-phenyl) | 1256940-03-0 |
| P14 | 7-F, 5-Me isoquinolin-1(2H)-one, 4-O-CH₂CH₂NH₂, 3-(3-OMe-4-Cl-phenyl) | 1256940-06-3 |
| P15 | 7-F, 5-Me isoquinolin-1(2H)-one, 4-O-(CH₂)₃-piperidinyl, 3-(3-OMe-4-Cl-phenyl) | 1256940-07-4 |

| # | Structure | Registry No. |
|---|---|---|
| P16 | 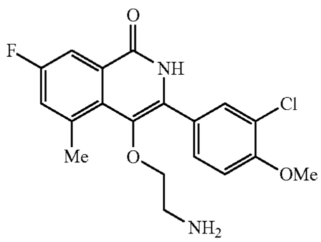 [SMILES: COc1ccc(-c2[nH]c(=O)c3cc(F)cc(C)c3c2OCCN)cc1Cl] | 1256940-08-5 |
| P17 | 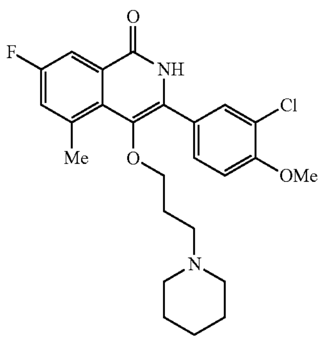 [SMILES: COc1ccc(-c2[nH]c(=O)c3cc(F)cc(C)c3c2OCCCN2CCCCC2)cc1Cl] | 1256940-09-6 |
| P18 | 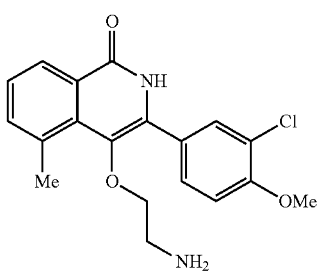 [SMILES: COc1ccc(-c2[nH]c(=O)c3cccc(C)c3c2OCCN)cc1Cl] | 1256940-10-9 |
| P19 | 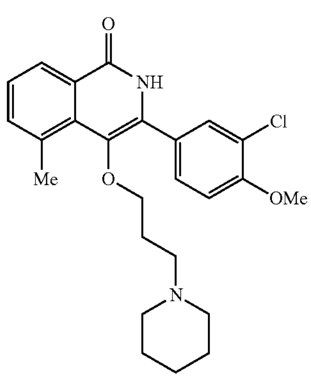 [SMILES: COc1ccc(-c2[nH]c(=O)c3cccc(C)c3c2OCCCN2CCCCC2)cc1Cl] | 1256940-11-0 |
| P20 | 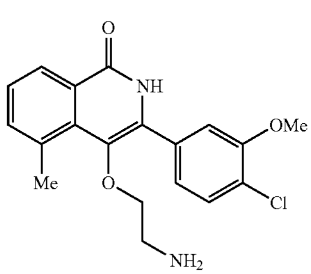 [SMILES: COc1cc(-c2[nH]c(=O)c3cccc(C)c3c2OCCN)ccc1Cl] | 1256940-12-1 |
| P21 | | 1256940-13-2 |
| P22 | | 1256940-16-5 |
| P23 | | 1256940-17-6 |
| P24 | | 1262335-24-9 |

It appears that the following 3-aryl-5-unsubstituted-2H-isoquinolin-1-ones are known.

| # | Structure | Registry No. |
|---|---|---|
| P25 | 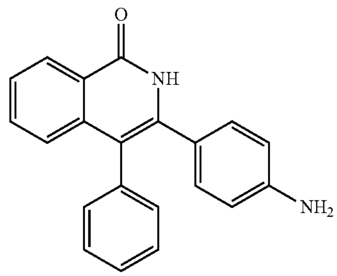 [SMILES: Nc1ccc(-c2[nH]c(=O)c3ccccc3c2-c2ccccc2)cc1] | 19069-81-9 |
| P26 | 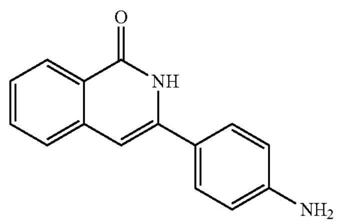 [SMILES: Nc1ccc(-c2cc3ccccc3c(=O)[nH]2)cc1] | 98659-53-1 |
| P27 | 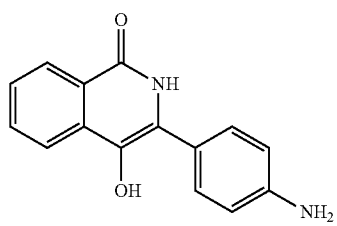 [SMILES: Nc1ccc(-c2[nH]c(=O)c3ccccc3c2O)cc1] | 98659-55-3 |
| P28 | 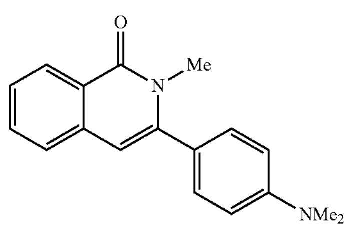 [SMILES: CN(C)c1ccc(-c2cc3ccccc3c(=O)n2C)cc1] | 145104-33-2 |
| P29 | 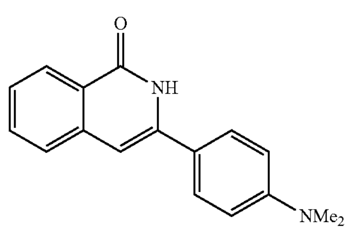 [SMILES: CN(C)c1ccc(-c2cc3ccccc3c(=O)[nH]2)cc1] | 223552-86-1 |
| P30 | 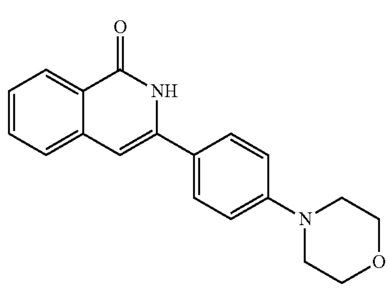 [SMILES: O=c1[nH]c(-c2ccc(N3CCOCC3)cc2)cc2ccccc12] | 223553-20-6 |

-continued

| # | Structure | Registry No. |
|---|-----------|--------------|
| P31 | 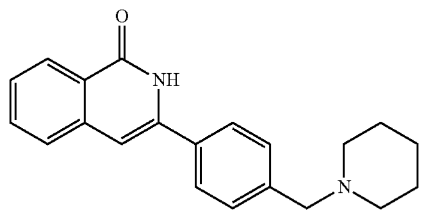 [SMILES: O=c1[nH]c(-c2ccc(CN3CCCCC3)cc2)cc2ccccc12] | 376354-94-8 |
| P32 | 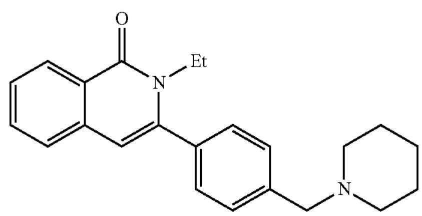 [SMILES: CCn1c(-c2ccc(CN3CCCCC3)cc2)cc2ccccc2c1=O] | 376354-97-1 |
| P33 | 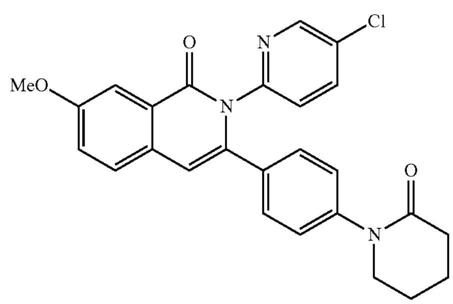 [SMILES: COc1ccc2cc(-c3ccc(N4CCCCC4=O)cc3)n(-c3ccc(Cl)cn3)c(=O)c2c1] | 503613-43-2 |
| P34 | 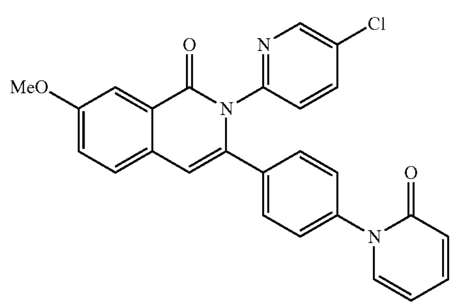 [SMILES: COc1ccc2cc(-c3ccc(-n4ccccc4=O)cc3)n(-c3ccc(Cl)cn3)c(=O)c2c1] | 503613-44-3 |
| P35 | 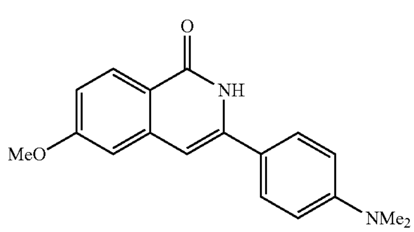 [SMILES: COc1ccc2c(=O)[nH]c(-c3ccc(N(C)C)cc3)cc2c1] | 630423-61-9 |
| P36 | 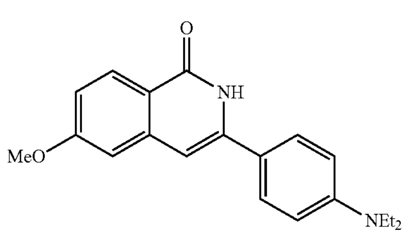 | 630423-64-2 |

-continued

| # | Structure | Registry No. |
|---|---|---|
| P37 | 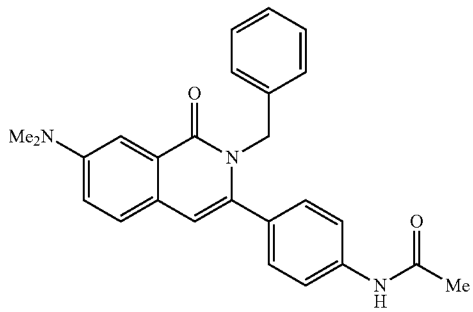 [SMILES: CC(=O)Nc1ccc(-c2cc3ccc(N(C)C)cc3c(=O)n2Cc2ccccc2)cc1] | 721960-58-3 |
| P38 | 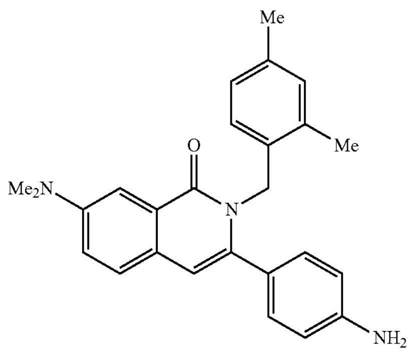 [SMILES: Cc1ccc(Cn2c(-c3ccc(N)cc3)cc3ccc(N(C)C)cc3c2=O)c(C)c1] | 721960-60-7 |
| P39 | 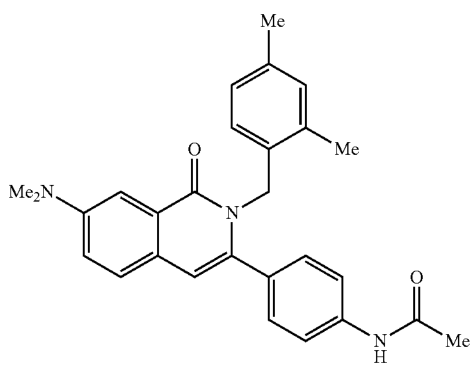 [SMILES: CC(=O)Nc1ccc(-c2cc3ccc(N(C)C)cc3c(=O)n2Cc2ccc(C)cc2C)cc1] | 721960-73-2 |
| P40 | 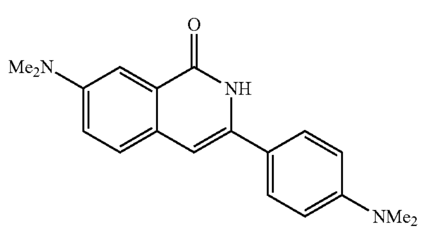 [SMILES: CN(C)c1ccc(-c2cc3ccc(N(C)C)cc3c(=O)[nH]2)cc1] | 862469-72-5 |
| P41 | 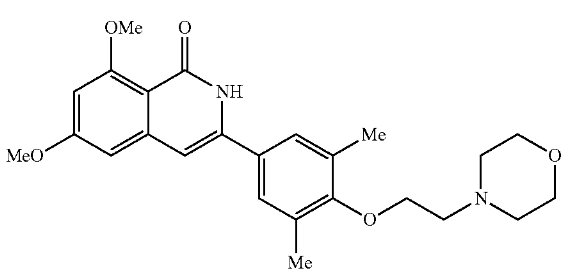 [SMILES: COc1cc(OC)c2c(=O)[nH]c(-c3cc(C)c(OCCN4CCOCC4)c(C)c3)cc2c1] | 924299-93-4 |

-continued

| # | Structure | Registry No. |
|---|---|---|
| P42 | 6,8-dimethoxy-3-[3,5-dimethyl-4-[2-(4-methylpiperazin-1-yl)ethoxy]phenyl]isoquinolin-1(2H)-one | 1044871-80-8 |
| P43 | 6,8-dimethoxy-3-[4-[2-(dimethylamino)ethoxy]-3,5-dimethylphenyl]isoquinolin-1(2H)-one | 1044871-83-1 |
| P44 | 3-(4-aminophenyl)-2-(4-hydroxybutyl)isoquinolin-1(2H)-one | 1193268-39-1 |
| P45 | 3-(4-aminophenyl)-2-(5-hydroxypentyl)isoquinolin-1(2H)-one | 1193268-40-4 |
| P46 | N-[2-[4-(6,8-dimethoxy-1-oxo-1,2-dihydroisoquinolin-3-yl)-2,6-dimethylphenoxy]ethyl]formamide | 1253733-07-1 |
| P47 | 3-[4-(2-aminoethoxy)-3,5-dimethylphenyl]-6,8-dimethoxyisoquinolin-1(2H)-one | 1253733-10-6 |

| # | Structure | Registry No. |
|---|---|---|
| P48 | 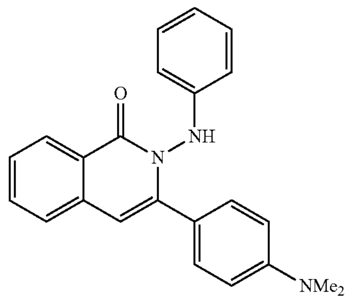 [SMILES: CN(C)c1ccc(-c2cc3ccccc3c(=O)n2Nc2ccccc2)cc1] | 1417652-57-3 |

SUMMARY OF THE INVENTION

One aspect of the invention pertains to certain 3-aryl-5-substituted-2H-isoquinolin-1-one compounds (referred to herein as IQ compounds), as described herein.

Another aspect of the invention pertains to a composition (e.g., a pharmaceutical composition) comprising an IQ compound, as described herein, and a pharmaceutically acceptable carrier or diluent.

Another aspect of the invention pertains to a method of preparing a composition (e.g., a pharmaceutical composition) comprising the step of mixing an IQ compound, as described herein, and a pharmaceutically acceptable carrier or diluent.

Another aspect of the present invention pertains to a method of inhibiting PARP (e.g., PARP1, TNKS1, TNKS2, etc.) function (e.g., in a cell), in vitro or in vivo, comprising contacting the cell with an effective amount of an IQ compound, as described herein.

Another aspect of the present invention pertains to a method of inhibiting Wnt signalling (e.g., in a cell), in vitro or in vivo, comprising contacting the cell with an effective amount of an IQ compound, as described herein.

Another aspect of the present invention pertains to a method of treatment comprising administering to a subject in need of treatment a therapeutically-effective amount of an IQ compound, as described herein, preferably in the form of a pharmaceutical composition.

Another aspect of the present invention pertains to an IQ compound as described herein for use in a method of treatment of the human or animal body by therapy.

Another aspect of the present invention pertains to use of an IQ compound, as described herein, in the manufacture of a medicament for use in treatment.

In one embodiment, the treatment is treatment of a proliferative condition.

In one embodiment, the treatment is treatment of cancer.

In one embodiment, the treatment is treatment of head cancer; neck cancer; nervous system cancer; lung/mediastinum cancer; breast cancer; oesophagus cancer; stomach cancer; liver cancer; biliary tract cancer; pancreatic cancer; small bowel cancer; large bowel cancer; gynaecological cancer; genito-urinary cancer; thyroid gland cancer; adrenal gland cancer; skin cancer; bone sarcoma; soft tissue sarcoma; paediatric malignancy; Hodgkin's disease; non-Hodgkin's lymphoma; myeloma; leukaemia; or metastasis from an unknown primary site.

In one embodiment, the treatment is treatment of: a neurodegenerative disorder, such as multiple sclerosis (MS); a neurological disorder associated with demyelination; neonatal hypoxic ischemic encephalopathy (HIE); neonatal periventricular leukomalacia (PVL); a cardiac related pathology, such as myocardial infarction; cardiac damage (e.g., to repair cardiac damage); an infectious disease, such as a pathology related to Herpes Simplex Virus (HSV); a pathology related to Epstein-Barr Virus (EBV); a metabolic disease, such as a metabolic disease where glucose uptake is dysfunctional, such as diabetes, such as type 2 diabetes; or fibrosis (e.g., lung fibrosis).

In one embodiment, the treatment is treatment of: a neurodegenerative disorder, such as multiple sclerosis (MS); neonatal hypoxic ischemic encephalopathy (HIE); neonatal periventricular leukomalacia (PVL); a cardiac related pathology, such as myocardial infarction; a pathology related to Herpes Simplex Virus (HSV); a pathology related to Epstein-Barr Virus (EBV); or a metabolic disease such as type 2 diabetes.

In one embodiment, the treatment is treatment of: Alzheimer's disease; late onset Alzheimer's disease; Dupuytren skin disease; tooth agenesis; vascular defects in the eye; Osteoperosis-pseudoglioma Syndrome (OPPG); exudative vitreoretinopathy; familial exudative vitreoretinopathy; retinal angiogenesis; schizophrenia; osteoporosis; dermal hypoplasia; XX sex reversal; Mullerian-duct regression and virilization; SERKAL syndrome; anonychia; hyponychia; sclerosteosis; van Buchem disease; Fuhrmann syndrome; odonto-onchyo-dermal hypoplasia; Type 2 diabetes; obesity; early onset obesity; a nephropathy, such as HIV-associated nephropathy; early coronary disease; bone density defects; tetra-amelia syndrome; split-hand/foot malformation; caudal duplication; Fuhrmann syndrome; odonto-onycho-dermal dysplasia; skeletal dysplasia; focal dermal hypoplasia; autosomal recessive anonychia; or neural tube defects.

In one embodiment, the treatment is treatment of: Alzheimer's disease; Dupuytren skin disease; tooth agenesis; exudative vitreoretinopathy; schizophrenia; osteoporosis; dermal hypoplasia; XX sex reversal; anonychia; hyponychia; sclerosteosis; van Buchem disease; Fuhrmann syndrome; odonto-onchyo-dermal hypoplasia; early onset obesity; or a nephropathy, such as HIV-associated nephropathy.

Another aspect of the present invention pertains to a kit comprising (a) an IQ compound, as described herein, preferably provided as a pharmaceutical composition and in a suitable container and/or with suitable packaging; and (b) instructions for use, for example, written instructions on how to administer the compound.

Another aspect of the present invention pertains to an IQ compound obtainable by a method of synthesis as described herein, or a method comprising a method of synthesis as described herein.

Another aspect of the present invention pertains to an IQ compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

One aspect of the present invention relates to certain compounds which are structurally related to 2H-isoquinolin-1-one.

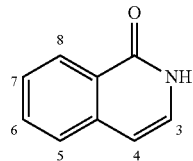

2H-Isoquinolin-1-one

More particularly, the present invention relates to certain 3-aryl-5-substituted-2H-isoquinolin-1-one compounds, as defined herein.

Yet more particularly, the present invention relates to certain 2H-isoquinolin-1-one compounds which have both:
(a) a particular substituent (denoted herein as $R^5$) at the 5-position; and
(b) a particular six-membered carboaryl or heteroaryl substituent (denoted herein as the ring containing W, X, Y, and Z) at the 3-position having a particular para-substituent (denoted herein as -$L^{3P}$-$R^{3N}$).

Thus, one aspect of the present invention pertains to compounds selected from compounds of the following formula, and pharmaceutically acceptable salts, N-oxides, hydrates, and solvates thereof, wherein —$R^{3N}$, -$L^{3P}$-, W, X, Y, Z, —$R^4$, —$R^5$, —$R^6$, —$R^7$, and —$R^8$ are as defined herein (for convenience, collectively referred to herein as "3-aryl-5-substituted-2H-isoquinolin-1-one compounds" or "IQ compounds"):

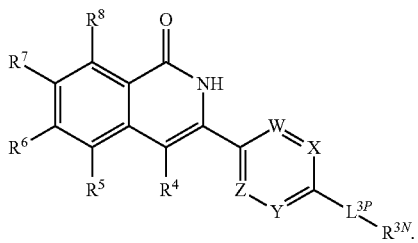

Some embodiments of the invention include the following:
(1) A compound selected from compounds of the following formula, and pharmaceutically acceptable salts, N-oxides, hydrates, and solvates thereof:

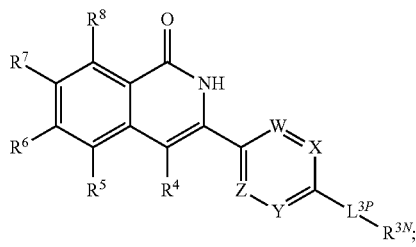

wherein:
W is $CR^W$, X is $CR^X$, Y is $CR^Y$, and Z is $CR^Z$ ("phenyl"); or
W is N, X is $CR^X$, Y is $CR^Y$, and Z is $CR^Z$ ("pyrid-2-yl"); or
W is $CR^W$, X is N, Y is $CR^Y$, and Z is $CR^Z$ ("pyrid-3-yl"); or
W is N, X is $CR^X$, Y is $CR^Y$, and Z is N ("pyrimidin-2-yl"); or
W is $CR^W$, X is N, Y is N, and Z is $CR^Z$ ("pyrimidin-5-yl"); or
W is N, X is $CR^X$, Y is N, and Z is $CR^Z$ ("pyrazin-2-yl"); or
W is N, X is N, Y is $CR^Y$, and Z is $CR^Z$ ("pyridazin-3-yl");
wherein:
—$R^W$ is independently —H or —$R^{WW}$;
—$R^X$ is independently —H or —$R^{XX}$;
—$R^Y$ is independently —H or —$R^{YY}$; and
—$R^Z$ is independently —H or —$R^{ZZ}$;
wherein:
—$R^{WW}$ is independently —$X^1$, —$R^1$, —OH, —$OR^1$, —$CF_3$, or —$OCF_3$;
—$R^{XX}$ is independently —$X^1$, —$R^1$, —OH, —$OR^1$, —$CF_3$, or —$OCF_3$;
—$R^{YY}$ is independently —$X^1$, —$R^1$, —OH, —$OR^1$, —$CF_3$, or —$OCF_3$; and
—$R^{ZZ}$ is independently —$X^1$, —$R^1$, —OH, —$OR^1$, —$CF_3$, or —$OCF_3$;
wherein:
each —$X^1$ is independently —F, —Cl, —Br, or —I; and
each —$R^1$ is independently linear or branched saturated $C_{1-4}$alkyl;
and wherein:
-$L^{3P}$- is independently a single covalent bond or -$L^{3PL}$-;
wherein:
-$L^{3PL}$- is independently -$L^{3PR1}$-, —C(=O)—, -$L^{3PR2}$-C(=O)—, —S(=O)$_2$—, -$L^{3PR3}$-S(=O)$_2$—, or —O-$L^{3PR4}$-;
wherein:
each -$L^{3PR1}$- is linear or branched saturated $C_{1-4}$alkylene;
each -$L^{3PR2}$- is linear or branched saturated $C_{1-4}$alkylene;
each -$L^{3PR3}$- is linear or branched saturated $C_{1-4}$alkylene;
each -$L^{3PR4}$- is linear or branched saturated $C_{1-4}$alkylene;
and wherein:
—$R^{3N}$ is independently —$NH_2$, —$NHR^A$, —$NR^AR^B$, or —$NR^CR^D$;
wherein:
each —$R^A$ is independently:
—$R^{A1}$, —$R^{A2}$, —$R^{A3}$, —$R^{A4}$, —$R^{A5}$, -$L^A$-$R^{A2}$, -$L^A$-$R^{A3}$, -$L^A$-$R^{A4}$, or -$L^A$-$R^{A5}$;
each —$R^{A1}$ is linear or branched $C_{1-6}$alkyl,
and is optionally substituted with one or more groups —$R^{S1}$;
each —$R^{A2}$ is saturated $C_{3-6}$cycloalkyl,
and is optionally substituted with one or more groups —$R^{S2C}$;
each —$R^{A3}$ is non-aromatic $C_{3-7}$heterocyclyl, and is optionally substituted on carbon with one or more groups —$R^{S2C}$, and is optionally substituted on secondary nitrogen, if present, with a group —$R^{SN}$;

each —$R^{A4}$ is independently phenyl or naphthyl,
and is optionally substituted with one or more groups —$R^{S3C}$;

each —$R^{A5}$ is $C_{6-10}$heteroaryl,
and is optionally substituted on carbon with one or more groups —$R^{S3C}$,
and is optionally substituted on secondary nitrogen, if present, with a group —$R^{SN}$;

each -$L^A$- is linear or branched saturated $C_{1-4}$alkylene;

and wherein:
each —$R^{S1}$ is independently:
—F, —Cl, —Br, —I,
—OH, —$OR^{TT}$,
—$OCF_3$,
—$NH_2$, —$NHR^{TT}$, —$NR^{TT}_2$, —$R^{TM}$,
—C(=O)OH, —C(=O)$OR^{TT}$, —OC(=O)$R^{TT}$,
—C(=O)$NH_2$, —C(=O)$NHR^{TT}$, —C(=O)$NR^{TT}_2$,
—C(=O)$R^{TM}$,
—NHC(=O)$R^{TT}$, —$NR^{TN}$C(=O)$R^{TT}$,
—NHC(=O)$NH_2$, —NHC(=O)$NHR^{TT}$, —NHC(=O)$NR^{TT}_2$, —NHC(=O)$R^{TM}$,
—$NR^{TN}$C(=O)$NH_2$, —$NR^{TN}$C(=O)$NHR^{TT}$,
—$NR^{TN}$C(=O)$NR^{TT}_2$, —$NR^{TN}$C(=O)$R^{TM}$,
—NHC(=O)$OR^{TT}$, —$NR^{TN}$C(=O)$OR^{TT}$,
—OC(=O)$NH_2$, —OC(=O)$NHR^{TT}$, —OC(=O)$NR^{TT}_2$, —OC(=O)$R^{TM}$,
—C(=O)$R^{TT}$,
—S(=O)$_2NH_2$, —S(=O)$_2NHR^{TT}$, —S(=O)$_2NR^{TT}_2$,
—S(=O)$_2R^{TM}$,
—NHS(=O)$_2R^{TT}$, —$NR^{TN}$S(=O)$_2R^{TT}$,
—S(=O)$_2R^{TT}$,
—CN, —$NO_2$, —$SR^{TT}$, or =O;

each —$R^{S2C}$ is independently:
—$R^{TT}$,
—F, —Cl, —Br, —I,
—OH, —$OR^{TT}$,
-$L^T$-OH, -$L^T$-$OR^{TT}$,
—$CF_3$, —$OCF_3$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$,
—C(=O)OH, —C(=O)$OR^{TT}$, —OC(=O)$R^{TT}$,
—C(=O)$NH_2$, —C(=O)$NHR^{TT}$, —C(=O)$NR^{TT}_2$,
—C(=O)$R^{TM}$,
—NHC(=O)$R^{TT}$, —$NR^{TN}$C(=O)$R^{TT}$,
—NHC(=O)$NH_2$, —NHC(=O)$NHR^{TT}$, —NHC(=O)$NR^{TT}_2$, —NHC(=O)$R^{TM}$,
—$NR^{TN}$C(=O)$NH_2$, —$NR^{TN}$C(=O)$NHR^{TT}$,
—$NR^{TN}$C(=O)$NR^{TT}_2$, —$NR^{TN}$C(=O)$R^{TM}$,
—NHC(=O)$OR^{TT}$, —$NR^{TN}$C(=O)$OR^{TT}$,
—OC(=O)$NH_2$, —OC(=O)$NHR^{TT}$, —OC(=O)$NR^{TT}_2$, —OC(=O)$R^{TM}$,
—C(=O)$R^{TT}$,
—S(=O)$_2NH_2$, —S(=O)$_2NHR^{TT}$, —S(=O)$_2NR^{TT}_2$,
—S(=O)$_2R^{TM}$,
—NHS(=O)$_2R^{TT}$, —$NR^{TN}$S(=O)$_2R^{TT}$,
—S(=O)$_2R^{TT}$,
—CN, —$NO_2$, —$SR^{TT}$, or =O;

each —$R^{S3C}$ is independently:
—$R^{TT}$,
—F, —Cl, —Br, —I,
—OH, —$OR^{TT}$,
-$L^T$-OH, -$L^T$-$OR^{TT}$,
—$CF_3$, —$OCF_3$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$,
—C(=O)OH, —C(=O)$OR^{TT}$, —OC(=O)$R^{TT}$,
—C(=O)$NH_2$, —C(=O)$NHR^{TT}$, —C(=O)$NR^{TT}_2$,
—C(=O)$R^{TM}$,
—NHC(=O)$R^{TT}$, —$NR^{TN}$C(=O)$R^{TT}$,
—NHC(=O)$NH_2$, —NHC(=O)$NHR^{TT}$, —NHC(=O)$NR^{TT}_2$, —NHC(=O)$R^{TM}$,
—$NR^{TN}$C(=O)$NH_2$, —$NR^{TN}$C(=O)$NHR^{TT}$,
—$NR^{TN}$C(=O)$NR^{TT}_2$, —$NR^{TN}$C(=O)$R^{TM}$,
—NHC(=O)$OR^{TT}$, —$NR^{TN}$C(=O)$OR^{TT}$,
—C(=O)$NH_2$, —C(=O)$NHR^{TT}$, —C(=O)$NR^{TT}_2$,
—OC(=O)$R^{TM}$,
—C(=O)$R^{TT}$,
—S(=O)$_2NH_2$, —S(=O)$_2NHR^{TT}$, —S(=O)$_2NR^{TT}_2$,
—S(=O)$_2R^{TM}$,
—NHS(=O)$_2R^{TT}$, —$NR^{TN}$S(=O)$_2R^{TT}$,
—S(=O)$_2R^{TT}$,
—CN, —$NO_2$, or —$SR^{TT}$;

and additionally, two adjacent groups —$R^{S3C}$, if present, may together form: —O—$CH_2$—O— or —O—$CH_2CH_2$—O—;

each —$R^{SN}$ is independently:
—$R^{TT}$,
-$L^T$-OH, -$L^T$-$OR^{TT}$,
-$L^T$-$NH_2$, -$L^T$-$NHR^{TT}$, -$L^T$-$NR^{TT}_2$, -$L^T$-$R^{TM}$,
—C(=O)$R^{TT}$,
—C(=O)$OR^{TT}$,
—C(=O)$NH_2$, —C(=O)$NHR^{TT}$, —C(=O)$NR^{TT}_2$,
—C(=O)$R^{TM}$, or
—S(=O)$_2R^{TT}$;

wherein:
each -$L^T$- is linear or branched saturated $C_{1-4}$alkylene;
each —$R^{TT}$ is independently linear or branched saturated $C_{1-4}$alkyl, saturated $C_{3-6}$cycloalkyl, saturated $C_{3-6}$cycloalkyl-methyl, phenyl, or benzyl; wherein said linear or branched saturated $C_{1-4}$alkyl is optionally substituted with —OH or —$OR^{TTT}$, wherein —$R^{TTT}$ is linear or branched saturated $C_{1-4}$alkyl;
each —$R^{TN}$ is linear or branched saturated $C_{1-4}$alkyl;
each —$R^{TM}$ is independently azetidino, pyrrolidino, piperidino, piperazino, morpholino, azepano, or diazepano, and is:
optionally substituted on carbon with one or more groups selected from: —$R^{TMM}$, —C(=O)$R^{TMM}$, —S(=O)$_2R^{TMM}$, —F, —$NH_2$, —$NHR^{TMM}$, —$NR^{TMM}_2$, —OH, and —$OR^{TMM}$; and
optionally substituted on secondary nitrogen, if present, with a group selected from: —$R^{TMM}$, —C(=O)$R^{TMM}$, —C(=O)$OR^{TMM}$, and —S(=O)$_2R^{TMM}$;
wherein each —$R^{TMM}$ is independently linear or branched saturated $C_{1-4}$alkyl, saturated $C_{3-6}$cycloalkyl, saturated $C_{3-6}$cycloalkyl-methyl, phenyl, or benzyl;

and wherein:
—$R^B$ is independently —$R^{B1}$, —$R^{B2}$, or -$L^B$-$R^{B2}$;
—$R^{B1}$ is linear or branched saturated $C_{1-6}$alkyl, and is optionally substituted with —OH or —$OR^{BB}$, wherein —$R^{BB}$ is linear or branched saturated $C_{1-4}$alkyl;
—$R^{B2}$ is saturated $C_{3-6}$cycloalkyl; and
-$L^B$- is linear or branched saturated $C_{1-4}$alkylene;

and wherein:
—$NR^CR^D$ is independently —$NR^{C1}R^{D1}$, —$NR^{C2}R^{D2}$, —$NR^{C3}R^{D3}$, —$NR^{C4}R^{D4}$, or —$NR^{C5}R^{D5}$;

wherein:
—$NR^{C1}R^{D1}$ is a monocyclic non-aromatic heterocyclyl group having from 4 to 8 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, wherein said S is optionally in the form of S(=O) or S(=O)$_2$;

and wherein said monocyclic non-aromatic heterocyclyl group is:

optionally substituted on carbon with one or more groups —R$^{NC}$, and optionally substituted on secondary nitrogen, if present, with a group —R$^{NN}$;

—NR$^{C2}$R$^{D2}$ is a fused bicyclic non-aromatic heterocyclyl group having from 7 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, wherein said S is optionally in the form of S(=O) or S(=O)$_2$, or exactly 3 of said ring atoms are ring heteroatoms, one of which is N, and each of the other two is independently N, O, or S, wherein said S is optionally in the form of S(=O) or S(=O)$_2$;

and wherein said fused bicyclic non-aromatic heterocyclyl group is:

optionally substituted on carbon with one or more groups —R$^{NC}$, and optionally substituted on secondary nitrogen, if present, with a group —R$^{NN}$;

—NR$^{C3}$R$^{D3}$ is a bridged non-aromatic heterocyclyl group having from 7 to 11 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, wherein said S is optionally in the form of S(=O) or S(=O)$_2$, or exactly 3 of said ring atoms are ring heteroatoms, one of which is N, and each of the other two is independently N, O, or S, wherein said S is optionally in the form of S(=O) or S(=O)$_2$;

and wherein said bridged non-aromatic heterocyclyl group is:

optionally substituted on carbon with one or more groups —R$^{NC}$, and optionally substituted on secondary nitrogen, if present, with a group —R$^{NN}$;

—NR$^{C4}$R$^{D4}$ is a spiro non-aromatic heterocyclyl group having from 6 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, or exactly 3 of said ring atoms are ring heteroatoms, one of which is N, and each of the other two is independently N, O, or S, wherein said S is optionally in the form of S(=O) or S(=O)$_2$;

and wherein said spiro non-aromatic heterocyclyl group is:

optionally substituted on carbon with one or more groups —R$^{NC}$, and optionally substituted on secondary nitrogen, if present, with a group —R$^{NN}$;

wherein:

each —R$^{NC}$ is independently:
—R$^{QQ}$,
—F, —Cl, —Br, —I,
—OH, —OR$^{QQ}$,
-L$^Q$-OH, -L$^Q$-OR$^{QQ}$,
—CF$_3$, —OCF$_3$,
—NH$_2$, —NHR$^{QQ}$, —NR$^{QQ}_2$, —R$^{QM}$,
-L$^Q$-NH$_2$, -L$^Q$-NHR$^{QQ}$, -L$^Q$-NR$^{QQ}_2$, -L$^Q$-R$^{QM}$,
—C(=O)OH, —C(=O)OR$^{QQ}$, —OC(=O)R$^{QQ}$,
—C(=O)NH$_2$, —C(=O)NHR$^{QQ}$, —C(=O)NR$^{QQ}_2$, —C(=O)R$^{QM}$,
—NHC(=O)R$^{QQ}$, —NR$^{QN}$C(=O)R$^{QQ}$,
—NHC(=O)NH$_2$, —NHC(=O)NHR$^{QQ}$, —NHC(=O)NR$^{QQ}_2$, —NHC(=O)R$^{QM}$,
—NR$^{QN}$C(=O)NH$_2$, —NR$^{QN}$C(=O)NHR$^{QQ}$,
—NR$^{QN}$C(=O)NR$^{QQ}_2$, —NR$^{QN}$C(=O)R$^{QM}$,
—NHC(=O)OR$^{QQ}$, —NR$^{QN}$C(=O)OR$^{QQ}$,
—OC(=O)NH$_2$, —OC(=O)NHR$^{QQ}$, —OC(=O)NR$^{QQ}_2$, —OC(=O)R$^{QM}$,
—C(=O)R$^{QQ}$,
—S(=O)$_2$NH$_2$, —S(=O)$_2$NHR$^{QQ}$, —S(=O)$_2$NR$^{QQ}_2$, —S(=O)$_2$R$^{QM}$,
—NHS(=O)$_2$R$^{QQ}$, —NR$^{QN}$S(=O)$_2$R$^{QQ}$,
—S(=O)$_2$R$^{QQ}$,
—CN, —NO$_2$, —SR$^{QQ}$, or =O;

each —R$^{NN}$ is independently:
—R$^{QQ}$,
-L$^Q$-OH, -L$^Q$-OR$^{QQ}$,
-L$^Q$-NH$_2$, -L$^Q$-NHR$^{QQ}$, -L$^Q$-NR$^{QQ}_2$, -L$^Q$-R$^{QM}$,
—C(=O)R$^{QQ}$,
—C(=O)OR$^{QQ}$,
—C(=O)NH$_2$, —C(=O)NHR$^{QQ}$, —C(=O)NR$^{QQ}_2$, —C(=O)R$^{QM}$, or
—S(=O)$_2$R$^{QQ}$;

wherein:

each -L$^Q$- is linear or branched saturated C$_{1-4}$alkylene;

each —R$^{QQ}$ is independently linear or branched saturated C$_{1-4}$alkyl, saturated C$_{3-6}$cycloalkyl, saturated C$_{3-6}$cycloalkyl-methyl, phenyl or benzyl; wherein said linear or branched saturated C$_{1-4}$alkyl is optionally substituted with —OH or —OR$^{QQQ}$, and said phenyl and benzyl are optionally substituted with —R$^{QQQ}$, wherein each —R$^{QQQ}$ is linear or branched saturated C$_{1-4}$alkyl;

each —R$^{QN}$ is linear or branched saturated C$_{1-4}$alkyl;

each —R$^{QM}$ is independently azetidino, pyrrolidino, piperidino, piperazino, morpholino, azepano, or diazepano, and is:

optionally substituted on carbon with one or more groups selected from: —R$^{QMM}$, —C(=O)R$^{QMM}$, —S(=O)$_2$R$^{QMM}$, —F, —NH$_2$, —NHR$^{QMM}$, —NR$^{QMM}_2$, —OH, and —OR$^{QMM}$; and optionally substituted on secondary nitrogen, if present, with a group selected from: —R$^{QMM}$, —C(=O)R$^{QMM}$, —C(=O)OR$^{QMM}$, and —S(=O)$_2$R$^{QMM}$;

wherein each —R$^{QMM}$ is independently linear or branched saturated C$_{1-4}$alkyl, saturated C$_{3-6}$cycloalkyl, saturated C$_{3-6}$cycloalkyl-methyl, phenyl, or benzyl;

and wherein:

—NR$^{C5}$R$^{D5}$ is independently: 1H-pyrrol-1-yl; 2H-isoindol-2-yl; 1H-indol-1-yl; 1H-pyrazol-1-yl; 1H-benzoimidazol-1-yl; 1H-imidazol-1-yl; 2H-indazol-2-yl; 1H-indazol-1-yl; 4H-[1,2,4]triazol-4-yl; 1H-[1,2,3]triazol-1-yl; 1H-[1,2,4]triazol-1-yl; 1H-benzotriazol-1-yl; or 1H-tetrazol-1-yl; and is optionally substituted with one or more groups —R$^H$;

wherein each —R$^H$ is independently:
—R$^{HH}$,
—F, —Cl, —Br, —I,
—OH, —OR$^{HH}$,
-L$^H$-OH, -L$^H$-OR$^{HH}$,
—CF$_3$, —OCF$_3$, —NH$_2$, —NHR$^{HH}$, —NR$^{HH}_2$, —R$^{HM}$,
-L$^H$-NH$_2$, -L$^H$-NHR$^{HH}$, -L$^H$-NR$^{HH}_2$, -L$^H$-R$^{HM}$,
—C(=O)OH, —C(=O)OR$^{HH}$, —OC(=O)R$^{HH}$,
—C(=O)NH$_2$, —C(=O)NHR$^{HH}$, —C(=O)NR$^{HH}_2$,
—C(=O)R$^{HM}$,
—NHC(=O)R$^{HH}$, —NR$^{HN}$C(=O)R$^{HH}$,
—NHC(=O)NH$_2$, —NHC(=O)NHR$^{HH}$, —NHC(=O)NR$^{HH}_2$, —NHC(=O)R$^{HM}$,
—NR$^{HN}$C(=O)NH$_2$, —NR$^{HN}$C(=O)NHR$^{HH}$,
—NR$^{HN}$C(=O)NR$^{HH}_2$, —NR$^{HN}$C(=O)R$^{HM}$,
—NHC(=O)OR$^{HH}$, —NR$^{HN}$C(=O)OR$^{HH}$,
—OC(=O)NH$_2$, —OC(=O)NHR$^{HH}$, —OC(=O)NR$^{HH}_2$, —OC(=O)R$^{HM}$,
—C(=O)R$^{HH}$,
—S(=O)$_2$NH$_2$, —S(=O)$_2$NHR$^{HH}$, —S(=O)$_2$NR$^{HH}_2$,
—S(=O)$_2$R$^{HM}$,
—NHS(=O)$_2$R$^{HH}$, —NR$^{HN}$S(=O)$_2$R$^{HH}$,
—S(=O)$_2$R$^{HH}$,
—CN, —NO$_2$, or —SR$^{HH}$;
wherein:
  each -L$^H$- is linear or branched saturated C$_{1-4}$alkylene;
  each —R$^{HH}$ is independently linear or branched saturated C$_{1-4}$alkyl, saturated C$_{3-6}$cycloalkyl, saturated C$_{3-6}$cycloalkyl-methyl, phenyl, or benzyl; wherein said linear or branched saturated C$_{1-4}$alkyl is optionally substituted with —OH or —OR$^{HHH}$, wherein —R$^{HHH}$ is linear or branched saturated C$_{1-4}$alkyl;
  each —R$^{HN}$ is linear or branched saturated C$_{1-4}$alkyl;
  each —R$^{HM}$ is independently azetidino, pyrrolidino, piperidino, piperazino, morpholino, azepano, or diazepano, and is:
  optionally substituted on carbon with one or more groups selected from: —R$^{HMM}$, —C(=O)R$^{HMM}$, —S(=O)$_2$R$^{HMM}$, —F, —NH$_2$, —NHR$^{HMM}$, —NR$^{HMM}_2$, —OH, and —OR$^{HMM}$; and
  optionally substituted on secondary nitrogen, if present, with a group selected from: —R$^{HMM}$, —C(=O)R$^{HMM}$, —C(=O)OR$^{HMM}$, and —S(=O)$_2$R$^{HMM}$;
  wherein each —R$^{HMM}$ is independently linear or branched saturated C$_{1-4}$alkyl, saturated C$_{3-6}$cycloalkyl, saturated C$_{3-6}$cycloalkyl-methyl, phenyl, or benzyl;
and wherein:
  —R$^5$ is independently —R$^{5A}$, —R$^{5B}$, —R$^{5C}$, —R$^{5D}$, or —R$^{5E}$;
  —R$^{5A}$ is linear or branched saturated C$_{1-4}$alkyl;
  —R$^{5B}$ is saturated C$_{3-6}$cycloalkyl;
  —R$^{5C}$ is independently —F, —Cl, —Br, or —I;
  —R$^{5D}$ is —CF$_3$; and
  —R$^{5E}$ is independently —C≡CH or C$_{3-6}$alkynyl optionally substituted with one or more groups —R$^{EE}$; wherein each —R$^{EE}$ is independently selected from —OH, —OR$^{EEE}$, —NH$_2$, —NHR$^{EEE}$, and —NR$^{EEE}_2$; wherein each —R$^{EEE}$ is linear or branched saturated C$_{1-4}$alkyl;
and wherein:
  —R$^4$ is —H;
  —R$^6$ is independently —H or —F; and
  —R$^7$ is independently —H or —F; and
  —R$^8$ is independently —H or —F.

For the avoidance of doubt, it is not intended that any two or more of —R$^{3N}$, -L$^{3P}$, W, X, Y, Z, —R$^4$, —R$^5$, —R$^6$, —R$^7$, and —R$^8$ together form a ring fused to the ring(s) to which they are attached. For example, it is not intended that —R$^4$ and —R$^5$ together form a ring fused to the ring to which they are attached. Similarly, it is not intended that —R$^4$ and Z together form a ring fused to the rings to which they are attached. Similarly, it is not intended that —R$^4$ and W together form a ring fused to the rings to which they are attached.

For the avoidance of doubt, the phrase "substituent on carbon" is intended to refer to a substituent which is attached to a carbon ring atom. Similarly, the phrase "substituent on secondary nitrogen" is intended to refer to a substituent which is attached to a nitrogen ring atom which, in the absence of the substituent, would be a secondary nitrogen ring atom (i.e., —NH—). Consequently, a pyridyl group may only have "substituents on carbon", whereas 1H-pyrrole may have both "substituents on carbon" and a "substituent on secondary nitrogen", as illustrated below.

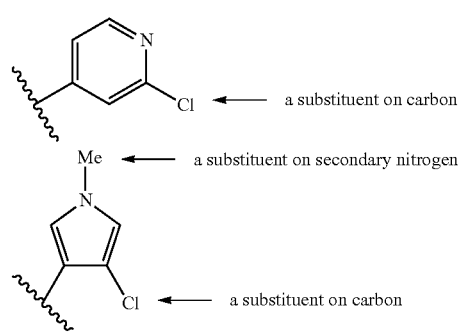

Similarly, a piperidino group may only have "substituents on carbon", whereas piperizino may have both "substituents on carbon" and a "substituent on secondary nitrogen", as illustrated below.

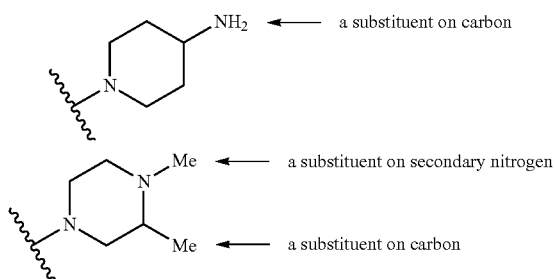

The Groups W, X, Y, and Z
(2) A compound according to (1), wherein:
  W is CR$^W$, X is CR$^X$, Y is CR$^Y$, and Z is CR$^Z$ ("phenyl"); or
  W is N, X is CR$^X$, Y is CR$^Y$, and Z is CR$^Z$ ("pyrid-2-yl"); or
  W is CR$^W$, X is N, Y is CR$^Y$, and Z is CR$^Z$ ("pyrid-3-yl"); or
  W is N, X is CR$^X$, Y is CR$^Y$, and Z is N ("pyrimidin-2-yl"); or
  W is CR$^W$, X is N, Y is N, and Z is CR$^Z$ ("pyrimidin-5-yl").
(3) A compound according to any (1), wherein:
  W is CR$^W$, X is CR$^X$, Y is CR$^Y$, and Z is CR$^Z$ ("phenyl"); or
  W is CR$^W$, X is N, Y is CR$^Y$, and Z is CR$^Z$ ("pyrid-3-yl"); or
  W is CR$^W$, X is N, Y is N, and Z is CR$^Z$ ("pyrimidin-5-yl").
(4) A compound according to (1), wherein:
  W is CR$^W$, X is CR$^X$, Y is CR$^Y$, and Z is CR$^Z$ ("phenyl").
(5) A compound according to (1), wherein:
  W is CR$^W$, X is N, Y is CR$^Y$, and Z is CR$^Z$ ("pyrid-3-yl").
(6) A compound according to (1), wherein:
  W is CR$^W$, X is N, Y is N, and Z is CR$^Z$ ("pyrimidin-5-yl").

The Group —R$^W$ (7) A compound according to any one of (1) to (6), wherein —R$^W$, if present, is —H.

(8) A compound according to any one of (1) to (6), wherein —R$^W$, if present, is —R$^{WW}$.

The Group —R$^X$ (9) A compound according to any one of (1) to (8), wherein —R$^X$, if present, is —H.

(10) A compound according to any one of (1) to (8), wherein —R$^X$, if present, is —R$^{XX}$.

The Group —R$^Y$

(11) A compound according to any one of (1) to (10), wherein —R$^Y$, if present, is —H.

(12) A compound according to any one of (1) to (10), wherein —R$^Y$, if present, is —R$^{YY}$.

The Group —R$^Z$

(13) A compound according to any one of (1) to (12), wherein —R$^Z$, if present, is —H.

(14) A compound according to any one of (1) to (12), wherein —R$^Z$, if present, is —R$^{ZZ}$.

The Group —R$^{WW}$

(15) A compound according to any one of (1) to (14), wherein —R$^{WW}$, if present, is independently —X$^1$, —R$^1$, or —CF$_3$.

(16) A compound according to any one of (1) to (14), wherein —R$^{WW}$, if present, is independently —X$^1$ or —R$^1$.

(17) A compound according to any one of (1) to (14), wherein —R$^{WW}$, if present, is independently —X$^1$.

(18) A compound according to any one of (1) to (14), wherein —R$^{WW}$, if present, is independently —R$^1$.

The Group —R$^{XX}$

(19) A compound according to any one of (1) to (18), wherein —R$^{XX}$, if present, is independently —X$^1$, —R$^1$, or —CF$_3$.

(20) A compound according to any one of (1) to (18), wherein —R$^{XX}$, if present, is independently —X$^1$ or —R$^1$.

(21) A compound according to any one of (1) to (18), wherein —R$^{XX}$, if present, is independently —X$^1$.

(22) A compound according to any one of (1) to (18), wherein —R$^{XX}$, if present, is independently —R$^1$.

The Group —R$^{YY}$

(23) A compound according to any one of (1) to (22), wherein —R$^{YY}$, if present, is independently —X$^1$, —R$^1$, or —CF$_3$.

(24) A compound according to any one of (1) to (22), wherein —R$^{YY}$, if present, is independently —X$^1$ or —R$^1$.

(25) A compound according to any one of (1) to (22), wherein —R$^{YY}$, if present, is independently —X$^1$.

(26) A compound according to any one of (1) to (22), wherein —R$^{YY}$, if present, is independently —R$^1$.

The Group —R$^{ZZ}$

(27) A compound according to any one of (1) to (26), wherein —R$^{ZZ}$, if present, is independently —X$^1$, —R$^1$, or —CF$_3$.

(28) A compound according to any one of (1) to (26), wherein —R$^{ZZ}$, if present, is independently —X$^1$ or —R$^1$.

(29) A compound according to any one of (1) to (26), wherein —R$^{ZZ}$, if present, is independently —X$^1$.

(30) A compound according to any one of (1) to (26), wherein —R$^{ZZ}$, if present, is independently —R$^1$.

The Group —X$^1$

(31) A compound according to any one of (1) to (30), wherein each —X$^1$, if present, is independently —F, —Cl, or —Br.

(32) A compound according to any one of (1) to (30), wherein each —X$^1$, if present, is —F or —Cl.

(33) A compound according to any one of (1) to (30), wherein each —X$^1$, if present, is —F.

(34) A compound according to any one of (1) to (30), wherein each —X$^1$, if present, is —Cl.

(35) A compound according to any one of (1) to (30), wherein each —X$^1$, if present, is —Br.

(36) A compound according to any one of (1) to (30), wherein each —X$^1$, if present, is —I.

The Group —R$^1$

(37) A compound according to any one of (1) to (36), wherein each —R$^1$, if present, is independently -Me, -Et, -nPr, -iPr, -nBu, -iBu, or -tBu.

(38) A compound according to any one of (1) to (36), wherein each —R$^1$, if present, is independently -Me, -Et, -nPr, or -iPr.

(39) A compound according to any one of (1) to (36), wherein each —R$^1$, if present, is independently -Me or -Et.

(40) A compound according to any one of (1) to (36), wherein each —R$^1$, if present, is -Me.

The Group -L$^{3P}$-

(41) A compound according to any one of (1) to (40), wherein -L$^{3P}$- is a single covalent bond.

(42) A compound according to any one of (1) to (40), wherein -L$^{3P}$- is -L$^{3PL}$-.

The Group -L$^{3PL}$-

(43) A compound according to any one of (1) to (42), wherein -L$^{3PL}$-, if present, is independently -L$^{3PR1}$-, —C(=O)—, -L$^{3PR2}$-C(=O)—, —O-L$^{3PR4}$-, or —S(=O)$_2$—.

(44) A compound according to any one of (1) to (42), wherein -L$^{3PL}$-, if present, is independently -L$^{3PR1}$-, —C(=O)—, —O-L$^{3PR4}$-, or —S(=O)$_2$—.

(45) A compound according to any one of (1) to (42), wherein -L$^{3PL}$-, if present, is -L$^{3PR1}$-.

(46) A compound according to any one of (1) to (42), wherein -L$^{3PL}$-, if present, is —C(=O)—.

(47) A compound according to any one of (1) to (42), wherein -L$^{3PL}$-, if present, is -L$^{3PR2}$-C(=O)—.

(48) A compound according to any one of (1) to (42), wherein -L$^{3PL}$-, if present, is —S(=O)$_2$—.

(49) A compound according to any one of (1) to (42), wherein -L$^{3PL}$-, if present, is -L$^{3PR3}$-S(=O)$_2$—.

(50) A compound according to any one of (1) to (42), wherein -L$^{3PL}$-, if present, is —O-L$^{3PR4}$-.

The Group -L$^{3PR1}$-

(51) A compound according to any one of (1) to (50), wherein each -L$^{3PR1}$-, if present, is independently —CH$_2$—, —CH(Me)-, —C(Me)$_2$-, —CH$_2$CH$_2$—, —CH(Me)CH$_2$—, —CH$_2$CH(Me)-, —C(Me)$_2$CH$_2$—, —CH$_2$C(Me)$_2$-, —CH$_2$CH$_2$CH$_2$—, or —CH$_2$CH$_2$CH$_2$CH$_2$—.

(52) A compound according to any one of (1) to (50), wherein each -L$^{3PR1}$-, if present, is independently —CH$_2$—, —CH(Me)—, —C(Me)$_2$-, —CH(Et)-, or —CH$_2$CH$_2$—.

(53) A compound according to any one of (1) to (50), wherein each -L$^{3PR1}$-, if present, is independently —CH$_2$—, —CH(Me)—, or —C(Me)$_2$-.

(54) A compound according to any one of (1) to (50), wherein each -L$^{3PR1}$-, if present, is independently —CH$_2$—, —CH$_2$CH$_2$—, —CH$_2$CH$_2$CH$_2$—, or —CH$_2$CH$_2$CH$_2$CH$_2$—.

(55) A compound according to any one of (1) to (50), wherein each -L$^{3PR1}$-, if present, is independently —CH$_2$CH$_2$—, —CH$_2$CH$_2$CH$_2$—, or —CH$_2$CH$_2$CH$_2$CH$_2$—.

(56) A compound according to any one of (1) to (50), wherein each -L$^{3PR1}$-, if present, is independently —CH$_2$— or —CH$_2$CH$_2$—.

(57) A compound according to any one of (1) to (50), wherein each -$L^{3PR1}$-, if present, is —$CH_2$—.

(58) A compound according to any one of (1) to (50), wherein each -$L^{3PR1}$-, if present, is independently —CH(Me)-.

(59) A compound according to any one of (1) to (50), wherein each -$L^{3PR1}$-, if present, is independently —$C(Me)_2$-.

(60) A compound according to any one of (1) to (50), wherein each -$L^{3PR1}$-, if present, is —$CH_2CH_2$—.

The Group -$L^{3PR2}$-

(61) A compound according to any one of (1) to (60), wherein each -$L^{3PR2}$-, if present, is independently —$CH_2$—, —CH(Me)—, —$C(Me)_2$-, —$CH_2CH_2$—, —CH(Me)$CH_2$—, —$CH_2$CH(Me)—, —$C(Me)_2CH_2$—, —$CH_2C(Me)_2$-, —$CH_2CH_2CH_2$—, or —$CH_2CH_2CH_2CH_2$—.

(62) A compound according to any one of (1) to (60), wherein each -$L^{3PR2}$-, if present, is independently —$CH_2$—, —CH(Me)—, —$C(Me)_2$-, —CH(Et)-, or —$CH_2CH_2$—.

(63) A compound according to any one of (1) to (60), wherein each -$L^{3PR2}$-, if present, is independently —$CH_2$—, —CH(Me)—, or —$C(Me)_2$-.

(64) A compound according to any one of (1) to (60), wherein each -$L^{3PR2}$-, if present, is independently —$CH_2$—, —$CH_2CH_2$—, —$CH_2CH_2CH_2$—, or —$CH_2CH_2CH_2CH_2$—.

(65) A compound according to any one of (1) to (60), wherein each -$L^{3PR2}$-, if present, is independently —$CH_2CH_2$—, —$CH_2CH_2CH_2$—, or —$CH_2CH_2CH_2CH_2$—.

(66) A compound according to any one of (1) to (60), wherein each -$L^{3PR2}$-, if present, is independently —$CH_2$— or —$CH_2CH_2$—.

(67) A compound according to any one of (1) to (60), wherein each -$L^{3PR2}$-, if present, is —$CH_2$—.

(68) A compound according to any one of (1) to (60), wherein each -$L^{3PR2}$-, if present, is independently —CH(Me)-.

(69) A compound according to any one of (1) to (60), wherein each -$L^{3PR2}$-, if present, is independently —$C(Me)_2$-.

(70) A compound according to any one of (1) to (60), wherein each -$L^{3PR2}$-, if present, is —$CH_2CH_2$—.

The Group -$L^{3PR3}$-

(71) A compound according to any one of (1) to (70), wherein each -$L^{3PR3}$-, if present, is independently —$CH_2$—, —CH(Me)—, —$C(Me)_2$-, —$CH_2CH_2$—, —CH(Me)$CH_2$—, —$CH_2$CH(Me)—, —$C(Me)_2CH_2$—, —$CH_2C(Me)_2$-, —$CH_2CH_2CH_2$—, or —$CH_2CH_2CH_2CH_2$—.

(72) A compound according to any one of (1) to (70), wherein each -$L^{3PR3}$-, if present, is independently —$CH_2$—, —CH(Me)—, —$C(Me)_2$-, —CH(Et)-, or —$CH_2CH_2$—.

(73) A compound according to any one of (1) to (70), wherein each -$L^{3PR3}$-, if present, is independently —$CH_2$—, —CH(Me)—, or —$C(Me)_2$-.

(74) A compound according to any one of (1) to (70), wherein each -$L^{3PR3}$-, if present, is independently —$CH_2$—, —$CH_2CH_2$—, —$CH_2CH_2CH_2$—, or —$CH_2CH_2CH_2CH_2$—.

(75) A compound according to any one of (1) to (70), wherein each -$L^{3PR3}$-, if present, is independently —$CH_2CH_2$—, —$CH_2CH_2CH_2$—, or —$CH_2CH_2CH_2CH_2$—.

(76) A compound according to any one of (1) to (70), wherein each -$L^{3PR3}$-, if present, is independently —$CH_2$— or —$CH_2CH_2$—.

(77) A compound according to any one of (1) to (70), wherein each -$L^{3PR3}$-, if present, is —$CH_2$—.

(78) A compound according to any one of (1) to (70), wherein each -$L^{3PR3}$-, if present, is —$CH_2CH_2$—.

The Group -$L^{3PR4}$-

(79) A compound according to any one of (1) to (78), wherein each -$L^{3PR4}$-, if present, is independently —$CH_2$—, —CH(Me)—, —$C(Me)_2$-, —$CH_2CH_2$—, —CH(Me)$CH_2$—, —$CH_2$CH(Me)—, —$C(Me)_2CH_2$—, —$CH_2C(Me)_2$-, —$CH_2CH_2CH_2$—, or —$CH_2CH_2CH_2CH_2$—.

(80) A compound according to any one of (1) to (78), wherein each -$L^{3PR4}$-, if present, is independently —$CH_2$—, —CH(Me)—, —$C(Me)_2$-, —CH(Et)-, or —$CH_2CH_2$—.

(81) A compound according to any one of (1) to (78), wherein each -$L^{3PR4}$-, if present, is independently —$CH_2$—, —CH(Me)—, or —$C(Me)_2$-.

(82) A compound according to any one of (1) to (78), wherein each -$L^{3PR4}$-, if present, is independently —$CH_2$—, —$CH_2CH_2$—, —$CH_2CH_2CH_2$—, or —$CH_2CH_2CH_2CH_2$—.

(83) A compound according to any one of (1) to (78), wherein each -$L^{3PR4}$-, if present, is independently —$CH_2CH_2$—, —$CH_2CH_2CH_2$—, or —$CH_2CH_2CH_2CH_2$—.

(84) A compound according to any one of (1) to (78), wherein each -$L^{3PR4}$-, if present, is independently —$CH_2$— or —$CH_2CH_2$—.

(85) A compound according to any one of (1) to (78), wherein each -$L^{3PR4}$-, if present, is —$CH_2$—.

(86) A compound according to any one of (1) to (78), wherein each -$L^{3PR4}$-, if present, is —$CH_2CH_2$—.

The Group —$R^{3N}$

(87) A compound according to any one of (1) to (86), wherein —$R^{3N}$ is independently —$NHR^A$, —$NR^AR^B$, or —$NR^CR^D$.

(88) A compound according to any one of (1) to (86), wherein —$R^{3N}$ is independently —$NR^AR^B$ or —$NR^CR^D$.

(89) A compound according to any one of (1) to (86), wherein —$R^{3N}$ is —$NH_2$.

(90) A compound according to any one of (1) to (86), wherein —$R^{3N}$ is —$NHR^A$.

(91) A compound according to any one of (1) to (86), wherein —$R^{3N}$ is —$NR^AR^B$.

(92) A compound according to any one of (1) to (86), wherein —$R^{3N}$ is —$NR^CR^D$.

The Group —$R^A$

(93) A compound according to any one of (1) to (92), wherein each —$R^A$, if present, is independently: —$R^{A1}$, —$R^{A2}$, —$R^{A3}$, -$L^A$-$R^{A2}$, or -$L^A$-$R^{A3}$.

(94) A compound according to any one of (1) to (92), wherein each —$R^A$, if present, is independently: —$R^{A1}$, —$R^{A3}$, or -$L^A$-$R^{A3}$.

(95) A compound according to any one of (1) to (92), wherein each —$R^A$, if present, is —$R^{A1}$.

(96) A compound according to any one of (1) to (92), wherein each —$R^A$, if present, is —$R^{A2}$.

(97) A compound according to any one of (1) to (92), wherein each —$R^A$, if present, is —$R^{A3}$.

(98) A compound according to any one of (1) to (92), wherein each —$R^A$, if present, is —$R^{A4}$.

(99) A compound according to any one of (1) to (92), wherein each —$R^A$, if present, is —$R^{A5}$.

(100) A compound according to any one of (1) to (92), wherein each —$R^A$, if present, is -$L^A$-$R^{A2}$.

(101) A compound according to any one of (1) to (92), wherein each —$R^A$, if present, is -$L^A$-$R^{A3}$.

(102) A compound according to any one of (1) to (92), wherein each —$R^A$, if present, is -$L^A$-$R^{A4}$.

(103) A compound according to any one of (1) to (92), wherein each —$R^A$, if present, is $L^A$-$R^{A5}$.

The Group —$R^{A1}$ (104) A compound according to any one of (1) to (103), wherein each —$R^{A1}$, if present, is independently linear or branched saturated $C_{1-4}$alkyl, and is optionally substituted with one or more groups —$R^{S1}$.

(105) A compound according to any one of (1) to (103), wherein each —$R^{A1}$, if present, is independently linear or branched saturated $C_{1-4}$alkyl, and is optionally substituted with one or more groups selected from: —OH, —$OR^{TT}$, —$NH_2$, —$NHR^{TT}$, and —$NR^{TT}_2$.

(106) A compound according to any one of (1) to (xx), wherein each —$R^{A1}$, if present, is independently linear or branched saturated $C_{1-4}$alkyl, and is optionally substituted with one or more groups selected from: —OH and —$OR^{TT}$.

(107) A compound according to any one of (1) to (103), wherein each —$R^{A1}$, if present, is independently -Me, -Et, -nPr, -iPr, -nBu, -iBu, or -tBu, and is optionally substituted with one or more groups —$R^{S1}$.

(108) A compound according to any one of (1) to (103), wherein each —$R^{A1}$, if present, is independently -Me, -Et, -nPr, -iPr, -nBu, -iBu, or -tBu, and is optionally substituted with one or more groups selected from: —OH, —$OR^{TT}$, —$NH_2$, —$NHR^{TT}$, and —$NR^{TT}_2$.

(109) A compound according to any one of (1) to (103), wherein each —$R^{A1}$, if present, is independently -Me, -Et, -nPr, or -iPr, and is optionally substituted with one or more groups —$R^{S1}$.

(110) A compound according to any one of (1) to (103), wherein each —$R^{A1}$, if present, is independently -Me, -Et, -nPr, or -iPr, and is optionally substituted with one or more groups selected from: —OH, —$OR^{TT}$, —$NH_2$, —$NHR^{TT}$, and —$NR^{TT}_2$.

(111) A compound according to any one of (1) to (103), wherein each —$R^{A1}$, if present, is independently -Me or -Et, and is optionally substituted with one or more groups —$R^{S1}$.

(112) A compound according to any one of (1) to (103), wherein each —$R^{A1}$, if present, is independently linear or branched saturated $C_{1-4}$alkyl.

(113) A compound according to any one of (1) to (103), wherein each —$R^{A1}$, if present, is independently -Me, -Et, -nPr, -iPr, -nBu, -iBu, or -tBu.

(114) A compound according to any one of (1) to (103), wherein each —$R^{A1}$, if present, is independently -Me, -Et, -nPr, or -iPr.

(115) A compound according to any one of (1) to (103), wherein each —$R^{A1}$, if present, is independently -Me or -Et.

(116) A compound according to any one of (1) to (103), wherein each —$R^{A1}$, if present, is -Me.

The Group —$R^{A2}$ (117) A compound according to any one of (1) to (116), wherein each —$R^{A2}$, if present, is independently cyclopropyl, cyclobutyl, cyclopentyl, or cyclohexyl, and is optionally substituted with one or more groups —$R^{S2C}$.

(118) A compound according to any one of (1) to (116), wherein each —$R^{A2}$, if present, is independently cyclopropyl, cyclobutyl, or cyclopentyl, and is optionally substituted with one or more groups —$R^{S2C}$.

(119) A compound according to any one of (1) to (116), wherein each —$R^{A2}$, if present, is independently cyclopropyl or cyclobutyl, and is optionally substituted with one or more groups —$R^{S2C}$.

The Group —$R^{A3}$ (120) A compound according to any one of (1) to (119), wherein each —$R^{A3}$, if present, is independently oxetanyl, tetrahydrofuranyl, tetrahydropyranyl, dioxanyl, azetidinyl, pyrrolidinyl, piperidinyl, piperazinyl, morpholinyl, azepanyl, or diazepanyl,
and is optionally substituted on carbon with one or more groups —$R^{S2C}$,
and is optionally substituted on secondary nitrogen, if present, with a group —$R^{SN}$.

(121) A compound according to any one of (1) to (119), wherein each —$R^{A3}$, if present, is independently tetrahydrofuranyl, tetrahydropyranyl, dioxanyl, pyrrolidinyl, piperidinyl, piperazinyl, morpholinyl,
and is optionally substituted on carbon with one or more groups —$R^{S2C}$,
and is optionally substituted on secondary nitrogen, if present, with a group —$R^{SN}$.

(122) A compound according to any one of (1) to (119), wherein each —$R^{A3}$, if present, is independently tetrahydropyranyl or piperidinyl,
and is optionally substituted on carbon with one or more groups —$R^{S2C}$,
and is optionally substituted on secondary nitrogen, if present, with a group —$R^{SN}$.

(123) A compound according to any one of (1) to (119), wherein each —$R^{A3}$, if present, is tetrahydropyranyl, and is optionally substituted on carbon with one or more groups —$R^{S2C}$.

(124) A compound according to any one of (1) to (119), wherein each —$R^{A3}$, if present, is piperidinyl,
and is optionally substituted on carbon with one or more groups —$R^{S2C}$,
and is optionally substituted on secondary nitrogen with a group —$R^{SN}$.

(125) A compound according to any one of (1) to (119), wherein each —$R^{A3}$, if present, is pyrrolidinyl,
and is optionally substituted on carbon with one or more groups —$R^{S2C}$,
and is optionally substituted on secondary nitrogen with a group —$R^{SN}$.

(126) A compound according to any one of (1) to (119), wherein each —$R^{A3}$, if present, is azetidinyl,
and is optionally substituted on carbon with one or more groups —$R^{S2C}$,
and is optionally substituted on secondary nitrogen with a group —$R^{SN}$.

The Group —$R^{A4}$ (127) A compound according to any one of (1) to (126), wherein each —$R^{A4}$, if present, is phenyl, and is optionally substituted with one or more groups —$R^{S3C}$.

(128) A compound according to any one of (1) to (126), wherein each —$R^{A4}$, if present, is naphthyl, and is optionally substituted with one or more groups —$R^{S3C}$.

The Group —$R^{A5}$ (129) A compound according to any one of (1) to (128), wherein each —$R^{A5}$, if present, is independently furanyl, thienyl, pyrrolyl, imidazolyl, oxazolyl, thiazolyl, pyrazolyl, isoxazolyl, isothiazolyl, pyridyl, pyridazinyl, pyrimidinyl, pyrazinyl, indolyl, benzoimidazolyl, indazolyl, benzofuranyl, benzothienyl, benzooxazolyl, benzothiazolyl, benzoisoxazolyl, benzoisothiazolyl, quinolinyl, isoquinolinyl, cinnolinyl, quinoxalinyl, quinazolinyl, or phthalazinyl,
and is optionally substituted on carbon with one or more groups —$R^{S3C}$,
and is optionally substituted on secondary nitrogen, if present, with a group —$R^{SN}$.

(130) A compound according to any one of (1) to (128), wherein each —$R^{A5}$, if present, is independently furanyl, thienyl, pyrrolyl, imidazolyl, oxazolyl, thiazolyl, pyrazolyl, isoxazolyl, isothiazolyl, pyridyl, pyridazinyl, pyrimidinyl, or pyrazinyl,
- and is optionally substituted on carbon with one or more groups —$R^{S3C}$,
- and is optionally substituted on secondary nitrogen, if present, with a group —$R^{SN}$.

(131) A compound according to any one of (1) to (128), wherein each —$R^{A5}$, if present, is independently furanyl, thienyl, pyrrolyl, imidazolyl, oxazolyl, thiazolyl, pyrazolyl, isoxazolyl, or isothiazolyl,
- and is optionally substituted on carbon with one or more groups —$R^{S3C}$,
- and is optionally substituted on secondary nitrogen, if present, with a group —$R^{SN}$.

(132) A compound according to any one of (1) to (128), wherein each —$R^{A5}$, if present, is imidazolyl,
- and is optionally substituted on carbon with one or more groups —$R^{S2C}$,
- and is optionally substituted on secondary nitrogen with a group —$R^{SN}$.

(133) A compound according to any one of (1) to (128), wherein each —$R^{A5}$, if present, is independently pyridyl, pyridazinyl, pyrimidinyl, or pyrazinyl,
- and is optionally substituted on carbon with one or more groups —$R^{S3C}$.

The Group -$L^A$-

(134) A compound according to any one of (1) to (133), wherein each -$L^A$-, if present, is independently —$CH_2$—, —CH(Me)—, —C(Me)$_2$-, —$CH_2CH_2$—, —CH(Me)CH$_2$—, —CH$_2$CH(Me)—, —C(Me)$_2$CH$_2$—, —CH$_2$C(Me)$_2$-, —CH$_2$CH$_2$CH$_2$—, or —CH$_2$CH$_2$CH$_2$CH$_2$—.

(135) A compound according to any one of (1) to (133), wherein each -$L^A$-, if present, is independently —$CH_2$—, —CH(Me)—, —C(Me)$_2$-, —CH(Et)-, or —CH$_2$CH$_2$—.

(136) A compound according to any one of (1) to (133), wherein each -$L^A$-, if present, is independently —$CH_2$—, —CH(Me)—, or —C(Me)$_2$-.

(137) A compound according to any one of (1) to (133), wherein each -$L^A$-, if present, is independently —$CH_2$—, —CH$_2$CH$_2$—, —CH$_2$CH$_2$CH$_2$—, or —CH$_2$CH$_2$CH$_2$CH$_2$—.

(138) A compound according to any one of (1) to (133), wherein each -$L^A$-, if present, is independently —CH$_2$CH$_2$—, —CH$_2$CH$_2$CH$_2$—, or —CH$_2$CH$_2$CH$_2$CH$_2$—.

(139) A compound according to any one of (1) to (133), wherein each -$L^A$-, if present, is independently —$CH_2$— or —CH$_2$CH$_2$—.

(140) A compound according to any one of (1) to (133), wherein each -$L^A$-, if present, is —$CH_2$—.

(141) A compound according to any one of (1) to (133), wherein each -$L^A$-, if present, is —CH$_2$CH$_2$—.

The Group —$R^{S1}$ (142) A compound according to any one of (1) to (141), wherein each —$R^{S1}$, if present, is independently:
- —F, —Cl, —Br, —I,
- —OH, —$OR^{TT}$,
- —OCF$_3$,
- —NH$_2$, —NHR$^{TT}$, —NR$^{TT}_2$, —R$^{TM}$,
- —C(=O)OH, —C(=O)OR$^{TT}$, —OC(=O)R$^{TT}$,
- —C(=O)NH$_2$, —C(=O)NHR$^{TT}$, —C(=O)NR$^{TT}_2$,
- —C(=O)R$^{TM}$,
- —C(=O)R$^{TT}$,
- —S(=O)$_2$NH$_2$, —S(=O)$_2$NHR$^{TT}$, —S(=O)$_2$NR$^{TT}_2$,
- —S(=O)$_2$R$^{TM}$,
- —NHS(=O)$_2$R$^{TT}$, —NR$^{TN}$S(=O)$_2$R$^{TT}$,
- —S(=O)$_2$R$^{TT}$,
- —CN, —NO$_2$, —SR$^{TT}$, or =O.

(143) A compound according to any one of (1) to (141), wherein each —$R^{S1}$, if present, is independently:
- —F, —Cl, —Br, —I,
- —OH, —$OR^{TT}$,
- —OCF$_3$,
- —NH$_2$, —NHR$^{TT}$, —NR$^{TT}_2$, —R$^{TM}$,
- —C(=O)OH, —C(=O)OR$^{TT}$, —OC(=O)R$^{TT}$,
- —C(=O)NH$_2$, —C(=O)NHR$^{TT}$, —C(=O)NR$^{TT}_2$,
- —C(=O)R$^{TM}$,
- —NHC(=O)R$^{TT}$, —NR$^{TN}$C(=O)R$^{TT}$,
- —C(=O)R$^{TT}$,
- —S(=O)$_2$NH$_2$, —S(=O)$_2$NHR$^{TT}$, —S(=O)$_2$NR$^{TT}_2$,
- —S(=O)$_2$R$^{TM}$,
- —NHS(=O)$_2$R$^{TT}$, —NR$^{TN}$S(=O)$_2$R$^{TT}$, or
- —S(=O)$_2$R$^{TT}$.

(144) A compound according to any one of (1) to (141), wherein each —$R^{S1}$, if present, is independently:
- —F, —Cl, —Br, —I,
- —OH, —$OR^{TT}$,
- —OCF$_3$,
- —NH$_2$, —NHR$^{TT}$, —NR$^{TT}_2$, —R$^{TM}$,
- —C(=O)OH, —C(=O)OR$^{TT}$, —OC(=O)R$^{TT}$,
- —C(=O)NH$_2$, —C(=O)NHR$^{TT}$, —C(=O)NR$^{TT}_2$,
- C(=O)R$^{TM}$,
- —NHC(=O)R$^{TT}$, —NR$^{TN}$C(=O)R$^{TT}$, or
- —C(=O)R$^{TT}$.

(145) A compound according to any one of (1) to (141), wherein each —$R^{S1}$, if present, is independently:
- —F,
- —OH, —$OR^{TT}$,
- —NH$_2$, —NHR$^{TT}$, —NR$^{TT}_2$, or —R$^{TM}$.

(146) A compound according to any one of (1) to (141), wherein each —$R^{S1}$, if present, is independently:
- —OH, —$OR^{TT}$,
- —NH$_2$, —NHR$^{TT}$, —NR$^{TT}_2$, or —R$^{TM}$.

(147) A compound according to any one of (1) to (141), wherein each —$R^{S1}$, if present, is independently —OH or —$OR^{TT}$.

The Group —$R^{S2C}$ (148) A compound according to any one of (1) to (148), wherein each —$R^{S2C}$, if present, is independently:
- —R$^{TT}$,
- —F, —Cl, —Br, —I,
- —OH, —$OR^{TT}$,
- -$L^T$-OH, -$L^T$-OR$^{TT}$,
- —CF$_3$, —OCF$_3$,
- —NH$_2$, —NHR$^{TT}$, —NR$^{TT}_2$, —R$^{TM}$,
- -$L^T$-NH$_2$, -$L^T$-NHR$^{TT}$, -$L^T$-NR$^{TT}_2$, -$L^T$-R$^{TM}$,
- —C(=O)OH, —C(=O)OR$^{TT}$, —OC(=O)R$^{TT}$,
- —C(=O)NH$_2$, —C(=O)NHR$^{TT}$, —C(=O)NRTT$_2$,
- C(=O)R$^{TM}$,
- —NHC(=O)R$^{TT}$, —NR$^{TN}$C(=O)R$^{TT}$,
- —C(=O)R$^{TT}$,
- —S(=O)$_2$NH$_2$, —S(=O)$_2$NHR$^{TT}$, —S(=O)$_2$NR$^{TT}_2$,
- —S(=O)$_2$R$^{TM}$,
- —NHS(=O)$_2$R$^{TT}$, —NR$^{TN}$S(=O)$_2$R$^{TT}$,
- —S(=O)$_2$R$^{TT}$,
- —CN, —NO$_2$, —SR$^{TT}$, or =O.

(149) A compound according to any one of (1) to (148), wherein each —$R^{S2C}$, if present, is independently:
- —R$^{TT}$,
- —F, —Cl, —Br, —I,
- —OH, —$OR^{TT}$,
- -$L^T$-OH, -$L^T$-OR$^{TT}$, —$CF_3$, —$OCF_3$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$,
—C(=O)OH, —C(=O)$OR^{TT}$, —OC(=O)$R^{TT}$,
—C(=O)$NH_2$, —C(=O)$NHR^{TT}$, —C(=O)$NR^{TT}_2$,
    —C(=O)$R^{TM}$,
—NHC(=O)$R^{TT}$, —$NR^{TN}$C(=O)$R^{TT}$,
—C(=O)$R^{TT}$,
—S(=O)$_2NH_2$, —S(=O)$_2NHR^{TT}$, —S(=O)$_2NR^{TT}_2$,
    —S(=O)$_2R^{TM}$,
—NHS(=O)$_2R^{TT}$, —$NR^{TN}$S(=O)$_2R^{TT}$,
—S(=O)$_2R^{TT}$, or
=O.

(150) A compound according to any one of (1) to (148), wherein each —$R^{S2C}$, if present, is independently:
—$R^{TT}$,
—F, —Cl, —Br, —I,
—OH, —$OR^{TT}$,
-$L^T$-OH, -$L^T$-$OR^{TT}$,
—$OCF_3$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$, or
=O.

(151) A compound according to any one of (1) to (148), wherein each —$R^{S2C}$, if present, is independently:
—$R^{TT}$,
—F,
—OH, —$OR^{TT}$,
-$L^T$-OH, -$L^T$-$OR^{TT}$,
—$OCF_3$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$, or
=O.

(152) A compound according to any one of (1) to (148), wherein each —$R^{S2C}$, if present, is independently:
—$R^{TT}$,
—F,
—OH, —$OR^{TT}$,
-$L^T$-OH, -$L^T$-$OR^{TT}$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$, or
=O.

(153) A compound according to any one of (1) to (148), wherein each —$R^{S2C}$, if present, is independently:
—$R^{TT}$,
—OH, —$OR^{TT}$,
-$L^T$-OH, -$L^T$-$OR^{TT}$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$, or
=O.

(154) A compound according to any one of (1) to (148), wherein each —$R^{S2C}$, if present, is independently:
—$R^{TT}$,
—OH, —$OR^{TT}$,
—$NH_2$, —$NHR^{TT}$, —$NR^{TT}_2$, —$R^{TM}$, or
=O.

The Group —$R^{S3C}$ (155) A compound according to any one of (1) to (154), wherein each —$R^{S3C}$, if present, is independently:
—$R^{TT}$,
—F, —Cl, —Br, —I,
—OH, —$OR^{TT}$,
-$L^T$-OH, -$L^T$-$OR^{TT}$,
—$CF_3$, —$OCF_3$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$,
—C(=O)OH, —C(=O)$OR^{TT}$, —OC(=O)$R^{TT}$,
—C(=O)$NH_2$, —C(=O)$NHR^{TT}$, —C(=O)$NR^{TT}_2$,
    —C(=O)$R^{TM}$,
—NHC(=O)$R^{TT}$, —$NR^{TN}$C(=O)$R^{TT}$,
—C(=O)$R^{TT}$,
—S(=O)$_2NH_2$, —S(=O)$_2NHR^{TT}$, —S(=O)$_2NR^{TT}_2$,
    —S(=O)$_2R^{TM}$,
—NHS(=O)$_2R^{TT}$, —$NR^{TN}$S(=O)$_2R^{TT}$,
—S(=O)$_2R^{TT}$,
—CN, —$NO_2$, or —$SR^{TT}$.

(156) A compound according to any one of (1) to (154), wherein each —$R^{S3C}$, if present, is independently:
—$R^{TT}$,
—F, —Cl, —Br, —I,
—OH, —$OR^{TT}$,
-$L^T$-OH, -$L^T$-$OR^{TT}$,
—$CF_3$, —$OCF_3$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, -$L^T$-$R^{TM}$,
—C(=O)OH, —C(=O)$OR^{TT}$, —OC(=O)$R^{TT}$,
—C(=O)$NH_2$, —C(=O)$NHR^{TT}$, —C(=O)NRTT$_2$,
    C(=O)$R^{TM}$,
—NHC(=O)$R^{TT}$, —$NR^{TN}$C(=O)$R^{TT}$, or
—C(=O)$R^{TT}$.

(157) A compound according to any one of (1) to (154), wherein each —$R^{S3C}$, if present, is independently:
—$R^{TT}$,
—F, —Cl, —Br, —I,
—OH, —$OR^{TT}$,
-$L^T$-OH, -$L^T$-$OR^{TT}$,
—$NH_2$, —$NHR^{TT}$, —$NR^{TT}_2$, —$R^{TM}$,
-$L^T$-$NH_2$, -$L^T$-$NHR^{TT}$, -$L^T$-$NR^{TT}_2$, or -$L^T$-$R^{TM}$.

(158) A compound according to any one of (1) to (154), wherein each —$R^{S3C}$, if present, is independently:
—$R^{TT}$,
—F, —Cl, —Br, —I,
—OH, —$OR^{TT}$,
—$NH_2$, —$NHR^{TT}$, —$NR^{TT}_2$, or —$R^{TM}$.

The Group —$R^{SN}$ (159) A compound according to any one of (1) to (158), wherein each —$R^{SN}$, if present, is independently:
—$R^{TT}$,
-$L^T$-OH, -$L^T$-$OR^{TT}$,
-$L^T$-$NH_2$, -$L^T$-$NHR^{TT}$, -$L^T$-$NR^{TT}_2$, -$L^T$-$R^{TM}$,
—C(=O)$R^{TT}$,
—C(=O)$OR^{TT}$,
—C(=O)$NH_2$, —C(=O)$NHR^{TT}$, —C(=O)$NR^{TT}_2$, or
—C(=O)$R^{TM}$.

(160) A compound according to any one of (1) to (158), wherein each —$R^{SN}$, if present, is independently:
—$R^{TT}$,
-$L^T$-OH, -$L^T$-$OR^{TT}$,
-$L^T NH_2$, -$L^T$-$NHR^{TT}$, -$L^T$-$NR^{TT}_2$, -$L^T$-$R^{TM}$,
—C(=O)$R^{TT}$, or
—C(=O)$OR^{TT}$.

(161) A compound according to any one of (1) to (158), wherein each —$R^{SN}$, if present, is independently:
—$R^{TT}$,
-$L^T$-OH, -$L^T$-$OR^{TT}$,
-$L^T$-$NH_2$, -$L^T$-$NHR^{TT}$, -$L^T$-$NR^{TT}_2$, -$L^T$-$R^{TM}$, or
—C(=O)$R^{TT}$.

(162) A compound according to any one of (1) to (158), wherein each —$R^{SN}$, if present, is independently:
—$R^{TT}$,
-$L^T$-OH, -$L^T$-$OR^{TT}$,
-$L^T$-$NH_2$, -$L^T$-$NHR^{TT}$, -$L^T$-$NR^{TT}_2$, or
—C(=O)$R^{TT}$.

(163) A compound according to any one of (1) to (158), wherein each —$R^{SN}$, if present, is independently:
—$R^{TT}$,
—C(=O)$R^{TT}$, or
—C(=O)O$R^{TT}$.

(164) A compound according to any one of (1) to (158), wherein each —$R^{SN}$, if present, is independently —$R^{TT}$ or —C(=O)$R^{TT}$.

(165) A compound according to any one of (1) to (158), wherein each —$R^{SN}$, if present, is independently —$R^{TT}$.

The Group -$L^T$-

(166) A compound according to any one of (1) to (165), wherein each -$L^T$-, if present, is independently —CH$_2$—, —CH(Me)—, —C(Me)$_2$-, —CH$_2$CH$_2$—, —CH(Me)CH$_2$—, —CH$_2$CH(Me)—, —C(Me)$_2$CH$_2$—, —CH$_2$C(Me)$_2$-, —CH$_2$CH$_2$CH$_2$—, or —CH$_2$CH$_2$CH$_2$CH$_2$—.

(167) A compound according to any one of (1) to (165), wherein each -$L^T$-, if present, is independently —CH$_2$—, —CH(Me)—, —C(Me)$_2$-, —CH(Et)-, or —CH$_2$CH$_2$—.

(168) A compound according to any one of (1) to (165), wherein each -$L^T$-, if present, is independently —CH$_2$—, —CH(Me)—, or —C(Me)$_2$-.

(169) A compound according to any one of (1) to (165), wherein each -$L^T$-, if present, is independently —CH$_2$—, —CH$_2$CH$_2$—, —CH$_2$CH$_2$CH$_2$—, or —CH$_2$CH$_2$CH$_2$CH$_2$—.

(170) A compound according to any one of (1) to (165), wherein each -$L^T$-, if present, is independently —CH$_2$CH$_2$—, —CH$_2$CH$_2$CH$_2$—, or —CH$_2$CH$_2$CH$_2$CH$_2$—.

(171) A compound according to any one of (1) to (165), wherein each -$L^T$-, if present, is independently —CH$_2$— or —CH$_2$CH$_2$—.

(172) A compound according to any one of (1) to (165), wherein each -$L^T$-, if present, is —CH$_2$—.

(173) A compound according to any one of (1) to (165), wherein each -$L^T$-, if present, is —CH$_2$CH$_2$—.

The Group —$R^{TT}$ (174) A compound according to any one of (1) to (173), wherein each —$R^{TT}$, if present, is independently linear or branched saturated C$_{1-4}$alkyl, saturated C$_{3-6}$cycloalkyl, saturated C$_{3-6}$cycloalkyl-methyl, phenyl, or benzyl.

(175) A compound according to any one of (1) to (173), wherein each —$R^{TT}$, if present, is independently linear or branched saturated C$_{1-4}$alkyl, saturated C$_{3-6}$cycloalkyl, phenyl, or benzyl.

(176) A compound according to any one of (1) to (173), wherein each —$R^{TT}$, if present, is independently linear or branched saturated C$_{1-4}$alkyl, phenyl, or benzyl.

(177) A compound according to any one of (1) to (173), wherein each —$R^{TT}$, if present, is independently linear or branched saturated C$_{1-4}$alkyl, saturated C$_{3-6}$cycloalkyl, or saturated C$_{3-6}$cycloalkyl-methyl; wherein said linear or branched saturated C$_{1-4}$alkyl is optionally substituted with —OH or —OR$^{TTT}$, wherein —R$^{TTT}$ is linear or branched saturated C$_{1-4}$alkyl.

(178) A compound according to any one of (1) to (173), wherein each —$R^{TT}$, if present, is independently linear or branched saturated C$_{1-4}$alkyl, saturated C$_{3-6}$cycloalkyl, or saturated C$_{3-6}$cycloalkyl-methyl.

(179) A compound according to any one of (1) to (173), wherein each —$R^{TT}$, if present, is independently linear or branched saturated C$_{1-4}$alkyl or saturated C$_{3-6}$cycloalkyl; wherein said linear or branched saturated C$_{1-4}$alkyl is optionally substituted with —OH or —OR$^{TTT}$, wherein —R$^{TTT}$ is linear or branched saturated C$_{1-4}$alkyl.

(180) A compound according to any one of (1) to (173), wherein each —$R^{TT}$, if present, is independently linear or branched saturated C$_{1-4}$alkyl or saturated C$_{3-6}$cycloalkyl.

(181) A compound according to any one of (1) to (173), wherein each —$R^{TT}$, if present, is linear or branched saturated C$_{1-4}$alkyl, and is optionally substituted with —OH or —OR$^{TTT}$, wherein —R$^{TTT}$ is linear or branched saturated C$_{1-4}$alkyl.

(182) A compound according to any one of (1) to (173), wherein each —$R^{TT}$, if present, is linear or branched saturated C$_{1-4}$alkyl.

(183) A compound according to any one of (1) to (173), wherein each —$R^{TT}$, if present, is independently -Me, -Et, -nPr, -iPr, -nBu, -iBu, or -tBu.

(184) A compound according to any one of (1) to (173), wherein each —$R^{TT}$, if present, is independently -Me or -tBu.

(185) A compound according to any one of (1) to (173), wherein each —$R^{TT}$, if present, is -Me.

(186) A compound according to any one of (1) to (173), wherein each —$R^{TT}$, if present, is -tBu.

The Group —$R^{TTT}$ (187) A compound according to any one of (1) to (186), wherein each —$R^{TTT}$, if present, is independently -Me, -Et, -nPr, -iPr, -nBu, -iBu, or -tBu.

(188) A compound according to any one of (1) to (186), wherein each —$R^{TTT}$, if present, is independently -Me or -Et.

(189) A compound according to any one of (1) to (186), wherein each —$R^{TTT}$, if present, is -Me.

The Group —$R^{TN}$ (190) A compound according to any one of (1) to (189), wherein each —$R^{TN}$, if present, is independently -Me, -Et, -nPr, -iPr, -nBu, -iBu, or -tBu.

(191) A compound according to any one of (1) to (189), wherein each —$R^{TN}$, if present, is independently -Me or -Et.

(192) A compound according to any one of (1) to (189), wherein each —$R^{TN}$, if present, is -Me.

The Group —$R^{TM}$ (193) A compound according to any one of (1) to (192), wherein each —$R^{TM}$, if present, is independently pyrrolidino, piperidino, piperazino, or morpholino, and is:
optionally substituted on carbon with one or more groups selected from: —R$^{TMM}$, —C(=O)R$^{TMM}$, —S(=O)$_2$R$^{TMM}$, —F, —NH$_2$, —NHR$^{TMM}$, —NR$^{TMM}_2$, —OH, and —OR$^{TMM}$; and
optionally substituted on secondary nitrogen, if present, with a group selected from: —R$^{TMM}$, —C(=O)R$^{TMM}$, —C(=O)OR$^{TMM}$, and —S(=O)$_2$R$^{TMM}$;
wherein each —R$^{TMM}$ is independently linear or branched saturated C$_{1-4}$alkyl, saturated C$_{3-6}$cycloalkyl, saturated C$_{3-6}$cycloalkyl-methyl, phenyl, or benzyl.

The Group —$R^{TMM}$ (194) A compound according to any one of (1) to (193), wherein each —$R^{TMM}$, if present, is independently linear or branched saturated C$_{1-4}$alkyl, saturated C$_{3-6}$cycloalkyl, phenyl, or benzyl.

(195) A compound according to any one of (1) to (193), wherein each —$R^{TMM}$, if present, is independently linear or branched saturated C$_{1-4}$alkyl, phenyl, or benzyl.

(196) A compound according to any one of (1) to (193), wherein each —$R^{TMM}$, if present, is independently linear or branched saturated C$_{1-4}$alkyl, saturated C$_{3-6}$cycloalkyl, or saturated C$_{3-6}$cycloalkyl-methyl.

(197) A compound according to any one of (1) to (193), wherein each —$R^{TMM}$, if present, is independently linear or branched saturated C$_{1-4}$alkyl or saturated C$_{3-6}$cycloalkyl.

(198) A compound according to any one of (1) to (193), wherein each —$R^{TMM}$, if present, is linear or branched saturated $C_{1-4}$alkyl.

(199) A compound according to any one of (1) to (193), wherein each —$R^{TMM}$, if present, is independently -Me, -Et, -nPr, -iPr, -nBu, -iBu, or -tBu.

(200) A compound according to any one of (1) to (193), wherein each —$R^{TMM}$, if present, is independently -Me or -Et.

(201) A compound according to any one of (1) to (193), wherein each —$R^{TMM}$, if present, is -Me.

(202) A compound according to any one of (1) to (193), wherein each —$R^{TMM}$, if present, is independently saturated $C_{3-6}$cycloalkyl.

(203) A compound according to any one of (1) to (193), wherein each —$R^{TMM}$, if present, is independently cyclopropyl, cyclobutyl, cyclopentyl, or cyclohexyl.

(204) A compound according to any one of (1) to (193), wherein each —$R^{TMM}$, if present, is cyclopropyl.

The Group —$R^B$ (205) A compound according to any one of (1) to (204), wherein —$R^B$, if present, is —$R^{B1}$.

(206) A compound according to any one of (1) to (204), wherein —$R^B$, if present, is —$R^{B2}$.

(207) A compound according to any one of (1) to (204), wherein —$R^B$, if present, is -$L^B$-$R^{B2}$.

The Group —$R^{B1}$ (208) A compound according to any one of (1) to (207), wherein —$R^{B1}$, if present, is linear or branched saturated $C_{1-6}$alkyl.

(209) A compound according to any one of (1) to (207), wherein —$R^{B1}$, if present, is independently -Me, -Et, -nPr, -iPr, -nBu, -iBu, or -tBu, and is optionally substituted with —OH or —$OR^{BB}$, wherein —$R^{BB}$ is linear or branched saturated $C_{1-4}$alkyl.

(210) A compound according to any one of (1) to (207), wherein —$R^{B1}$, if present, is independently -Me, -Et, -nPr, -iPr, -nBu, -iBu, or -tBu.

(211) A compound according to any one of (1) to (207), wherein —$R^{B1}$, if present, is independently -Me, -Et, -nPr, or -iPr.

(212) A compound according to any one of (1) to (207), wherein —$R^{B1}$, if present, is independently: -Me; or -Et that is optionally substituted with —OH or —$OR^{BB}$, wherein —$R^{BB}$ is linear or branched saturated $C_{1-4}$alkyl.

(213) A compound according to any one of (1) to (207), wherein —$R^{B1}$, if present, is independently -Me, -Et, —CH$_2$CH$_2$OH, or —CH$_2$CH$_2$OMe.

(214) A compound according to any one of (1) to (207), wherein —$R^{B1}$, if present, is independently -Me, -Et, or —CH$_2$CH$_2$OH.

(215) A compound according to any one of (1) to (207), wherein —$R^{B1}$, if present, is independently -Me or -Et.

(216) A compound according to any one of (1) to (207), wherein —$R^{B1}$, if present, is -Me.

The Group —$R^{BB}$ (217) A compound according to any one of (1) to (216), wherein —$R^{BB}$, if present, is independently -Me or -Et.

(218) A compound according to any one of (1) to (216), wherein —$R^{BB}$, if present, is -Me.

The Group —$R^{B2}$ (219) A compound according to any one of (1) to (218), wherein —$R^{B2}$, if present, is independently cyclopropyl, cyclobutyl, cyclopentyl, or cyclohexyl.

(220) A compound according to any one of (1) to (218), wherein —$R^{B2}$, if present, is independently cyclopropyl, cyclobutyl, or cyclopentyl.

(221) A compound according to any one of (1) to (218), wherein —$R^{B2}$, if present, is independently cyclopropyl or cyclobutyl.

(222) A compound according to any one of (1) to (218), wherein —$R^{B2}$, if present, is cyclopropyl.

The Group -$L^B$-

(223) A compound according to any one of (1) to (222), wherein each -$L^B$-, if present, is independently —CH$_2$—, —CH(Me)—, —C(Me)$_2$-, —CH$_2$CH$_2$—, —CH(Me)CH$_2$—, —CH$_2$CH(Me)—, —C(Me)$_2$CH$_2$—, —CH$_2$C(Me)$_2$-, —CH$_2$CH$_2$CH$_2$—, or —CH$_2$CH$_2$CH$_2$CH$_2$—.

(224) A compound according to any one of (1) to (222), wherein each -$L^B$-, if present, is independently —CH$_2$—, —CH(Me)—, —C(Me)$_2$-, —CH(Et), or —CH$_2$CH$_2$—.

(225) A compound according to any one of (1) to (222), wherein each -$L^B$-, if present, is independently —CH$_2$—, —CH(Me)—, or —C(Me)$_2$-.

(226) A compound according to any one of (1) to (222), wherein each -$L^B$-, if present, is independently —CH$_2$—, —CH$_2$CH$_2$—, —CH$_2$CH$_2$CH$_2$—, or —CH$_2$CH$_2$CH$_2$CH$_2$—.

(227) A compound according to any one of (1) to (222), wherein each -$L^B$-, if present, is independently —CH$_2$CH$_2$—, —CH$_2$CH$_2$CH$_2$—, or —CH$_2$CH$_2$CH$_2$CH$_2$—.

(228) A compound according to any one of (1) to (222), wherein each -$L^B$-, if present, is independently —CH$_2$— or —CH$_2$CH$_2$—.

(229) A compound according to any one of (1) to (222), wherein each -$L^B$-, if present, is —CH$_2$—.

(230) A compound according to any one of (1) to (222), wherein each -$L^B$-, if present, is —CH$_2$CH$_2$—.

The Group —$NR^CR^D$ (231) A compound according to any one of (1) to (230), wherein —$NR^CR^D$, if present, is —$NR^{C1}R^{D1}$.

(232) A compound according to any one of (1) to (230), wherein —$NR^CR^D$, if present, is —$NR^{C2}R^{D2}$.

(233) A compound according to any one of (1) to (230), wherein —$NR^CR^D$, if present, is —$NR^{C3}R^{D3}$.

(234) A compound according to any one of (1) to (230), wherein —$NR^CR^D$, if present, is —$NR^{C4}R^{D4}$.

(235) A compound according to any one of (1) to (230), wherein —$NR^CR^D$, if present, is —$NR^{C5}R^{D5}$.

The Group —$NR^{C1}R^{D1}$ (236) A compound according to any one of (1) to (235), wherein —$NR^{C1}R^{D1}$, if present, is a monocyclic non-aromatic heterocyclyl group having from 4 to 7 ring atoms.

(237) A compound according to any one of (1) to (235), wherein —$NR^{C1}R^{D1}$, if present, is a monocyclic non-aromatic heterocyclyl group having from 5 to 7 ring atoms.

(238) A compound according to any one of (1) to (235), wherein —$NR^{C1}R^{D1}$, if present, is a monocyclic non-aromatic heterocyclyl group having 5 ring atoms.

(239) A compound according to any one of (1) to (235), wherein —$NR^{C1}R^{D1}$, if present, is a monocyclic non-aromatic heterocyclyl group having 6 ring atoms.

(240) A compound according to any one of (1) to (235), wherein —$NR^{C1}R^{D1}$, if present, is a monocyclic non-aromatic heterocyclyl group having 7 ring atoms.

(241) A compound according to any one of (1) to (235), wherein, in —$NR^{C1}R^{D1}$, if present, exactly 1 of said ring atoms is a ring heteroatom, and is N.

(242) A compound according to any one of (1) to (235), wherein, in —$NR^{C1}R^{D1}$, if present, exactly 2 of said ring atoms are ring heteroatoms, and are both N.

(243) A compound according to any one of (1) to (235), wherein, in —$NR^{C1}R^{D1}$, if present, exactly 2 of said ring atoms are ring heteroatoms, and are N and O.

(244) A compound according to any one of (1) to (235), wherein, in —NR$^{C1}$R$^{D1}$, if present, exactly 2 of said ring atoms are ring heteroatoms, and are N and S, wherein said S is optionally in the form of S(=O) or S(=O)$_2$.

(245) A compound according to any one of (1) to (235), wherein, in —NR$^{C1}$R$^{D1}$, if present, exactly 2 of said ring atoms are ring heteroatoms, and are N and S.

(246) A compound according to any one of (1) to (235), wherein, —NR$^{C1}$R$^{D1}$, if present, is independently selected from the following groups, wherein S, if present, is optionally in the form of S(=O) or S(=O)$_2$, and is:

optionally substituted on carbon with one or more groups —R$^{NC}$, and optionally substituted on secondary nitrogen, if present, with a group —R$^{NN}$:

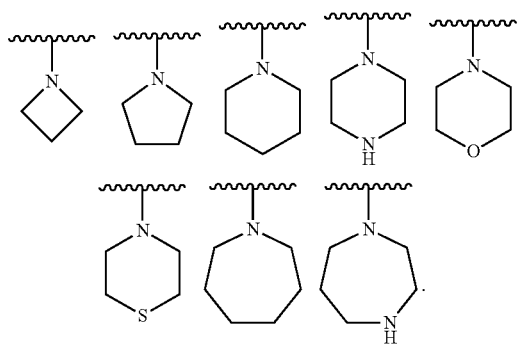

(247) A compound according to any one of (1) to (235), wherein, —NR$^{C1}$R$^{D1}$, if present, is independently selected from the following groups, and is:

optionally substituted on carbon with one or more groups —R$^{NC}$, and optionally substituted on secondary nitrogen, if present, with a group —R$^{NN}$:

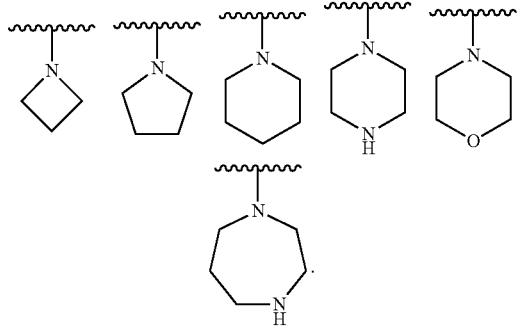

(248) A compound according to any one of (1) to (235), wherein, —NR$^{C1}$R$^{D1}$, if present, is independently selected from the following groups, and is:

optionally substituted on carbon with one or more groups —R$^{NC}$, and optionally substituted on secondary nitrogen, if present, with a group —R$^{NN}$:

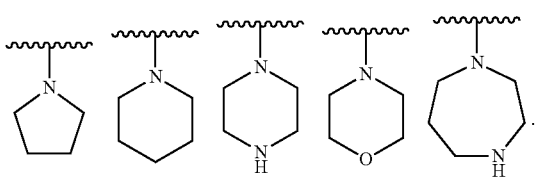

(249) A compound according to any one of (1) to (235), wherein, —NR$^{C1}$R$^{D1}$, if present, is the following group, and is optionally substituted on carbon with one or more groups —R$^{NC}$:

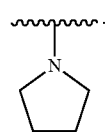

(250) A compound according to any one of (1) to (235), wherein, —NR$^{C1}$R$^{D1}$, if present, is the following group, and is optionally substituted on carbon with one or more groups —R$^{NC}$:

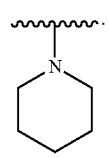

(251) A compound according to any one of (1) to (235), wherein, —NR$^{C1}$R$^{D1}$, if present, is the following group, and is:

optionally substituted on carbon with one or more groups —R$^{NC}$, and optionally substituted on secondary nitrogen with a group —R$^{NN}$:

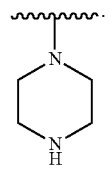

(252) A compound according to any one of (1) to (235), wherein, —NR$^{C1}$R$^{D1}$, if present, is the following group, and is optionally substituted on carbon with one or more groups —R$^{NC}$:

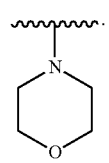

(253) A compound according to any one of (1) to (235), wherein, —NR$^{C1}$R$^{D1}$, if present, is the following group, and is:

optionally substituted on carbon with one or more groups —R$^{NC}$, and optionally substituted on secondary nitrogen with a group —R$^{NN}$:

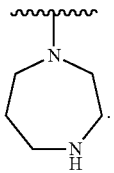 [SMILES: *N1CCCNCC1]

The Group —NR$^{C2}$R$^{D2}$ (254) A compound according to any one of (1) to (253), wherein —NR$^{C2}$R$^{D2}$, if present, is a fused bicyclic non-aromatic heterocyclyl group having from 7 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, wherein said S is optionally in the form of S(=O) or S(=O)$_2$;

and wherein said fused bicyclic non-aromatic heterocyclyl group is:

optionally substituted on carbon with one or more groups —R$^{NC}$, and optionally substituted on secondary nitrogen, if present, with a group —R$^{NN}$.

(255) A compound according to any one of (1) to (253), wherein —NR$^{C2}$R$^{D2}$, if present, is a fused bicyclic non-aromatic heterocyclyl group having from 8 to 10 ring atoms.

(256) A compound according to any one of (1) to (253), wherein —NR$^{C2}$R$^{D2}$, if present, is a fused bicyclic non-aromatic heterocyclyl group having 8 ring atoms.

(257) A compound according to any one of (1) to (253), wherein —NR$^{C2}$R$^{D2}$, if present, is a fused bicyclic non-aromatic heterocyclyl group having 9 ring atoms.

(258) A compound according to any one of (1) to (253), wherein —NR$^{C2}$R$^{D2}$, if present, is a fused bicyclic non-aromatic heterocyclyl group having 10 ring atoms.

(259) A compound according to any one of (1) to (258), wherein, in —NR$^{C2}$R$^{D2}$, if present, exactly 1 of said ring atoms is a ring heteroatom, and is N.

(260) A compound according to any one of (1) to (258), wherein, in —NR$^{C2}$R$^{D2}$, if present, exactly 2 of said ring atoms are ring heteroatoms, and are both N.

(261) A compound according to any one of (1) to (258), wherein, in —NR$^{C2}$R$^{D2}$, if present, exactly 2 of said ring atoms are ring heteroatoms, and are N and O.

(262) A compound according to any one of (1) to (258), wherein, in —NR$^{C2}$R$^{D2}$, if present, exactly 2 of said ring atoms are ring heteroatoms, and are N and S, wherein said S is optionally in the form of S(=O) or S(=O)$_2$.

(263) A compound according to any one of (1) to (258), wherein, in —NR$^{C2}$R$^{D2}$, if present, exactly 2 of said ring atoms are ring heteroatoms, and are N and S.

(264) A compound according to any one of (1) to (253), wherein, —NR$^{C2}$R$^{D2}$, if present, is independently selected from the following groups, and is:

optionally substituted on carbon with one or more groups —R$^{NC}$, and optionally substituted on secondary nitrogen, if present, with a group —R$^{NN}$:

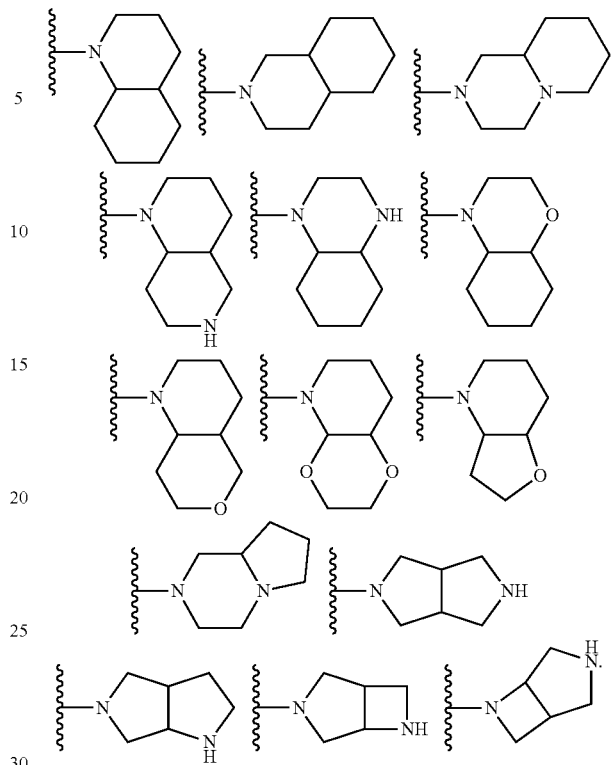

(265) A compound according to any one of (1) to (253), wherein, —NR$^{C2}$R$^{D2}$, if present, is independently selected from the following groups, and is:

optionally substituted on carbon with one or more groups —R$^{NC}$, and optionally substituted on secondary nitrogen, if present, with a group —R$^{NN}$:

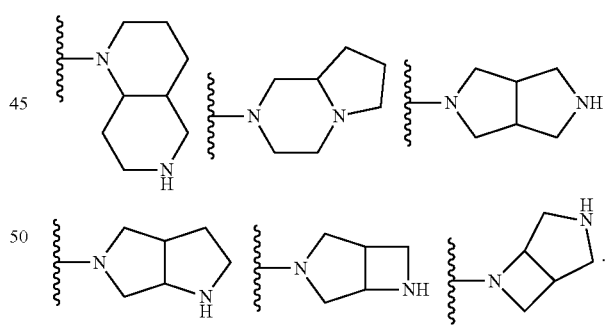

(266) A compound according to any one of (1) to (253), wherein, —NR$^{C2}$R$^{D2}$, if present, is the following group, and is optionally substituted on carbon with one or more groups —R$^{NC}$:

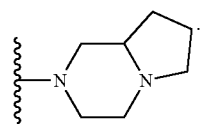 [SMILES: *N1CCN2CCCC2C1]

47

(267) A compound according to any one of (1) to (253), wherein, —NR$^{C2}$R$^{D2}$, if present, is the following group, and is:
optionally substituted on carbon with one or more groups —R$^{NC}$, and
optionally substituted on secondary nitrogen with a group —R$^{NN}$:

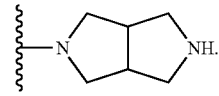

The Group —NR$^{C3}$R$^{D3}$ (268) A compound according to any one of (1) to (267), wherein —NR$^{C3}$R$^{D3}$, if present, is a bridged non-aromatic heterocyclyl group having from 7 to 11 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O;
and wherein said bridged non-aromatic heterocyclyl group is:
optionally substituted on carbon with one or more groups —R$^{NC}$, and
optionally substituted on secondary nitrogen, if present, with a group —R$^{NN}$.

(269) A compound according to any one of (1) to (267), wherein —NR$^{C3}$R$^{D3}$, if present, is a bridged non-aromatic heterocyclyl group having 7 ring atoms.

(270) A compound according to any one of (1) to (267), wherein —NR$^{C3}$R$^{D3}$, if present, is a bridged non-aromatic heterocyclyl group having 8 ring atoms.

(271) A compound according to any one of (1) to (267), wherein —NR$^{C3}$R$^{D3}$, if present, is a bridged non-aromatic heterocyclyl group having 9 ring atoms.

(272) A compound according to any one of (1) to (267), wherein —NR$^{C3}$R$^{D3}$, if present, is a bridged non-aromatic heterocyclyl group having 11 ring atoms.

(273) A compound according to any one of (1) to (272), wherein, in —NR$^{C3}$R$^{D3}$, if present, exactly 1 of said ring atoms is a ring heteroatom, and is N.

(274) A compound according to any one of (1) to (272), wherein, in —NR$^{C3}$R$^{D3}$, if present, exactly 2 of said ring atoms are ring heteroatoms, and are both N.

(275) A compound according to any one of (1) to (272), wherein, in —NR$^{C3}$R$^{D3}$, if present, exactly 2 of said ring atoms are ring heteroatoms, and are N and O.

(276) A compound according to any one of (1) to (272), wherein, in —NR$^{C3}$R$^{D3}$, if present, exactly 2 of said ring atoms are ring heteroatoms, and are N and S, wherein said S is optionally in the form of S(=O) or S(=O)$_2$.

(277) A compound according to any one of (1) to (272), wherein, in —NR$^{C3}$R$^{D3}$, if present, exactly 2 of said ring atoms are ring heteroatoms, and are N and S.

(278) A compound according to any one of (1) to (272), wherein, in —NR$^{C3}$R$^{D3}$, if present, exactly 3 of said ring atoms are ring heteroatoms, one of which is N, and each of the other two is independently N, O, or S, wherein said S is optionally in the form of S(=O) or S(=O)$_2$.

(279) A compound according to any one of (1) to (272), wherein, in —NR$^{C3}$R$^{D3}$, if present, exactly 3 of said ring atoms are ring heteroatoms, one of which is N, and each of the other two is independently N, O, or S.

48

(280) A compound according to any one of (1) to (267), wherein, —NR$^{C3}$R$^{D3}$, if present, is independently selected from the following groups, and is:
optionally substituted on carbon with one or more groups —R$^{NC}$, and
optionally substituted on secondary nitrogen, if present, with groups —R$^{NN}$:

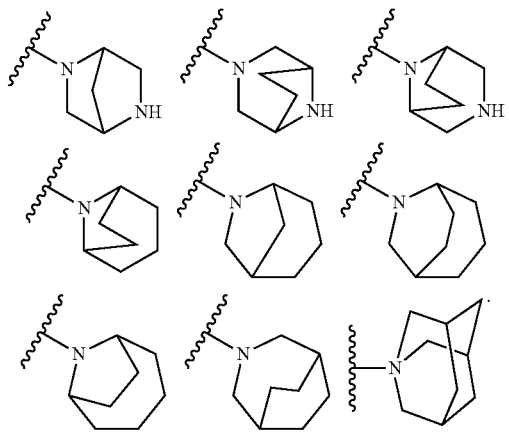

(281) A compound according to any one of (1) to (267), wherein, —NR$^{C3}$R$^{D3}$, if present, is independently selected from the following groups, and is:
optionally substituted on carbon with one or more groups —R$^{NC}$, and
optionally substituted on secondary nitrogen, if present, with groups —R$^{NN}$:

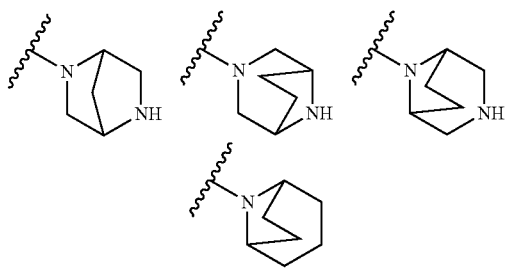

(282) A compound according to any one of (1) to (267), wherein, —NR$^{C3}$R$^{D3}$, if present, is independently selected from the following groups, and is:
optionally substituted on carbon with one or more groups —R$^{NC}$, and
optionally substituted on secondary nitrogen, if present, with groups —R$^{NN}$:

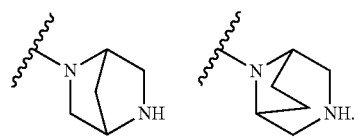 [SMILES: *N1CC2CC1CN2 ; *N1C2CCC1CNC2]

(283) A compound according to any one of (1) to (267), wherein, —NR$^{C3}$R$^{D3}$, if present, is the following group, and is:
optionally substituted on carbon with one or more groups —R$^{NC}$, and optionally substituted on secondary nitrogen with a group —R$^{NN}$:

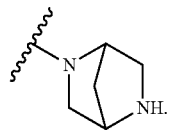 [SMILES: *N1CC2CC1CN2]

(284) A compound according to any one of (1) to (267), wherein, —NR$^{C3}$R$^{D3}$, if present, is the following group, and is:

optionally substituted on carbon with one or more groups —R$^{NC}$, and optionally substituted on secondary nitrogen with groups —R$^{NN}$:

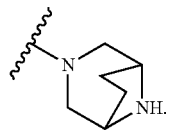 [SMILES: *N1CC2CCC(C1)N2]

The Group —NR$^{C4}$R$^{D4}$ (285) A compound according to any one of (1) to (284), wherein —NR$^{C4}$R$^{D4}$, if present, is a spiro non-aromatic heterocyclyl group having 7 ring atoms.

(286) A compound according to any one of (1) to (284), wherein —NR$^{C4}$R$^{D4}$, if present, is a spiro non-aromatic heterocyclyl group having 8 ring atoms.

(287) A compound according to any one of (1) to (284), wherein —NR$^{C4}$R$^{D4}$, if present, is a spiro non-aromatic heterocyclyl group having 9 ring atoms.

(288) A compound according to any one of (1) to (284), wherein —NR$^{C4}$R$^{D4}$, if present, is a spiro non-aromatic heterocyclyl group having 10 ring atoms.

(289) A compound according to any one of (1) to (284), wherein —NR$^{C4}$R$^{D4}$, if present, is a spiro non-aromatic heterocyclyl group having 11 ring atoms.

(290) A compound according to any one of (1) to (284), wherein —NR$^{C4}$R$^{D4}$, if present, is a spiro non-aromatic heterocyclyl group having 12 ring atoms.

(291) A compound according to any one of (1) to (290), wherein, in —NR$^{C4}$R$^{D4}$, if present, exactly 1 of said ring atoms is a ring heteroatom, and is N.

(292) A compound according to any one of (1) to (290), wherein, in —NR$^{C4}$R$^{D4}$, if present, exactly 2 of said ring atoms are ring heteroatoms, and are both N.

(293) A compound according to any one of (1) to (290), wherein, in —NR$^{C4}$R$^{D4}$, if present, exactly 2 of said ring atoms are ring heteroatoms, and are N and O.

(294) A compound according to any one of (1) to (290), wherein, in —NR$^{C4}$R$^{D4}$, if present, exactly 2 of said ring atoms are ring heteroatoms, and are N and S, wherein said S is optionally in the form of S(═O) or S(═O)$_2$.

(295) A compound according to any one of (1) to (290), wherein, in —NR$^{C4}$R$^{D4}$, if present, exactly 2 of said ring atoms are ring heteroatoms, and are N and S.

(296) A compound according to any one of (1) to (290), wherein, in —NR$^{C4}$R$^{D4}$, if present, exactly 3 of said ring atoms are ring heteroatoms, one of which is N, and each of the other two is independently N, O, or S, wherein said S is optionally in the form of S(═O) or S(═O)$_2$.

(297) A compound according to any one of (1) to (290), wherein, in —NR$^{C4}$R$^{D4}$, if present, exactly 3 of said ring atoms are ring heteroatoms, one of which is N, and each of the other two is independently N, O, or S.

(298) A compound according to any one of (1) to (284), wherein, —NR$^{C4}$R$^{D4}$, if present, is independently selected from the following groups, and is:

optionally substituted on carbon with one or more groups —R$^{NC}$, and optionally substituted on secondary nitrogen, if present, with a group —R$^{NN}$:

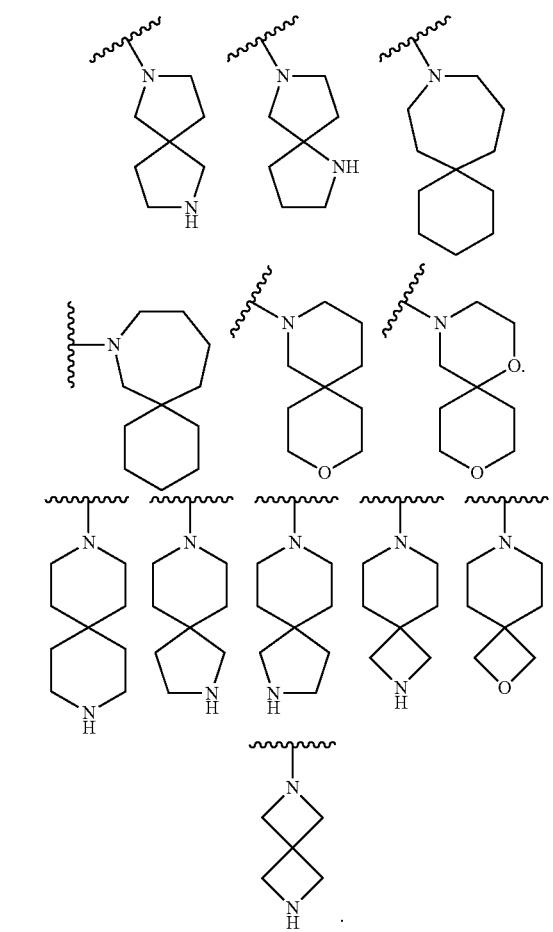

(299) A compound according to any one of (1) to (284), wherein, —NR$^{C4}$R$^{D4}$, if present, is independently selected from the following groups, and is:

optionally substituted on carbon with one or more groups —R$^{NC}$, and optionally substituted on secondary nitrogen, if present, with a group —R$^{NN}$:

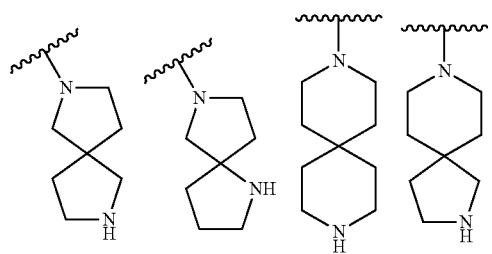

-continued

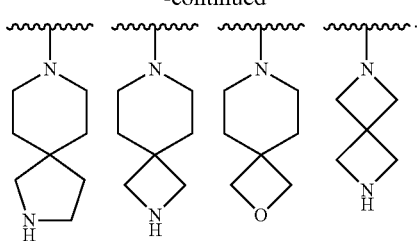

(300) A compound according to any one of (1) to (284), wherein, —NR$^{C4}$R$^{D4}$, if present, is independently selected from the following groups, and is:
  optionally substituted on carbon with one or more groups —R$^{NC}$, and
  optionally substituted on secondary nitrogen with a group —R$^{NN}$:

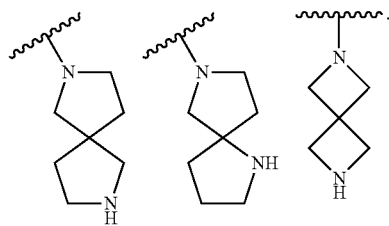

(301) A compound according to any one of (1) to (284), wherein, —NR$^{C4}$R$^{D4}$, if present, is the following group, and is:
  optionally substituted on carbon with one or more groups —R$^{NC}$, and
  optionally substituted on secondary nitrogen with a group —R$^{NN}$:

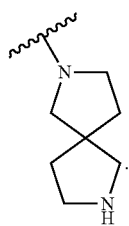 [SMILES: *N1CCC2(CCNC2)C1]

The Group —R$^{NC}$ (302) A compound according to any one of (1) to (301), wherein each —R$^{NC}$, if present, is independently:
  —R$^{QQ}$,
  —F, —Cl, —Br, —I,
  —OH, —OR$^{QQ}$,
  -L$^{Q}$-OH, -L$^{Q}$-OR$^{QQ}$,
  —NH$_2$, —NHR$^{QQ}$, —NR$^{QQ}$$_2$, —R$^{QM}$,
  -L$^{Q}$-NH$_2$, -L$^{Q}$-NHR$^{QQ}$, -L$^{Q}$-NR$^{QQ}$$_2$, -L$^{Q}$-R$^{QM}$, or
  =O.

(303) A compound according to any one of (1) to (301), wherein each —R$^{NC}$, if present, is independently:
  —R$^{QQ}$,
  —OH, —OR$^{QQ}$,
  —NH$_2$, —NHR$^{QQ}$, —NR$^{QQ}$$_2$, —R$^{QM}$, or
  =O.

(304) A compound according to any one of (1) to (301), wherein each —R$^{NC}$, if present, is independently —R$^{QQ}$.

The Group —R$^{NN}$ (305) A compound according to any one of (1) to (304), wherein each —R$^{NN}$, if present, is independently:
  —R$^{QQ}$,
  -L$^{Q}$-OH, -L$^{Q}$-OR$^{QQ}$,
  -L$^{Q}$-NH$_2$, -L$^{Q}$-NHR$^{QQ}$, -L$^{Q}$-NR$^{QQ}$$_2$, -L$^{Q}$-R$^{QM}$,
  —C(=O)R$^{QQ}$,
  —C(=O)OR$^{QQ}$,
  —C(=O)NH$_2$, —C(=O)NHR$^{QQ}$, —C(=O)NR$^{QQ}$$_2$, or
  —C(=O)R$^{QM}$.

(306) A compound according to any one of (1) to (304), wherein each —R$^{NN}$, if present, is independently:
  —R$^{QQ}$,
  -L$^{Q}$-OH, -L$^{Q}$-OR$^{QQ}$,
  -L$^{Q}$-NH$_2$, -L$^{Q}$-NHR$^{QQ}$, -L$^{Q}$-NR$^{QQ}$$_2$, -L$^{Q}$-R$^{QM}$,
  —C(=O)R$^{QQ}$, or
  —C(=O)OR$^{QQ}$.

(307) A compound according to any one of (1) to (304), wherein each —R$^{NN}$, if present, is independently:
  —R$^{QQ}$,
  -L$^{Q}$-OH, -L$^{Q}$-OR$^{QQ}$,
  -L$^{Q}$-NH$_2$, -L$^{Q}$-NHR$^{QQ}$, -L$^{Q}$-NR$^{QQ}$$_2$, -L$^{Q}$-R$^{QM}$, or
  —C(=O)R$^{QQ}$.

(308) A compound according to any one of (1) to (304), wherein each —R$^{NN}$, if present, is independently:
  —R$^{QQ}$,
  -L$^{Q}$-OH, -L$^{Q}$-OR$^{QQ}$,
  -L$^{Q}$-NH$_2$, -L$^{Q}$-NHR$^{QQ}$, -L$^{Q}$-NR$^{QQ}$$_2$, or
  —C(=O)R$^{QQ}$.

(309) A compound according to any one of (1) to (304), wherein each —R$^{NN}$, if present, is independently:
  —R$^{QQ}$,
  —C(=O)R$^{QQ}$, or
  —C(=O)OR$^{QQ}$.

(310) A compound according to any one of (1) to (304), wherein each —R$^{NN}$, if present, is independently —R$^{QQ}$ or —C(=O)R$^{QQ}$.

(311) A compound according to any one of (1) to (304), wherein each —R$^{NN}$, if present, is independently —R$^{QQ}$.

(312) A compound according to any one of (1) to (304), wherein each —R$^{NN}$, if present, is independently: —R$^{QQ}$, -L$^{Q}$-OH, or -L$^{Q}$-OR$^{QQ}$.

(313) A compound according to any one of (1) to (304), wherein each —R$^{NN}$, if present, is independently: -L$^{Q}$-OH or -L$^{Q}$-OR$^{QQ}$.

(314) A compound according to any one of (1) to (304), wherein each —R$^{NN}$, if present, is independently: -L$^{Q}$-OH.

The Group -L$^{Q}$-

(315) A compound according to any one of (1) to (314), wherein each -L$^{Q}$-, if present, is independently —CH$_2$—, —CH(Me)—, —C(Me)$_2$-, —CH$_2$CH$_2$—, —CH(Me)CH$_2$—, —CH$_2$CH(Me)—, —C(Me)$_2$CH$_2$—, —CH$_2$C(Me)$_2$-, —CH$_2$CH$_2$CH$_2$—, or —CH$_2$CH$_2$CH$_2$CH$_2$—.

(316) A compound according to any one of (1) to (314), wherein each -L$^{Q}$-, if present, is independently —CH$_2$—, —CH(Me)—, —C(Me)$_2$-, —CH(Et)-, or —CH$_2$CH$_2$—.

(317) A compound according to any one of (1) to (314), wherein each -L$^{Q}$-, if present, is independently —CH$_2$—, —CH(Me)—, or —C(Me)$_2$-.

(318) A compound according to any one of (1) to (314), wherein each -L$^{Q}$-, if present, is independently —CH$_2$—, —CH$_2$CH$_2$—, —CH$_2$CH$_2$CH$_2$—, or —CH$_2$CH$_2$CH$_2$CH$_2$—.

(319) A compound according to any one of (1) to (314), wherein each -L$^{Q}$-, if present, is independently —CH$_2$CH$_2$—, —CH$_2$CH$_2$CH$_2$—, or —CH$_2$CH$_2$CH$_2$CH$_2$—.

(320) A compound according to any one of (1) to (314), wherein each -$L^Q$-, if present, is independently —$CH_2$— or —$CH_2CH_2$—.

(321) A compound according to any one of (1) to (314), wherein each -$L^Q$-, if present, is —$CH_2$—.

(322) A compound according to any one of (1) to (314), wherein each -$L^Q$-, if present, is —$CH_2CH_2$—.

The Group —$R^{QQ}$ (323) A compound according to any one of (1) to (322), wherein each —$R^{QQ}$, if present, is independently linear or branched saturated $C_{1-4}$alkyl, saturated $C_{3-6}$cycloalkyl, saturated $C_{3-6}$cycloalkyl-methyl, phenyl, or benzyl; wherein said linear or branched saturated $C_{1-4}$alkyl is optionally substituted with —OH or —$OR^{QQQ}$, wherein —$R^{QQQ}$ is linear or branched saturated $C_{1-4}$alkyl.

(324) A compound according to any one of (1) to (322), wherein each —$R^{QQ}$, if present, is independently linear or branched saturated $C_{1-4}$alkyl, saturated $C_{3-6}$cycloalkyl, saturated $C_{3-6}$cycloalkyl-methyl, phenyl, or benzyl.

(325) A compound according to any one of (1) to (322), wherein each —$R^{QQ}$, if present, is independently linear or branched saturated $C_{1-4}$alkyl, saturated $C_{3-6}$cycloalkyl, phenyl, or benzyl.

(326) A compound according to any one of (1) to (322), wherein each —$R^{QQ}$, if present, is independently linear or branched saturated $C_{1-4}$alkyl, phenyl, or benzyl.

(327) A compound according to any one of (1) to (322), wherein each —$R^{QQ}$, if present, is independently linear or branched saturated $C_{1-4}$alkyl, saturated $C_{3-6}$cycloalkyl, or saturated $C_{3-6}$cycloalkyl-methyl; wherein said linear or branched saturated $C_{1-4}$alkyl is optionally substituted with —OH or —$OR^{QQ}$, wherein —$R^{QQ}$ is linear or branched saturated $C_{1-4}$alkyl.

(328) A compound according to any one of (1) to (322), wherein each —$R^{QQ}$, if present, is independently linear or branched saturated $C_{1-4}$alkyl, saturated $C_{3-6}$cycloalkyl, or saturated $C_{3-6}$cycloalkyl-methyl.

(329) A compound according to any one of (1) to (322), wherein each —$R^{QQ}$, if present, is independently linear or branched saturated $C_{1-4}$alkyl or saturated $C_{3-6}$cycloalkyl; wherein said linear or branched saturated $C_{1-4}$alkyl is optionally substituted with —OH or —$OR^{QQ}$, wherein —$R^{QQ}$ is linear or branched saturated $C_{1-4}$alkyl.

(330) A compound according to any one of (1) to (322), wherein each —$R^{QQ}$, if present, is independently linear or branched saturated $C_{1-4}$alkyl or saturated $C_{3-6}$cycloalkyl.

(331) A compound according to any one of (1) to (322), wherein each —$R^{QQ}$, if present, is linear or branched saturated $C_{1-4}$alkyl, and is optionally substituted with —OH or —$OR^{QQ}$, wherein —$R^{QQ}$ is linear or branched saturated $C_{1-4}$alkyl.

(332) A compound according to any one of (1) to (322), wherein each —$R^{QQ}$, if present, is linear or branched saturated $C_{1-4}$alkyl.

(333) A compound according to any one of (1) to (322), wherein each —$R^{QQ}$, if present, is independently -Me, -Et, -nPr, -iPr, -nBu, -iBu, or -tBu.

(334) A compound according to any one of (1) to (322), wherein each —$R^{QQ}$, if present, is independently -Me or -tBu.

(335) A compound according to any one of (1) to (322), wherein each —$R^{QQ}$, if present, is -Me.

(336) A compound according to any one of (1) to (322), wherein each —$R^{QQ}$, if present, is -tBu.

(337) A compound according to any one of (1) to (322), wherein each —$R^{QQ}$, if present, is saturated $C_{3-6}$cycloalkyl.

(338) A compound according to any one of (1) to (322), wherein each —$R^{QQ}$, if present, is independently cyclopropyl, cyclobutyl, cyclopentyl, or cyclohexyl.

(339) A compound according to any one of (1) to (322), wherein each —$R^{QQ}$, if present, is cyclopropyl.

(340) A compound according to any one of (1) to (322), wherein each —$R^{QQ}$, if present, is saturated $C_{3-6}$cycloalkyl-methyl.

(341) A compound according to any one of (1) to (322), wherein each —$R^{QQ}$, if present, is independently cyclopropyl-methyl, cyclobutyl-methyl, cyclopentyl-methyl, or cyclohexyl-methyl.

(342) A compound according to any one of (1) to (322), wherein each —$R^{QQ}$, if present, is cyclopropyl-methyl.

The Group —$R^{QQQ}$ (343) A compound according to any one of (1) to (342), wherein each —$R^{QQQ}$, if present, is independently -Me, -Et, -nPr, -iPr, -nBu, -iBu, or -tBu.

(344) A compound according to any one of (1) to (342), wherein each —$R^{QQQ}$, if present, is independently -Me or -Et.

(345) A compound according to any one of (1) to (342), wherein each —$R^{QQQ}$, if present, is independently -Me.

The Group —$R^{QN}$ (346) A compound according to any one of (1) to (345), wherein each —$R^{QN}$, if present, is independently -Me, -Et, -nPr, -iPr, -nBu, -iBu, or -tBu.

(347) A compound according to any one of (1) to (345), wherein each —$R^{QN}$, if present, is independently -Me or -Et.

(348) A compound according to any one of (1) to (345), wherein each —$R^{QN}$, if present, is independently -Me.

The Group —$R^{QM}$ (349) A compound according to any one of (1) to (348), wherein each —$R^{QM}$, if present, is independently pyrrolidino, piperidino, piperazino, or morpholino, and is:

optionally substituted on carbon with one or more groups selected from: —$R^{QMM}$, —C(=O)$R^{QMM}$, —S(=O)$_2$$R^{QMM}$, —F, —$NH_2$, —$NHR^{QMM}$, —$NR^{QMM}{}_2$, —OH, and —$OR^{QMM}$; and optionally substituted on secondary nitrogen, if present, with a group selected from: —$R^{QMM}$, —C(=O)$R^{QMM}$, —C(=O)O$R^{QMM}$, and —S(=O)$_2$$R^{QMM}$;

wherein each —$R^{QMM}$ is independently linear or branched saturated $C_{1-4}$alkyl, saturated $C_{3-6}$cycloalkyl, saturated $C_{3-6}$cycloalkyl-methyl, phenyl, or benzyl.

The Group —$R^{QMM}$ (350) A compound according to any one of (1) to (349), wherein each —$R^{QMM}$, if present, is independently linear or branched saturated $C_{1-4}$alkyl, saturated $C_{3-6}$cycloalkyl, phenyl, or benzyl.

(351) A compound according to any one of (1) to (349), wherein each —$R^{QMM}$, if present, is independently linear or branched saturated $C_{1-4}$alkyl, phenyl, or benzyl.

(352) A compound according to any one of (1) to (349), wherein each —$R^{QMM}$, if present, is independently linear or branched saturated $C_{1-4}$alkyl, saturated $C_{3-6}$cycloalkyl, or saturated $C_{3-6}$cycloalkyl-methyl.

(353) A compound according to any one of (1) to (349), wherein each —$R^{QMM}$, if present, is independently linear or branched saturated $C_{1-4}$alkyl or saturated $C_{3-6}$cycloalkyl.

(354) A compound according to any one of (1) to (349), wherein each —$R^{QMM}$, if present, is linear or branched saturated $C_{1-4}$alkyl.

(355) A compound according to any one of (1) to (349), wherein each —$R^{QMM}$, if present, is independently -Me, -Et, -nPr, -iPr, -nBu, -iBu, or -tBu.

(356) A compound according to any one of (1) to (349), wherein each —$R^{QMM}$, if present, is independently -Me or -Et.

(357) A compound according to any one of (1) to (349), wherein each —$R^{QMM}$, if present, is -Me.

(358) A compound according to any one of (1) to (349), wherein each —$R^{QMM}$, if present, is independently saturated $C_{3-6}$cycloalkyl.

(359) A compound according to any one of (1) to (349), wherein each —$R^{QMM}$, if present, is independently cyclopropyl, cyclobutyl, cyclopentyl, or cyclohexyl.

(360) A compound according to any one of (1) to (349), wherein each —$R^{QMM}$, if present, is cyclopropyl.

The Group —$NR^{C5}R^{D5}$ (361) A compound according to any one of (1) to (360), wherein —$NR^{C5}R^{D5}$, if present, is independently: 1H-pyrrol-1-yl; 2H-isoindol-2-yl; 1H-indol-1-yl; 1H-pyrazol-1-yl; 1H-benzoimidazol-1-yl; 1H-imidazol-1-yl; 2H-indazol-2-yl; 1H-indazol-1-yl; 4H-[1,2,4]triazol-4-yl; 1H-[1,2,3]triazol-1-yl; 1H-[1,2,4]triazol-1-yl; 1H-benzotriazol-1-yl; or 1H-tetrazol-1-yl; and is optionally substituted with one or more groups —$R^H$.

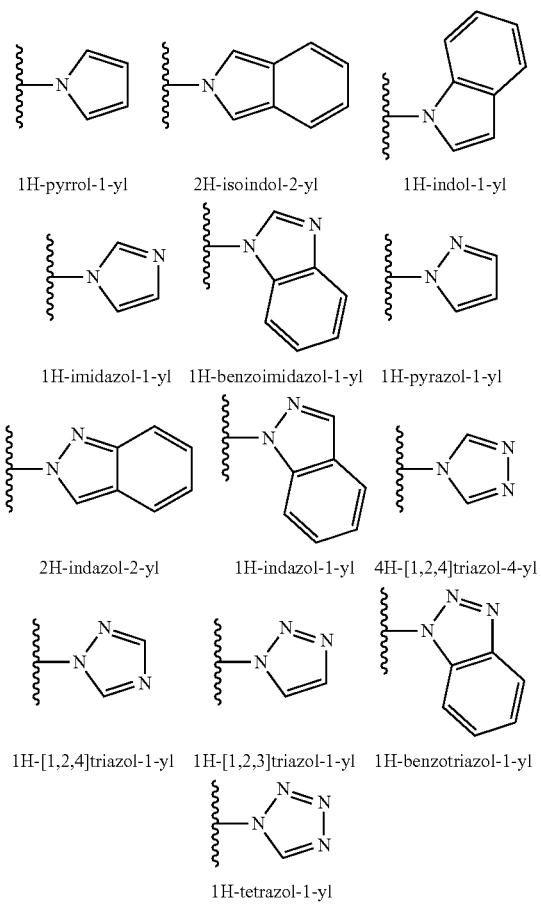

(362) A compound according to any one of (1) to (360), wherein —$NR^{C5}R^{D5}$, if present, is independently: 1H-pyrrol-1-yl; 1H-pyrazol-1-yl; 1H-imidazol-1-yl; 4H-[1,2,4]triazol-4-yl; 1H-[1,2,3]triazol-1-yl; 1H-[1,2,4]triazol-1-yl; or 1H-tetrazol-1-yl; and is optionally substituted with one or more groups —$R^H$.

(363) A compound according to any one of (1) to (360), wherein —$NR^{C5}R^{D5}$, if present, is: 1H-pyrrol-1-yl; 1H-pyrazol-1-yl; or 1H-imidazol-1-yl; and is optionally substituted with one or more groups —$R^H$.

(364) A compound according to any one of (1) to (360), wherein —$NR^{C5}R^{D5}$, if present, is 1H-pyrrol-1-yl; and is optionally substituted with one or more groups —$R^H$.

(365) A compound according to any one of (1) to (360), wherein —$NR^{C5}R^{D5}$, if present, is 1H-pyrazol-1-yl; and is optionally substituted with one or more groups —$R^H$.

(366) A compound according to any one of (1) to (360), wherein —$NR^{C5}R^{D5}$, if present, is 1H-imidazol-1-yl; and is optionally substituted with one or more groups —$R^H$.

(367) A compound according to any one of (1) to (360), wherein —$NR^{C5}R^{D5}$, if present, is 1H-[1,2,4]triazol-1-yl; and is optionally substituted with one or more groups —$R^H$.

(368) A compound according to any one of (1) to (360), wherein —$NR^{C5}R^{D5}$, if present, is 1H-benzoimidazol-1-yl; and is optionally substituted with one or more groups —$R^H$.

(369) A compound according to any one of (1) to (360), wherein —$NR^{C5}R^{D5}$, if present, is 1H-indol-1-yl; and is optionally substituted with one or more groups —$R^H$.

The Group —$R^H$ (370) A compound according to any one of (1) to (369), wherein each —$R^H$, if present, is independently:
- —$R^{HH}$,
- —F, —Cl, —Br, —I,
- —OH, —$OR^{HH}$,
- -$L^H$-OH, -$L^H$-$OR^{HH}$,
- —$CF_3$, —$OCF_3$,
- —$NH_2$, —$NHR^{HH}$, —$NR^{HH}_2$, —$R^{TM}$,
- -$L^H$-$NH_2$, -$L^H$-$NHR^{HH}$, -$L^H$-$NR^{HH}_2$, -$L^H$-$R^{HM}$,
- —C(=O)OH, —C(=O)$OR^{HH}$, —OC(=O)$R^{HH}$,
- —C(=O)$NH_2$, —C(=O)$NHR^{HH}$, —C(=O)$NR^{HH}_2$,
- —C(=O)$R^{HM}$,
- —NHC(=O)$R^{HH}$, —$NR^{HN}$C(=O)$R^{HH}$, or
- —C(=O)$R^{HH}$.

(371) A compound according to any one of (1) to (369), wherein each —$R^H$, if present, is independently:
- —$R^{HH}$,
- —F, —Cl, —Br, —I,
- —OH, —$OR^{HH}$,
- -$L^H$-OH, -$L^{HH}$-$OR^{HH}$,
- —$NH_2$, —$NHR^{HH}$, —$NR^{HH}_2$, —$R^{HM}$,
- -$L^H$-$NH_2$, -$L^H$-$NHR^{HH}$, -$L^H$-$NR^{HH}_2$, or -$L^H$-$R^{HM}$.

(372) A compound according to any one of (1) to (369), wherein each —$R^H$, if present, is independently:
- —$R^{HH}$,
- —OH, —$OR^{HH}$,
- —$NH_2$, —$NHR^{HH}$, —$NR^{HH}_2$, or —$R^{HM}$.

(373) A compound according to any one of (1) to (369), wherein each —$R^H$, if present, is independently —$R^{HH}$.

The Group -$L^H$-

(374) A compound according to any one of (1) to (373), wherein each -$L^H$-, if present, is independently —$CH_2$—, —CH(Me)—, —C(Me)$_2$-, —$CH_2CH_2$—, —CH(Me)$CH_2$—, —$CH_2$CH(Me)—, —C(Me)$_2CH_2$—, —$CH_2$C(Me)$_2$-, —$CH_2CH_2CH_2$—, or —$CH_2CH_2CH_2CH_2$—.

(375) A compound according to any one of (1) to (373), wherein each -$L^H$-, if present, is independently —$CH_2$—, —CH(Me)—, —C(Me)$_2$-, —CH(Et)-, or —$CH_2CH_2$—.

(376) A compound according to any one of (1) to (373), wherein each -$L^H$-, if present, is independently —$CH_2$—, —CH(Me)—, or —C(Me)$_2$-.

(377) A compound according to any one of (1) to (373), wherein each -$L^H$-, if present, is independently —$CH_2$—, —$CH_2CH_2$—, —$CH_2CH_2CH_2$—, or —$CH_2CH_2CH_2CH_2$—.

(378) A compound according to any one of (1) to (373), wherein each -$L^H$-, if present, is independently —CH$_2$CH$_2$—, —CH$_2$CH$_2$CH$_2$—, or —CH$_2$CH$_2$CH$_2$CH$_2$—.

(379) A compound according to any one of (1) to (373), wherein each -$L^H$-, if present, is independently —CH$_2$— or —CH$_2$CH$_2$—.

(380) A compound according to any one of (1) to (373), wherein each -$L^H$-, if present, is —CH$_2$—.

(381) A compound according to any one of (1) to (373), wherein each -$L^H$-, if present, is —CH$_2$CH$_2$—.

The Group —$R^{HH}$ (382) A compound according to any one of (1) to (381), wherein each —$R^{HH}$, if present, is independently linear or branched saturated C$_{1-4}$alkyl, saturated C$_{3-6}$cycloalkyl, saturated C$_{3-6}$cycloalkyl-methyl, phenyl, or benzyl.

(383) A compound according to any one of (1) to (381), wherein each —$R^{HH}$, if present, is independently linear or branched saturated C$_{1-4}$alkyl, saturated C$_{3-6}$cycloalkyl, phenyl, or benzyl.

(384) A compound according to any one of (1) to (381), wherein each —$R^{HH}$, if present, is independently linear or branched saturated C$_{1-4}$alkyl, phenyl, or benzyl.

(385) A compound according to any one of (1) to (381), wherein each —$R^{HH}$, if present, is independently linear or branched saturated C$_{1-4}$alkyl, saturated C$_{3-6}$cycloalkyl, or saturated C$_{3-6}$cycloalkyl-methyl; wherein said linear or branched saturated C$_{1-4}$alkyl is optionally substituted with —OH or —OR$^{HHH}$, wherein —R$^{HHH}$ is linear or branched saturated C$_{1-4}$alkyl.

(386) A compound according to any one of (1) to (381), wherein each —$R^{HH}$, if present, is independently linear or branched saturated C$_{1-4}$alkyl, saturated C$_{3-6}$cycloalkyl, or saturated C$_{3-6}$cycloalkyl-methyl.

(387) A compound according to any one of (1) to (381), wherein each —$R^{HH}$, if present, is independently linear or branched saturated C$_{1-4}$alkyl or saturated C$_{3-6}$cycloalkyl; wherein said linear or branched saturated C$_{1-4}$alkyl is optionally substituted with —OH or —OR$^{HHH}$, wherein —R$^{QQ}$ is linear or branched saturated C$_{1-4}$alkyl.

(388) A compound according to any one of (1) to (381), wherein each —$R^{HH}$, if present, is independently linear or branched saturated C$_{1-4}$alkyl or saturated C$_{3-6}$cycloalkyl.

(389) A compound according to any one of (1) to (381), wherein each —$R^{HH}$, if present, is linear or branched saturated C$_{1-4}$alkyl, and is optionally substituted with —OH or —OR$^{HHH}$, wherein —R$^{HHH}$ is linear or branched saturated C$_{1-4}$alkyl.

(390) A compound according to any one of (1) to (381), wherein each —$R^{HH}$, if present, is linear or branched saturated C$_{1-4}$alkyl.

(391) A compound according to any one of (1) to (381), wherein each —$R^{HH}$, if present, is independently -Me, -Et, -nPr, -iPr, -nBu, -iBu, or -tBu.

(392) A compound according to any one of (1) to (381), wherein each —$R^{HH}$, if present, is independently -Me or -tBu.

(393) A compound according to any one of (1) to (381), wherein each —$R^{HH}$, if present, is -Me.

(394) A compound according to any one of (1) to (381), wherein each —$R^{HH}$, if present, is -tBu.

(395) A compound according to any one of (1) to (381), wherein each —$R^{HH}$, if present, is saturated C$_{3-6}$cycloalkyl.

(396) A compound according to any one of (1) to (381), wherein each —$R^{HH}$, if present, is independently cyclopropyl, cyclobutyl, cyclopentyl, or cyclohexyl.

(397) A compound according to any one of (1) to (381), wherein each —$R^{HH}$, if present, is cyclopropyl.

The Group —$R^{HHH}$ (398) A compound according to any one of (1) to (397), wherein each —$R^{HHH}$, if present, is independently -Me, -Et, -nPr, -iPr, -nBu, -iBu, or -tBu.

(399) A compound according to any one of (1) to (397), wherein each —$R^{HHH}$, if present, is independently -Me or -Et.

(400) A compound according to any one of (1) to (397), wherein each —$R^{HH}$, if present, is independently -Me.

The Group —$R^{HN}$ (401) A compound according to any one of (1) to (400), wherein each —$R^{HN}$, if present, is independently -Me, -Et, -nPr, -iPr, -nBu, -iBu, or -tBu.

(402) A compound according to any one of (1) to (400), wherein each —$R^{HN}$, if present, is independently -Me or -Et.

(403) A compound according to any one of (1) to (400), wherein each —$R^{HN}$, if present, is independently -Me.

The Group —$R^{HM}$ (404) A compound according to any one of (1) to (403), wherein each —$R^{HM}$, if present, is independently pyrrolidino, piperidino, piperazino, or morpholino, and is:

optionally substituted on carbon with one or more groups selected from: —R$^{HMM}$, —C(=O)R$^{HMM}$, —S(=O)$_2$R$^{HMM}$, —F, —NH$_2$, —NHR$^{HMM}$, —NR$^{HMM}{}_2$, —OH, and —OR$^{HMM}$; and optionally substituted on secondary nitrogen, if present, with a group selected from: —R$^{HMM}$, —C(=O)R$^{HMM}$, —C(=O)OR$^{HMM}$, and —S(=O)$_2$R$^{HMM}$;

wherein each —R$^{HMM}$ is independently linear or branched saturated C$_{1-4}$alkyl, saturated C$_{3-6}$cycloalkyl, saturated C$_{3-6}$cycloalkyl-methyl, phenyl, or benzyl.

The Group —$R^{HMM}$ (405) A compound according to any one of (1) to (404), wherein each —$R^{HMM}$, if present, is independently linear or branched saturated C$_{1-4}$alkyl, saturated C$_{3-6}$cycloalkyl, phenyl, or benzyl.

(406) A compound according to any one of (1) to (404), wherein each —$R^{HMM}$, if present, is independently linear or branched saturated C$_{1-4}$alkyl, phenyl, or benzyl.

(407) A compound according to any one of (1) to (404), wherein each —$R^{HMM}$, if present, is independently linear or branched saturated C$_{1-4}$alkyl, saturated C$_{3-6}$cycloalkyl, or saturated C$_{3-6}$cycloalkyl-methyl.

(408) A compound according to any one of (1) to (404), wherein each —$R^{HMM}$, if present, is independently linear or branched saturated C$_{1-4}$alkyl or saturated C$_{3-6}$cycloalkyl.

(409) A compound according to any one of (1) to (404), wherein each —$R^{HMM}$, if present, is linear or branched saturated C$_{1-4}$alkyl.

(410) A compound according to any one of (1) to (404), wherein each —$R^{HMM}$, if present, is independently -Me, -Et, -nPr, -iPr, -nBu, -iBu, or -tBu.

(411) A compound according to any one of (1) to (404), wherein each —$R^{HMM}$, if present, is independently -Me or -Et.

(412) A compound according to any one of (1) to (404), wherein each —$R^{HMM}$, if present, is -Me.

(413) A compound according to any one of (1) to (404), wherein each —$R^{HMM}$, if present, is independently saturated C$_{3-6}$cycloalkyl.

(414) A compound according to any one of (1) to (404), wherein each —$R^{HMM}$, if present, is independently cyclopropyl, cyclobutyl, cyclopentyl, or cyclohexyl.

(415) A compound according to any one of (1) to (404), wherein each —$R^{HMM}$, if present, is cyclopropyl.

The Group —$R^5$ (416) A compound according to any one of (1) to (415), wherein —$R^5$ is independently —$R^{5A}$, —$R^{5B}$, —$R^{5C}$, or —$R^{5D}$.

(417) A compound according to any one of (1) to (415), wherein —$R^5$ is —$R^{5A}$.

(418) A compound according to any one of (1) to (415), wherein —$R^5$ is —$R^{5B}$.

(419) A compound according to any one of (1) to (415), wherein —$R^5$ is —$R^{5C}$.

(420) A compound according to any one of (1) to (415), wherein —$R^5$ is —$R^{5D}$.

(421) A compound according to any one of (1) to (415), wherein —$R^5$ is —$R^{5E}$.

The Group —$R^{5A}$ (422) A compound according to any one of (1) to (421), wherein —$R^{5A}$, if present, is independently -Me, -Et, -nPr, -iPr, -nBu, -iBu, or -tBu.

(423) A compound according to any one of (1) to (421), wherein —$R^{5A}$, if present, is independently -Me, -Et, -nPr, or -iPr.

(424) A compound according to any one of (1) to (421), wherein —$R^{5A}$, if present, is independently -Me or -Et.

(425) A compound according to any one of (1) to (421), wherein —$R^{5A}$, if present, is -Me.

The Group —$R^{5B}$ (426) A compound according to any one of (1) to (425), wherein —$R^{5B}$, if present, is independently cyclopropyl, cyclobutyl, cyclopentyl, or cyclohexyl.

(427) A compound according to any one of (1) to (425), wherein —$R^{5B}$, if present, is independently cyclopropyl, cyclobutyl, or cyclopentyl.

(428) A compound according to any one of (1) to (425), wherein —$R^{5B}$, if present, is independently cyclopropyl or cyclobutyl.

(429) A compound according to any one of (1) to (425), wherein —$R^{5B}$, if present, is cyclopropyl.

The Group —$R^{5C}$ (430) A compound according to any one of (1) to (429), wherein —$R^{5C}$, if present, is independently —F, —Cl, or —Br.

(431) A compound according to any one of (1) to (429), wherein —$R^{5C}$, if present, is independently —F or —Cl.

(432) A compound according to any one of (1) to (429), wherein —$R^{5C}$, if present, is —F.

(433) A compound according to any one of (1) to (429), wherein —$R^{5C}$, if present, is —Cl.

(434) A compound according to any one of (1) to (429), wherein —$R^{5C}$, if present, is —Br.

(435) A compound according to any one of (1) to (429), wherein —$R^{5C}$, if present, is —I.

The Group —$R^{5E}$ (436) A compound according to any one of (1) to (435), wherein —$R^{5E}$, if present, is independently —C≡CH or $C_{3-4}$alkynyl optionally substituted with one or more groups —$R^{EE}$; wherein each —$R^{EE}$ is independently selected from —OH, —$OR^{EEE}$, —$NH_2$, —$NHR^{EEE}$, and —$NR^{EEE}_2$; wherein each —$R^{EEE}$ is linear or branched saturated $C_{1-4}$alkyl.

(437) A compound according to any one of (1) to (435), wherein —$R^{5E}$, if present, is —C≡CH.

(438) A compound according to any one of (1) to (435), wherein —$R^{5E}$, if present, is $C_{3-4}$alkynyl optionally substituted with one or more groups —$R^{EE}$; wherein each —$R^{EE}$ is independently selected from —OH, —$OR^{EEE}$, —$NH_2$, —$NHR^{EEE}$, and —$NR^{EEE}_2$; wherein each —$R^{EEE}$ is linear or branched saturated $C_{1-4}$alkyl.

(439) A compound according to any one of (1) to (435), wherein —$R^{5E}$, if present, is independently —C≡CH, —C≡CH—$CH_3$, —C≡CH—$CH_2R^{EE}$, —C≡CH—$CH_2CH_3$ or —C≡CH—$CH_2CH_2R^{EE}$; wherein each —$R^{EE}$ is independently selected from —OH, —$OR^{EEE}$, —$NH_2$, —$NHR^{EEE}$, and —$NR^{EEE}_2$; wherein each —$R^{EEE}$ is linear or branched saturated $C_{1-4}$alkyl.

(440) A compound according to any one of (1) to (435), wherein —$R^{5E}$, if present, is independently —C≡CH—$CH_3$ or —C≡CH—$CH_2R^{EE}$; wherein each —$R^{EE}$ is independently selected from —OH, —$OR^{EEE}$, —$NH_2$, —$NHR^{EEE}$, and —$NR^{EEE}_2$; wherein each —$R^{EEE}$ is linear or branched saturated $C_{1-4}$alkyl.

(441) A compound according to any one of (1) to (435), wherein —$R^{5E}$, if present, is independently —C≡CH—$CH_2CH_3$ or —C≡CH—$CH_2CH_2R^{EE}$; wherein each —$R^{EE}$ is independently selected from —OH, —$OR^{EEE}$, —$NH_2$, —$NHR^{EEE}$, and —$NR^{EEE}_2$; wherein each —$R^{EEE}$ is linear or branched saturated $C_{1-4}$alkyl.

The Group —$R^{EE}$ (442) A compound according to any one of (1) to (441), wherein —$R^{EE}$, if present, is independently —OH or —$OR^{EEE}$.

(443) A compound according to any one of (1) to (441), wherein —$R^{EE}$, if present, is independently —$NH_2$, —$NHR^{EEE}$, or —$NR^{EEE}_2$.

The Group —$R^{EEE}$ (444) A compound according to any one of (1) to (443), wherein each —$R^{EEE}$, if present, is independently -Me, -Et, -nPr, -iPr, -nBu, -iBu, or -tBu.

(445) A compound according to any one of (1) to (443), wherein each —$R^{EEE}$, if present, is independently -Me, -Et, -nPr, or -iPr.

(446) A compound according to any one of (1) to (443), wherein each —$R^{EEE}$, if present, is independently -Me or -Et.

(447) A compound according to any one of (1) to (443), wherein each —$R^{EEE}$, if present, is -Me.

The Group —$R^6$ (448) A compound according to any one of (1) to (447), wherein —$R^6$ is —H.

(449) A compound according to any one of (1) to (447), wherein —$R^6$ is —F.

The Group —$R^7$ (450) A compound according to any one of (1) to (449), wherein —$R^7$ is —H.

(451) A compound according to any one of (1) to (449), wherein —$R^7$ is —F.

The Group —$R^8$ (452) A compound according to any one of (1) to (451), wherein —$R^8$ is —H.

(453) A compound according to any one of (1) to (451), wherein —$R^8$ is —F.

Specific Compounds (454) A compound according to (1), selected from compounds of the following formulae and pharmaceutically acceptable salts, N-oxides, hydrates, and solvates thereof:

| Pat. Code | Structure |
|---|---|
| IQ-001 | 5-methyl-3-(4-(dimethylamino)phenyl)isoquinolin-1(2H)-one |
| IQ-002 | 5-chloro-3-(6-(4-methylpiperazin-1-yl)pyridin-3-yl)isoquinolin-1(2H)-one |
| IQ-003 | 5-methyl-3-(6-(4-methylpiperazin-1-yl)pyridin-3-yl)isoquinolin-1(2H)-one |
| IQ-004 | 3-(6-(4-cyclopropylpiperazin-1-yl)pyridin-3-yl)-5-methylisoquinolin-1(2H)-one |
| IQ-005 | 3-(6-(4-acetylpiperazin-1-yl)pyridin-3-yl)-5-methylisoquinolin-1(2H)-one |
| IQ-006 | 3-(6-(4-(dimethylamino)piperidin-1-yl)pyridin-3-yl)-5-methylisoquinolin-1(2H)-one |
| IQ-007 | 5-chloro-3-(6-(4-(dimethylamino)piperidin-1-yl)pyridin-3-yl)isoquinolin-1(2H)-one |
| IQ-008 | 3-(6-(3-(dimethylamino)pyrrolidin-1-yl)pyridin-3-yl)-5-methylisoquinolin-1(2H)-one |
| IQ-009 | 5-chloro-3-(6-(3-(dimethylamino)pyrrolidin-1-yl)pyridin-3-yl)isoquinolin-1(2H)-one |
| IQ-010 | tert-butyl 4-(4-(5-chloro-1-oxo-1,2-dihydroisoquinolin-3-yl)phenyl)piperazine-1-carboxylate |

| Pat. Code | Structure |
|---|---|
| IQ-011 | 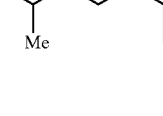 |
| IQ-012 | |
| IQ-013 | |
| IQ-014 | |
| IQ-015 | |
| Pat. Code | Structure |
|---|---|
| IQ-016 | 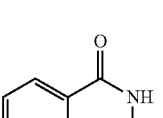 |
| IQ-017 | |
| IQ-018 | |
| IQ-019 | |
| IQ-020 | |

| Pat. Code | Structure |
|---|---|
| IQ-021 | 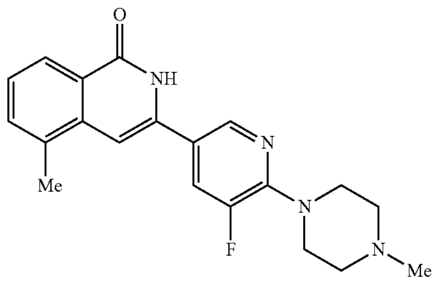 [SMILES: Cc1cccc2c(=O)[nH]c(-c3cnc(N4CCN(C)CC4)c(F)c3)cc12] |
| IQ-022 | 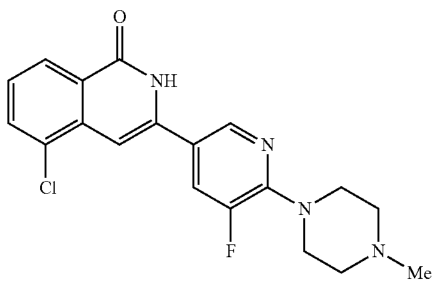 [SMILES: CN1CCN(c2ncc(-c3cc4c(Cl)cccc4c(=O)[nH]3)cc2F)CC1] |
| IQ-023 | 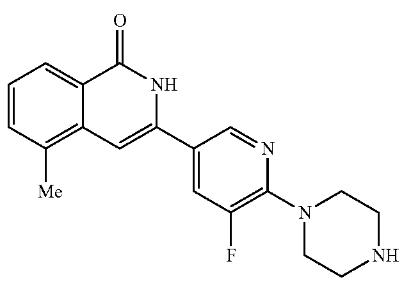 [SMILES: Cc1cccc2c(=O)[nH]c(-c3cnc(N4CCNCC4)c(F)c3)cc12] |
| IQ-024 | 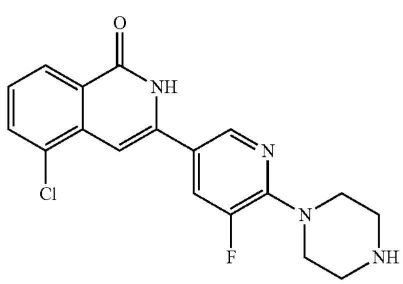 [SMILES: O=c1[nH]c(-c2cnc(N3CCNCC3)c(F)c2)cc2c(Cl)cccc12] |
| IQ-025 | 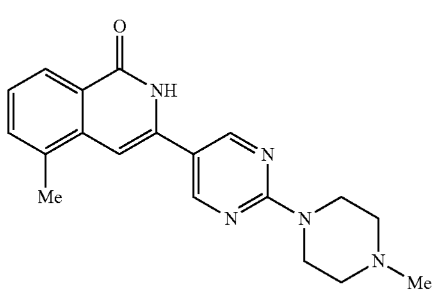 [SMILES: Cc1cccc2c(=O)[nH]c(-c3cnc(N4CCN(C)CC4)nc3)cc12] |
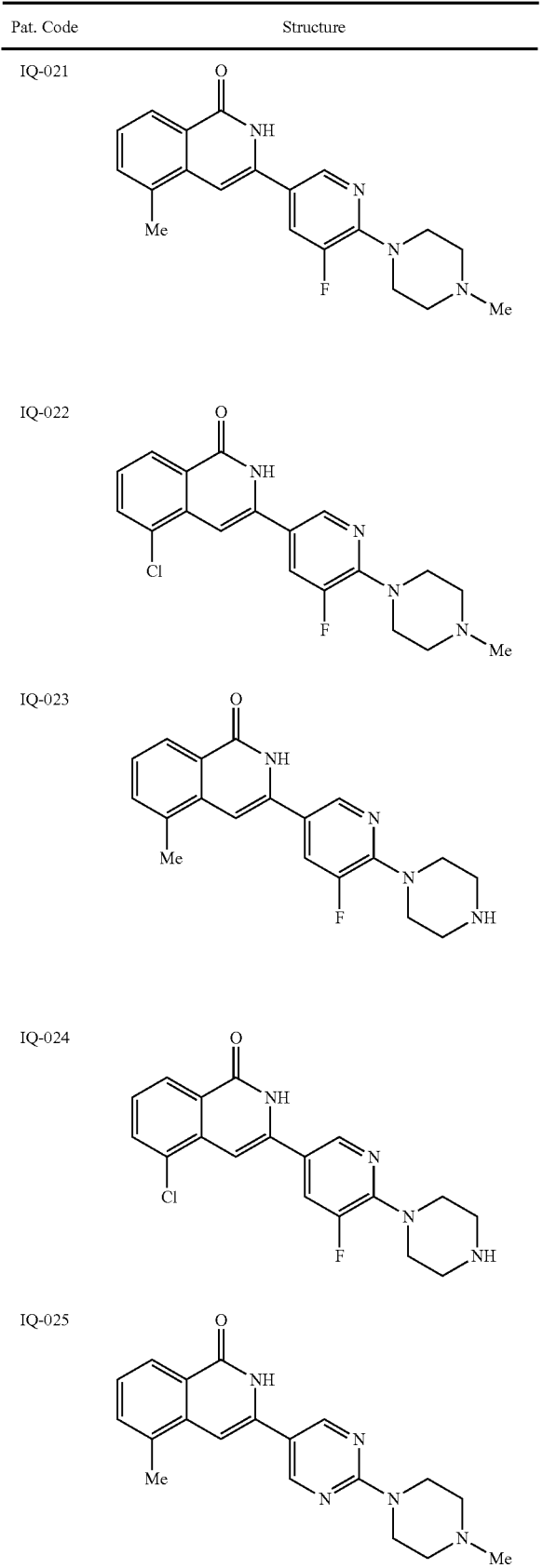
| Pat. Code | Structure |
|---|---|
| IQ-026 | 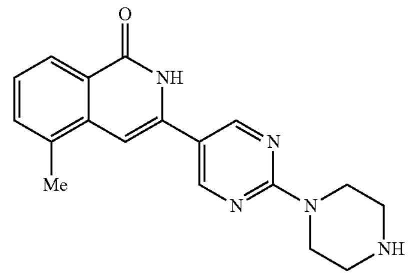 [SMILES: Cc1cccc2c(=O)[nH]c(-c3cnc(N4CCNCC4)nc3)cc12] |
| IQ-027 | 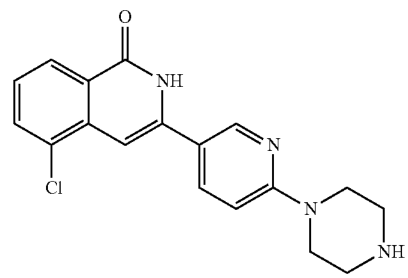 [SMILES: O=c1[nH]c(-c2ccc(N3CCNCC3)nc2)cc2c(Cl)cccc12] |
| IQ-028 | 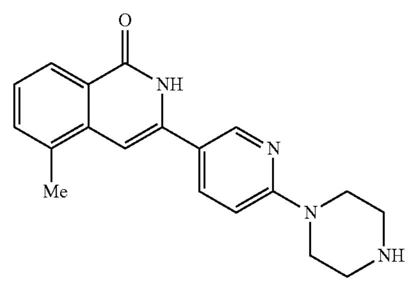 [SMILES: Cc1cccc2c(=O)[nH]c(-c3ccc(N4CCNCC4)nc3)cc12] |
| IQ-029 | 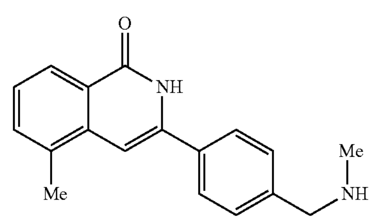 [SMILES: CNCc1ccc(-c2cc3c(C)cccc3c(=O)[nH]2)cc1] |
| IQ-030 | 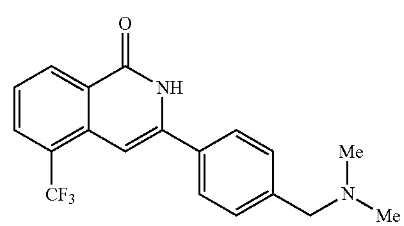 |
| IQ-031 | 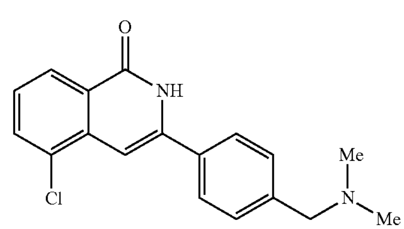 [SMILES: CN(C)Cc1ccc(-c2cc3c(Cl)cccc3c(=O)[nH]2)cc1] |
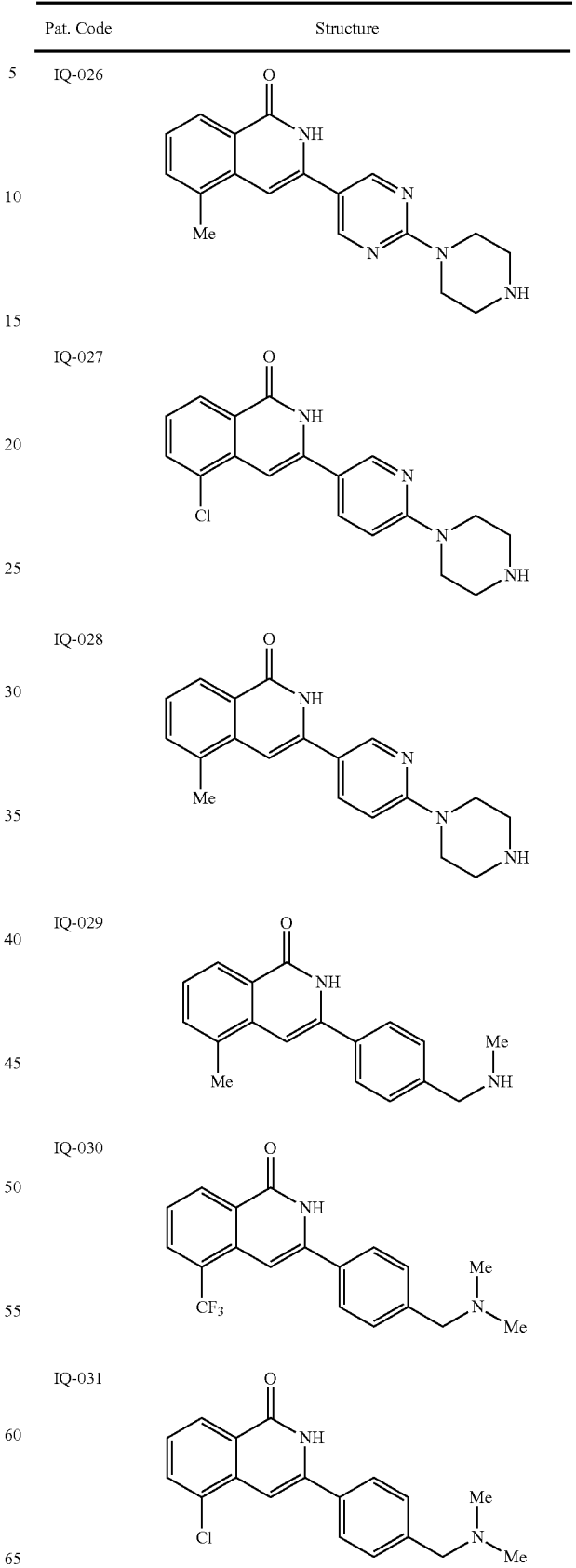

-continued
| Pat. Code | Structure |
|---|---|
| IQ-032 | 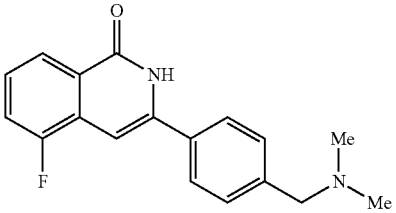 [SMILES: CN(C)Cc1ccc(-c2cc3c(F)cccc3c(=O)[nH]2)cc1] |
| IQ-033 | 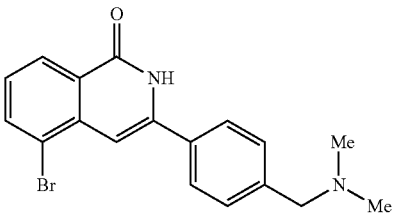 [SMILES: CN(C)Cc1ccc(-c2cc3c(Br)cccc3c(=O)[nH]2)cc1] |
| IQ-034 | 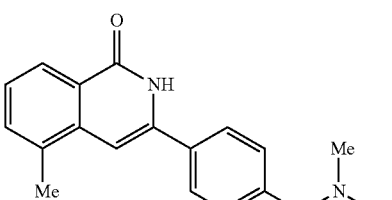 |
| IQ-035 | 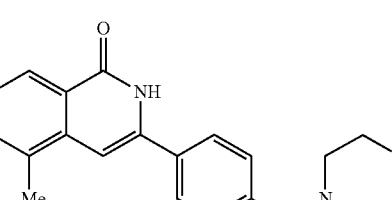 |
| IQ-036 | 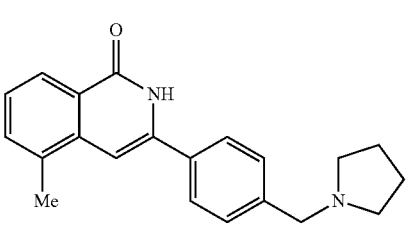 [SMILES: Cc1cccc2c(=O)[nH]c(-c3ccc(CN4CCCC4)cc3)cc12] |
| IQ-037 | 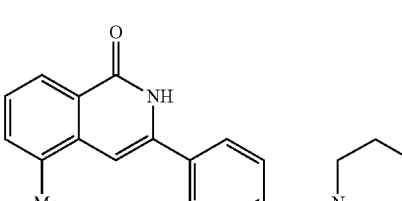 |
| IQ-038 | 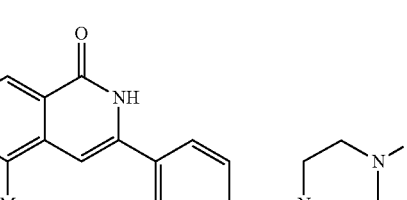 |
-continued
| Pat. Code | Structure |
|---|---|
| IQ-039 | 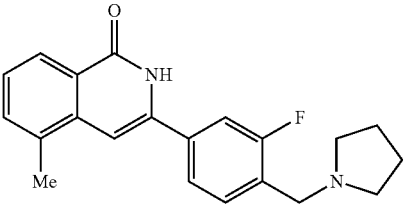 [SMILES: Cc1cccc2c(=O)[nH]c(-c3ccc(CN4CCCC4)c(F)c3)cc12] |
| IQ-040 | 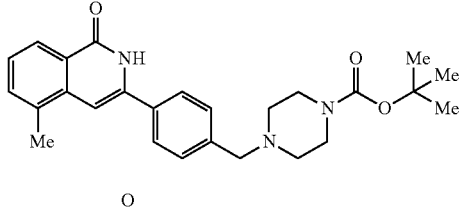 |
| IQ-041 | 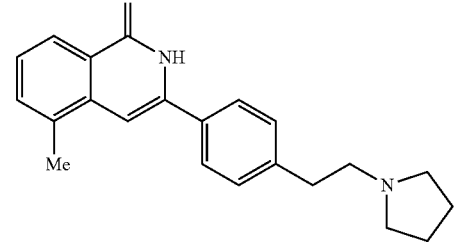 |
| IQ-042 | 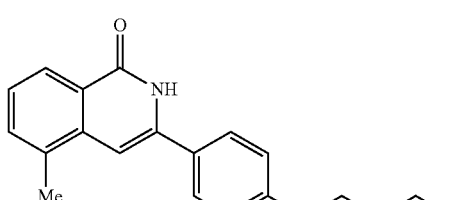 |
| IQ-043 | 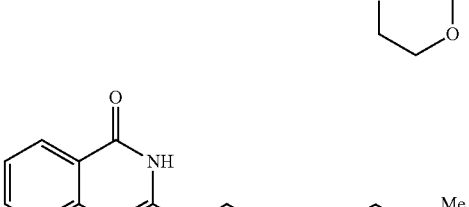 |
| IQ-044 | 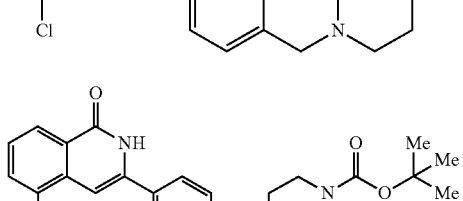 |
| IQ-045 | 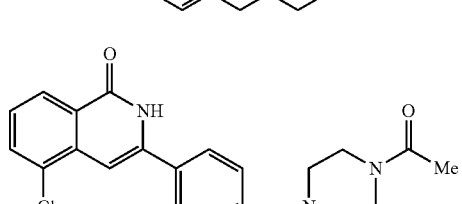 |

| Pat. Code | Structure |
|---|---|
| IQ-046 | 5-cyclopropyl-3-[4-((4-methylpiperazin-1-yl)methyl)phenyl]isoquinolin-1(2H)-one |
| IQ-047 | tert-butyl 4-(4-(5-cyclopropyl-1-oxo-1,2-dihydroisoquinolin-3-yl)benzyl)piperazine-1-carboxylate |
| IQ-048 | 5-methyl-3-(4-(1-(4-methylpiperazin-1-yl)ethyl)phenyl)isoquinolin-1(2H)-one |
| IQ-049 | 5-cyclopropyl-3-(4-(piperazin-1-ylmethyl)phenyl)isoquinolin-1(2H)-one |
| IQ-050 | 3-(4-((4-cyclopropylpiperazin-1-yl)methyl)phenyl)-5-methylisoquinolin-1(2H)-one |
| IQ-051 | 5-methyl-3-(4-((2-methylpiperazin-1-yl)methyl)phenyl)isoquinolin-1(2H)-one |
| IQ-052 | 3-(4-((2,4-dimethylpiperazin-1-yl)methyl)phenyl)-5-methylisoquinolin-1(2H)-one |
| IQ-053 | 3-(4-((4-(dimethylamino)piperidin-1-yl)methyl)phenyl)-5-methylisoquinolin-1(2H)-one |
| IQ-054 | 5-methyl-3-(4-((4-methyl-3-oxopiperazin-1-yl)methyl)phenyl)isoquinolin-1(2H)-one |
| IQ-055 | 3-(4-((4-acetylpiperazin-1-yl)methyl)phenyl)-5-methylisoquinolin-1(2H)-one |
| IQ-056 | 5-chloro-3-(4-((4-methyl-3-oxopiperazin-1-yl)methyl)phenyl)isoquinolin-1(2H)-one |
| IQ-057 | 5-methyl-3-(6-((4-methylpiperazin-1-yl)methyl)pyridin-3-yl)isoquinolin-1(2H)-one |
| IQ-058 | tert-butyl 4-(2-fluoro-4-(5-methyl-1-oxo-1,2-dihydroisoquinolin-3-yl)benzyl)piperazine-1-carboxylate |
| IQ-059 | 3-(3-fluoro-4-(piperazin-1-ylmethyl)phenyl)-5-methylisoquinolin-1(2H)-one |

| Pat. Code | Structure |
|---|---|
| IQ-060 | 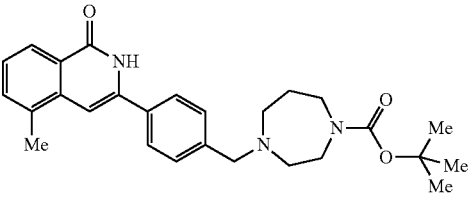 [SMILES: Cc1cccc2c(=O)[nH]c(-c3ccc(CN4CCCN(C(=O)OC(C)(C)C)CC4)cc3)cc12] |
| IQ-061 | 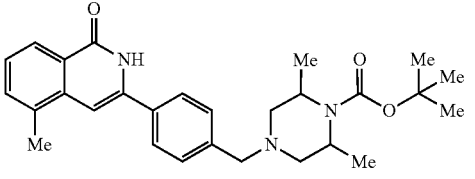 [SMILES: Cc1cccc2c(=O)[nH]c(-c3ccc(CN4CC(C)N(C(=O)OC(C)(C)C)C(C)C4)cc3)cc12] |
| IQ-062 | 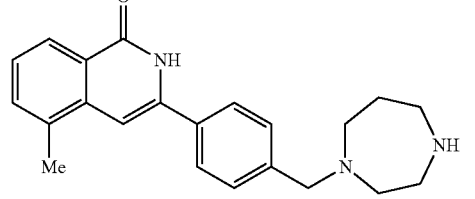 |
| IQ-063 | 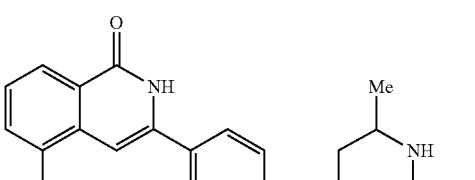 |
| IQ-064 | 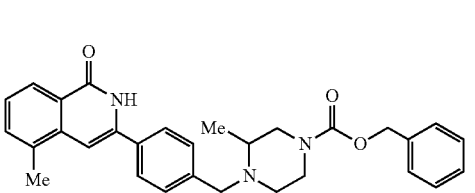 |
| IQ-065 | 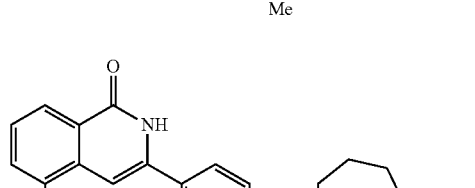 |
| IQ-066 | 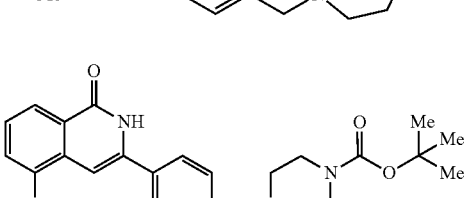 |
| IQ-067 | 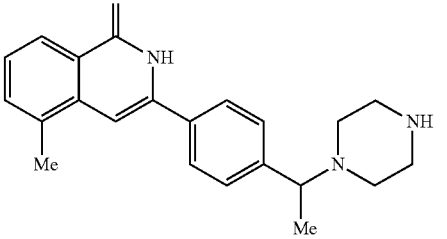 |
| IQ-068 | 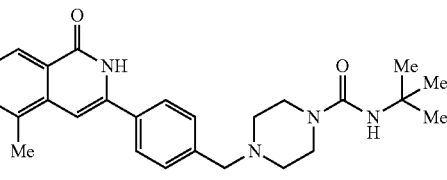 |
| IQ-069 | 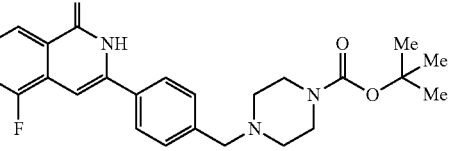 |
| IQ-070 | 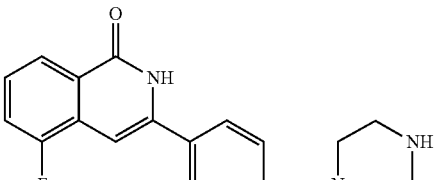 |
| IQ-071 | 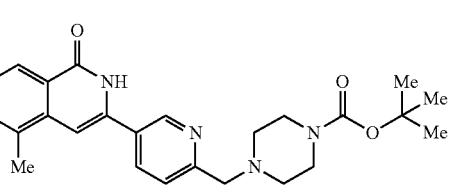 |
| IQ-072 | 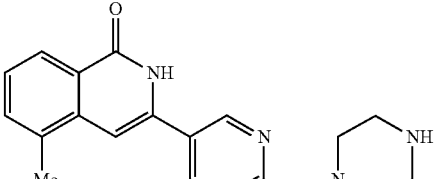 |
| IQ-073 | 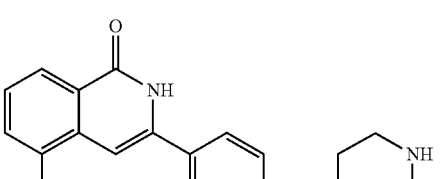 |

| Pat. Code | Structure |
|---|---|
| IQ-074 | 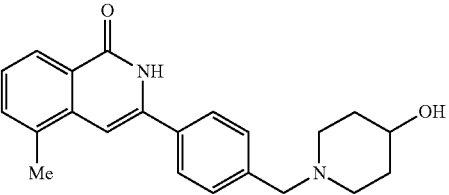 [SMILES: Cc1cccc2c(=O)[nH]c(-c3ccc(CN4CCC(O)CC4)cc3)cc12] |
| IQ-075 | 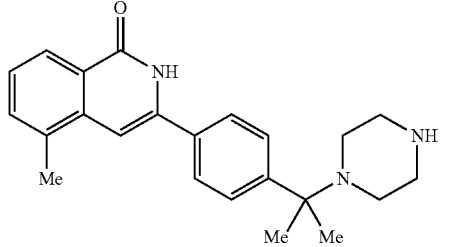 [SMILES: Cc1cccc2c(=O)[nH]c(-c3ccc(C(C)(C)N4CCNCC4)cc3)cc12] |
| IQ-076 | 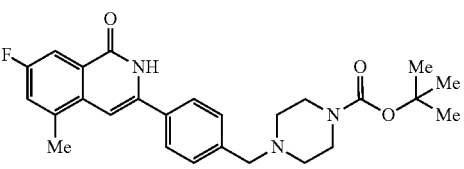 [SMILES: Cc1cc(F)cc2c(=O)[nH]c(-c3ccc(CN4CCN(C(=O)OC(C)(C)C)CC4)cc3)cc12] |
| IQ-077 | 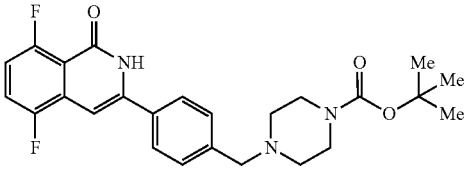 [SMILES: CC(C)(C)OC(=O)N1CCN(Cc2ccc(-c3cc4c(F)ccc(F)c4c(=O)[nH]3)cc2)CC1] |
| IQ-078 | 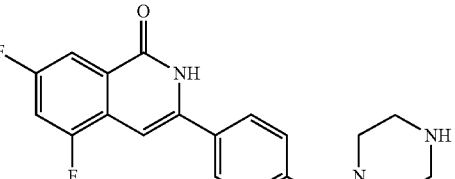 |
| IQ-079 | 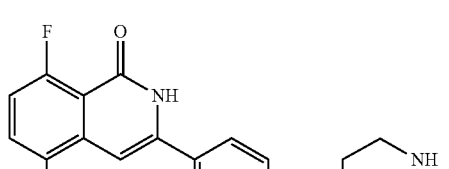 |
| IQ-080 | 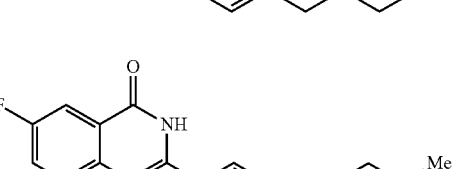 |
| Pat. Code | Structure |
|---|---|
| IQ-081 | 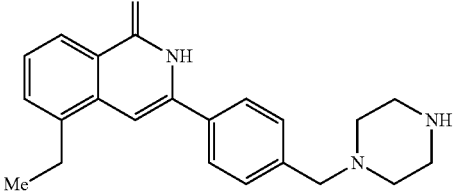 |
| IQ-082 | 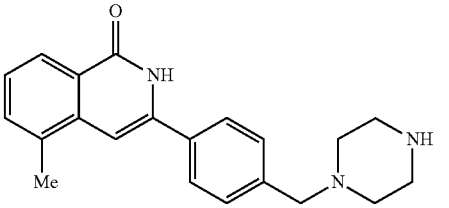 |
| IQ-083 | 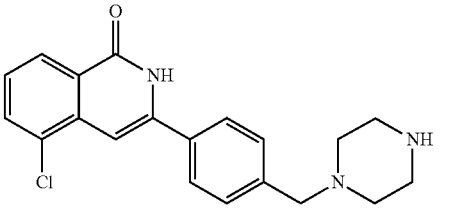 |
| IQ-084 | 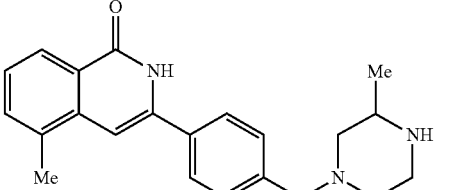 |
| IQ-085 | 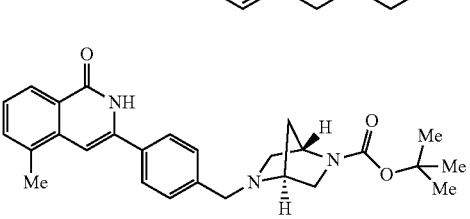 |
| IQ-086 | 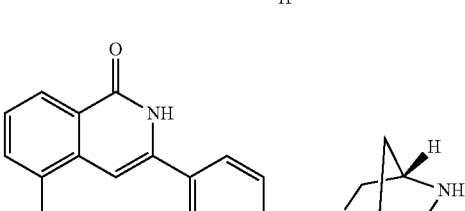 |
| IQ-087 | 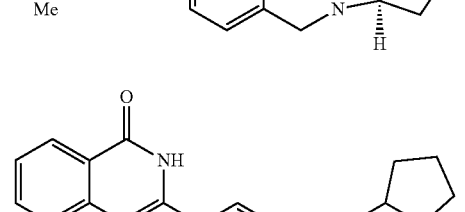 |

| Pat. Code | Structure |
|---|---|
| IQ-088 | 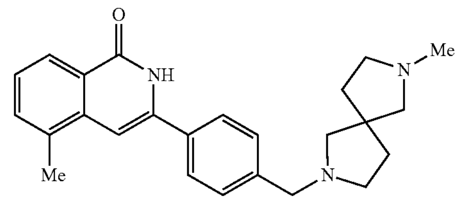 [SMILES: Cc1cccc2c(=O)[nH]c(-c3ccc(CN4CCC5(CCN(C)C5)C4)cc3)cc12] |
| IQ-089 | 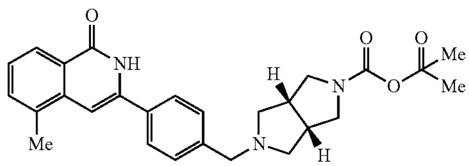 |
| IQ-090 | 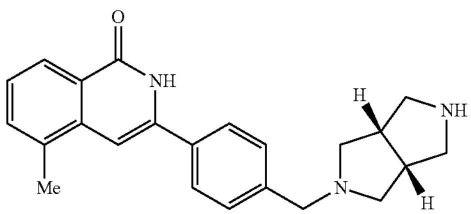 [SMILES: Cc1cccc2c(=O)[nH]c(-c3ccc(CN4C[C@H]5CNC[C@H]5C4)cc3)cc12] |
| IQ-091 | 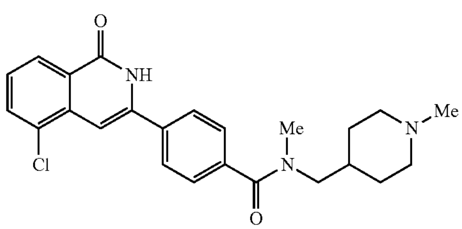 [SMILES: CN1CCC(CN(C)C(=O)c2ccc(-c3cc4c(Cl)cccc4c(=O)[nH]3)cc2)CC1] |
| IQ-092 | 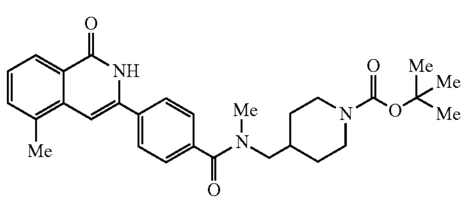 [SMILES: Cc1cccc2c(=O)[nH]c(-c3ccc(C(=O)N(C)CC4CCN(C(=O)OC(C)(C)C)CC4)cc3)cc12] |
| IQ-093 | 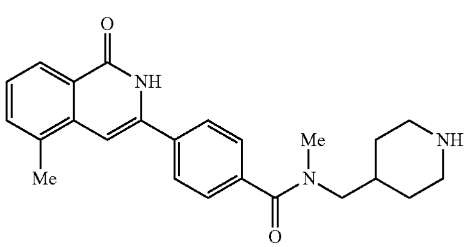 [SMILES: Cc1cccc2c(=O)[nH]c(-c3ccc(C(=O)N(C)CC4CCNCC4)cc3)cc12] |
| IQ-094 | 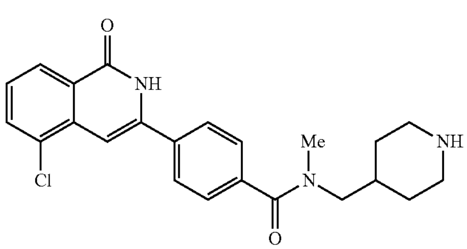 [SMILES: CN(CC1CCNCC1)C(=O)c1ccc(-c2cc3c(Cl)cccc3c(=O)[nH]2)cc1] |

| Pat. Code | Structure |
|---|---|
| IQ-095 | 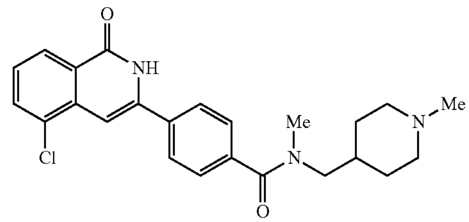 [SMILES: CN1CCC(CN(C)C(=O)c2ccc(-c3cc4c(Cl)cccc4c(=O)[nH]3)cc2)CC1] |
| IQ-096 | 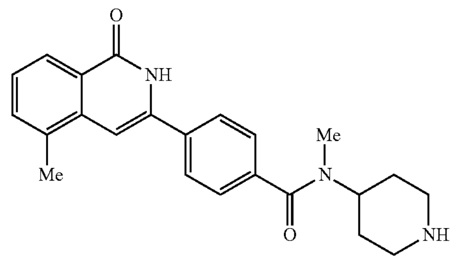 [SMILES: Cc1cccc2c(=O)[nH]c(-c3ccc(C(=O)N(C)C4CCNCC4)cc3)cc12] |
| IQ-097 | 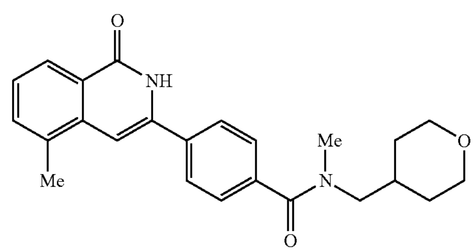 [SMILES: Cc1cccc2c(=O)[nH]c(-c3ccc(C(=O)N(C)CC4CCOCC4)cc3)cc12] |
| IQ-098 | 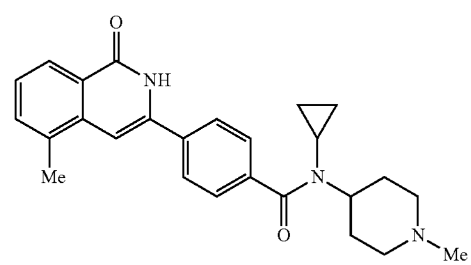 [SMILES: Cc1cccc2c(=O)[nH]c(-c3ccc(C(=O)N(C4CC4)C4CCN(C)CC4)cc3)cc12] |
| IQ-099 | 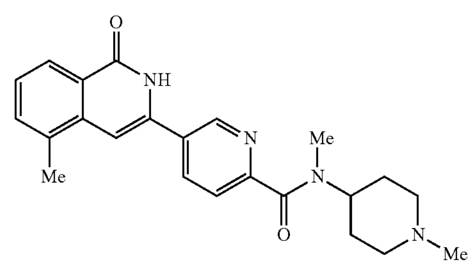 [SMILES: Cc1cccc2c(=O)[nH]c(-c3ccc(C(=O)N(C)C4CCN(C)CC4)nc3)cc12] |
| IQ-100 | 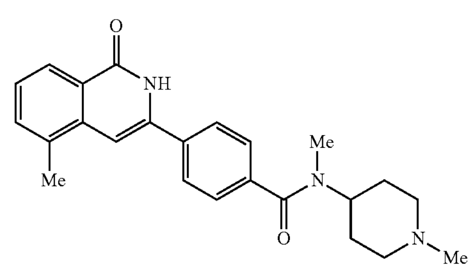 [SMILES: Cc1cccc2c(=O)[nH]c(-c3ccc(C(=O)N(C)C4CCN(C)CC4)cc3)cc12] |

| Pat. Code | Structure |
|---|---|
| IQ-101 | 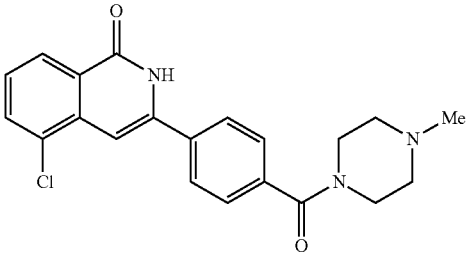 [SMILES: CN1CCN(C(=O)c2ccc(-c3cc4c(Cl)cccc4c(=O)[nH]3)cc2)CC1] |
| IQ-102 | 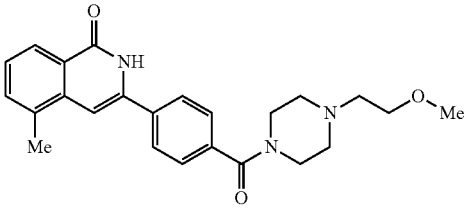 [SMILES: COCCN1CCN(C(=O)c2ccc(-c3cc4c(C)cccc4c(=O)[nH]3)cc2)CC1] |
| IQ-103 | 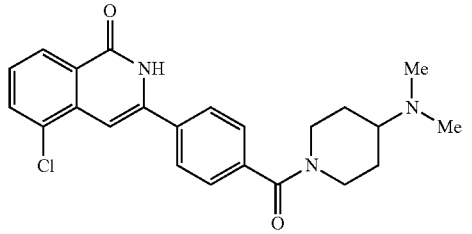 [SMILES: CN(C)C1CCN(C(=O)c2ccc(-c3cc4c(Cl)cccc4c(=O)[nH]3)cc2)CC1] |
| IQ-104 | 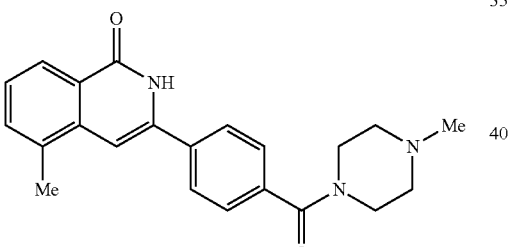 |
| IQ-105 | 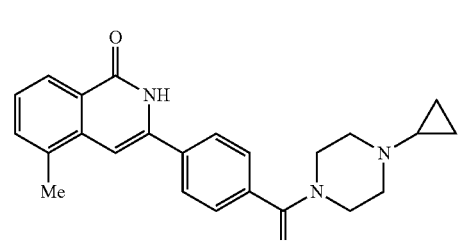 |
| IQ-106 | 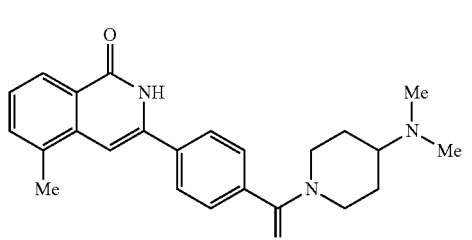 |
| IQ-107 | 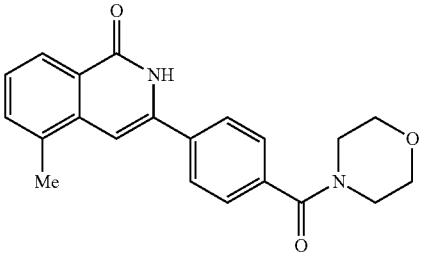 [SMILES: Cc1cccc2c(=O)[nH]c(-c3ccc(C(=O)N4CCOCC4)cc3)cc12] |
| IQ-108 | 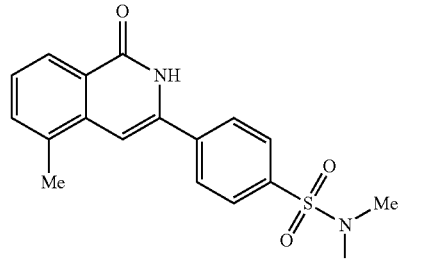 |
| IQ-109 | 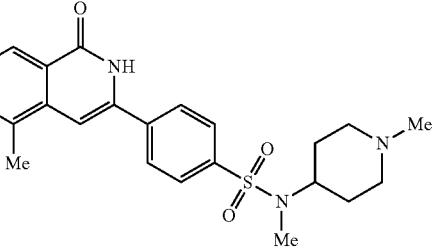 |
| IQ-110 | 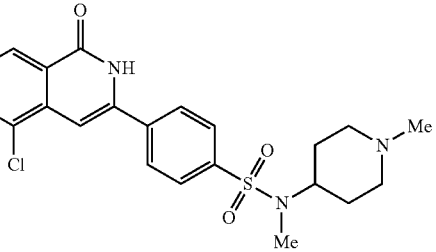 |
| IQ-111 | 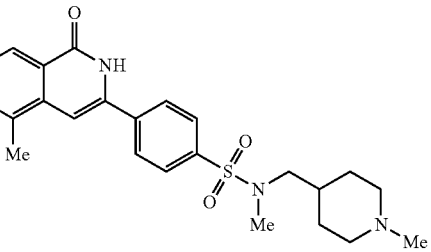 |
| IQ-112 | 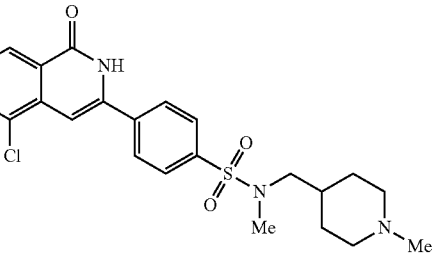 |

| Pat. Code | Structure |
|---|---|
| IQ-113 | 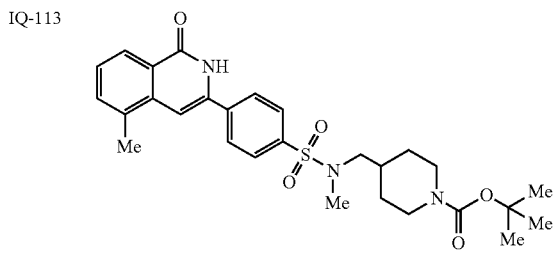 |
| IQ-114 | 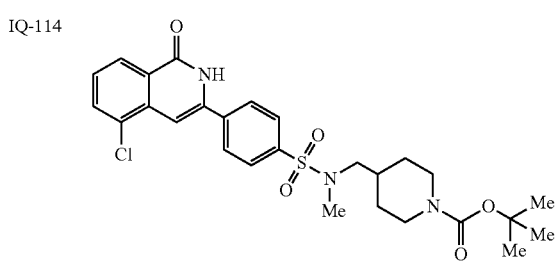 |
| IQ-115 | 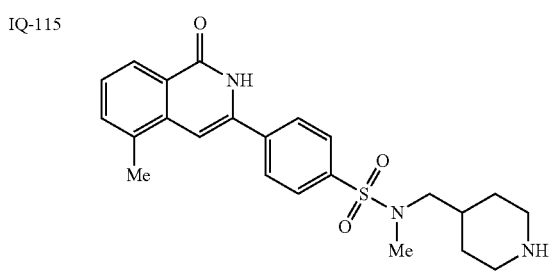 |
| IQ-116 | 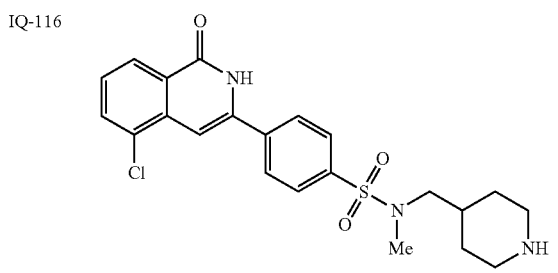 |
| IQ-117 | 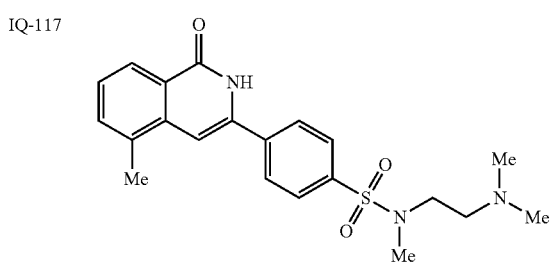 |
| IQ-118 | 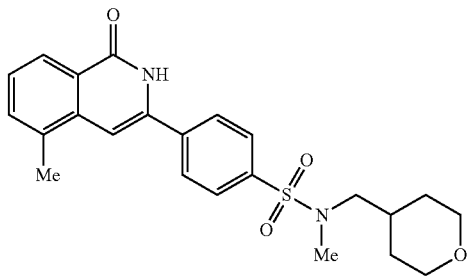 [SMILES: Cc1cccc2c(=O)[nH]c(-c3ccc(S(=O)(=O)N(C)CC4CCOCC4)cc3)cc12] |
| IQ-119 | 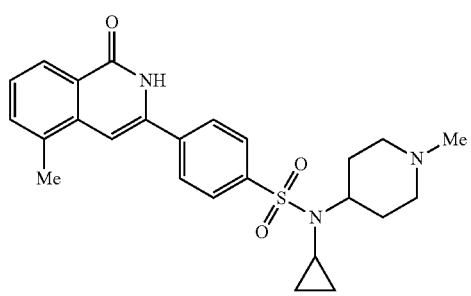 [SMILES: Cc1cccc2c(=O)[nH]c(-c3ccc(S(=O)(=O)N(C4CC4)C4CCN(C)CC4)cc3)cc12] |
| IQ-120 | 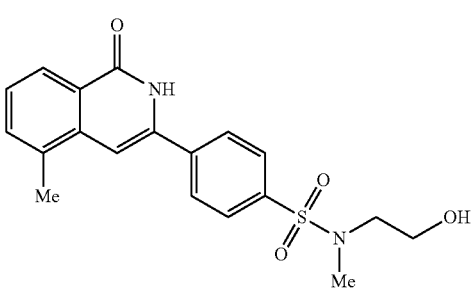 [SMILES: Cc1cccc2c(=O)[nH]c(-c3ccc(S(=O)(=O)N(C)CCO)cc3)cc12] |
| IQ-121 | 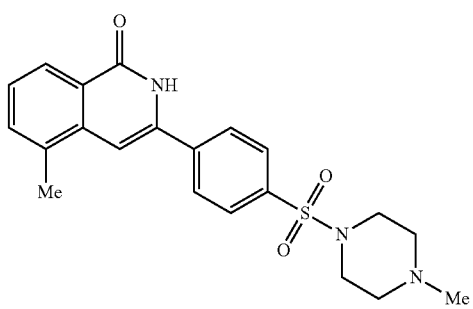 [SMILES: Cc1cccc2c(=O)[nH]c(-c3ccc(S(=O)(=O)N4CCN(C)CC4)cc3)cc12] |
| IQ-122 | 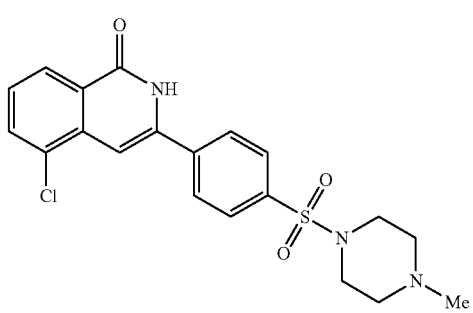 [SMILES: CN1CCN(S(=O)(=O)c2ccc(-c3cc4c(Cl)cccc4c(=O)[nH]3)cc2)CC1] |

| Pat. Code | Structure |
|---|---|
| IQ-123 | 5-Me isoquinolin-1(2H)-one, 3-[4-(piperazin-1-ylsulfonyl)phenyl] |
| IQ-124 | 5-Cl isoquinolin-1(2H)-one, 3-[4-(piperazin-1-ylsulfonyl)phenyl] |
| IQ-125 | 5-Me isoquinolin-1(2H)-one, 3-{4-[(4-(dimethylamino)piperidin-1-yl)sulfonyl]phenyl} |
| IQ-126 | 5-Cl isoquinolin-1(2H)-one, 3-{4-[(4-(dimethylamino)piperidin-1-yl)sulfonyl]phenyl} |
| IQ-127 | 5-Me isoquinolin-1(2H)-one, 3-{4-[2-(methylamino)ethoxy]phenyl} |

| Pat. Code | Structure |
|---|---|
| IQ-128 | 5-Cl isoquinolin-1(2H)-one, 3-{4-[2-(dimethylamino)ethoxy]phenyl} |
| IQ-129 | 5-F isoquinolin-1(2H)-one, 3-{4-[2-(dimethylamino)ethoxy]phenyl} |
| IQ-130 | 5-Me isoquinolin-1(2H)-one, 3-{4-[2-(dimethylamino)ethoxy]phenyl} |
| IQ-131 | 5-CF₃ isoquinolin-1(2H)-one, 3-{4-[2-(dimethylamino)ethoxy]phenyl} |
| IQ-132 | 5-Br isoquinolin-1(2H)-one, 3-{4-[2-(dimethylamino)ethoxy]phenyl} |
| IQ-133 | 5-Me isoquinolin-1(2H)-one, 3-{4-[2-(morpholin-4-yl)ethoxy]phenyl} |
| IQ-134 | 5-Me isoquinolin-1(2H)-one, 3-{4-[2-(pyrrolidin-1-yl)ethoxy]phenyl} |

| Pat. Code | Structure |
|---|---|
| IQ-135 | 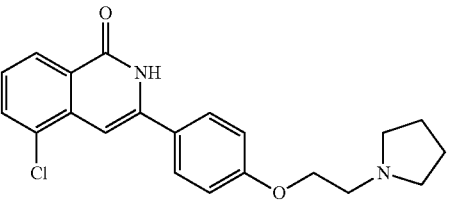 [SMILES: O=c1[nH]c(-c2ccc(OCCN3CCCC3)cc2)cc2c(Cl)cccc12] |
| IQ-136 | 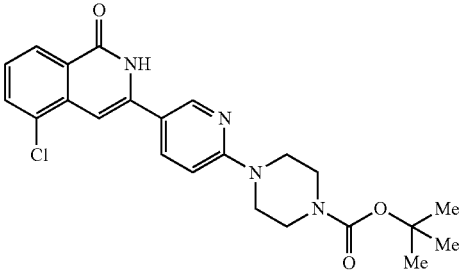 [SMILES: CC(C)(C)OC(=O)N1CCN(c2ccc(-c3cc4c(Cl)cccc4c(=O)[nH]3)cn2)CC1] |
| IQ-137 | 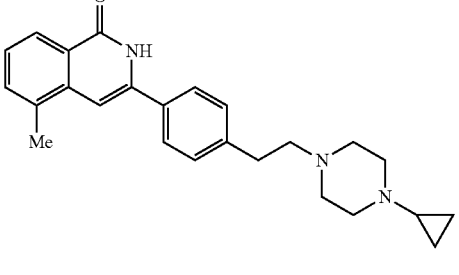 |
| IQ-138 | 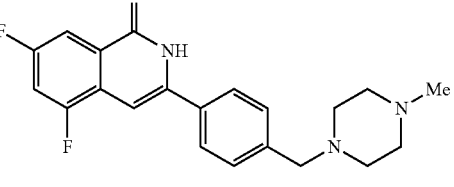 |
| IQ-139 | 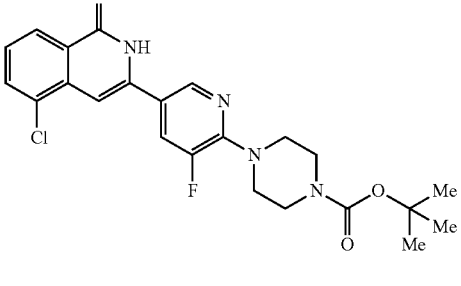 |
| IQ-140 | 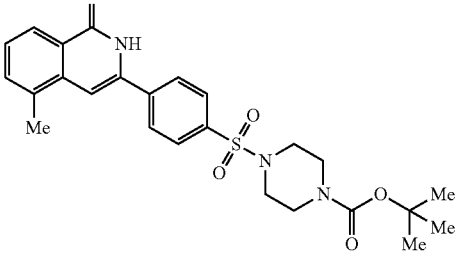 |
| Pat. Code | Structure |
|---|---|
| IQ-141 | 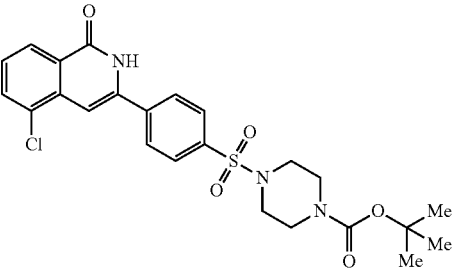 [SMILES: CC(C)(C)OC(=O)N1CCN(S(=O)(=O)c2ccc(-c3cc4c(Cl)cccc4c(=O)[nH]3)cc2)CC1] |
| IQ-142 | 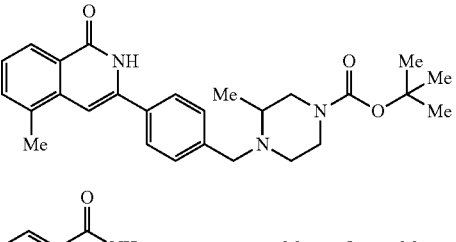 |
| IQ-143 | 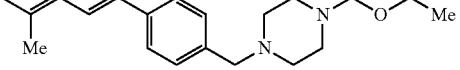 |
| IQ-144 | 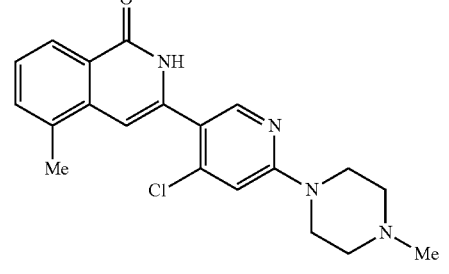 |
| IQ-145 | 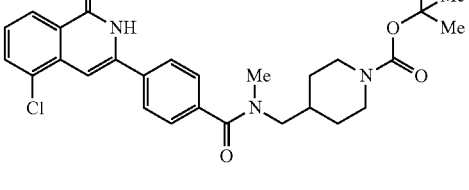 |
| IQ-146 | 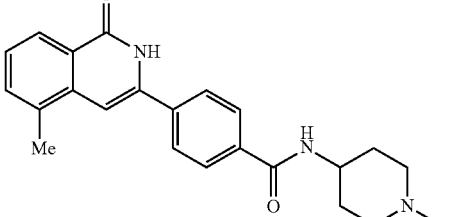 |
| IQ-147 | 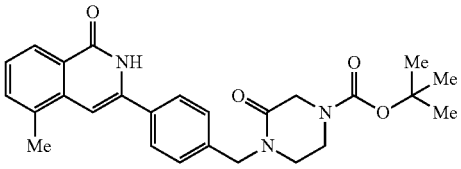 [SMILES: Cc1cccc2c(=O)[nH]c(-c3ccc(CN4CCN(C(=O)OC(C)(C)C)CC4=O)cc3)cc12] |

| Pat. Code | Structure |
|---|---|
| IQ-148 | 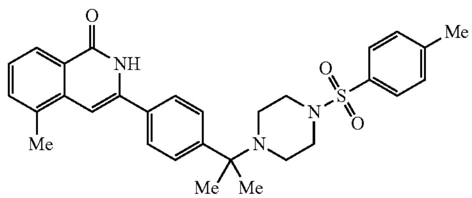 [SMILES: Cc1ccc(S(=O)(=O)N2CCN(C(C)(C)c3ccc(-c4cc5c(C)cccc5c(=O)[nH]4)cc3)CC2)cc1] |
| IQ-149 | 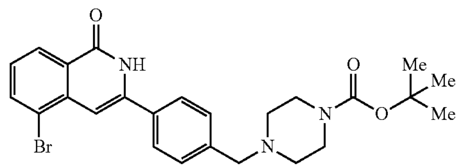 [SMILES: CC(C)(C)OC(=O)N1CCN(Cc2ccc(-c3cc4c(Br)cccc4c(=O)[nH]3)cc2)CC1] |
| IQ-150 | 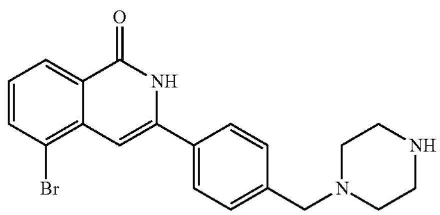 |
| IQ-151 | 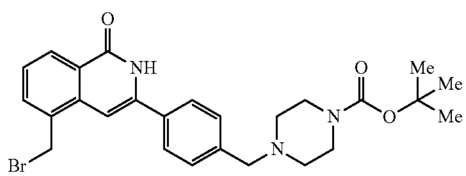 [SMILES: CC(C)(C)OC(=O)N1CCN(Cc2ccc(-c3cc4c(CBr)cccc4c(=O)[nH]3)cc2)CC1] |
| IQ-152 | 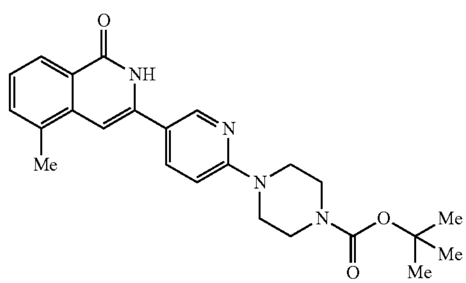 |
| IQ-153 | 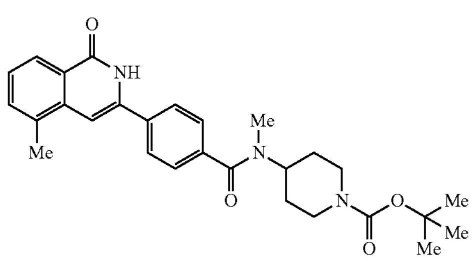 [SMILES: Cc1cccc2c(=O)[nH]c(-c3ccc(C(=O)N(C)C4CCN(C(=O)OC(C)(C)C)CC4)cc3)cc12] |
| IQ-154 | 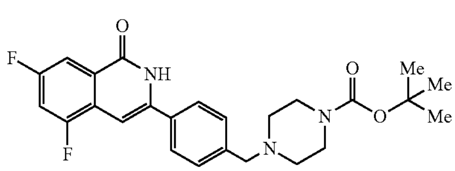 [SMILES: CC(C)(C)OC(=O)N1CCN(Cc2ccc(-c3cc4c(F)cc(F)cc4c(=O)[nH]3)cc2)CC1] |

| Pat. Code | Structure |
|---|---|
| IQ-155 | 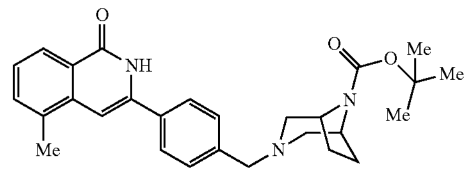 [SMILES: Cc1cccc2c(=O)[nH]c(-c3ccc(CN4CC5CCC(C4)N5C(=O)OC(C)(C)C)cc3)cc12] |
| IQ-156 | 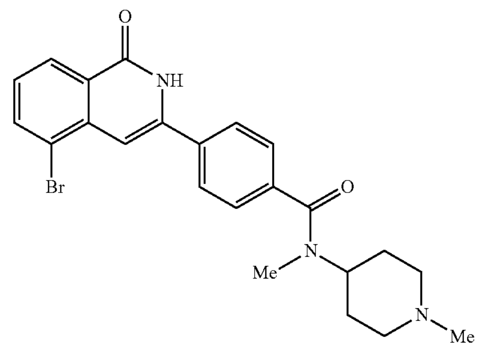 [SMILES: CN1CCC(N(C)C(=O)c2ccc(-c3cc4c(Br)cccc4c(=O)[nH]3)cc2)CC1] |
| IQ-157 | 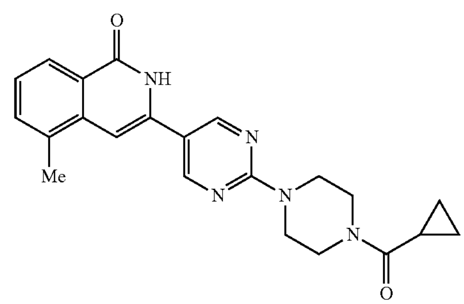 [SMILES: Cc1cccc2c(=O)[nH]c(-c3cnc(N4CCN(C(=O)C5CC5)CC4)nc3)cc12] |
| IQ-158 | 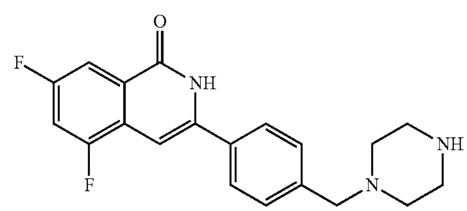 [SMILES: O=c1[nH]c(-c2ccc(CN3CCNCC3)cc2)cc2c(F)cc(F)cc12] |
| IQ-159 | 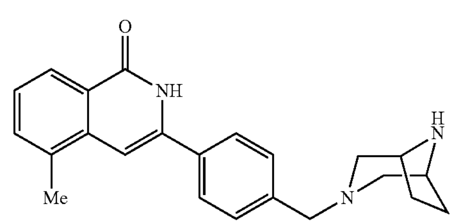 [SMILES: Cc1cccc2c(=O)[nH]c(-c3ccc(CN4CC5CCC(C4)N5)cc3)cc12] |

| Pat. Code | Structure |
|---|---|
| IQ-160 |  |
| IQ-161 | |
| IQ-162 | |
| IQ-163 | |
| IQ-164 | |
| IQ-165 | |
| Pat. Code | Structure |
|---|---|
| IQ-166 | 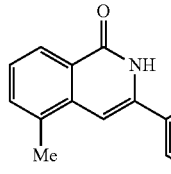 |
| IQ-167 | |
| IQ-168 | |
| IQ-169 | |
| IQ-170 | |
| IQ-171 | |

| Pat. Code | Structure |
|---|---|
| IQ-172 | 3-(4-((3-hydroxy-3-methylazetidin-1-yl)methyl)phenyl)-5-methylisoquinolin-1(2H)-one |
| IQ-173 | 3-(4-((3-(dimethylamino)pyrrolidin-1-yl)methyl)phenyl)-5-methylisoquinolin-1(2H)-one |
| IQ-174 | 3-(4-((3-(dimethylamino)azetidin-1-yl)methyl)phenyl)-5-methylisoquinolin-1(2H)-one |
| IQ-175 | 5-methyl-3-(4-(2-(4-methylpiperazin-1-yl)-2-oxoethyl)phenyl)isoquinolin-1(2H)-one |
| IQ-176 | 5-methyl-3-(4-(2-(methyl(1-methylpiperidin-4-yl)amino)-2-oxoethyl)phenyl)isoquinolin-1(2H)-one |
| IQ-177 | 5-methyl-3-(4-((3-(methylamino)azetidin-1-yl)methyl)phenyl)isoquinolin-1(2H)-one |
| IQ-178 | 7-fluoro-5-methyl-3-(4-((3-(methylamino)azetidin-1-yl)methyl)phenyl)isoquinolin-1(2H)-one |
| IQ-179 | 3-(4-((2-methyl-1H-benzo[d]imidazol-1-yl)methyl)phenyl)-5-methylisoquinolin-1(2H)-one |
| IQ-180 | 3-(4-((1H-imidazol-1-yl)methyl)phenyl)-5-methylisoquinolin-1(2H)-one |
| IQ-181 | 3-(4-((1H-benzo[d]imidazol-1-yl)methyl)phenyl)-5-methylisoquinolin-1(2H)-one |
| IQ-182 | 3-(4-((1H-pyrazol-1-yl)methyl)phenyl)-5-methylisoquinolin-1(2H)-one |
| IQ-183 | 3-(4-((1H-indol-1-yl)methyl)phenyl)-5-methylisoquinolin-1(2H)-one |
| IQ-184 | 3-(4-((1H-pyrrol-1-yl)methyl)phenyl)-5-methylisoquinolin-1(2H)-one |

| Pat. Code | Structure |
|---|---|
| IQ-185 | 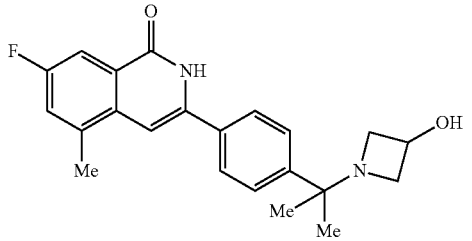 [SMILES: Cc1cc(F)cc2c(=O)[nH]c(-c3ccc(C(C)(C)N4CC(O)C4)cc3)cc12] |
| IQ-186 | 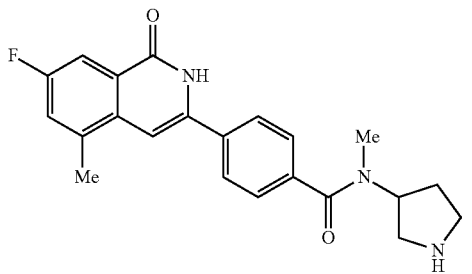 [SMILES: Cc1cc(F)cc2c(=O)[nH]c(-c3ccc(C(=O)N(C)C4CCNC4)cc3)cc12] |
| IQ-187 | 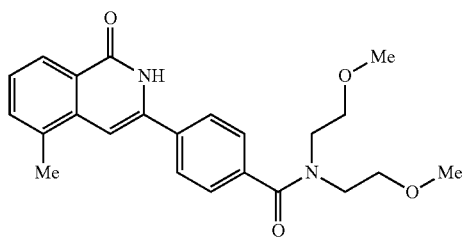 [SMILES: COCCN(CCOC)C(=O)c1ccc(-c2cc3c(C)cccc3c(=O)[nH]2)cc1] |
| IQ-188 | 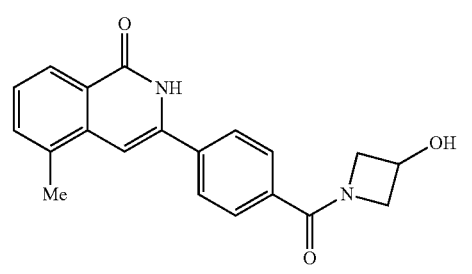 [SMILES: Cc1cccc2c(=O)[nH]c(-c3ccc(C(=O)N4CC(O)C4)cc3)cc12] |
| IQ-189 | 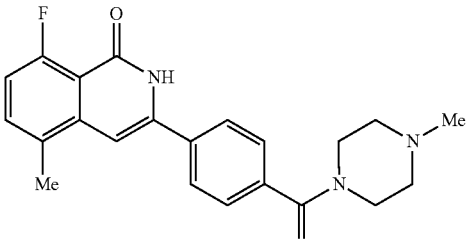 |
| IQ-190 | 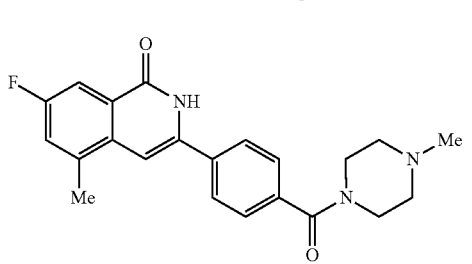 |
| IQ-191 | 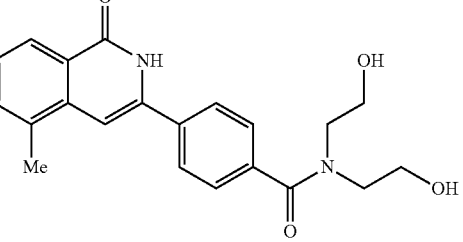 |
| IQ-192 | 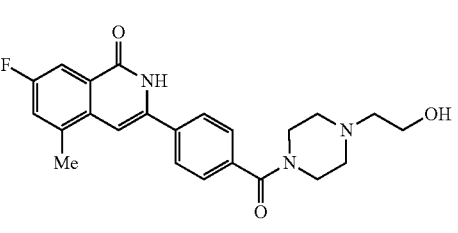 [SMILES: Cc1cc(F)cc2c(=O)[nH]c(-c3ccc(C(=O)N4CCN(CCO)CC4)cc3)cc12] |
| IQ-193 | 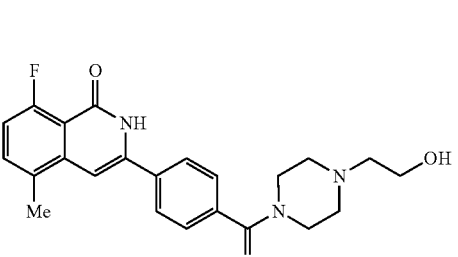 |
| IQ-194 | 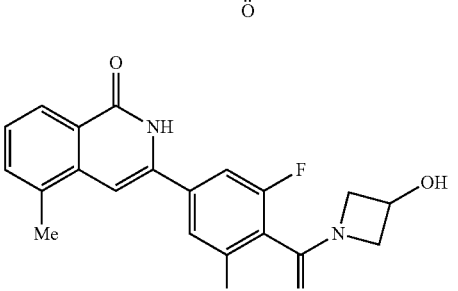 |
| IQ-195 | 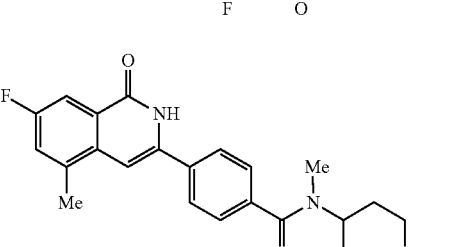 |
| IQ-196 | 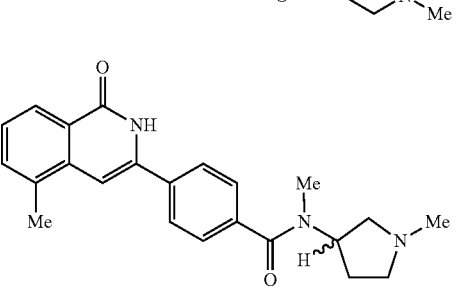 |

| Pat. Code | Structure |
|---|---|
| IQ-197 | 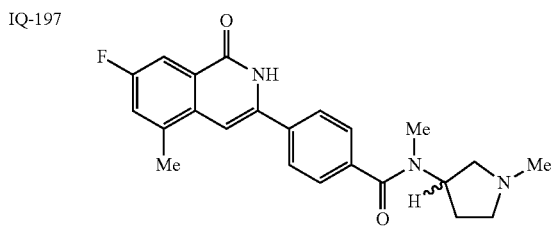 |
| IQ-198 | 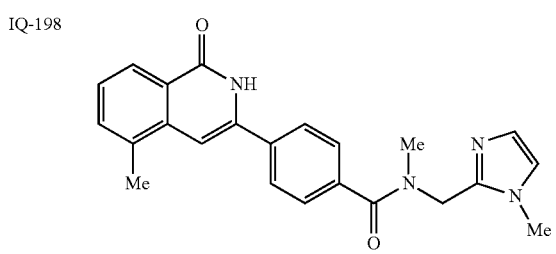 |
| IQ-199 | 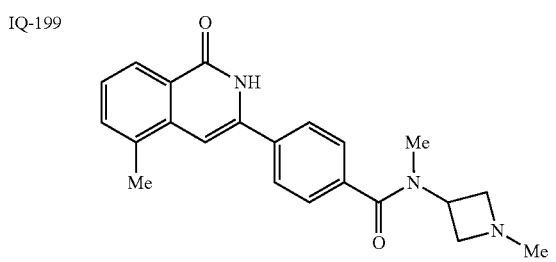 |
| IQ-200 | 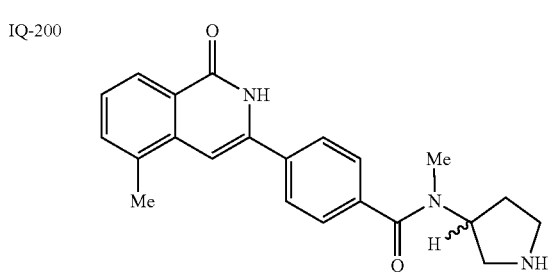 |
| IQ-201 | 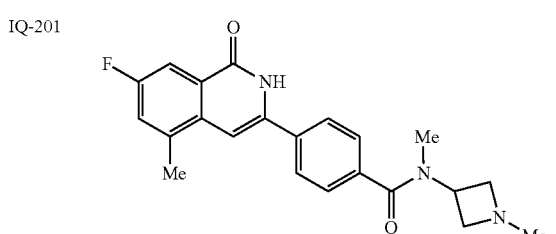 |
| IQ-202 | 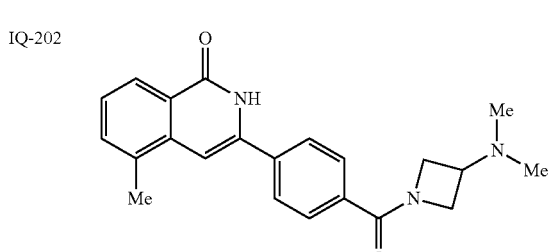 |
| Pat. Code | Structure |
|---|---|
| IQ-203 | 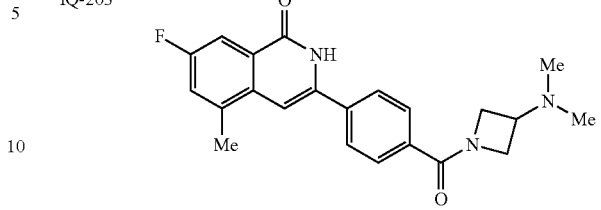 |
| IQ-204 | 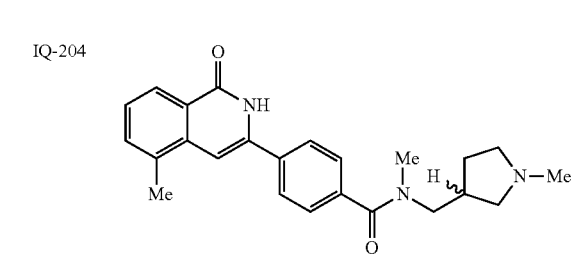 |
| IQ-205 | 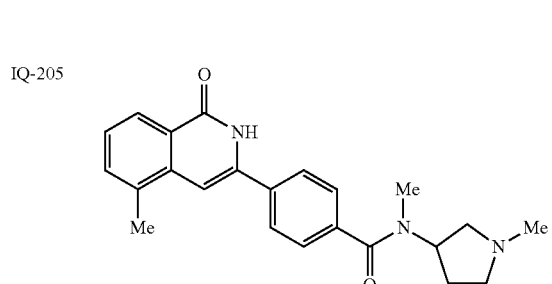 |
| IQ-206 | 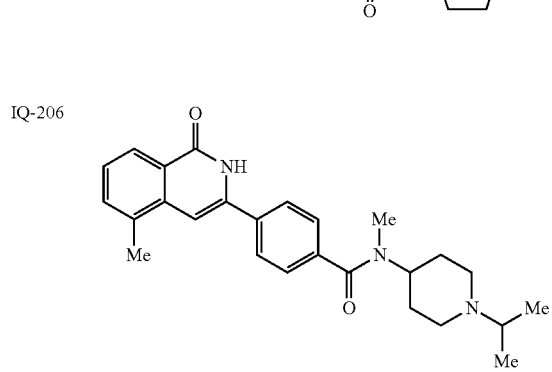 |
| IQ-207 | 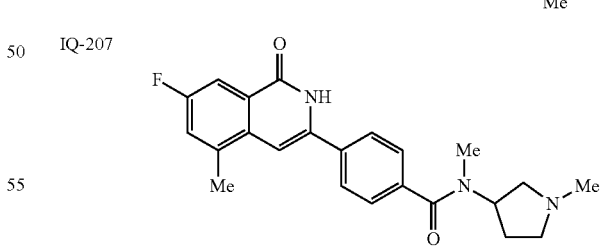 |
| IQ-208 | 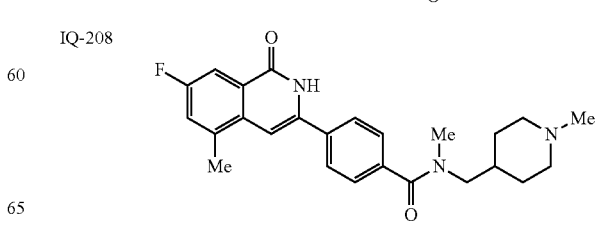 |

| Pat. Code | Structure |
|---|---|
| IQ-209 | 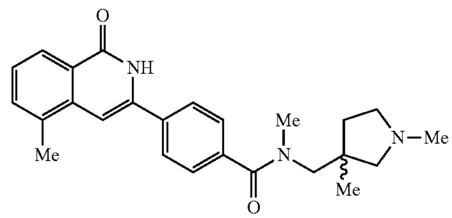 [SMILES: Cc1cccc2c(=O)[nH]c(-c3ccc(C(=O)N(C)CC4(C)CCN(C)C4)cc3)cc12] |
| IQ-210 | 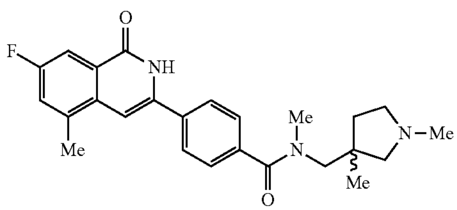 [SMILES: Cc1cc(F)cc2c(=O)[nH]c(-c3ccc(C(=O)N(C)CC4(C)CCN(C)C4)cc3)cc12] |
| IQ-211 | 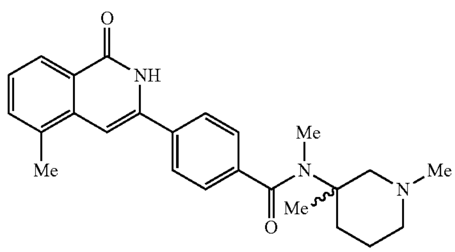 [SMILES: Cc1cccc2c(=O)[nH]c(-c3ccc(C(=O)N(C)C4(C)CCCN(C)C4)cc3)cc12] |
| IQ-212 | 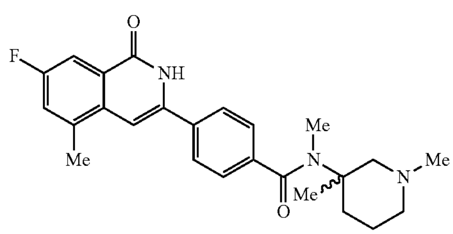 [SMILES: Cc1cc(F)cc2c(=O)[nH]c(-c3ccc(C(=O)N(C)C4(C)CCCN(C)C4)cc3)cc12] |
| IQ-213 | 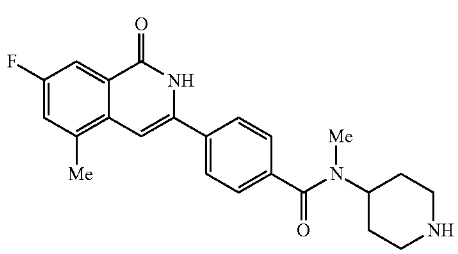 [SMILES: Cc1cc(F)cc2c(=O)[nH]c(-c3ccc(C(=O)N(C)C4CCNCC4)cc3)cc12] |
| IQ-214 | 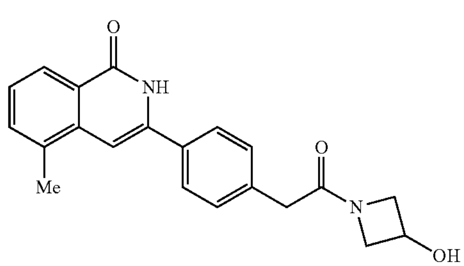 [SMILES: Cc1cccc2c(=O)[nH]c(-c3ccc(CC(=O)N4CC(O)C4)cc3)cc12] |
| IQ-215 | |
| IQ-216 | |
| IQ-217 | |
| IQ-218 | |
| IQ-219 | |
| IQ-220 | |

| Pat. Code | Structure |
|---|---|
| IQ-221 | 8-fluoro-5-methyl-3-[6-(4-methylpiperazine-1-carbonyl)pyridin-3-yl]isoquinolin-1(2H)-one |
| IQ-222 | 7-fluoro-5-methyl-3-[6-(4-methylpiperazine-1-carbonyl)pyridin-3-yl]isoquinolin-1(2H)-one |
| IQ-223 | 3-{6-[4-(cyclopropylmethyl)piperazine-1-carbonyl]pyridin-2-yl}-5-methylisoquinolin-1(2H)-one |
| IQ-224 | 5-methyl-3-[2-(4-methylpiperazine-1-carbonyl)pyrimidin-5-yl]isoquinolin-1(2H)-one |
| IQ-225 | 8-fluoro-5-methyl-3-[2-(4-methylpiperazine-1-carbonyl)pyrimidin-5-yl]isoquinolin-1(2H)-one |
| IQ-226 | 5,8-difluoro-3-[4-(4-methylpiperazine-1-carbonyl)phenyl]isoquinolin-1(2H)-one |
| IQ-227 | 5,7-difluoro-3-[4-(4-methylpiperazine-1-carbonyl)phenyl]isoquinolin-1(2H)-one |
| IQ-228 | 5,7-difluoro-3-{4-[4-(2-hydroxyethyl)piperazine-1-carbonyl]phenyl}isoquinolin-1(2H)-one |
| IQ-229 | 3-{2-[4-(cyclopropylmethyl)piperazine-1-carbonyl]pyrimidin-5-yl}-5,8-difluoroisoquinolin-1(2H)-one |
| IQ-230 | 5-ethynyl-3-{4-[(piperazin-1-yl)methyl]phenyl}isoquinolin-1(2H)-one |
| IQ-231 | 5-(3-hydroxyprop-1-yn-1-yl)-3-{4-[(4-methylpiperazin-1-yl)methyl]phenyl}isoquinolin-1(2H)-one |
| IQ-232 | 3-{4-[2-(dimethylamino)ethoxy]phenyl}-5-(3-hydroxyprop-1-yn-1-yl)isoquinolin-1(2H)-one |

*Note: Structure descriptions are approximate based on visual inspection of the chemical diagrams.*

-continued

| Pat. Code | Structure |
|---|---|
| IQ-233 | (structure) |
| IQ-234 | (structure) |
| IQ-235 | (structure) |
| IQ-236 | (structure) |
| IQ-237 | (structure) |
| IQ-238 | (structure) |

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., W, X, Y, Z, $-R^W$, $-R^X$, $-R^Y$, $-R^Z$, $-R^{WW}$, $-R^{XX}$, $-R^{YY}$, $-R^{ZZ}$, $-X^1$, $-R^1$, $-L^{3P}-$, $-L^{3PL}-$, $-L^{3PR1}-$, $-L^{3PR2}-$, $-L^{3PR3}-$, $-L^{3PR4}-$, $-R^{3N}$, $-R^A$, $-R^{A1}$, $-R^{A2}$, $-R^{A3}$, $-R^{A4}$, $-R^{A5}$, $-L^A-$, $-R^{S1}$, $-R^{S2C}$, $-R^{S3C}$, $-R^{SN}$, $-L^T-$, $-R^{TT}$, $-R^{TTT}$, $-R^{TN}$, $-R^{TM}$, $-R^{TMM}$, $-R^B$, $-R^{B1}$, $-R^{B2}$, $-L^B-$, $-R^{BB}$, $-NR^CR^D$, $-NR^{C1}R^{D1}$, $-NR^{C2}R^{D2}$, $-NR^{C3}R^{D3}$, $-NR^{C4}R^{D4}$, $-NR^{C5}R^{D5}$, $-R^{NC}$, $-R^{NN}$, $-L^Q-$, $-R^{QQ}$, $-R^{QN}$, $-R^{QM}$, $-R^{QMM}$, $-R^H$, $-L^H-$, $-R^{HH}$, $-R^{HN}$, $-R^{HM}$, $-R^{HMM}$, $-R^5$, $-R^{5A}$, $-R^{5B}$, $-R^{5C}$, $-R^{5D}$, $-R^{5E}$, $-R^{5EE}$, $-R^{5EEE}$, $-R^4$, $-R^6$, $-R^7$, $-R^8$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to IQ compounds, as described herein, in substantially purified form and/or in a form substantially free from contaminants.

In one embodiment, the compound is in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the compound is in a substantially purified form with an optical purity of at least 60% (i.e., 60% of the compound, on a molar basis, is the desired stereoisomer or enantiomer, and 40% is undesired stereoisomer(s) or enantiomer), e.g., at least 70%, e.g., at least 80%, e.g., at least 90%, e.g., at least 95%, e.g., at least 97%, e.g., at least 98%, e.g., at least 99%.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

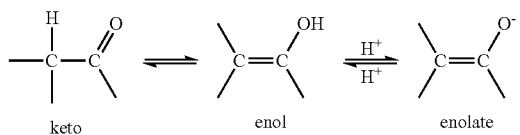

For example, 1H-pyridin-2-one-5-yl and 2-hydroxyl-pyridin-5-yl (shown below) are tautomers of one another. A reference herein to one is intended to encompass both.

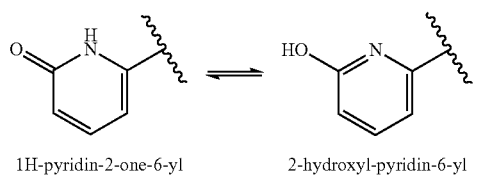 [SMILES: *c1cccc(=O)[nH]1 ; *c1cccc(O)n1]

1H-pyridin-2-one-6-yl     2-hydroxyl-pyridin-6-yl

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, formic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

N-Oxides

It may be convenient or desirable to prepare, purify, and/or handle a corresponding N-oxide of the compound. For example, a compound having a pyridyl group may be prepared, purified, and/or handled as the corresponding N-oxide.

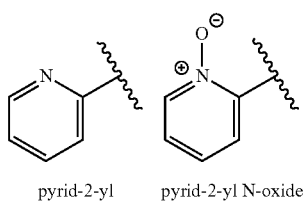

pyrid-2-yl     pyrid-2-yl N-oxide

Unless otherwise specified, a reference to a particular compound also includes N-oxide forms thereof.

Hydrates and Solvates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Greene and P. Wuts; 4th Edition; John Wiley and Sons, 2006).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl(diphenylmethyl), or trityl(triphenylmethyl)ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxycarbonyl amide (—NHCO—OCH$_2$C$_6$H$_5$, —NH-Cbz); as a t-butoxycarbonyl amine (—NHCO—OC(CH$_3$)$_3$, —NH-Boc); a 2-biphenyl-2-propoxycarbonyl amine (—NHCO—OC(CH$_3$)$_2$C$_6$H$_4$C$_6$H$_5$, —NH-Bpoc), as a 9-fluorenylmethoxycarbonyl amine (—NH-Fmoc), as a 6-nitroveratryloxycarbonyl amine (—NH-Nvoc), as a 2-trimethylsilylethyloxycarbonyl amine (—NH-Teoc), as a 2,2,2-trichloroethyloxycarbonyl amine (—NH-Troc), as an allyloxycarbonyl amine (—NH-Alloc), as a 2(-phenylsulfonyl)ethyloxycarbonyl amine (—NH-Psec); or, in suitable cases (e.g., cyclic amines), as a nitroxide radical (>N—O●).

For example, a carboxylic acid group may be protected as an ester for example, as: an $C_{1-7}$alkyl ester (e.g., a methyl ester; a t-butyl ester); a $C_{1-7}$haloalkyl ester (e.g., a $C_{1-7}$trihaloalkyl ester); a tri$C_{1-7}$alkylsilyl-$C_{1-7}$alkyl ester; or a $C_{5-20}$aryl-$C_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

General Chemical Synthesis

Several methods for the chemical synthesis of IQ compounds are described herein. These and/or other well known methods may be modified and/or adapted in known ways in order to facilitate the synthesis of additional compounds described herein.

All reagents were either purchased from common commercial sources or synthesised in accordance with known literature procedures. Commercial reagents were used without further purification unless otherwise stated. Microwave reactions were conducted using a CEM Discover. Flash column chromatography was conducted using pre-packed silica Biotage® SNAP (KP-Sil) cartridges. Ion exchange chromatography was performed using Isolute® Flash SCX-2 cartridges.

ABBREVIATIONS

APCI: atmospheric pressure chemical ionisation.
BBr$_3$: boron tribromide.

BINAP: 2,2'-bis(diphenylphosphino)-1,1'-binaphthyl.
Boc: tert-butyloxycarbonyl.
$CH_2Cl_2$: dichloromethane.
CV: column volume.
DEAD: diethylazodicarboxylate.
DIAD: diisopropyl azodicarboxylate.
DIPEA: N,N-diisopropylamine
DMA: dimethyl acetamide.
DMAP: 4-dimethylaminopyridine
DME: dimethoxyethane.
DMF: N,N-dimethylformamide.
Dppf: 1,1'-Bis(diphenylphosphino)ferrocene.
EDCl: 1-ethyl-3-(3-dimethylaminopropyl) carbodiimide.
ES: electrospray.
EtOAc: ethyl acetate.
h: hour(s).
HATU: 2-(7-Aza-1H-benzotriazole-1-yl)-1,1,3,3-tetramethyluronium hexafluorophosphate.
IPA: isopropyl alcohol.
LDA: lithium diisopropylamide.
MCPBA: meta-Chloroperoxybenzoic acid
min: minute(s).
Ms/mesyl: methane sulfonyl
PFPA: perfluorophthalic anhydride.
$PPh_3$: triphenyl phosphine.
PS: polymer supported.
Py: pyridine.
$R_f$: retention factor
Rt: retention time.
RT: room temperature.
SCX: strong cation exchange
SEM: 2-(trimethylsilyl)ethoxymethyl.
TBAF: tetra-n-butylammonium fluoride.
TBDMS: tert-butyldimethylsilyl.
TBDPS: tert-butyldiphenyllsilyl.
TBTU: O-(benzotriazol-1-yl)-N,N,N',N'-tetramethyluronium tetrafluoroborate.
TFA: trifluoroacetic acid.
THF: tetrahydrofuran.
Ts/tosyl; 4-toluenesulfonyl.

The general synthetic methods for the synthesis of 2H-isoquinolin-1-ones 5 are illustrated below:

Route 1: Synthesis of 2H-isoquinolin-1-ones 5 via Cyclisation

Scheme 1

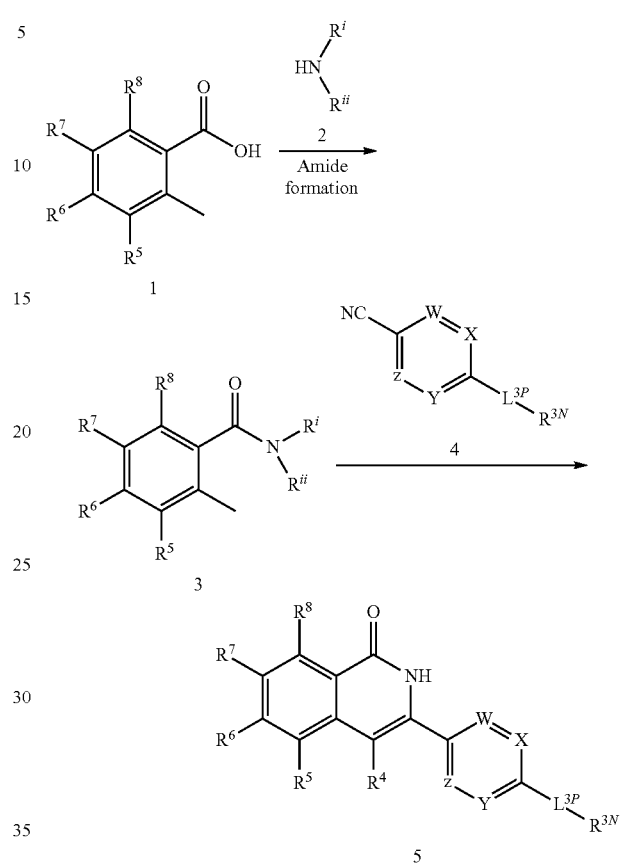

Acid 1 can be reacted with amine 2 (e.g., N,N-diethylamine) to yield amide 3, either by utilising standard amine coupling procedures (e.g., EDCI, HATU, etc.) or converting the acid 1 into the corresponding acid chloride (or mixed anhydride) and reacting with the amine 2 (see, e.g., Le et al., 2004). The 2-H-isoquinolin-1-one 5 can be prepared by in situ deprotonation of 2-methyl-benzamide derivative 3 with a suitable base (e.g., n-BuLi, sec-BuLi, t-BuLi, LDA, etc.) in THF (or similar suitable aprotic solvent) at −78° C., then reacting with the required nitrile 4 (see, e.g., Hattori et al., 2006).

Route 2: Synthesis of 2H-isoquinolin-1-ones 5 via Organopalladium Cross-Coupling Scheme 2

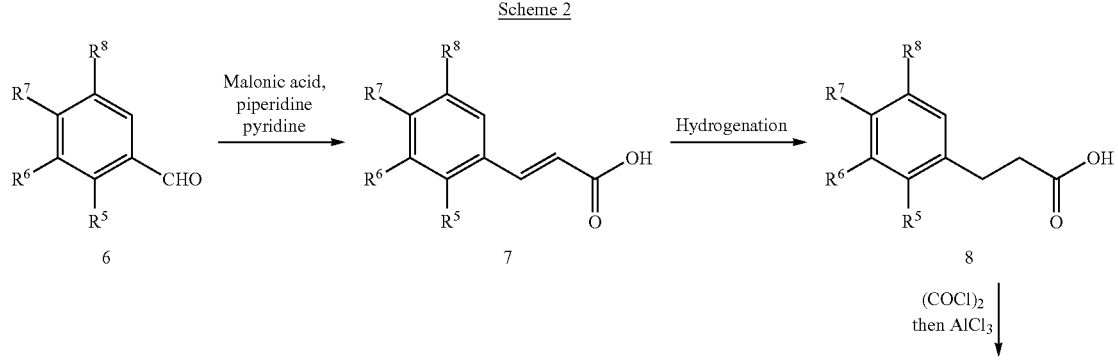

(COCl)$_2$
then AlCl$_3$

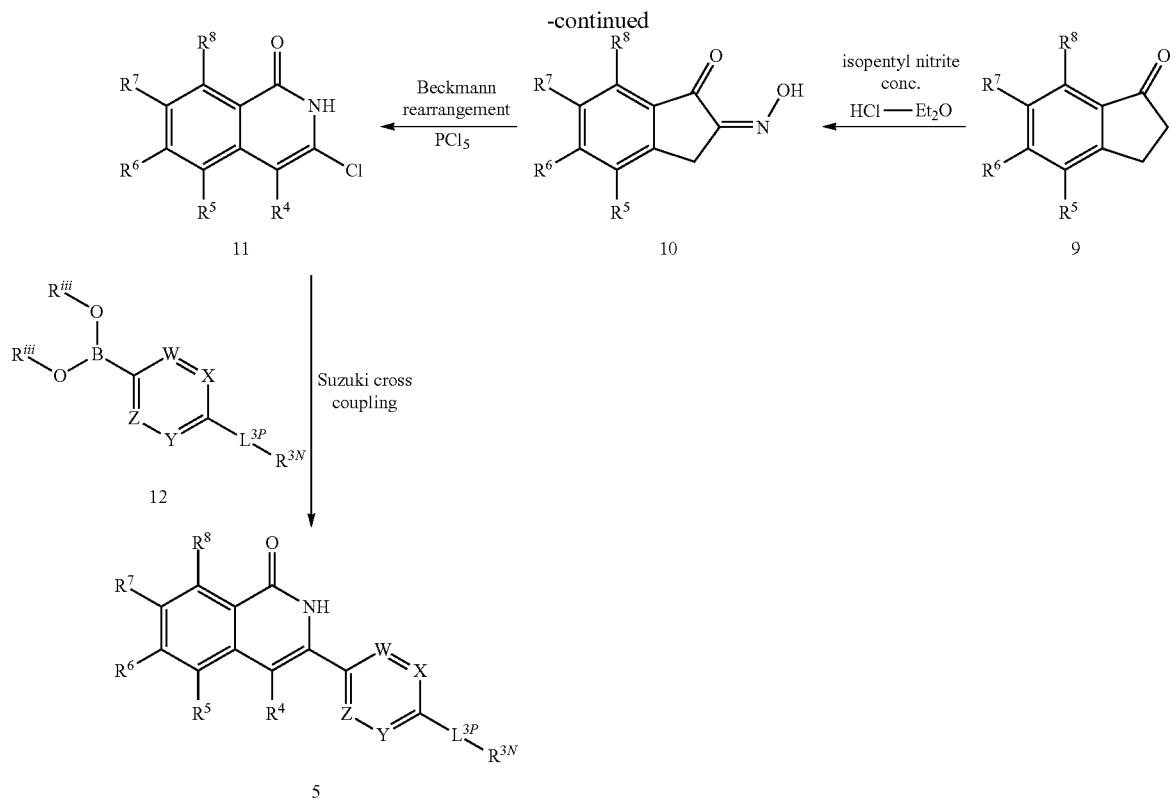

The 2H-isoquinolin-1-one 5 can be synthesised by a palladium-mediated cross-coupling from the corresponding aryl halide 11 (e.g. chloride) and the corresponding boronic acid or ester (Suzuki cross-coupling).

Route 2a: Alternative synthesis of 2H-isoquinolin-1-ones 5 via Organopalladium Cross-Coupling Scheme 2a

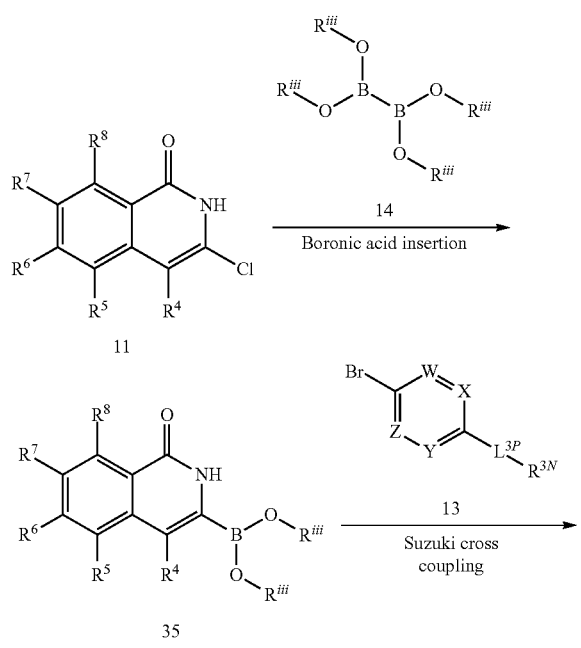

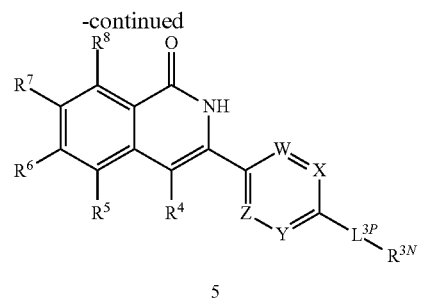

In an alternative route, the 2H-isoquinolin-1-one 5 can be synthesised by a palladium-mediated cross-coupling from the corresponding aryl or heteroaryl halides 13 (e.g., bromide) and the corresponding boronic ester 35 (Suzuki cross-coupling). The boronic ester 35 can be accessed by a palladium-mediated cross-coupling from the corresponding 3-halo-2H-isoquinolin-1-one 11 (e.g., chloride) with a suitable diboron reagent (e.g. bis(pinacolato)diboron), and a suitable source of palladium (e.g., $Pd(PPh_3)_4$, $PdCl_2(PPh_3)_2$) in an appropriate solvent (e.g., THF, DMF, DME, DCE, toluene, etc.).

For the Suzuki cross-coupling, 3-halo-2H-isoquinolin-1-one (e.g chloride) 11 can be reacted with a suitable boronic acid or ester 12 in the presence of a suitable base (e.g., $K_2CO_3$, NaOt-Bu, $K_3PO_4$, etc.), a suitable source of palladium (e.g., $Pd(PPh_3)_4$, $PdCl_2(PPh_3)_2$, etc.) and a ligand (e.g., $P(t-Bu)_3$, BINAP, etc.) in an appropriate solvent (e.g., THF, DME, DCE, toluene, etc.).

The 3-chloro-2H-isoquinolin-1-one 11 can be synthesised from indan-1,2-dione 2-oxime 10 (see, e.g., Merchant et al., 1984) via Beckmann rearrangement followed by treatment with $PCl_5$.

Indan-1,2-dione 2-oxime 10 can be accessed from commercial sources or prepared from commercially available indanones 9 by nitrosation or from aldehyde 6 via chain extension, cyclisation and nitrosation (see, e.g., Musso et al., 2003).

The general synthetic methods for the synthesis of nitrile intermediates 4 and boronic acid or boronic ester intermediates 12 are illustrated below:

Synthesis of Aryl Nitrile 4 from Aryl Bromide 13

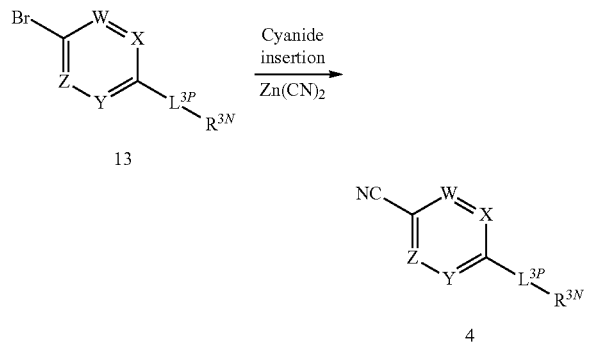

The nitrile 4 can be accessed by a palladium-mediated cyanide insertion from the corresponding carboaryl or heteroaryl halide 13 (e.g., iodide, bromide, chloride) with a source of cyanide e.g., $Zn(CN)_2$, $Cu(CN)_2$, and a suitable source of palladium (e.g., $Pd(PPh_3)_4$, $PdCl_2(PPh_3)_2$) in an appropriate solvent (e.g., THF, DMF, DME, DCE, toluene, etc.).

Synthesis of Boronic Acid or Boronic Ester Intermediate 12 from Aryl Halide 13

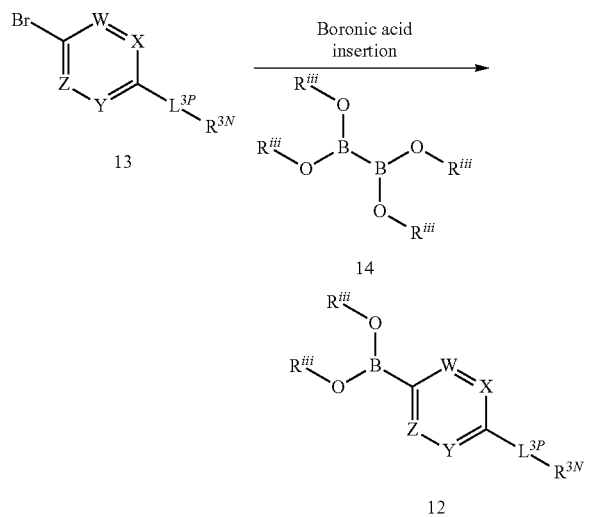

The boronic acid or ester 12 can be accessed by a palladium-mediated cross-coupling from the corresponding aryl (heteroaryl) halide 13 (e.g., iodide, bromide, chloride) with bis(pinacolato)diboron, and a suitable source of palladium (e.g., $Pd(PPh_3)_4$, $PdCl_2(PPh_3)_2$) in an appropriate solvent (e.g., THF, DMF, DME, DCE, toluene, etc.).

Synthesis of Amine 17 from Alkyl Bromide 15

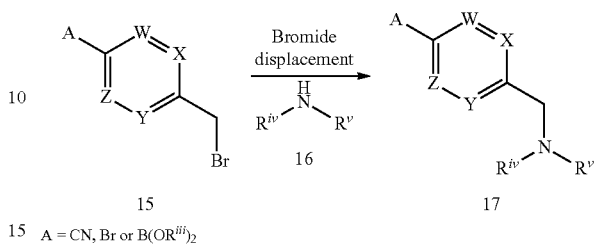

$A = CN$, Br or $B(OR^{iii})_2$

The amine 17 can be accessed by bromide displacement from the corresponding halide 15 (e.g., iodide, bromide, chloride) and an appropriate amine 16 in an appropriate solvent (e.g., THF, DMF, $CH_2Cl_2$ etc.).

This method is exemplified in Scheme 5 with benzyl or heteroarylmethyl bromides, but it is understood that the same approach can be extended to other examples of A-aryl-$L^{3PR1}$-Br. The same method can be used for any amine 16 as defined in the claims, including aromatic heterocycles $HNR^{C5}R^{D5}$ (e.g., imidazole, pyrazole, etc.).

Synthesis of Amine 17 from Aldehyde 18

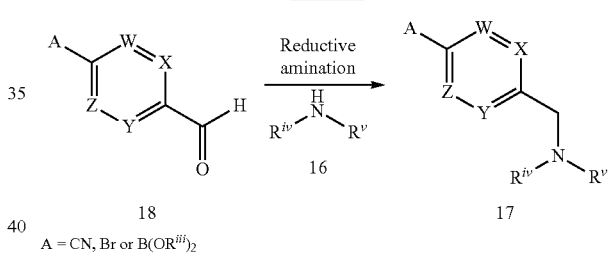

$A = CN$, Br or $B(OR^{iii})_2$

The amine 17 can be accessed by standard reductive amination conditions from the corresponding aldehyde 18 and an appropriate amine 16 in an appropriate solvent (e.g., DCE etc.), with the use a standard reducing reagent (e.g., sodium triacetoxy borohydride, sodium borohydride, etc.).

Synthesis of Amide 20 from Acid 19

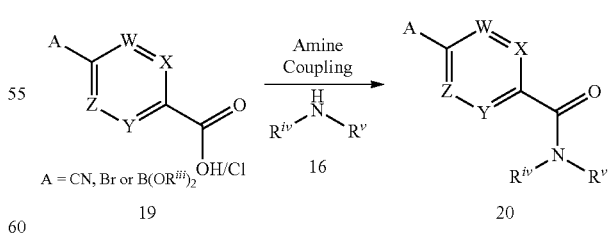

$A = CN$, Br or $B(OR^{iii})_2$ OH/Cl

The amide 20 can be accessed by standard amine coupling conditions from the corresponding acid (or acid chloride) 19 and an appropriate amine 16 in an appropriate solvent (e.g., THF, DMF, $CH_2Cl_2$ etc.), with a suitable base (e.g., DIPEA, $Et_3N$ etc.) with the use a standard amine coupling reagent (e.g., HATU, TBTU, EDCI etc.).

Alternatively, the amide 20 can be accessed by standard amine coupling conditions from the corresponding acid chloride 19 and an appropriate amine 16 in an appropriate solvent (e.g., THF, DMF, $CH_2Cl_2$ etc.), with a suitable base (e.g., DIPEA, $Et_3N$ etc.).

Synthesis of Amide 20 from Acid 19

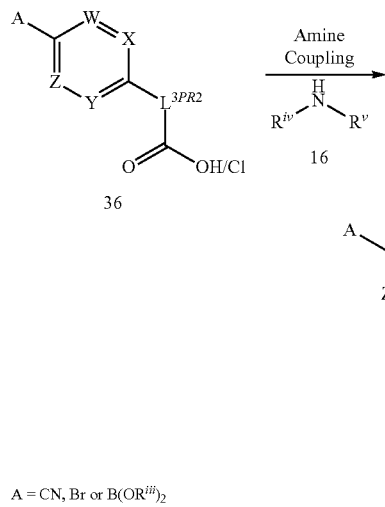

A = CN, Br or $B(OR^{iii})_2$

The same method from Scheme 7 can be applied using a carboxylic acid (or acid chloride) 36, with an amine 16, to afford amide 37.

Synthesis of Sulfonamide 22 from Sulfonyl Chloride 21

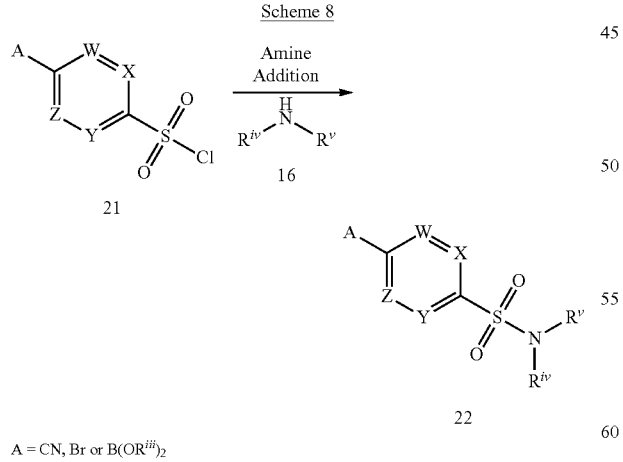

A = CN, Br or $B(OR^{iii})_2$

The sulfonamide 22 can be prepared from the corresponding sulfonyl chloride 21 and an appropriate amine 16 in an appropriate solvent (e.g., THF, $CH_2Cl_2$ etc.), with a suitable base (e.g., DIPEA, $Et_3N$ etc.).

Synthesis of Amino-Heteroaryl Nitrile 24 from Halo-Heteroaryl Nitrile 23

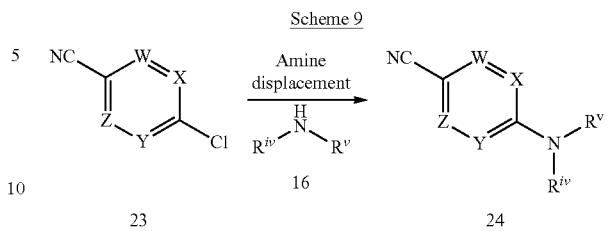

Halo-heteroaryl 23 can be reacted with amine 16 to yield amino-heteroaryl 24 (see, e.g., Nettekoven et al., 2006) either by heating in acetonitrile (or other suitable solvent) or by irradiation using microwave heating in acetonitrile (or other suitable solvent).

The general synthetic methods for the synthesis of 2H-isoquinolin-1-ones 5 are illustrated below:

Synthesis of 2H-isoquinolin-1-ones 5 via Organometal Cross-Coupling

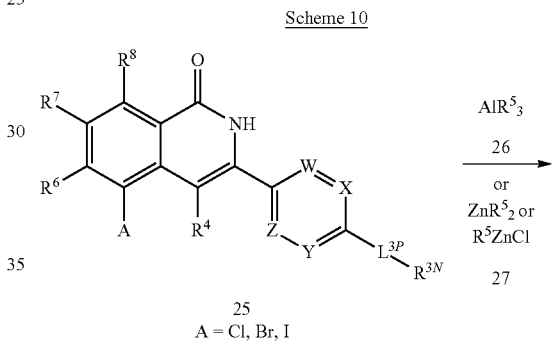

The 2H-isoquinolin-1-one 5 can be synthesised by palladium-mediated cross-coupling of an aryl halide 25 and a suitable trialkylaluminium reagent 26 (see, e.g., Molander et al., 2003) in the presence of a suitable source of palladium (e.g., $Pd(PPh_3)_4$, $PdCl_2(PPh_3)_2$, etc.) and $CeCl_3$ in an appropriate solvent (e.g., THF, DME, DCE, toluene, dioxane, etc.).

The aryl halide 25 can alternatively be reacted with a suitable organo-zinc halide or diorgano-zinc compound 27 (see, e.g., Hughes et al., 2007) in the presence of a suitable source of palladium (e.g., $Pd(PPh_3)_4$, $PdCl_2(PPh_3)_2$, etc.), a ligand (e.g., $P(t-Bu)_3$, BINAP, etc.) in an appropriate solvent (e.g., THF, DME, DCE, toluene, dioxane, etc.).

Synthesis of 2H-isoquinolin-1-ones 5 via Sonogashira Coupling

Scheme 10a

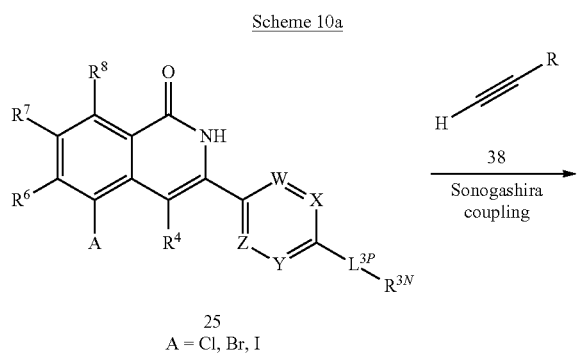

25
A = Cl, Br, I

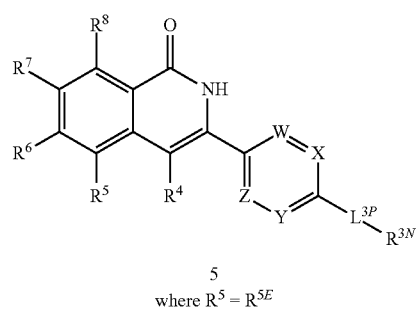

5
where $R^5 = R^{5E}$

The 2H-isoquinolin-1-one 5 can be synthesised by palladium/copper-mediated cross-coupling (Sonogashira coupling) of an aryl halide 25 and a suitable alkynyl reagent 38 in the presence of a base (e.g., DIPEA, triethylamine, pyrrolidine, piperidine, $Cs_2CO_3$, etc.), a suitable source of palladium (e.g., $Pd(PPh_3)_4$, $PdCl_2(PPh_3)_2$, etc.) and a ligand (e.g., $PPh_3$, $P(t-Bu)_3$, etc.) in an appropriate solvent (e.g., THF, DMF, DME, DCE, toluene, dioxane, etc.).

Synthesis of 2H-isoquinolin-1-ones 30 via N-Acylation

Scheme 11

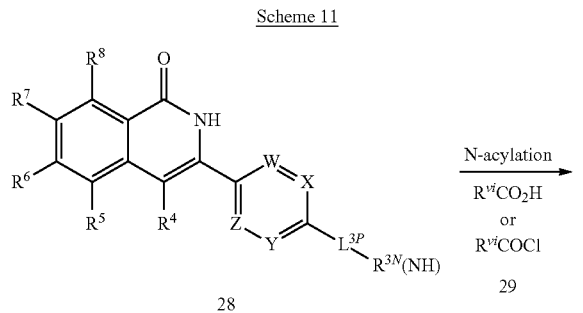

28

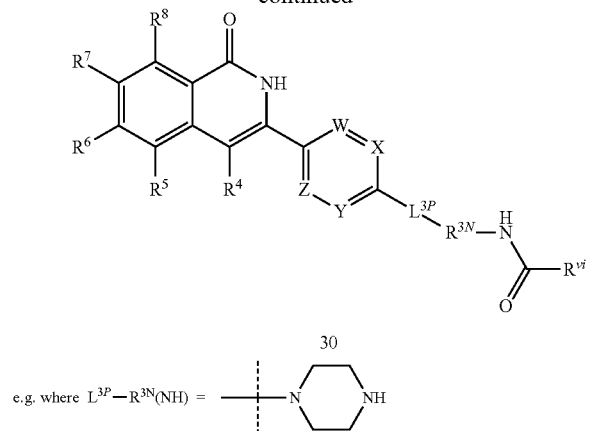

30 e.g. where $L^{3P}-R^{3N}(NH) = $

The amide 30 can be accessed by standard amine coupling conditions from the corresponding amine 28 and an appropriate acid 29 in an appropriate solvent (e.g., THF, DMF, $CH_2Cl_2$ etc.), with a suitable base (e.g., DIPEA, $Et_3N$ etc.) with the use a standard amine coupling reagent (e.g., HATU, TBTU, EDCI etc.).

Alternatively, the amide 30 can be accessed by standard amine coupling conditions from the corresponding amine 28 and an appropriate acid chloride 29 in an appropriate solvent (e.g., THF, DMF, $CH_2Cl_2$ etc.), with a suitable base (e.g., DIPEA, $Et_3N$ etc.).

Synthesis of 2H-isoquinolin-1-ones 32 via Urea Formation

Scheme 12

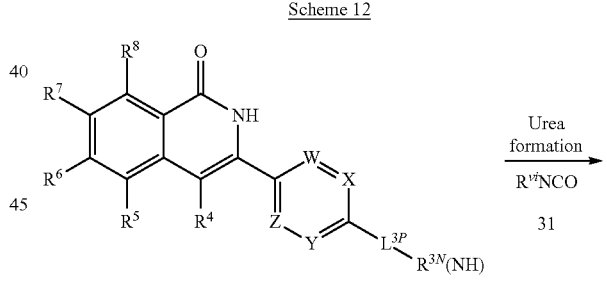

32 e.g. where $L^{3P}-R^{3N}(NH) = $

The urea 32 can be accessed by standard urea formation conditions from the corresponding amine 28 and an appropriate isocyanate 31 in an appropriate solvent (e.g, DMF, CH$_2$Cl$_2$ etc.).

Synthesis of 2H-isoquinolin-1-ones 34 via N-Acylation

Scheme 13

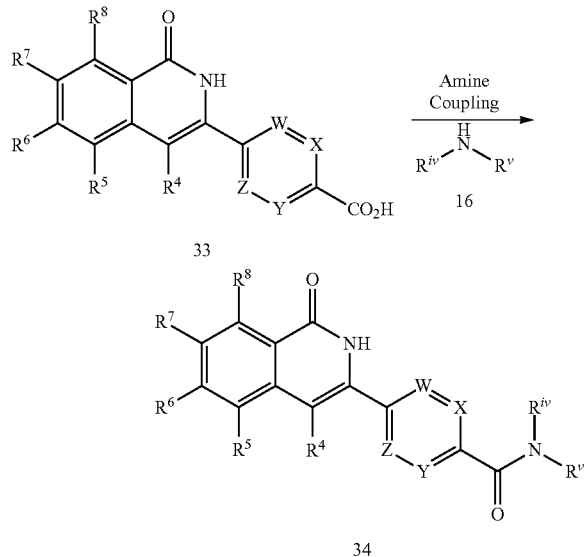

The amide 34 can be accessed by standard amine coupling conditions from the corresponding acid 33 and an appropriate amine 16 in an appropriate solvent (e.g., THF, DMF, CH$_2$Cl$_2$ etc.), with a suitable base (e.g., DIPEA, Et$_3$N etc.) with the use a standard amine coupling reagent (e.g., HATU, TBTU, EDCI etc.).

Synthesis of 2H-isoquinolin-1-ones 40 via N-Acylation

Scheme 13a

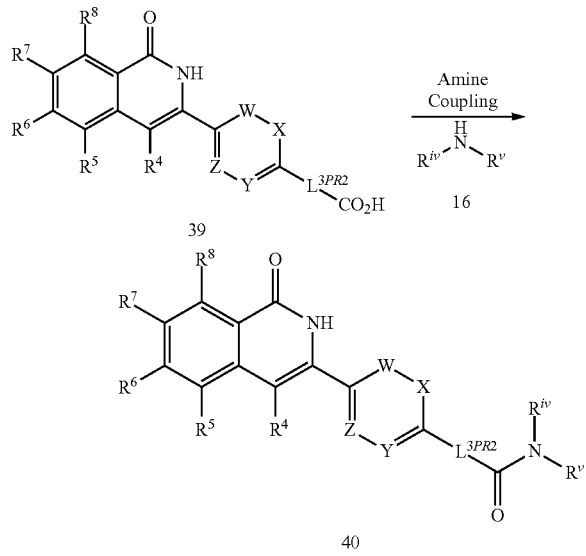

The same method from Scheme 13 can be applied using a carboxylic acid 39, with an amine 16, to afford amide 40.

Compositions

One aspect of the present invention pertains to a composition (e.g., a pharmaceutical composition) comprising an IQ compound, as described herein, and a pharmaceutically acceptable carrier, diluent, or excipient.

Another aspect of the present invention pertains to a method of preparing a composition (e.g., a pharmaceutical composition) comprising mixing an IQ compound, as described herein, and a pharmaceutically acceptable carrier, diluent, or excipient.

Uses

The IQ compounds, as described herein, are useful, for example, in the treatment of disorders (e.g., diseases) that are ameliorated by the inhibition of PARP (e.g., PARP1, TNKS1, TNKS2, etc.) and/or the inhibition of Wnt signalling, as described herein.

Use in Methods of Inhibiting PARP (e.g., PARP1, TNKS1, TNKS2, etc.)

One aspect of the present invention pertains to a method of inhibiting PARP (e.g., PARP1, TNKS1, TNKS2, etc.) in a cell, in vitro or in vivo, comprising contacting the cell with an effective amount of an IQ compound, as described herein.

One aspect of the present invention pertains to a method of inhibiting TNKS1 and/or TNKS2 in a cell, in vitro or in vivo, comprising contacting the cell with an effective amount of an IQ compound, as described herein.

One of ordinary skill in the art is readily able to determine whether or not a candidate compound inhibits PARP (e.g., PARP1, TNKS1, TNKS2, etc.). For example, suitable assays are described herein or are known in the art.

In one embodiment, the method is performed in vitro.

In one embodiment, the method is performed in vivo.

In one embodiment, the IQ compound is provided in the form of a pharmaceutically acceptable composition.

Any type of cell may be treated, including but not limited to, adipose, lung, gastrointestinal (including, e.g., bowel, colon), breast (mammary), ovarian, prostate, liver (hepatic), kidney (renal), bladder, pancreas, brain, and skin.

For example, a sample of cells may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Inhibiting Wnt Signalling

One aspect of the present invention pertains to a method of inhibiting Wnt signalling in a cell, in vitro or in vivo, comprising contacting the cell with an effective amount of an IQ compound, as described herein.

One of ordinary skill in the art is readily able to determine whether or not a candidate compound inhibits Wnt signalling. For example, suitable assays are described herein or are known in the art.

In one embodiment, the method is performed in vitro.

In one embodiment, the method is performed in vivo.

In one embodiment, the IQ compound is provided in the form of a pharmaceutically acceptable composition.

Use in Methods of Inhibiting Cell Proliferation, etc.

The IQ compounds described herein, e.g., (a) regulate (e.g., inhibit) cell proliferation; (b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of an IQ compound, as described herein.

In one embodiment, the method is a method of regulating (e.g., inhibiting) cell proliferation (e.g., proliferation of a cell), in vitro or in vivo, comprising contacting a cell with an effective amount of an IQ compound, as described herein.

In one embodiment, the method is performed in vitro.

In one embodiment, the method is performed in vivo.

In one embodiment, the IQ compound is provided in the form of a pharmaceutically acceptable composition.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to an IQ compound, as described herein, for use in a method of treatment of the human or animal body by therapy.

Use in the Manufacture of Medicaments

Another aspect of the present invention pertains to use of an IQ compound, as described herein, in the manufacture of a medicament for use in treatment.

In one embodiment, the medicament comprises the IQ compound.

Methods of Treatment

Another aspect of the present invention pertains to a method of treatment comprising administering to a patient in need of treatment a therapeutically effective amount of an IQ compound, as described herein, preferably in the form of a pharmaceutical composition.

Disorders Treated—Disorders Ameliorated by the Inhibition of PARP (e.g., PARP1, TNKS1, TNKS2, etc.)

In one embodiment (e.g., of use in methods of therapy, of use in the manufacture of medicaments, of methods of treatment), the treatment is treatment of a disorder (e.g., a disease) that is ameliorated by the inhibition of PARP.

In one embodiment (e.g., of use in methods of therapy, of use in the manufacture of medicaments, of methods of treatment), the treatment is treatment of a disorder (e.g., a disease) that is ameliorated by the inhibition of TNKS1 and/or TNKS2.

Disorders Treated—Proliferative Conditions

In one embodiment (e.g., of use in methods of therapy, of use in the manufacture of medicaments, of methods of treatment), the treatment is treatment of: a proliferative condition.

The term "proliferative condition," as used herein, pertains to an unwanted or uncontrolled cellular proliferation of excessive or abnormal cells which is undesired, such as neoplastic or hyperplastic growth.

In one embodiment, the treatment is treatment of: a proliferative condition characterised by benign, pre-malignant, or malignant cellular proliferation, including for example: neoplasms, hyperplasias, and tumours (e.g., histocytoma, glioma, astrocyoma, osteoma), cancers (see below), psoriasis, bone diseases, fibroproliferative disorders (e.g., of connective tissues), pulmonary fibrosis, atherosclerosis, smooth muscle cell proliferation in the blood vessels, such as stenosis or restenosis following angioplasty.

Disorders Treated—Cancer

In one embodiment (e.g., of use in methods of therapy, of use in the manufacture of medicaments, of methods of treatment), the treatment is treatment of cancer.

In one embodiment, the treatment is treatment of cancer characterised by, or further characterised by, cancer cells which overexpress PARP.

In one embodiment, the treatment is treatment of cancer characterised by, or further characterised by, cancer cells which overexpress TNKS1 and/or TNKS2.

In one embodiment, the treatment is treatment of lung cancer, small cell lung cancer, non-small cell lung cancer, gastrointestinal cancer, stomach cancer, bowel cancer, colon cancer, rectal cancer, colorectal cancer, thyroid cancer, breast cancer, ovarian cancer, endometrial cancer, prostate cancer, testicular cancer, liver cancer, kidney cancer, renal cell carcinoma, bladder cancer, pancreatic cancer, brain cancer, glioma, sarcoma, osteosarcoma, bone cancer, nasopharyngeal cancer (e.g., head cancer, neck cancer), skin cancer, squamous cancer, Kaposi's sarcoma, melanoma, malignant melanoma, lymphoma, or leukemia.

In one embodiment, the treatment is treatment of:
a carcinoma, for example a carcinoma of the bladder, breast, colon (e.g., colorectal carcinomas such as colon adenocarcinoma and colon adenoma), kidney, epidermal, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, prostate, skin (e.g., squamous cell carcinoma);
a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma;
a hematopoietic tumour of myeloid lineage, for example acute and chronic myelogenous leukemias, myelodysplastic syndrome, or promyelocytic leukemia;
a tumour of mesenchymal origin, for example fibrosarcoma or habdomyosarcoma;
a tumour of the central or peripheral nervous system, for example astrocytoma, neuroblastoma, glioma or schwannoma;
melanoma; seminoma; teratocarcinoma; osteosarcoma; xenoderoma pigmentoum; keratoctanthoma; thyroid follicular cancer; or Kaposi's sarcoma.

In one embodiment, the treatment is treatment of solid tumour cancer.

In one embodiment, the treatment is treatment of cancer head and neck cancer; nervous system cancer; lung/mediastinum cancer; breast cancer; oesophagus cancer; stomach cancer; liver cancer; biliary tract cancer; pancreatic cancer; small bowel cancer; large bowel cancer; gynaecological cancer; genito-urinary cancer; thyroid gland cancer; adrenal gland cancer; skin cancer; bone sarcoma; soft tissue sarcoma; paediatric malignancy; Hodgkin's disease; non-Hodgkin's lymphoma; myeloma; leukaemia; or metastasis from an unknown primary site.

In one embodiment, the treatment is treatment of cancer metastasis.

In one embodiment, the cancer is characterised by, or further characterised by, cancer stem cells.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of cell migration (the spread of cancer cells to other parts of the body), the inhibition of invasion (the spread of tumour cells into neighbouring normal structures), or the promotion of apoptosis (programmed cell death). The compounds of the present invention may be used in the treatment of the cancers described herein, independent of the mechanisms discussed herein.

Disorders Treated—Non-Cancer Indications Related to Tankyrase Inhibition

In one embodiment, the treatment is treatment of: a neurodegenerative disorder, such as multiple sclerosis (MS); a neurological disorder associated with demyelination; neonatal hypoxic ischemic encephalopathy (HIE); neonatal periventricular leukomalacia (PVL); a cardiac related pathology, such as myocardial infarction; cardiac damage (e.g., to repair cardiac damage); an infectious disease, such as a pathology related to Herpes Simplex Virus (HSV); a pathology related to Epstein-Barr Virus (EBV); a metabolic disease, such as a metabolic disease where glucose uptake is dysfunctional, such as diabetes, such as type 2 diabetes; or fibrosis (e.g., lung fibrosis).

In one embodiment, the treatment is treatment of: a neurodegenerative disorder, such as multiple sclerosis (MS); neonatal hypoxic ischemic encephalopathy (HIE); neonatal periventricular leukomalacia (PVL); a cardiac related pathology, such as myocardial infarction; a pathology related to Herpes Simplex Virus (HSV); a pathology related to Epstein-Barr Virus (EBV); or a metabolic disease such as type 2 diabetes.

Disorder Treated—Non-Cancer Indications Related to Wnt Signalling

In one embodiment, the treatment is treatment of: Alzheimer's disease; late onset Alzheimer's disease; Dupuytren skin disease; tooth agenesis; vascular defects in the eye; Osteoperosis-pseudoglioma Syndrome (OPPG); exudative vitreoretinopathy; familial exudative vitreoretinopathy; retinal angiogenesis; schizophrenia; osteoporosis; dermal hypoplasia; XX sex reversal; Mullerian-duct regression and virilization; SERKAL syndrome; anonychia; hyponychia; sclerosteosis; van Buchem disease; Fuhrmann syndrome; odonto-onchyo-dermal hypoplasia; Type 2 diabetes; obesity; early onset obesity; a nephropathy, such as HIV-associated nephropathy; early coronary disease; bone density defects; tetra-amelia syndrome; split-hand/foot malformation; caudal duplication; Fuhrmann syndrome; odonto-onycho-dermal dysplasia; skeletal dysplasia; focal dermal hypoplasia; autosomal recessive anonychia; or neural tube defects.

In one embodiment, the treatment is treatment of: Alzheimer's disease; Dupuytren skin disease; tooth agenesis; exudative vitreoretinopathy; schizophrenia; osteoporosis; dermal hypoplasia; XX sex reversal; anonychia; hyponychia; sclerosteosis; van Buchem disease; Fuhrmann syndrome; odonto-onchyo-dermal hypoplasia; early onset obesity; or a nephropathy, such as HIV-associated nephropathy.

Treatment

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

One aspect of the present invention pertains to a compound as described herein, in combination with one or more (e.g., 1, 2, 3, 4, etc.) additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Examples of additional agents/therapies that may be co-administered/combined with treatment with the IQ compounds described herein include the following: antimetabolites; alkylating agents; spindle poisons; topoisomerase inhibitors; DNA binding agents; kinase inhibitors; therapeutic antibodies; PARP inhibitors; NAD metabolism inhibitors; metabolic inhibitors; targeted agents; endocrine agents; etc.

Other Uses

The IQ compounds described herein may also be used as cell culture additives to inhibit PARP (e.g., PARP1, TNKS1, TNKS2, etc.), to inhibit Wnt signalling, etc.

The IQ compounds described herein may also be used as part of an in vitro assay, for example, in order to determine whether a candidate host is likely to benefit from treatment with the compound in question.

The IQ compounds described herein may also be used as a standard, for example, in an assay, in order to identify other active compounds, other PARP (e.g., PARP1, TNKS1, TNKS2, etc.) inhibitors, other Wnt signalling inhibitors, etc.

Kits

One aspect of the invention pertains to a kit comprising (a) an IQ compound as described herein, or a composition comprising an IQ compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The IQ compound or pharmaceutical composition comprising the IQ compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for an IQ compound to be administered alone, it is preferable to present it as a pharmaceutical formulation (e.g., composition, preparation, medicament) comprising at least one IQ compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising mixing at least one IQ compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or mixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oilin-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 µg/mL, for example from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use.

Extemporaneous injection solutions and suspensions may be prepared from sterile powders, granules, and tablets.

Dosage

It will be appreciated by one of skill in the art that appropriate dosages of the IQ compounds, and compositions comprising the IQ compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular IQ compound, the route of administration, the time of administration, the rate of excretion of the IQ compound, the duration of the treatment, other drugs, compounds, and/or materials used in combination, the severity of the disorder, and the species, sex, age, weight, condition, general health, and prior medical history of the patient. The amount of IQ compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the IQ compound is in the range of about 10 µg to about 250 mg (more typically about 100 µg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

Chemical Synthesis

The following examples are provided solely to illustrate the present invention and are not intended to limit the scope of the invention, as described herein.

Analytical Methods

Reverse Phase Preparative HPLC-MS: Mass-directed purification by preparative LC-MS using a preparative C-18 column (Phenomenex Luna C18 (2), 100×21.2 mm, 5 µm).

Analysis of products and intermediates has been carried out using reverse phase analytical HPLC-MS using the parameters set out below.

HPLC Analytical Methods:

AnalpH2_MeOH_4 min: Phenomenex Luna C18 (2) 3 µm, 50×4.6 mm; A=water+0.1% formic acid; B=MeOH; 45° C.; % B: 0 min 5%, 1 min 37.5%, 3 min 95%, 3.51 min 5%, 4.5 min 5%; 2.25 mL/min.

AnalpH2_MeOH_4 min(1): Phenomenex Luna C18 (2) 3 µm, 50×4.6 mm; A=water+0.1% formic acid; B=MeOH+0.1% formic acid; 45° C.; % B: 0 min 5%, 1 min 37.5%, 3 min 95%, 3.51 min 5%, 4.5 min 5%; 2.25 mL/min.

AnalpH2_MeOH_4 min(2): Phenomenex Luna C18 (2) 3 µm, 50×4.6 mm; A=water+0.1% formic acid; B=MeOH+0.1% formic acid; 40° C.; % B: 0 min 5%, 1 min 37.5%, 3 min 95%, 3.51 min 5%, 4.5 min 5%; 2.25 mL/min.

AnalpH2_MeOH_4 min(3): Phenomenex Luna C18 (2) 3 µm, 50×4.6 mm; A=water+0.1% formic acid; B=MeOH+0.1% formic acid; 45° C.; % B: 0 min 5%, 1 min 37.5%, 3 min 95%, 3.51 min 5%, 4.0 min 5%; 2.25 mL/min.

AnalpH9_MeOH_4 min: Phenomenex Luna C18 (2) 3 µm, 50×4.6 mm; A=water pH9 (Ammonium Bicarbonate 10 mM); B=MeOH; 45° C.; % B: 0 min 5%, 1 min 37.5%, 3 min 95%, 3.51 min 5%, 4.5 min 5%; 2.25 mL/min.

AnalpH9_MeOH_4 min(1): Phenomenex Luna C18 (2) 3 µm, 50×4.6 mm; A=water pH9 (Ammonium Bicarbonate 10 mM); B=MeOH+0.1% formic acid; 45° C.; % B: 0 min 5%, 1 min 37.5%, 3 min 95%, 3.51 min 5%, 4.5 min 5%; 2.25 mL/min.

AnalpH9_MeOH_4 min(2): Phenomenex Luna C18 (2) 3 µm, 50×4.6 mm; A=water pH9 (Ammonium Bicarbonate 10 mM); B=MeOH; 45° C.; % B: 0 min 5%, 1 min 37.5%, 3 min 95%, 3.51 min 5%, 4.0 min 5%; 2.25 mL/min.

AnalpH2_MeCN_TFA_4 min: Acquity UPLC BEH C18 1.7 µm, 50×2.1 mm; A=water+0.025% TFA; B=Acetonitrile+0.025% TFA; % B: 0 min 15%, 3 min 95%, 4 min 95%, 4.1 min 15%; 0.4 mL/min.

AnalpH2_MeCN_TFA_4 min(1): Acquity UPLC BEH C18 1.7 µm, 50×2.1 mm; A=water+0.025% TFA; B=Acetonitrile+0.025% TFA; % B: 0 min 50%, 4 min 80%, 6 min 80%, 6.1 min 50%; 0.3 mL/min.

AnalpH2_MeCN_FA_7 min(XTERRA1.m): Xterra C18 2.5 µm, 50×4.6 mm; A=water+0.1% FA; B=Acetonitrile+0.1% FA; % B: 0 min 20%, 4 min 90%, 7 min 90%, 7.1 min 20%; 1.0 mL/min.

AnalpH9_MeCN_AB_10 min (Develosil): Develosil C18 2.7 µm, 150×4.6 mm; A=water+0.01 M Ammonium bicarbonate; B=Acetonitrile; % B: 0 min 50%, 4 min 90%, 10 min 90%, 10.1 min 50%; 1.0 mL/min.

AnalpH2_MeOH_QC: Phenomenex Luna C18 (2) 3 µm, 150×4.6 mm; A=water+0.1% formic acid; B=MeOH; 35° C.; % B: 0 min 5%, 7.5 min 95%, 10 min 95%, 10.10 min 5%, 13.0 min 5%; 1.5 mL/min.

AnalpH2_MeOH_QC(1): Phenomenex Luna C18 (2) 3 µm, 150×4.6 mm; A=water+0.1% formic acid; B=MeOH+0.1% formic acid; 40° C.; % B: 0 min 5%, 7.5 min 95%, 10 min 95%, 10.10 min 5%, 13.0 min 5%; 1.5 mL/min.

AnalpH2_MeOH_QC(2): Phenomenex Gemini C18 5 µm, 150×4.6 mm; A=water+0.1% formic acid; B=MeOH+0.1% formic acid; 40° C.; % B: 0 min 5%, 7.5 min 95%, 10 min 95%, 10.10 min 5%, 13.0 min 5%; 1.5 mL/min.

AnalpH2_MeOH_QC(3): Phenomenex Gemini C18 5 µm, 250×4.6 mm; A=water+0.1% formic acid; B=MeOH+0.1% formic acid; 40° C.; % B: 0 min 5%, 16 min 95%, 18 min 95%, 18.10 min 5%, 24.0 min 5%; 1.5 mL/min.

AnalpH9_MeOH_QC: Phenomenex Luna C18 (2)) 3 µm, 50×4.6 mm; A=water+pH9 (Ammonium Bicarbonate 10 mM); B=MeOH; 35° C.; % B: 0 min 5%, 7.5 min 95%, 10 min 95%, 10.10 min 5%, 13.0 min 5%; 1.5 mL/min.

AnalpH9_MeOH_QC(1): Phenomenex Luna C18 (2) 3 µm, 50×4.6 mm; A=water+pH9 (Ammonium Bicarbonate 10 mM); B=MeOH+0.1% formic acid; 35° C.; % B: 0 min 5%, 7.5 min 95%, 10 min 95%, 10.10 min 5%, 13.0 min 5%; 1.5 mL/min.

AnalpH2_MeOH_QC(Sunfire): Waters Sunfire C18 (2) 5 µm, 100×4.6 mm; A=water+0.1% formic acid; B=MeOH; 35° C.; % B: 0 min 5%, 7.5 min 95%, 10 min 95%, 10.10 min 5%, 13.0 min 5%; 1.5 mL/min.

AnalpH2_MeOH_QC(Sunfire1): Waters Sunfire C18 (2) 5 µm, 100×4.6 mm; A=water+0.1% formic acid; B=MeOH+0.1% formic acid; 40° C.; % B: 0 min 5%, 7.5 min 95%, 10 min 95%, 10.10 min 5%, 13.0 min 5%; 1.5 mL/min.

AnalpH9_MeOH_QC(Sunfire): Waters Sunfire C18 (2) 5 μm, 100×4.6 mm; A=water+pH9 (Ammonium Bicarbonate 10 mM); B=MeOH; 35° C.; % B: 0 min 5%, 7.5 min 95%, 10 min 95%, 10.10 min 5%, 13.0 min 5%; 1.5 mL/min.

AnalpH9_MeOH_QC(Sunfire1): Waters Sunfire C18 (2) 5 μm, 100×4.6 mm; A=water+pH9 (Ammonium Bicarbonate 10 mM); B=MeOH+0.1% formic acid; 35° C.; % B: 0 min 5%, 7.5 min 95%, 10 min 95%, 10.10 min 5%, 13.0 min 5%; 1.5 mL/min.

Chiral HPLC Preparative Methods:
Chiral_Method_1: Daicel IA, 10 μm, 250×20 mm; MeOH+0.2% diethylamine
Chiral_Method_2: Daicel IA, 10 μm, 250×20 mm; 50% (MeCN+3% diethylamine)+50% EtOH
Chiral_Method_3: Daicel IA, 10 μm, 250×20 mm; EtOH+0.05% diethylamine Synthesis of 2H-isoquinolin-1-ones of Formula 4-6

Scheme A (via Route 1)

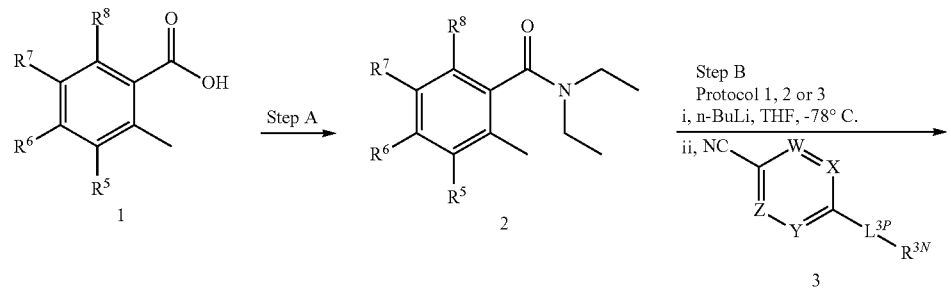

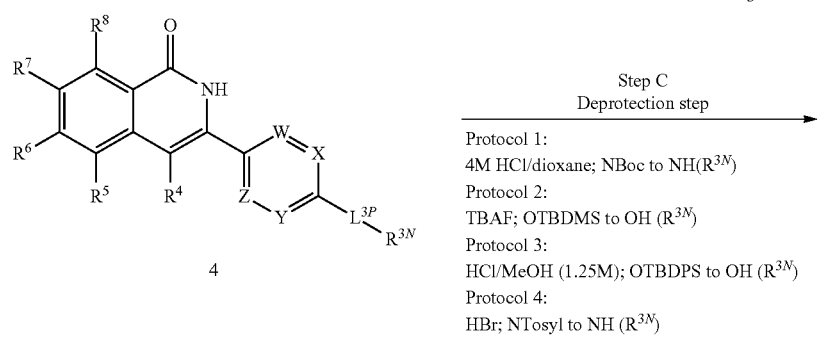

Step C
Deprotection step

Protocol 1:
4M HCl/dioxane; NBoc to NH(R$^{3N}$)
Protocol 2:
TBAF; OTBDMS to OH (R$^{3N}$)
Protocol 3:
HCl/MeOH (1.25M); OTBDPS to OH (R$^{3N}$)
Protocol 4:
HBr; NTosyl to NH (R$^{3N}$)

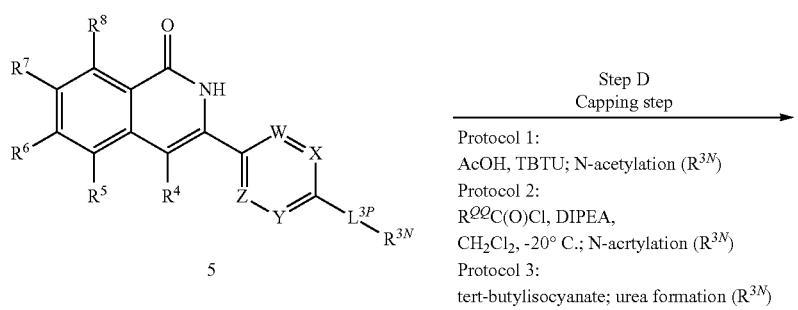

Step D
Capping step

Protocol 1:
AcOH, TBTU; N-acetylation (R$^{3N}$)
Protocol 2:
R$^{QQ}$C(O)Cl, DIPEA, CH$_2$Cl$_2$, -20° C.; N-acrtylation (R$^{3N}$)
Protocol 3:
tert-butylisocyanate; urea formation (R$^{3N}$)

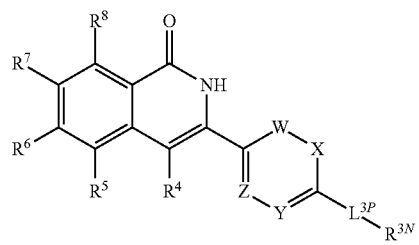

Scheme A, Step A: Synthesis of N,N-Diethyl-benzamide Derivatives 2

N,N-Diethyl-2,3-dimethyl-benzamide

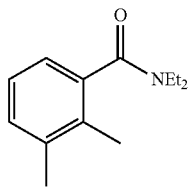

To a stirred solution of 2,3-dimethyl-benzoic acid (1.52 g, 10.1 mmol) in $CH_2Cl_2$/DMF (118 mL/12 mL) was added N,N-diisopropylethylamine (1.76 mL, 10.1 mmol) and TBTU (3.25 g, 10.1 mmol) and the reaction mixture stirred at RT for 50 min. N,N-diethylamine (1.58 mL, 15.2 mmol) was added and the reaction mixture stirred for 18 h. The reaction mixture was washed with 10% $Na_2CO_3$ solution (2×100 mL) and concentrated in vacuo. The crude material was purified by silica gel column chromatography, eluting with isohexane and increasing the polarity to 30% EtOAc/isohexane to obtain N,N-diethyl-2,3-dimethyl-benzamide as a colourless liquid (1.48 g, 72%).

$^1$H NMR (400 MHz, DMSO-$d_6$): δ 7.20-7.10 (m, 2H), 6.90 (d, J=8 Hz, 1H), 3.70-3.55 (m, 1H), 3.35-3.20 (m, 1H), 3.15-2.90 (m, 2H), 2.25 (s, 3H), 2.07 (s, 3H), 1.17 (t, J=7 Hz, 3H), 0.95 (t, J=7 Hz, 3H).

AnalpH2_MeOH_4 min: Rt 2.75 min; m/z 206 [M+1]$^+$.

The following N,N-diethyl-benzamide derivatives are prepared using analogous procedures.

TABLE 1

N,N-Diethyl-benzamide Derivatives of Formula 2

| Compound | Reference | Analytical Data | Mass, % Yield, State |
|---|---|---|---|
| (structure with Cl) | Compound reported by Snieckus et al., 1989 | AnalpH2_MeOH_ 4 min: Rt 2.84 min; m/z 226 [M + 1]$^+$ | 10 g, 77%, colourless oil |
| (structure with F) | Compound reported by Fujio et al., 2009 | AnalpH2_MeOH_ 4 min: Rt 2.63 min; m/z 210 [M + 1]$^+$ | 1.15 g, 86%, colourless oil |
| (structure with CF$_3$) | | AnalpH2_MeOH_ 4 min: Rt 2.94 min; m/z 260 [M + 1]$^+$ | 1.17 g, 92%, colourless oil |
| (structure with Br) | Compound reported by Naoto et al., 2009 | AnalpH2_MeOH_ 4 min: Rt 2.80 min; m/z 269 [M + 1]$^+$ | 4.93 g, 98%, colourless oil |

3-Cyclopropyl-N,N-diethyl-2-methyl-benzamide 7

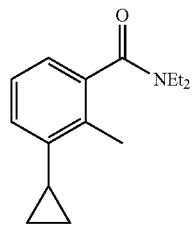

A solution of 3-bromo-N—N-diethyl-2-methylbenzamide (2.5 g, 9 mmol), cyclopropyl boronic acid (955 mg, 11 mmol), $K_3PO_4$ (9.81 g, 46 mmol) and water (10 mL) in toluene (40 mL) was de-gassed using $N_2$ for 1.5 h, Pd(OAc)$_2$ (207 mg, 0.9 mmol) and triphenyl phosphine (42 mg, 0.92 mmol) was added and the reaction mixture degassed for 1 h and heated at 90° C. for 16 h. The reaction mixture was cooled to RT, diluted with EtOAc (40 mL), washed with water (10 mL), dried over $Na_2SO_4$ and concentrated in vacuo. The crude compound was purified by silica gel column chromatography eluting with 3% EtOAc/$CH_2Cl_2$ to obtain 3-cyclopropyl-N,N-diethyl-2-methyl-benzamide as a pale yellow liquid (1.3 g, 61%).

$^1$H NMR (400 MHz, CDCl$_3$): δ 7.13-7.09 (m, 1H), 7.00-6.98 (m, 2H), 3.91-3.70 (m, 1H), 3.55-3.35 (m, 1H), 3.20-3.05 (m, 2H), 2.34 (s, 3H), 1.95-1.80 (m, 1H), 1.26 (t, J=7 Hz, 3H), 1.02 (d, J=7 Hz, 3H), 0.99-090 (m, 2H), 0.75-0.60 (m, 2H).

AnalpH2_MeOH_4 min: Rt 2.92 min; m/z 232 [M+1]$^+$.

Synthesis of Nitrile Intermediates 3 of Formula 10 (required for Step B, Scheme A)

Scheme B

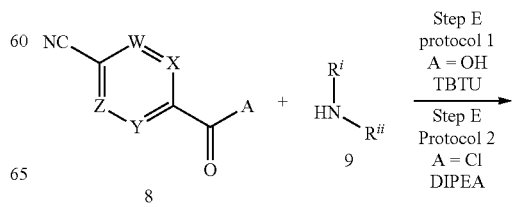

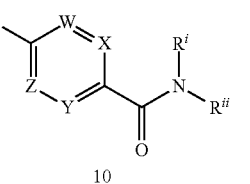

Scheme A, Step E (Protocol 1): Synthesis of Amide-Substituted Benzonitriles 10 (via Acid Coupling)

4-{[(4-Cyano-benzoyl)-methyl-amino]-methyl}-piperidine-1-carboxylic acid tert-butyl ester

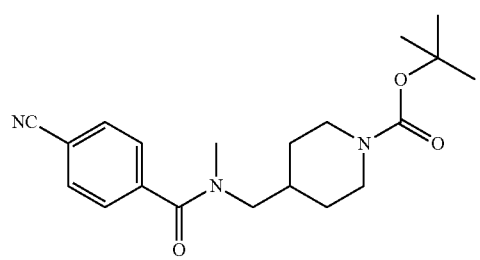 [SMILES: CN(CC1CCN(C(=O)OC(C)(C)C)CC1)C(=O)c1ccc(C#N)cc1]

To a stirred solution of 4-cyanobenzoic acid (322 mg, 2.19 mmol) in CH$_2$Cl$_2$ (10 mL) was added TBTU (702 mg, 2.19 mmol) and N,N-diisopropylethylamine (1.14 mL, 6.54 mmol) and the reaction mixture stirred at RT for 10 min. 4-Methylaminomethyl-piperidine-1-carboxylic acid tert-butyl ester (500 mg, 2.19 mmol) in DMF (4 mL) was added and the reaction mixture was stirred at RT for 2 h. The crude material was concentrated in vacuo and purified by silica gel column chromatography, eluting with isohexane and increasing the polarity to 100% EtOAc to afford 4-{[(4-cyano-benzoyl)-methyl-amino]-methyl}-piperidine-1-carboxylic acid tert-butyl ester as a orange solid (700 mg, 89%).

AnalpH2_MeOH_4 min(1): Rt 2.73 min; m/z 358 [M+1]$^+$.

The following nitrile benzamide derivatives are prepared using analogous procedures.

TABLE 2

Amide-substituted Benzonitrile Intermediates 3 of Formula 10

| Compound | Analytical Data | Mass, % Yield, State |
|---|---|---|
| (4-cyanobenzoyl-piperazinyl-ethoxy-OMe) | AnalpH9_MeOH_ 4 min: Rt 1.87 min; m/z 274 [M + 1]$^+$ | 1.46 g (92%), yellow semi-solid |
| (4-cyanobenzoyl-piperidinyl-N(CH$_3$)$_2$) | AnalpH9_MeOH_ 4 min: Rt 1.82 min; m/z 258 [M + 1]$^+$ | 1.27 g (97%), white solid |
| (4-cyanobenzoyl-N-methyl-piperidinyl) | AnalpH9_MeOH_ 4 min: Rt 1.89 min; m/z 258 [M + 1]$^+$ | 1.0 g (99%), white solid |
| (4-cyanobenzoyl-piperazinyl-cyclopropyl) | AnalpH9_MeOH_ 4 min: Rt 2.21 min; m/z 256 [M + 1]$^+$ | 992 mg (99%), white solid |

Scheme B, Step E (Protocol 2): Synthesis of Amide-Substituted Benzonitriles 10 (via Acid Chloride Coupling)

4-Cyano-N-methyl-N-(1-methyl-piperidin-4-ylmethyl)-benzamide

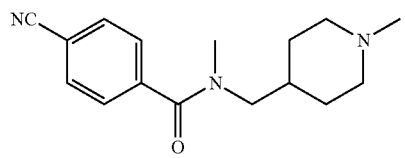 [SMILES: CN1CCC(CN(C)C(=O)c2ccc(C#N)cc2)CC1]

4-cyanobenzoylchloride (200 mg, 1.21 mmol) was dissolved in anhydrous CH$_2$Cl$_2$ (4 mL) and cooled to 0° C. Methyl-(1-methyl-piperidin-4-ylmethyl)-amine (172 mg, 1.21 mmol) in anhydrous CH$_2$Cl$_2$ (1 mL) was added followed by N,N-diisopropylethylamine (0.63 mL, 3.62 mmol). The reaction mixture was allowed to warm to RT over 2 h. The reaction mixture was concentrated in vacuo and the crude product purified by reverse phase preparative HPLC-MS to obtain 4-cyano-N-methyl-N-(1-methyl-piperidin-4-ylmethyl)-benzamide as an off-white solid (213 mg, 65%).

AnalpH9_MeOH_4 min(1): Rt 1.77 min; m/z 272 [M+1]⁺.

Synthesis of Nitrile intermediates 3 of Formula 12 (required for Step B-Scheme A)

Scheme C

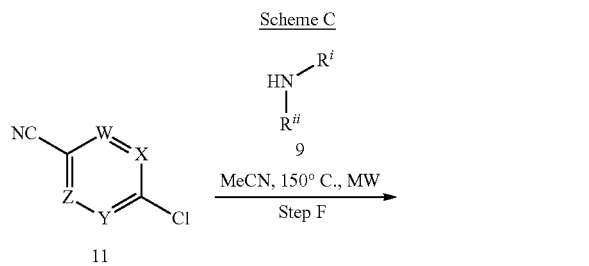

Step F: Synthesis of Amino-Substituted Pyridine-Carbonitrile Derivatives 12

6-(4-Acetyl-piperazin-1-yl)-nicotinonitrile

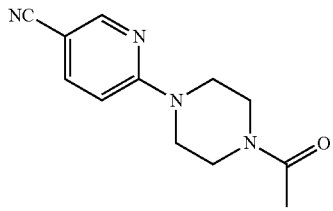 [SMILES: CC(=O)N1CCN(c2ccc(C#N)cn2)CC1]

6-Chloropyridine-2-carbonitrile (104 mg, 0.75 mmol) and 1-acetylpiperazine (384 mg, 0.75 mmol) in acetonitrile (2.5 mL) were stirred and irradiated using a microwave reactor (300 W, 150° C., 60 min). The reaction mixture was concentrated in vacuo and purified by silica gel column chromatography, eluting with CH$_2$Cl$_2$ and increasing the polarity to 10% MeOH/CH$_2$Cl$_2$ to afford 6-(4-acetyl-piperazin-1-yl)-nicotinonitrile as an off-white solid (172 mg, quant.).

AnalpH2_MeOH_4 min: Rt 1.77 min; m/z 231 [M+1]⁺.

The following substituted pyridine-carbonitrile derivatives are prepared using analogous procedures.

TABLE 3

| Substituted Amino-Pyridine-Carbonitrile Derivatives 3 of formula 12 | | |
|---|---|---|
| Compound | Analytical Data | Mass, % Yield, State |
| 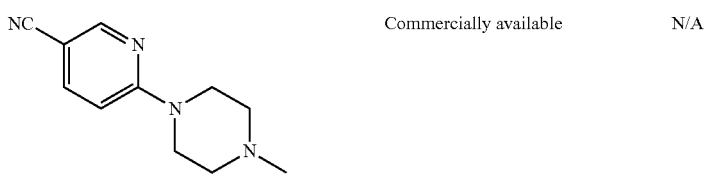 | AnalpH9_MeOH_4 min: Rt 2.55 min; m/z 231 [M + 1]⁺ | 157 mg, 91%, light brown crystalline solid |
| 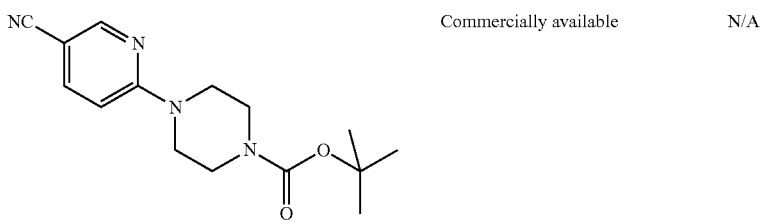 | Commercially available | N/A |
| | Commercially available | N/A |

TABLE 3-continued

Substituted Amino-Pyridine-Carbonitrile Derivatives 3 of formula 12

| Compound | Analytical Data | Mass, % Yield, State |
|---|---|---|
| (structure: 4-chloro-5-cyano-2-(4-methylpiperazin-1-yl)pyridine) | AnalpH9_MeOH_4 min: Rt 2.30 min; m/z 237 [M + 1]+ | 94 mg, 17%, yellow solid |
| (structure: tert-butyl 4-(5-cyano-3-fluoropyridin-2-yl)piperazine-1-carboxylate) | AnalpH2_MeOH_4 min: Rt 3.10 min; m/z not observed | 731 mg, 94%, yellow solid |
| (structure: 5-fluoro-6-(4-methylpiperazin-1-yl)nicotinonitrile) | AnalpH9_MeOH_4 min: Rt 1.80 min; m/z 221 [M + 1]+ | 496 mg, 88%, yellow solid |
| (structure: 6-(4-(2-(dimethylamino)ethyl)piperazin-1-yl)nicotinonitrile) | AnalpH9_MeOH_4 min: Rt 1.46 min; m/z 260 [M + 1]+ | 485 mg, 65%, yellow oil |
| (structure: 6-(4-(2-hydroxyethyl)piperazin-1-yl)nicotinonitrile) | AnalpH9_MeOH_4 min: Rt 1.85 min; m/z 233 [M + 1]+ | 350 mg, 70%, pale yellow solid |

TABLE 3-continued

Substituted Amino-Pyridine-Carbonitrile Derivatives 3 of formula 12

| Compound | Analytical Data | Mass, % Yield, State |
|---|---|---|
| (5-cyanopyridin-2-yl)-3-(dimethylamino)pyrrolidine | AnalpH9_MeOH_4 min: Rt 2.12 min; m/z 217 [M + 1]⁺ | 312 mg, 80%, light brown oil |
| (5-cyanopyridin-2-yl)-4-(dimethylamino)piperidine | AnalpH9_MeOH_4 min: Rt 2.22 min; m/z 231 [M + 1]⁺ | 449 mg, 87%, cream solid |
| 6-(4-cyclopropylpiperazin-1-yl)nicotinonitrile | AnalpH9_MeOH_4 min: Rt 2.56 min; m/z 229 [M + 1]⁺ | 340 mg, 85%, beige solid |
| 6-[(1,3-dihydroxypropan-2-yl)amino]nicotinonitrile | AnalpH2_MeOH_4 min(3): Rt 0.98 min; m/z 194 [M + 1]⁺ | Used in next step as crude material |

Synthesis of Nitrile Intermediates 3 of Formula 14 (required for Step B, Scheme A)

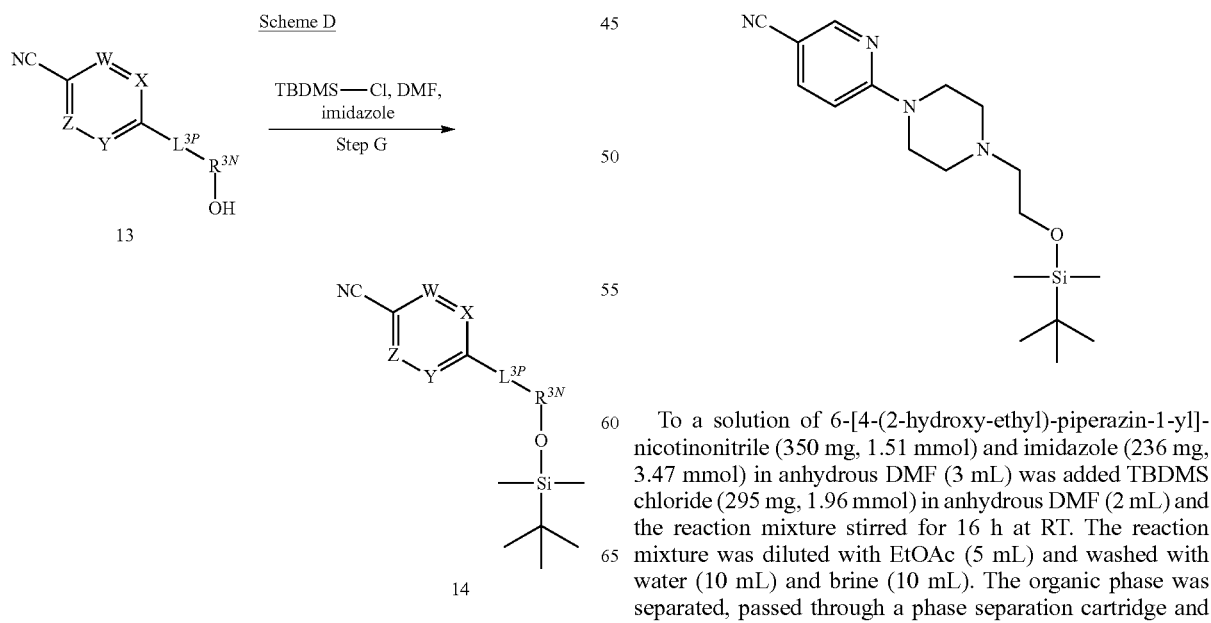

6-{4-[2-(tert-Butyl-dimethyl-silanyloxy)-ethyl]-piperazin-1-yl}-nicotinonitrile

To a solution of 6-[4-(2-hydroxy-ethyl)-piperazin-1-yl]-nicotinonitrile (350 mg, 1.51 mmol) and imidazole (236 mg, 3.47 mmol) in anhydrous DMF (3 mL) was added TBDMS chloride (295 mg, 1.96 mmol) in anhydrous DMF (2 mL) and the reaction mixture stirred for 16 h at RT. The reaction mixture was diluted with EtOAc (5 mL) and washed with water (10 mL) and brine (10 mL). The organic phase was separated, passed through a phase separation cartridge and concentrated in vacuo. The crude residue was purified on silica gel column chromatography eluting with 30% EtOAc/isohexane, and increasing the polarity to 50% EtOAc/isohexane to afford 6-{4-[2-(tert-butyl-dimethyl-silanyloxy)-ethyl]-piperazin-1-yl}-nicotinonitrile as a pale yellow solid (394 mg, 75%).

AnalpH2_MeOH_4 min: Rt 2.17 min; m/z 347 [M+1]$^+$.

The following TBDMS-protected nicotinonitrile derivatives are prepared using analogous procedures.

(2-Hydroxy-ethyl)-methyl-carbamic acid tert-butyl ester (400 mg, 2.28 mmol), TBDPS chloride (593 µL, 2.28 mmol) and imidazole (342 mg, 5.02 mmol) in DMF (2 mL) were stirred at RT for 12 h. The reaction mixture was diluted with brine and extracted with CH$_2$Cl$_2$. The combined organics were passed through a phase separation cartridge and concentrated in vacuo. The crude material was purified by silica gel column chromatography, eluting with isohexane and increasing the polarity to 50% EtOAc/isohexane to obtain [2-(tert-butyl-diphenyl-silanyloxy)-ethyl]-methyl-carbamic acid tert-butyl ester as a colourless oil (572 mg, 61%).

TABLE 4

Nitrile Intermediates 3 of formula 14

| Compound | Reference | Analytical Data | Mass, % Yield, State |
|---|---|---|---|
| 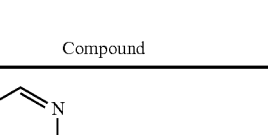 | Intermediate for IQ-219 | AnalpH2_MeOH_4 min(3): Rt 3.76 min; m/z 422 [M + 1]$^+$ | 1.34 g, 88%, white solid |

Synthesis of Nitrile Intermediates 3 of Formula 16
(Required for Step B, Scheme A)
Scheme E

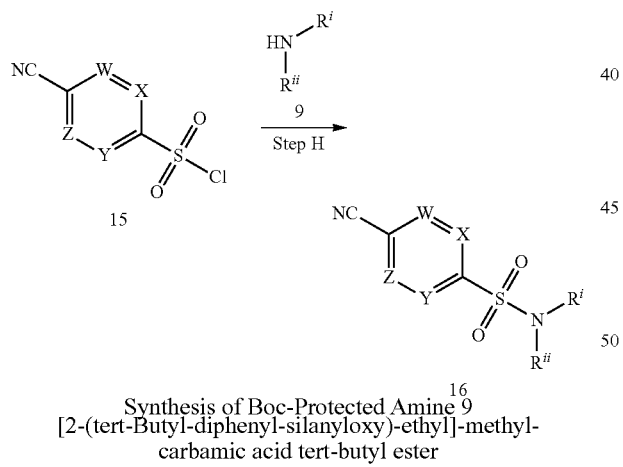

Synthesis of Boc-Protected Amine 9
[2-(tert-Butyl-diphenyl-silanyloxy)-ethyl]-methyl-carbamic acid tert-butyl ester

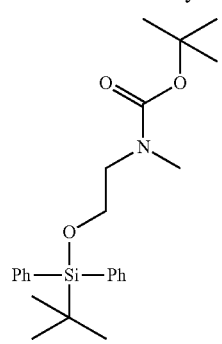

AnalpH2_MeOH_4 min(1): Rt 3.74 min; m/z 414 [M+1]$^+$.

[2-(tert-Butyl-diphenyl-silanyloxy)-ethyl]-methyl-amine

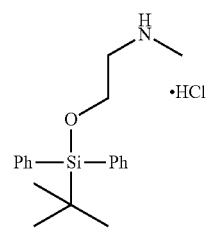

[2-(tert-Butyl-diphenyl-silanyloxy)-ethyl]-methyl-carbamic acid tert-butyl ester (572 mg, 1.38 mmol) and 4M HCl/dioxane (3 mL) in CH$_2$Cl$_2$ (5 mL) were stirred at RT for 3 h. The reaction mixture was concentrated in vacuo and the crude material was purified by silica gel column chromatography, eluting with CH$_2$Cl$_2$ and increasing the polarity to 10% MeOH/CH$_2$Cl$_2$ to obtain [2-(tert-butyl-diphenyl-silanyloxy)-ethyl]-methyl-amine as a yellow solid (105 mg, 21%).

Step H: Synthesis of Sulfonamide Derivatives 16

4-{[(4-Cyano-benzenesulfonyl)-methyl-amino]-methyl}-piperidine-1-carboxylic acid tert butyl ester

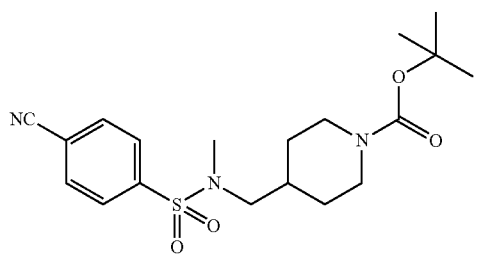 [SMILES: CN(CC1CCN(C(=O)OC(C)(C)C)CC1)S(=O)(=O)c1ccc(C#N)cc1]

To a stirred solution of 4-cyanobenzenesulfonyl chloride (411 mg, 2.2 mmol) in $CH_2Cl_2$ (10 mL) was added 4-methylaminomethyl-piperidine-1-carboxylic acid tert-butyl ester (500 mg, 2.2 mmol) and triethylamine (0.91 mL, 6.5 mmol) and the reaction stirred at RT for 2 h after which time silica was added and solvent removed. The crude residue was purified by silica gel chromatography eluting with isohexane, and increasing the polarity to 100% EtOAc to afford 4{[4-cyano-benzenesulfonyl)-methyl-amino]-methyl}-piperidine-1-carboxylic acid tert-butyl ester as a white solid (750 mg, 87%).

AnalpH2_MeOH_4 min(1): Rt 2.91 min; m/z 416 $[M+23]^+$.

The following substituted sulfonamide derivatives are prepared using analogous procedures.

TABLE 5

Sulfonamide Derivatives 3 of formula 16

| Compound | Reference | Analytical Data | Mass, % Yield, State |
|---|---|---|---|
|  |  | AnalpH2_MeOH_ 4 min: Rt 2.72 min; m/z 374 $[M + 23]^+$ | 669 mg, 96%, white solid |
|  | Commercially available |  | N/A |
|  |  | AnalpH2_MeOH_ 4 min(1): Rt 1.24 min; m/z 320 $[M + 1]^+$ | 300 mg, 94%, cream solid |
|  |  | AnalpH2_MeOH_ 4 min(1): Rt 2.29 min; m/z not observed | 310 mg, quant., white solid |
|  |  | AnalpH2_MeOH_ 4 min(1): Rt 2.07 min; m/z 268 $[M + 1]^+$ | 367 mg, quant., cream solid |

TABLE 5-continued

Sulfonamide Derivatives 3 of formula 16

| Compound | Reference | Analytical Data | Mass, % Yield, State |
|---|---|---|---|
| (NC-phenyl-SO₂-N-piperidine-N(CH₃)₂) | | AnalpH2_MeOH_ 4 min: Rt 1.80 min; m/z 294 [M + 1]⁺ | 560 mg, quant., white solid |
| (NC-phenyl-SO₂-N(CH₃)-CH₂-N-methylpiperidine) | | AnalpH2_MeOH_ 4 min: Rt 1.05 min; m/z 308 [M + 1]⁺ | 669 mg, quant., white solid |
| (NC-phenyl-SO₂-N(CH₃)-N-methylpiperidine) | | AnalpH9_MeOH_ 4 min(1): Rt 1.86 min; m/z 294 [M + 1]⁺ | 129 mg, 65%, yellow solid |
| (NC-phenyl-SO₂-N-methylpiperazine) | | AnalpH2_MeOH_ 4 min: Rt 0.85 min; m/z 266 [M + 1]⁺ | 268 mg, quant., off-white solid |
| (NC-phenyl-SO₂-N(CH₃)-CH₂CH₂-OTBDPS) | | AnalpH2_MeOH_ 4 min(1): Rt 3.49 min; m/z 479 [M + 1]⁺ | 131 mg, 91%, yellow solid |

Synthesis of Nitriles 3 of Formula 22

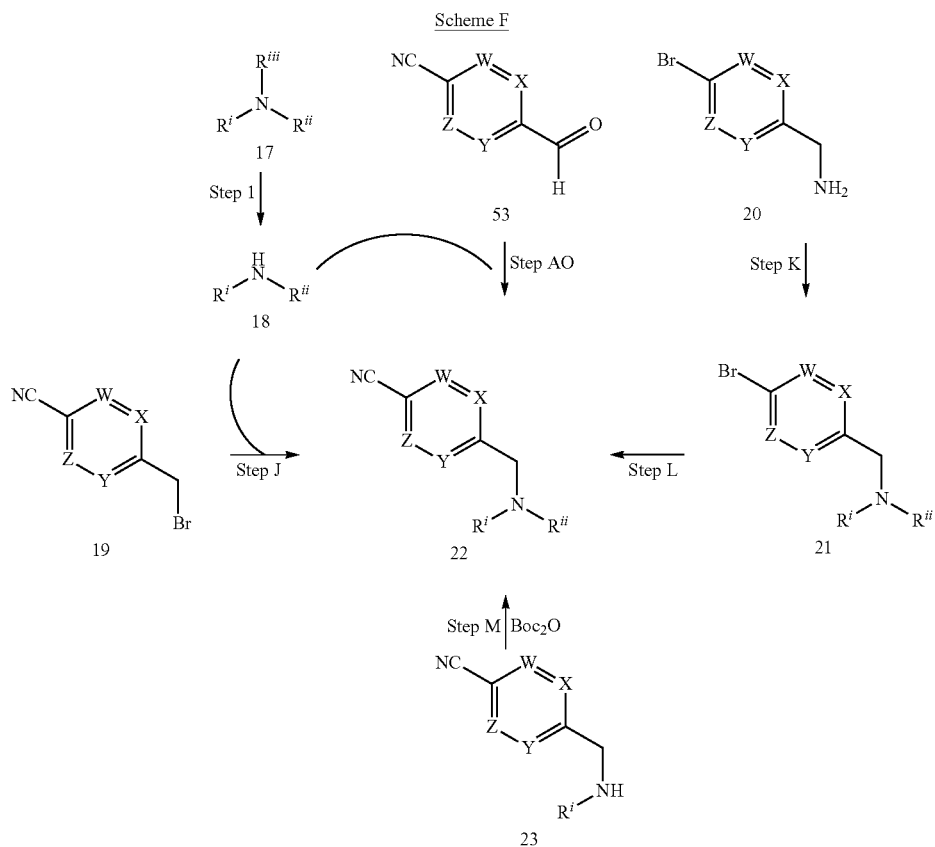

Scheme F, Step I: Synthesis of Amine Intermediates 18

4-(tert-Butyl-diphenyl-silanyloxy)-piperidine-1-carboxylic acid tert-butyl ester

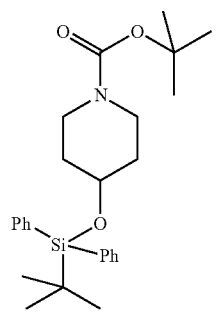 [SMILES: CC(C)(C)OC(=O)N1CCC(O[Si](c2ccccc2)(c2ccccc2)C(C)(C)C)CC1]

To a stirred solution of 4-hydroxy-piperidine-1-carboxylic acid tert-butyl ester (400 mg, 1.98 mmol) in DMF (2 mL) was added TBDPS chloride (0.52 mL, 1.98 mmol) and imidazole (297 mg, 4.47 mmol) and the reaction stirred at RT for 16 h afterwhich time the reaction mixture was diluted with brine (10 mL), washed with $CH_2Cl_2$ (3×25 mL) and the organics combined and dried through a phase separation cartridge and concentrated in vacuo. The crude material was purified by silica gel column chromatography, eluting with EtOAc and increasing the polarity to 30% EtOAc/isohexane to obtain 4-(tert-butyl-diphenyl-silanyloxy)-piperidine-1-carboxylic acid tert-butyl ester as a colourless oil (545 mg, 62%).

AnalpH2_MeOH_4 min(1): Rt 3.92 min; m/z 440 $[M+1]^+$.

The following substituted amine derivatives are prepared using analogous procedures.

TABLE 6

Boc-protected Amine Intermediates 17

| Compound | Code | Analytical Data | Mass, % Yield, State |
|---|---|---|---|
| | IQ-167 | AnalpH2_MeOH_ 4 min(3): Rt 3.68 min; m/z 412 $[M + 1]^+$ | 2.14 g, 90%, colourless oil |

TABLE 6-continued

Boc-protected Amine Intermediates 17

| Compound | Code | Analytical Data | Mass, % Yield, State |
|---|---|---|---|
| 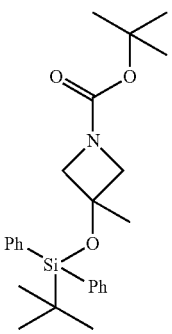 [SMILES: CC(C)(C)OC(=O)N1CC(C)(O[Si](c2ccccc2)(c2ccccc2)C(C)(C)C)C1] | IQ-172 | AnalpH2_MeOH_ 4 min(3): Rt 3.75 min; m/z 326 [M − (Boc)]⁺ | 1.07 g, 95%, colourless oil |

4-(tert-Butyl-diphenyl silanyloxy)-piperidine

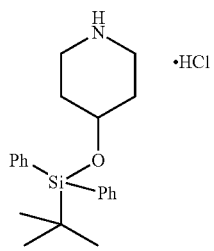 [SMILES: CC(C)(C)[Si](OC1CCNCC1)(c1ccccc1)c1ccccc1 ; Cl]

To 4-(tert-butyl-diphenyl-silanyloxy)-piperidine-1-carboxylic acid tert-butyl ester (54 mg, 0.124 mmol) was added 4M HCl/dioxane (2 mL) and CH₂Cl₂ (5 mL). The reaction mixture was stirred at RT for 2 h. 4M HCl/dioxane (3 mL) added and reaction stirred for a further 1 hr. The reaction mixture was concentrated in vacuo. The crude material was purified by silica gel column chromatography eluting with CH₂Cl₂ and increasing the polarity to 10% MeOH/CH₂Cl₂ to obtain 4-(tert-butyl-diphenyl silanyloxy)-piperidine as a cream foam (370 mg, 79%).

AnalpH2_MeOH_4 min(1): Rt 2.54 min; m/z 340 [M+1]⁺.

The following substituted amine derivatives are prepared using analogous procedures.

TABLE 7

Boc-deprotected Amine Intermediates 18

| Compound | Reference | Analytical Data | Mass, % Yield, State |
|---|---|---|---|
| 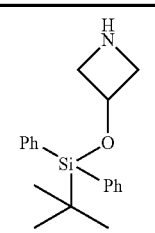 | Intermediate for IQ-167 or IQ-169 | AnalpH2_MeOH_ 4 min(3): Rt 2.39 min; m/z 312 [M + 1]⁺ | 950 mg, 59%, pale oil |
| 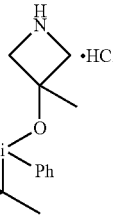 | Intermediate for IQ-172 | AnalpH2_MeOH_ 4 min(3): Rt 2.46 min; m/z 326 [M + 1]⁺ | 188 mg, 21%, white solid |

Scheme F, Step J: Synthesis of Nitrile Intermediates 3 of Formula 22 (via Bromide displacement)

(3aS,6aR)-5-(4-Cyano-benzyl)-hexahydro-pyrrolo[3,4-c]pyrrole-2-carboxylic acid tert-butyl ester

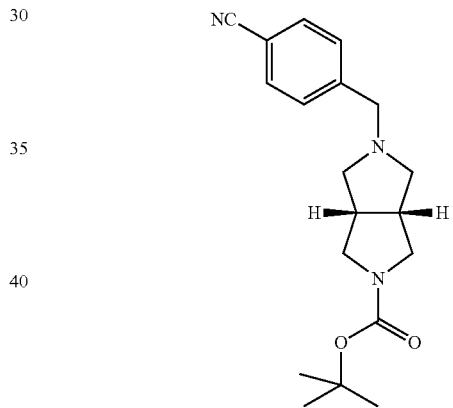

To 4-(bromomethyl)benzonitrile (277 mg, 1.41 mmol) was added hexahydro-pyrrolo[3,4-c]pyrrole-2-carboxylic acid (300 mg, 1.41 mmol), potassium carbonate (215 mg, 1.55 mmol) and acetone (7 mL) and the reaction mixture stirred for 16 h. The reaction mixture was concentrated in vacuo, dissolved in CH₂Cl₂ (4 mL) and washed with water (4 mL).

The organic phase was separated and the aqueous layer washed with CH₂Cl₂ (4 mL). The organic phases were combined, passed through a phase separation cartridge and concentrated in vacuo. The crude material was purified by silica gel column chromatography, eluting with CH₂Cl₂ and increasing the polarity to 3.5% MeOH/CH₂Cl₂ to obtain (3aS, 6aR)-5-(4-cyano-benzyl)-hexahydro-pyrrolo[3,4-c]pyrrole-2-carboxylic acid tert-butyl ester as a yellow oil (278 mg, 60%).

AnalpH2_MeOH_4 min(1): Rt 1.54 min; m/z 328 [M+1]⁺.

The following nitrile derivatives are prepared using analogous procedures.

TABLE 8

Nitrile Intermediates 3 of formula 22

| Compound | Reference | Analytical Data | Mass, % Yield, State |
|---|---|---|---|
| 4-cyanobenzyl-substituted 3-oxo-piperazine-1-carboxylic acid tert-butyl ester | | AnalpH2_MeOH_4 min(1): Rt 2.53 min; m/z 316 [M + 1]⁺ | 630 mg, 100%, white solid |
| 4-(1-(4-cyanophenyl)ethyl)piperazine-1-carboxylic acid tert-butyl ester | | AnalpH2_MeOH_4 min(1): Rt 1.82 min; m/z 316 [M + 1]⁺ | 220 mg, 73%, colourless oil |
| 4-(4-cyanobenzyl)-2,5-dimethylpiperazine-1-carboxylic acid benzyl ester | | AnalpH2_MeOH_4 min(1): Rt 2.51 min; m/z 364 [M + 1]⁺ | 197 mg, 85%, colourless oil |
| 4-(4-cyanobenzyl)-2,6-dimethylpiperazine-1-carboxylic acid tert-butyl ester | | AnalpH2_MeOH_4 min(1): Rt 3.20 min; m/z 330 [M + 1]⁺ | 280 mg, 83%, colourless oil |
| 4-(4-cyanobenzyl)-1,4-diazepane-1-carboxylic acid tert-butyl ester | | AnalpH2_MeOH_4 min(1): Rt 1.55 min; m/z 316 [M + 1]⁺ | 294 mg, 92%, colourless oil |

TABLE 8-continued

Nitrile Intermediates 3 of formula 22

| Compound | Reference | Analytical Data | Mass, % Yield, State |
|---|---|---|---|
| (4-cyanobenzyl) 2,5-diazabicyclo[2.2.1]heptane, N-Boc | | AnalpH2_MeOH_4 min: Rt 1.43 min; m/z 314 [M + 1]⁺ | 445 mg, 69%, colourless oil |
| 4-(4-cyanobenzyl)-2-methylpiperazine-1-carboxylic acid tert-butyl ester | | AnalpH2_MeOH_4 min: Rt 2.54 min; m/z 316 [M + 1]⁺ | 550 mg, 85%, colourless oil |
| 4-(4-cyanobenzyl)-3-methylpiperazine-1-carboxylic acid tert-butyl ester | | AnalpH2_MeOH_4 min: Rt 1.85 min; m/z 316 [M + 1]⁺ | 420 mg, 65%, white solid |
| 4-(4-cyanobenzyl)piperazine-1-carboxylic acid tert-butyl ester | Commercially available | | N/A |
| 4-((dimethylamino)methyl)benzonitrile | Commercially available | | N/A |

TABLE 8-continued

Nitrile Intermediates 3 of formula 22

| Compound | Reference | Analytical Data | Mass, % Yield, State |
|---|---|---|---|
| NC-C6H3(F)-CH2-N(pyrrolidine) | | AnalpH9_MeOH_ 4 min: Rt 2.51 min; m/z 205 [M + 1]+ | 760 mg, 80%, pale yellow liquid |
| NC-C6H4-CH2-N(N-methylpiperazine) | Commercially available | | N/A |
| NC-C6H4-CH(CH3)-N(N-methylpiperazine) | | AnalpH9_MeCN_ 4 min; Rt 1.83 min; m/z 230 [M + 1]+ | 189 mg, 89%, colourless oil |
| NC-C6H4-CH2-N(4-methyl-3-oxopiperazine) | | AnalpH9_MeCN_ 4 min(1): Rt 1.39 min; m/z 230 [M + 1]+ | 1.02 g, 85%, orange oil |
| NC-C6H4-CH2-N(4-methyl-1,4-diazepane) | | AnalpH9_MeOH_ 4 min(1): Rt 1.81 min; m/z 230 [M + 1]+ | 150 mg, 64%, colourless oil |

TABLE 8-continued
Nitrile Intermediates 3 of formula 22
| Compound | Reference | Analytical Data | Mass, % Yield, State |
|---|---|---|---|
| 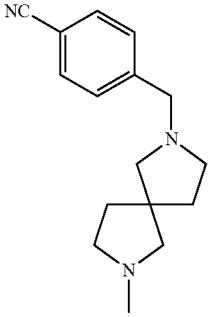 [SMILES: CN1CCC2(CCN(Cc3ccc(C#N)cc3)C2)C1] | | AnalpH9_MeCN_4 min(1): Rt 1.72 min; m/z 256 [M + 1]+ | 63 mg, 15%, brown oil |
| 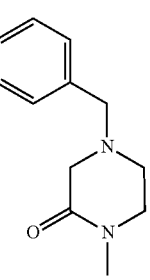 | | AnalpH2_MeOH_4 min(1): Rt 1.47 min; m/z 230 [M + 1]+ | 212 mg, 45%, orange glass |
| 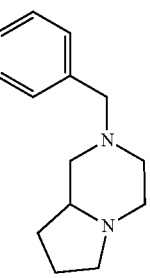 | | AnalpH9_MeCN_4 min: Rt 1.94 min; m/z 242 [M + 1]+ | 171 mg, 34%, pale orange oil |
| 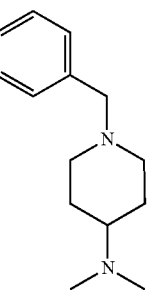 | | AnalpH9_MeCN_4 min: Rt 1.72 min; m/z 244 [M + 1]+ | 231 mg, 37%, white solid |
| 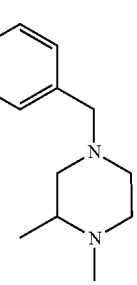 | | AnalpH2_MeOH_4 min: Rt 0.95 min, m/z 230 [M + 1]+ | 110 mg, 23%, orange oil |

TABLE 8-continued

Nitrile Intermediates 3 of formula 22

| Compound | Reference | Analytical Data | Mass, % Yield, State |
|---|---|---|---|
| NC-C6H4-CH2-N(piperazine)-cyclopropyl | | AnalpH9_MeCN_4 min: Rt 2.19 min; m/z 242 [M + 1]+ | 68 mg, 13%, pale orange oil |
| NC-C6H4-CH2-N(piperidine) | | AnalpH2_MeOH_4 min: Rt 0.34, 0.74 min; m/z 201 [M + 1]+ | 700 mg, 68%, pale yellow liquid |
| NC-C6H4-CH2-N(pyrrolidine) | | AnalpH2_MeOH_4 min: Rt 0.33, 0.57 min; m/z 187 [M + 1]+, 373 [2M + 1]+ | 700 mg, 73%, pale yellow liquid |
| NC-C6H4-CH2-N(morpholine) | Commercially available | | N/A |
| NC-C6H4-CH2-N(piperidine)-O-Si(Ph)2(tBu) | | AnalpH2_MeOH_4 min(1): Rt 2.69 min; m/z 455 [M + 1]+ | 360 mg, 80%, yellow glass |
| NC-C6H4-CH2-N(bicyclic diamine)-Boc | | AnalpH2_MeOH_4 min: Rt 2.82 min; m/z 328 [M + 1]+ | 194 mg, 100%, cream solid |

TABLE 8-continued

Nitrile Intermediates 3 of formula 22

| Compound | Reference | Analytical Data | Mass, % Yield, State |
|---|---|---|---|
| | Intermediate for IQ-167 | AnalpH2_MeOH_4 min(3): Rt 2.56 min; m/z 427 [M + 1]+ | 180 mg, 28%, colourless glass |
| | Commercially available | | N/A |
| | Commercially available | | N/A |
| | Intermediate for IQ-169 | AnalpH2_MeOH_4 min(3): Rt 2.75 min; m/z 445 [M + 1]+ | 50 mg, 6%, yellow oil |
| | Intermediate for IQ-173 | AnalpH2_MeOH_4 min(3): Rt 0.39 min; m/z 230 [M + 1]+ | 414 mg, 51%, orange oil |
| | Intermediate for IQ-174 | AnalpH9_MeOH_4 min(2): Rt 0.39 min; m/z 230 [M + 1]+ | 469 mg, 65%, bright yellow oil |
| | Commercially available | | N/A |

Synthesis of Nitriles 3 of Formula 22

Scheme F, Step K: Synthesis of Aryl Bromide Intermediates 21 (via Amine dialkylation)

1-[1-(4-Bromo-phenyl)-1-methyl-ethyl]-4-(toluene-4-sulfonyl)-piperazine

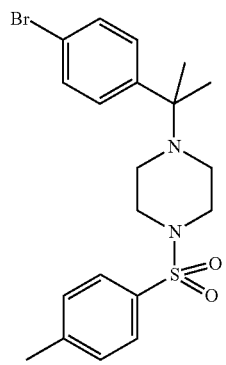 [SMILES: Cc1ccc(S(=O)(=O)N2CCN(C(C)(C)c3ccc(Br)cc3)CC2)cc1]

To a solution of 1-(4-bromo-phenyl)-1-methyl-ethylamine (400 mg, 1.84 mmol) in diisopropylethylamine (4 mL) was added N,N-bis(2-chloroethyl)-4-methylbenzene sulphonamide (500 mg, 1.68 mmol) and the reaction subjected to microwave irradiation at 150° C. for 9 h afterwhich time the reaction was concentrated in vacuo and the crude residue purified by reverse phase preparative HPLC-MS to afford 1-[1-(4-bromo-phenyl)-1-methyl-ethyl]-4-(toluene-4-sulfonyl)-piperazine as a peach solid (375 mg, 47%).
AnalpH2_MeOH_4 min(1): RT 3.04 min; m/z 437/439 [M+1]+.

Scheme F, Step L: Synthesis of Nitrile Intermediates 22

4-{1-Methyl-1-[4-(toluene-4-sulfonyl)-piperazin-1-yl]-ethyl}-benzonitrile

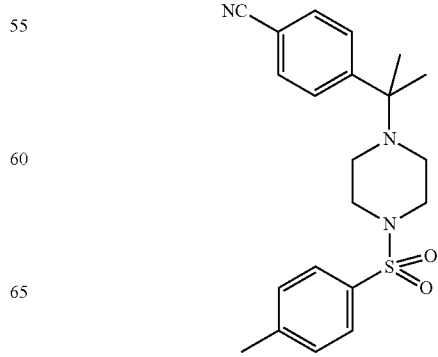

To a solution of 1-[1-(4-bromo-phenyl)-1-methyl-ethyl]-4-(toluene-4-sulfonyl)-piperazine (200 mg, 0.45 mmol) in DMF (3 mL) was added zinc cyanide (64.41 mg, 0.54 mmol) and tetrakis(triphenylphosphine)palladium(0) (52 mg, 0.045 mmol) and the reaction mixture degassed for 10 min under $N_2$. The reaction mixture was then subjected to microwave irradiation for 30 min at 180° C., afterwhich time the reaction was diluted with 1:1 $CH_2Cl_2$/EtOAc (20 mL), washed with water (2×10 mL), passed through a phase separation cartridge and concentrated in vacuo. The crude residue was purified by reverse phase preparative HPLC-MS to afford 4-{1-methyl-1-[4-(toluene-4-sulfonyl)-piperazin-1-yl]-ethyl]-benzonitrile as a cream solid (70 mg, 47%).

AnalpH2_MeOH_4 min(1): Rt 2.78 min; m/z 384 [M+1]$^+$.

Scheme F, Step M: Synthesis of Nitrile Intermediates 22 (via BOC Protection)

(4-Cyano-benzyl)-methyl-carbamic acid tert-butyl ester

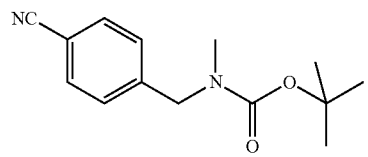 [SMILES: CN(Cc1ccc(C#N)cc1)C(=O)OC(C)(C)C]

To 4-[(methylamine)methyl]benzonitrile (1 g, 6.8 mmol) in $CH_2Cl_2$ (50 mL) was added DMAP (0.93 g, 7.6 mmol), di-tert-butyl dicarbonate (1.7 g, 7.6 mmol) and the reaction stirred for 48 h at RT. The reaction mixture was washed with saturated, aqueous $NaHCO_3$ and brine. The organic phase was separated and concentrated in vacuo. The crude residue was purified on silica gel chromatography eluting with isohexane, and increasing the polarity to 20% EtOAc/isohexane to afford (4-cyano-benzyl)-methyl-carbamic acid tert-butyl ester as a colourless oil (1.48 g, 89%).

AnalpH2_MeOH_4 min: Rt 2.75 min; m/z 247 [M+1]$^+$.

Scheme F, Step AO: Synthesis of Nitrile Intermediates 22 (via Reductive Amination)

4-[3-(tert-Butyl-diphenyl-silanyloxy)-3-methyl-azetidin-1-ylmethyl]-benzonitrile

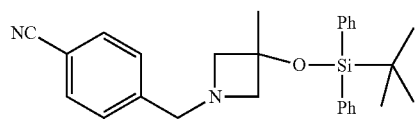 [SMILES: CC1(O[Si](c2ccccc2)(c2ccccc2)C(C)(C)C)CN(Cc2ccc(C#N)cc2)C1]

To a stirred solution of 4-formylbenzonitrile (68 mg, 0.51 mmol) and 3-(tert-Butyl-diphenyl-silanyloxy)-3-methyl-azetidine hydrochloride (188 mg, 0.51 mmol) in 1:1 MeOH/DMF (26 mL) was added acetic acid (catalytic). The reaction mixture was stirred under $N_2$ at 0° C. for 1 h. Sodium cyanoborohydride (1M in THF, 0.6 mL, 0.57 mmol) was added and the reaction mixture stirred at RT, under $N_2$ for 18 h. The reaction mixture was concentrated in vacuo, the residue suspended in $H_2O$ (10 mL), washed with $CH_2Cl_2$ (2×10 mL) and the solution passed through a phase separation cartridge. The combined organic layers were concentrated in vacuo and the crude residue purified by silica gel chromatography eluting with 100% isohexane and increasing the polarity 100% EtOAc to afford 4-[3-(tert-butyl-diphenyl-silanyloxy)-3-methyl-azetidin-1-ylmethyl]-benzonitrile as a colourless oil (196 mg, 86%).

AnalpH2_MeOH_4 min(3): Rt 2.71 min; m/z 441 [M+1]$^+$.

Synthesis of Nitrile Intermediates 3 of Formula 26 (Required for Step B, Scheme A)

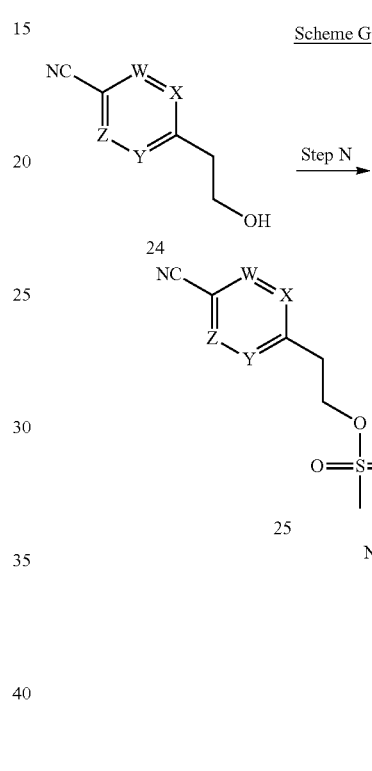

Scheme G, Step N: Mesylation of Alcohol 24

4-Cyano phenethyl methanesulfonate

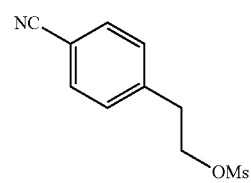 [SMILES: CS(=O)(=O)OCCc1ccc(C#N)cc1]

To a solution of 4-(2-hydroxy-ethyl)-benzonitrile (2 g, 13.6 mmol) in $CH_2Cl_2$ (10 mL) was added $Et_3N$ (6.8 mL, 47.52 mmol) and mesyl chloride (1.4 mL, 17.63 mmol) at 0° C. and stirred for 2 h. The reaction mixture was diluted with $CH_2Cl_2$ (30 mL), washed with saturated $NaHCO_3$ solution (2×10 mL), the organic layer was dried over $Na_2SO_4$, filtered and concentrated in vacuo to obtain 4-cyano phenethyl methanesulfonate (3 g) as a pale yellow gummy liquid. The crude compound was used for the next step without further purification.

R$_f$: 0.6 (50% EtOAc/petroleum ether 60-80).

Scheme G, Step O: Synthesis of Amines (Via Mesylate Displacement)

4-(2-Morpholinoethyl)benzonitrile

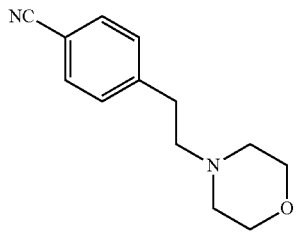 [SMILES: N#Cc1ccc(CCN2CCOCC2)cc1]

To a stirred solution of 4-cyano phenethyl methanesulfonate (6.04 mmol) in CH$_2$Cl$_2$ (10 mL) at 0° C. was added morpholine (3.5 g, 40.22 mmol) and heated 50° C. for 16 h. The reaction mixture was diluted with CH$_2$Cl$_2$ (100 mL), washed with saturated NaHCO$_3$ solution (2×10 mL), the organic layer was dried over Na$_2$SO$_4$ and concentrated in vacuo. The crude material was purified by silica gel column chromatography, eluting with 3% MeOH/CHCl$_3$ to obtain 4-(2-morpholinoethyl)benzonitrile as a pale yellow solid (700 mg, 48%).

$^1$H NMR (400 MHz, CDCl$_3$): δ 7.58 (d, J=8 Hz, 2H), 7.30 (d, J=8 Hz, 2H), 3.72 (t, J=4.8 Hz, 4H), 2.85 (t, J=8 Hz, 2H), 2.61-2.49 (6H, m).

AnalpH9_MeOH_4 min: Rt 2.20 min; m/z 217 [M+1]$^+$.

The following nitrile derivatives are prepared using analogous procedures.

Scheme A, Step B (Protocol 1): Synthesis of Boc-Protected 2H-isoquinolin-1-one Derivatives of Formula 4

4-({Methyl-[4-(5-methyl-1-oxo-1,2-dihydro-isoquinolin-3-yl)-benzoyl]-amino}-methyl)-piperidine-1-carboxylic acid tert-butyl ester (IQ-092)

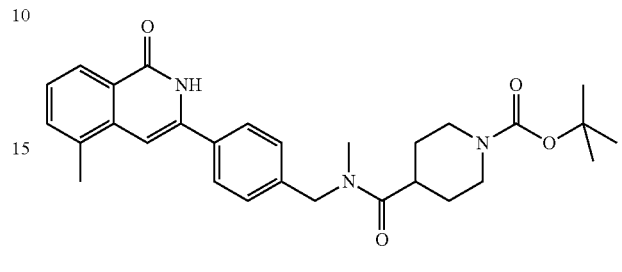

N,N-Diethyl-2,3-dimethyl-benzamide (200 mg, 0.97 mmol) was dissolved in anhydrous THF (4 mL) under a N$_2$ and cooled to −78° C. n-BuLi (2.5M in n-hexanes, 0.82 mL, 2.04 mmol) was added dropwise to yield a deep red coloured solution and the reaction mixture was stirred at −78° C. for 30 minutes. 4-{[(4-Cyano-benzoyl)-methyl-amino]-methyl}-piperidine-1-carboxylic acid tert-butyl ester (348 mg, 0.97 mmol) was dissolved in anhydrous THF (4 mL) and added dropwise, and the reaction stirred at −78° C. for 2 h. The reaction mixture was quenched with ice/water, allowed to warm to RT and extracted with CH$_2$Cl$_2$ and EtOAc. The combined organic phase was passed through a phase separation cartridge and concentrated in vacuo. The crude compound was triturated with isohexane/diethyl ether (80:20), the solid filtered and dried in vacuo to give 4-({methyl-[4-(5-methyl-1-oxo-1,2-dihydro-isoquinolin-3-yl)-benzoyl]-amino}-methyl)-piperidine-1-carboxylic acid tert-butyl ester as a light beige solid (171 mg, 36%).

TABLE 9

Nitrile Intermediates 3 of formula 26

| Compound | Analytical Data | Mass, % Yield, State |
|---|---|---|
| NC-phenyl-CH$_2$CH$_2$-pyrrolidine | AnalpH9_MeOH_4 min: Rt 2.39 min; m/z 201 [M + 1]$^+$ | Pale yellow solid |
| NC-phenyl-CH$_2$CH$_2$-piperazine-N-cyclopropyl | AnalpH9_MeOH_4 min: Rt 2.62 min; m/z 256 [M + 1]$^+$ | Pale yellow solid |

AnalpH2_MeOH_QC(Sunfire1): Rt 7.81 min; m/z 490 [M+1]⁺.

4-(5-Chloro-1-oxo-1,2-dihydro-isoquinolin-3-yl)-N-(1-methyl-piperidin-4-ylmethyl)-benzamide (IQ-091)

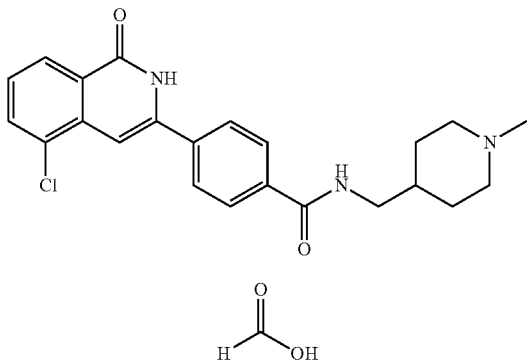

3-Chloro-N,N-diethyl-2-methyl-benzamide (150 mg, 0.66 mmol) was dissolved in anhydrous THF (2 mL) under N$_2$ and cooled to −78° C. n-BuLi (2.5M in n-hexanes, 558 µL, 1.39 mmol) was added dropwise and the reaction mixture was stirred at −78° C. for 30 minutes. 4-Cyano-N-(1-methyl-piperidin-4-ylmethyl)-benzamide (180 mg, 0.66 mmol) in anhydrous THF (2 mL) was added dropwise to the reaction mixture and stirred at −78° C. continued for 1 h. The reaction mixture was poured into ice/water, allowed to warm to RT and extracted with CH$_2$Cl$_2$ (×3) and the organic phase dried (MgSO$_4$). The solution was filtered and concentrated in vacuo. The crude material was purified by reverse phase preparative HPLC-MS to afford 4-(5-chloro-1-oxo-1,2-dihydro-isoquinolin-3-yl)-N-(1-methyl-piperidin-4-ylmethyl)-benzamide as a white solid (37 mg, 13%).

$^1$H NMR (400 MHz, DMSO-d$_6$): δ11.91 (br s, 1H), 8.25 (s, formic acid, 1H), 8.21 (d, J=8. Hz, 1H), 7.9 (dd, J=8 Hz, 1H), 7.85 (d, J=8 Hz, 2H), 7.53 (d, J=8 Hz, 1H), 7.51 (t, J=8 Hz, 1H), 7.46 (d, J=8 Hz, 1H), 6.97 (s, 1H), 3.42-3.38 (m, 1H), 3.20-3.12 (m, 1H), 2.95 (s, 1H), 2.90 (s, 2H), 2.82-2.78 (m, 1H), 2.68-2.64 (m, 1H), 2.18 (s, 2H), 2.09 (s, 1H), 1.86-1.92 (m, 1H), 1.79-1.81 (m, 1H), 1.68-1.65 (m, 2H), 1.49-1.42 (m, 1H), 1.30-1.23 (m, 1H), 0.90-0.79 (m, 1H).

AnalpH2_MeOH_QC: Rt 5.70 min; m/z 424 [M+1]⁺.

TABLE 10

2H-Isoquinolin-1-one Derivatives of Formula 4

| Compound | Code | Analytical Data | Mass, % Yield, State |
|---|---|---|---|
|  | IQ-145 | AnalpH2_MeOH_QC (Sunfire 1): Rt 8.08 min; m/z 510 [M + 1]⁺ | 142 mg, 31%, light beige solid |
|  | IQ-101 | AnalpH2_MeOH_QC: Rt 5.21 min; m/z 382 [M + 1]⁺ | 10 mg, 3%, pale yellow solid |

TABLE 10-continued

2H-Isoquinolin-1-one Derivatives of Formula 4

| Compound | Code | Analytical Data | Mass, % Yield, State |
|---|---|---|---|
| (structure) | IQ-102 | AnalpH2_MeOH_QC: Rt 5.08 min; m/z 407 [M + 1]⁺ | 24 mg, 5%, beige solid |
| (structure) | IQ-103 | AnalpH2_MeOH_QC: Rt 5.33 min; m/z 410 [M + 1]⁺ | 5 mg, 3%, white solid |
| (structure) | IQ-104 | AnalpH2_MeOH_QC: Rt 4.93 min; m/z 362 [M + 1]⁺ | 27 mg, 9%, white solid<br>$^1$H NMR (400 MHz, DMSO-$d_6$): δ 11.61 (br s, 1H), 8.09 (d, J = 7.8 Hz, 1H), 7.90 (d, J = 8.6 Hz, 2H), 7.58 (d, J = 7.3 Hz, 1H), 7.50 (d, J = 8.6 Hz, 2H), 7.4 (t, J = 7.8 Hz, 1H), 6.92 (s, 1H), 3.63 (br s, 2H), 3.38 (br s, 2H), 2.57 (s, 3H), 2.34 (br s, 4H), 2.21 (s, 3H). |
| (structure) | IQ-001 | AnalpH2_MeOH_QC: Rt 8.49 min; m/z 279 [M + 1]⁺ | 143 mg, 64%, pale yellow solid |

TABLE 10-continued

2H-Isoquinolin-1-one Derivatives of Formula 4

| Compound | Code | Analytical Data | Mass, % Yield, State |
|---|---|---|---|
| | IQ-013 | AnalpH2_MeOH_QC: Rt 8.84 min; m/z 420 [M + 1]$^+$ | 123 mg, 43%, yellow solid |
| | IQ-010 | AnalpH2_MeOH_QC: Rt 9.14 min; m/z 440 [M + 1]$^+$ | 231 mg, 60%, cream solid |
| | IQ-042 | AnalpH2_MeOH_4 min: Rt 5.21 min; m/z 349 [M + 1]$^+$ | 46 mg, 26%, off-white solid |
| | IQ-041 | AnalpH2_MeOH_4 min: Rt 5.30 min; m/z 333 [M + 1]$^+$ | 30 mg, 9%, off-white solid |

TABLE 10-continued
2H-Isoquinolin-1-one Derivatives of Formula 4
| Compound | Code | Analytical Data | Mass, % Yield, State |
|---|---|---|---|
| 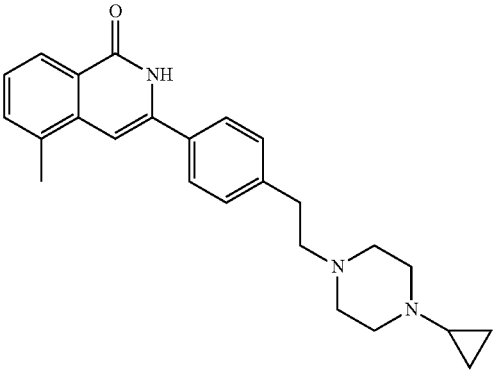 [SMILES: Cc1cccc2c(=O)[nH]c(-c3ccc(CCN4CCN(C5CC5)CC4)cc3)cc12] | IQ-137 | AnalpH2_MeOH_4 min: Rt 5.55 min; m/z 388 [M + 1]+ | 12 mg, 6%, white solid |
| 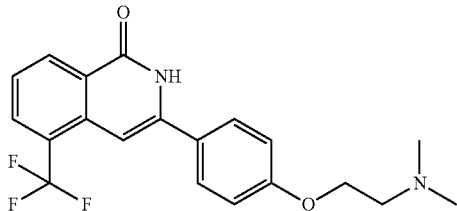 [SMILES: CN(C)CCOc1ccc(-c2cc3c(C(F)(F)F)cccc3c(=O)[nH]2)cc1] | IQ-131 | AnalpH2_MeOH_QC: Rt 5.74 min; m/z 377 [M + 1]+ | 22 mg, 10%, pale brown gum |
| 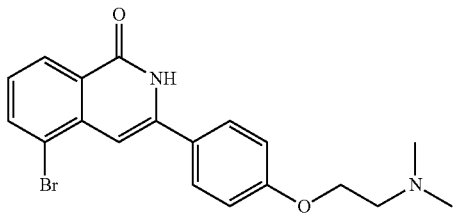 [SMILES: CN(C)CCOc1ccc(-c2cc3c(Br)cccc3c(=O)[nH]2)cc1] | IQ-132 | AnalpH2_MeOH_QC: Rt 5.69 min; m/z 387 [M + 1]+ | 1.23 g, 86%, cream solid |
| 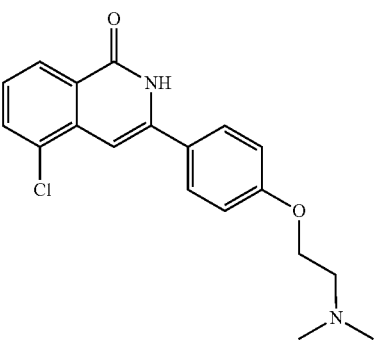 [SMILES: CN(C)CCOc1ccc(-c2cc3c(Cl)cccc3c(=O)[nH]2)cc1] | IQ-128 | AnalpH2_MeOH_QC: Rt 5.59 min; m/z 343 [M + 1]+ | 86 mg, 32%, beige solid |
| 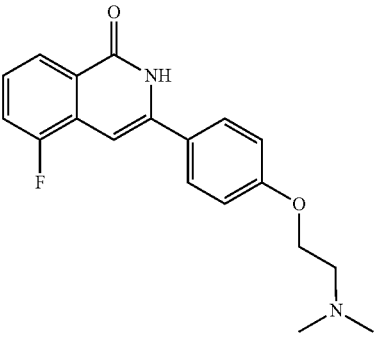 [SMILES: CN(C)CCOc1ccc(-c2cc3c(F)cccc3c(=O)[nH]2)cc1] | IQ-129 | AnalpH2_MeOH_QC: Rt 5.21 min; m/z 327 [M + 1]+ | 135 mg, 52%, beige solid |

TABLE 10-continued
2H-Isoquinolin-1-one Derivatives of Formula 4
| Compound | Code | Analytical Data | Mass, % Yield, State |
|---|---|---|---|
| 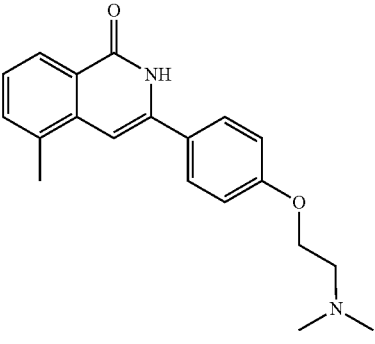 [SMILES: Cc1cccc2c(=O)[nH]c(-c3ccc(OCCN(C)C)cc3)cc12] | IQ-130 | AnalpH2_MeOH_QC: Rt 5.27 min; m/z 323 [M + 1]⁺ | 101 mg, 40%, pale yellow solid |
| 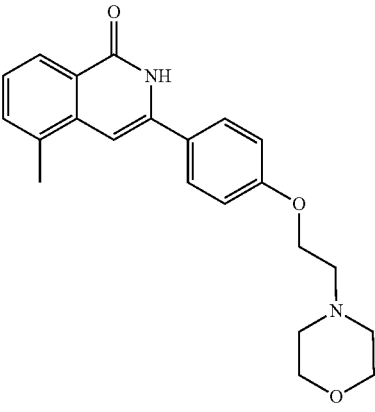 [SMILES: Cc1cccc2c(=O)[nH]c(-c3ccc(OCCN4CCOCC4)cc3)cc12] | IQ-133 | AnalpH2_MeOH_QC: Rt 5.37 min; m/z 365 [M + 1]⁺ | 230 mg, 63%, white solid |
| 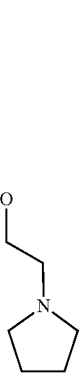 | IQ-134 | AnalpH2_MeOH_QC: Rt 5.53 min; m/z 349 [M + 1]⁺ | 42 mg, 24%, off-white solid |
| 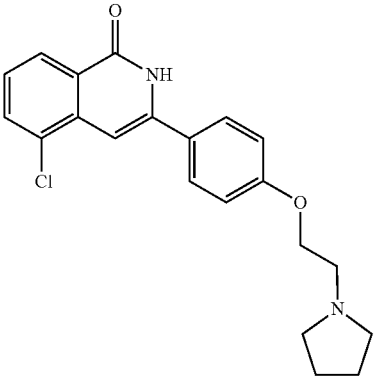 [SMILES: O=c1[nH]c(-c2ccc(OCCN3CCCC3)cc2)cc2c(Cl)cccc12] | IQ-135 | AnalpH2_MeOH_QC: Rt 8.84 min; m/z 369 [M + 1]⁺ | 40 mg, 22%, off-white solid |

TABLE 10-continued

2H-Isoquinolin-1-one Derivatives of Formula 4

| Compound | Code | Analytical Data | Mass, % Yield, State |
|---|---|---|---|
| | IQ-003 | AnalpH2_MeOH_QC: Rt 5.16 min; m/z 335 [M + 1]⁺ | 14 mg, 4%, off-white solid |
| | IQ-002-1 | AnalpH2_MeOH_QC: Rt 5.45 min; m/z 355 [M + 1]⁺ | 196 mg, 84%, pale yellow solid |
| | IQ-153 | AnalpH9_MeOH_QC: Rt 8.51 min; m/z 421 [M + 1]⁺ | 24 mg, 6%, yellow solid |
| | IQ-136 | AnalpH2_MeOH_QC: Rt 8.79 min; m/z 441 [M + 1]⁺ | 126 mg, 29%, off-white solid |
| | IQ-144 | AnalpH2_MeOH_QC: Rt 5.55 min; m/z 369 [M + 1]⁺ | 5.5 mg, 4%, white solid |

TABLE 10-continued

2H-Isoquinolin-1-one Derivatives of Formula 4

| Compound | Code | Analytical Data | Mass, % Yield, State |
|---|---|---|---|
| | IQ-139 | AnalpH2_MeOH_QC: Rt 9.37 min; m/z 459 [M + 1]$^+$ | 139 mg, 34%, orange solid |
| | IQ-020 | AnalpH2_MeOH_QC: Rt 9.03 min; m/z 439 [M + 1]$^+$ | 63 mg, 15%, cream solid |
| | IQ-021 | AnalpH2_MeOH_QC: Rt 5.37 min; m/z 353 [M + 1]$^+$ | 8 mg, 3%, cream solid |
| | IQ-022 | AnalpH2_MeOH_QC: Rt 5.69 min; m/z 373 [M + 1]$^+$ | 56 mg, 23%, cream solid |

TABLE 10-continued

2H-Isoquinolin-1-one Derivatives of Formula 4

| Compound | Code | Analytical Data | Mass, % Yield, State |
|---|---|---|---|
| (5-chloro-isoquinolin-1-one with pyridine-piperazine-N,N-dimethylaminoethyl) | IQ-019 | AnalpH2_MeOH_QC: Rt 5.59 min; m/z 412 [M + 1]$^+$ | 49 mg, 26%, off-white solid |
| (5-methyl-isoquinolin-1-one with pyridine-piperazine-N,N-dimethylaminoethyl) | IQ-018 | AnalpH2_MeOH_QC: Rt 5.10 min; m/z 392 [M + 1]$^+$ | 50 mg, 28%, pale yellow solid |
| (5-chloro-isoquinolin-1-one with pyridine-piperazine-ethyl-OTBDMS) | | AnalpH2_MeOH_4 min: Rt 2.68 min; m/z 499 [M + 1]$^+$ | 222 mg, 99%, yellow solid |
| (5-methyl-isoquinolin-1-one with pyridine-piperazine-ethyl-OTBDMS) | | AnalpH2_MeOH_4 min: Rt 2.58 min; m/z 479 [M + 1]$^+$ | 214 mg, 99%, orange solid |

TABLE 10-continued

2H-Isoquinolin-1-one Derivatives of Formula 4

| Compound | Code | Analytical Data | Mass, % Yield, State |
|---|---|---|---|
| (5-chloro-isoquinolin-1(2H)-one with pyridine-pyrrolidine-NMe2 substituent) | IQ-009 | AnalpH2_MeOH_QC: Rt 5.29 min; m/z 369 [M + 1]$^+$ | 25.5 mg, 15%, tan solid |
| (5-methyl-isoquinolin-1(2H)-one with pyridine-pyrrolidine-NMe2 substituent) | IQ-008 | AnalpH2_MeOH_QC: Rt 4.77 min; m/z 349 [M + 1]$^+$ | 28 mg, 18%, pale yellow solid |
| (5-chloro-isoquinolin-1(2H)-one with pyridine-piperidine-NMe2 substituent) | IQ-007 | AnalpH2_MeOH_QC: Rt 5.51 min; m/z 384 [M + 1]$^+$ | 72 mg, 42%, yellow solid<br>$^1$H NMR (400 MHz, DMSO-d$_6$):<br>δ 11.72 (br s, 1H), 8.54 (d, J = 2.8 Hz, 1H), 8.16 (dt, J = 7.6 Hz, 1H), 7.92 (dd, J = 9.1 Hz, 1H), 7.84 (dd, J = 7.6 Hz, 1H), 7.42 (t, J = 7.8 Hz, 1H), 6.94 (d, J = 8.8 Hz, 1H), 6.82 (s, 1H), 4.4 (br d, J = 13.1 Hz, 2H), 2.91 (t, J = 11.9 Hz, 2H), 2.39-2.38 (m, 1H), 2.19 (s, 6H), 1.83 (br d, J = 12.6 Hz, 2H), 1.39-1.29 (m, 2H). |
| (5-methyl-isoquinolin-1(2H)-one with pyridine-piperidine-NMe2 substituent) | IQ-006 | AnalpH2_MeOH_QC: Rt 5.09 min; m/z 364 [M + 1]$^+$ | 26 mg, 16%, pale yellow solid |

TABLE 10-continued

2H-Isoquinolin-1-one Derivatives of Formula 4

| Compound | Code | Analytical Data | Mass, % Yield, State |
|---|---|---|---|
| 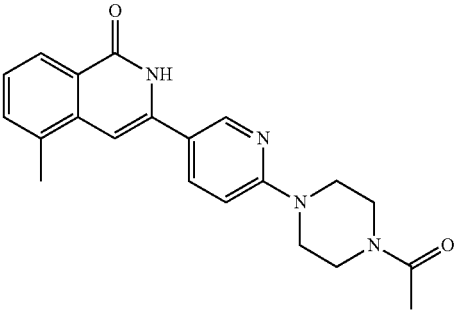 [SMILES: CC(=O)N1CCN(c2ccc(-c3cc4c(C)cccc4c(=O)[nH]3)cn2)CC1] | IQ-005 | AnalpH2_MeOH_QC: Rt 7.39 min; m/z 363 [M + 1]⁺ | 24.5 mg, 8%, pale yellow solid |
| 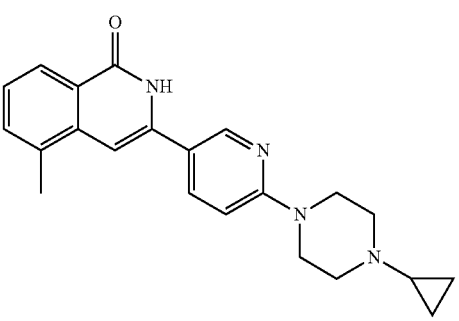 [SMILES: Cc1cccc2c(=O)[nH]c(-c3ccc(N4CCN(C5CC5)CC4)nc3)cc12] | IQ-004 | AnalpH2_MeOH_QC: Rt 5.45 min; m/z 362 [M + 1]⁺ | 53 mg, 33%, pale yellow solid |
| 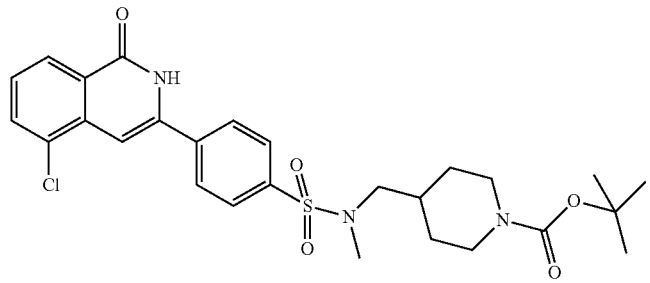 [SMILES: CN(CC1CCN(C(=O)OC(C)(C)C)CC1)S(=O)(=O)c1ccc(-c2cc3c(Cl)cccc3c(=O)[nH]2)cc1] | IQ-114 | AnalpH2_MeOH_QC (Sunfire 1): Rt 8.21 min; m/z 546 [M + 1]⁺ | 210 mg, 43%, white solid |
| 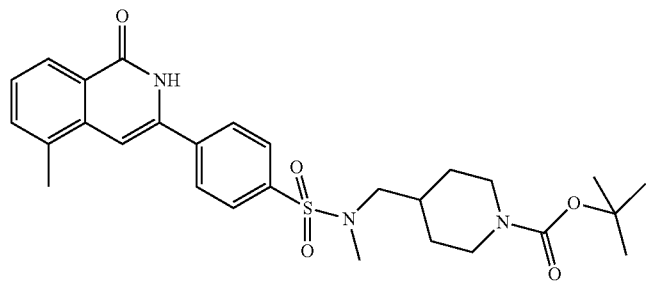 [SMILES: Cc1cccc2c(=O)[nH]c(-c3ccc(S(=O)(=O)N(C)CC4CCN(C(=O)OC(C)(C)C)CC4)cc3)cc12] | IQ-113 | AnalpH2_MeOH_QC (Sunfire): Rt 7.98 min; m/z 526 [M + 1]⁺ | 230 mg, 45%, cream solid |
| 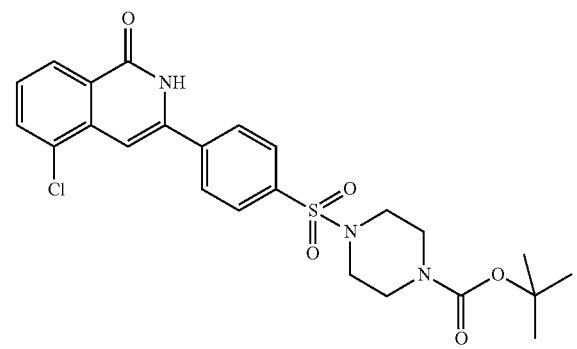 [SMILES: CC(C)(C)OC(=O)N1CCN(S(=O)(=O)c2ccc(-c3cc4c(Cl)cccc4c(=O)[nH]3)cc2)CC1] | IQ-141 | AnalpH2_MeOH_QC: Rt 8.71 min; m/z 504 [M + 1]⁺ | 189 mg, 57%, yellow solid |

TABLE 10-continued

2H-Isoquinolin-1-one Derivatives of Formula 4

| Compound | Code | Analytical Data | Mass, % Yield, State |
|---|---|---|---|
| | IQ-140 | AnalpH2_MeOH_QC: Rt 8.42 min; m/z 484 [M + 1]+ | 107 mg, 31%, yellow solid |
| | IQ-108 | AnalpH2_MeOH_QC: Rt 7.56 min; m/z 343 [M + 1]+ | 32.5 mg, 12%, cream solid |
| | IQ-119 | AnalpH2_MeOH_QC(1): Rt 5.71 min; m/z 452 [M + 1]+ | 83 mg, 20%, cream solid |
| | IQ-118 | AnalpH2_MeOH_QC(1): Rt 7.98 min; m/z 427 [M + 1]+ | 120 mg, 28%, pale yellow solid |
| | IQ-117 | AnalpH2_MeOH_QC(1): Rt 5.38 min; m/z 400 [M + 1]+ | 193 mg, 43%, pale yellow solid |

TABLE 10-continued

2H-Isoquinolin-1-one Derivatives of Formula 4

| Compound | Code | Analytical Data | Mass, % Yield, State |
|---|---|---|---|
| | IQ-126 | AnalpH2_MeOH_QC: Rt 5.85 min; m/z 446 [M + 1]$^+$ | 163 mg, 56%, yellow yellow solid |
| | IQ-125 | AnalpH2_MeOH_QC: Rt 5.55 min; m/z 426 [M + 1]$^+$ | 104 mg, 33%, yellow yellow solid |
| | IQ-110 | AnalpH2_MeOH_QC: Rt 5.87 min; m/z 446 [M + 1]$^+$ | 130 mg, 48%, white solid |
| | IQ-111 | AnalpH2_MeOH_QC: Rt 5.72 min; m/z 440 [M + 1]$^+$ | 47 mg, 15%, white solid |

TABLE 10-continued

2H-Isoquinolin-1-one Derivatives of Formula 4

| Compound | Code | Analytical Data | Mass, % Yield, State |
|---|---|---|---|
| 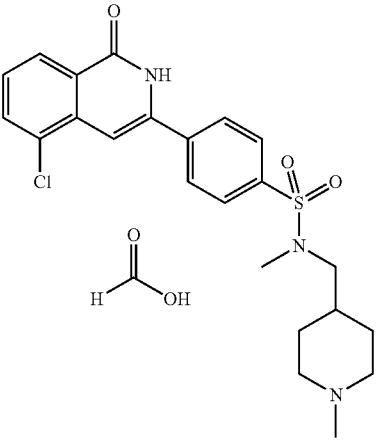 [SMILES: CN1CCC(CN(C)S(=O)(=O)c2ccc(-c3cc4c(Cl)cccc4c(=O)[nH]3)cc2)CC1 ; O=CO] | IQ-112 | AnalpH2_MeOH_QC: Rt 6.02 min; m/z 461 [M + 1]⁺ | 52 mg, 18%, white solid<br>$^1$H NMR (400 MHz, DMSO-d$_6$): δ 11.99 (br s, 1H), 8.23-8.21 (m, 1H), 8.21 (s, formic acid CHO, 0.4H), 8.06-8.03 (m, 2H), 7.92-7.88 (m, 3H), 7.54 (t, J = 7.6 Hz, 1H), 7.02 (s, 1H), 2.84 (d, J = 7.6 Hz, 2H), 2.80-2.74 (m, 2H), 2.70 (s, 3H), 2.18 (s, 3H), 1.92-1.86 (m, 2H), 1.65-1.50 (m, 2H), 1.59-1.50 (m, 1H), 1.21-1.10 (m, 2H). |
| 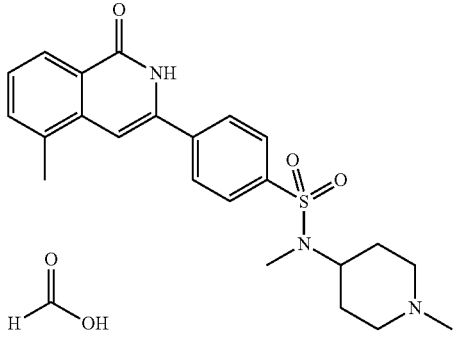 [SMILES: Cc1cccc2c(=O)[nH]c(-c3ccc(S(=O)(=O)N(C)C4CCN(C)CC4)cc3)cc12 ; O=CO] | IQ-109 | AnalpH2_MeOH_QC: Rt 5.58 min; m/z 426 [M + 1]⁺ | 10 mg, 4%, white solid |
| 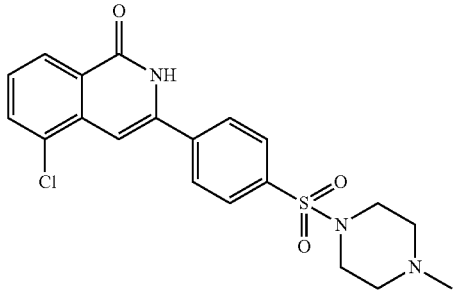 [SMILES: CN1CCN(S(=O)(=O)c2ccc(-c3cc4c(Cl)cccc4c(=O)[nH]3)cc2)CC1] | IQ-122 | AnalpH2_MeOH_QC: Rt 5.80 min; m/z 418 [M + 1]⁺ | 142 mg, 68%, cream solid |
| 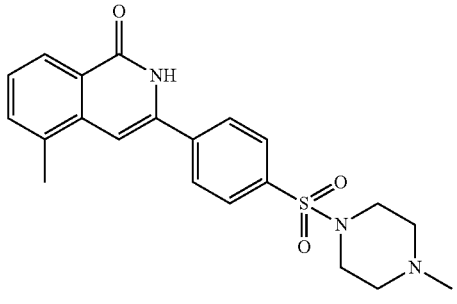 [SMILES: Cc1cccc2c(=O)[nH]c(-c3ccc(S(=O)(=O)N4CCN(C)CC4)cc3)cc12] | IQ-121 | AnalpH2_MeOH_QC: Rt 5.49 min; m/z 398 [M + 1]⁺ | 77 mg, 39%, cream solid |

TABLE 10-continued

2H-Isoquinolin-1-one Derivatives of Formula 4

| Compound | Code | Analytical Data | Mass, % Yield, State |
|---|---|---|---|
| (structure: 5-methyl isoquinolin-1-one with 4-(N-methyl-N-(2-OTBDPS-ethyl)sulfonamido)phenyl) | | AnalpH2_MeOH_QC(1): Rt 9.80 min; m/z 611 [M + 1]⁺ | 3.8 mg, 2%, white solid |
| (structure: 5-chloro isoquinolin-1-one with 4-(dimethylaminomethyl)phenyl) | IQ-031 | AnalpH2_MeOH_QC: Rt 5.44 min; m/z 313 [M + 1]⁺ | 138 mg, 67%, cream solid |
| (structure: 5-trifluoromethyl isoquinolin-1-one with 4-(dimethylaminomethyl)phenyl) | IQ-030 | AnalpH2_MeOH_QC: Rt 4.83 min; m/z 347 [M + 1]⁺ | 2 mg, 1% yellow solid |
| (structure: 5-fluoro isoquinolin-1-one with 4-(dimethylaminomethyl)phenyl) | IQ-032 | AnalpH2_MeOH_QC: Rt 4.90 min; m/z 297 [M + 1]⁺ | 175.1 mg, 91% cream solid |
| (structure: 5-methyl isoquinolin-1-one with 4-(methylaminomethyl)phenyl) | IQ-034 | AnalpH2_MeOH_QC: Rt 4.94 min; m/z 293 [M + 1]⁺ | 133 mg, 58% pale yellow solid |

TABLE 10-continued
2H-Isoquinolin-1-one Derivatives of Formula 4
| Compound | Code | Analytical Data | Mass, % Yield, State |
|---|---|---|---|
| 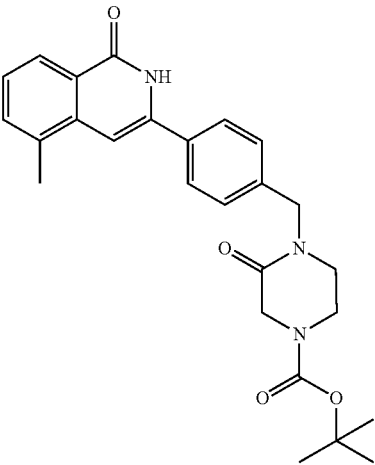 [SMILES: Cc1cccc2c(=O)[nH]c(-c3ccc(CN4CCN(C(=O)OC(C)(C)C)CC4=O)cc3)cc12] | IQ-147 | AnalpH2_MeOH_QC(1): Rt 8.32 min; m/z 448 [M + 1]+ | 36 mg, 8%, white solid |
| 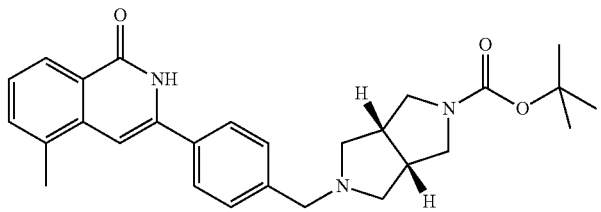 [SMILES: Cc1cccc2c(=O)[nH]c(-c3ccc(CN4C[C@@H]5CN(C(=O)OC(C)(C)C)C[C@@H]5C4)cc3)cc12] | IQ-089 | AnalpH2_MeOH_QC(1): Rt 6.02 min; m/z 460 [M + 1]+ | 11.8 mg, 31%, off-white foam |
| 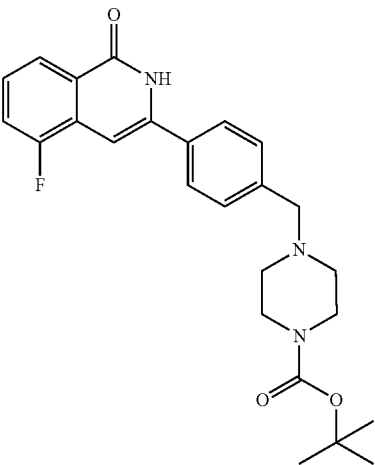 [SMILES: CC(C)(C)OC(=O)N1CCN(Cc2ccc(-c3cc4c(F)cccc4c(=O)[nH]3)cc2)CC1] | IQ-069 | AnalpH2_MeOH_QC(1): Rt 6.51 min; m/z 438 [M + 1]+ | 111 mg, 51%, pink solid |

TABLE 10-continued
2H-Isoquinolin-1-one Derivatives of Formula 4
| Compound | Code | Analytical Data | Mass, % Yield, State |
|---|---|---|---|
| 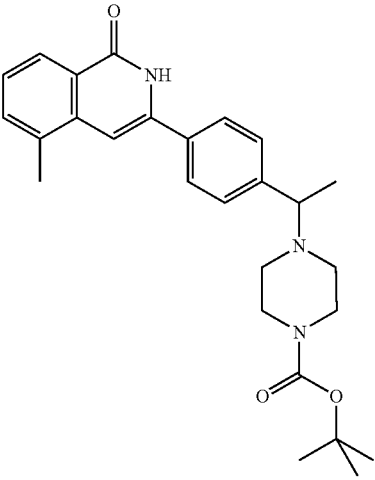 [SMILES: Cc1cccc2c(=O)[nH]c(-c3ccc(C(C)N4CCN(C(=O)OC(C)(C)C)CC4)cc3)cc12] | IQ-066 | AnalpH2_MeOH_QC(1): Rt 6.45 min; m/z 448 [M + 1]+ | 131 mg, 43%, cream solid |
| 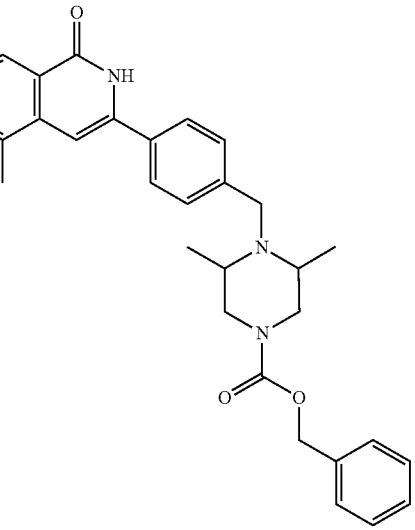 | IQ-064 | AnalpH2_MeOH_QC(1): Rt 7.05 min; m/z 496 [M + 1]+ | 28 mg, 7.3%, white solid |
| 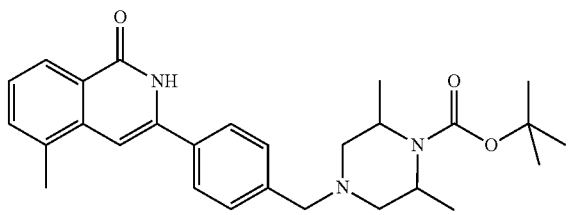 [SMILES: Cc1cccc2c(=O)[nH]c(-c3ccc(CN4CC(C)N(C(=O)OC(C)(C)C)C(C)C4)cc3)cc12] | IQ-061 | AnalpH2_MeOH_QC(1): Rt 8.89 min; m/z 462 [M + 1]+ | 180 mg, 46%, cream solid |
| 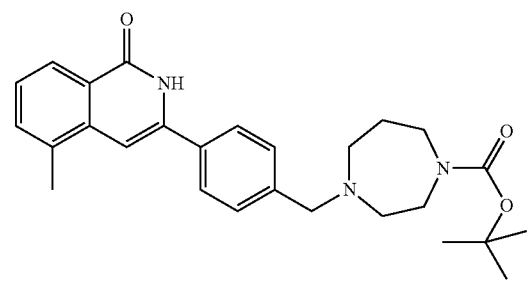 [SMILES: Cc1cccc2c(=O)[nH]c(-c3ccc(CN4CCCN(C(=O)OC(C)(C)C)CC4)cc3)cc12] | IQ-060 | AnalpH2_MeOH_QC(1): Rt 6.03 min; m/z 448 [M + 1]+ | 160 mg, 38%, off-white solid |

TABLE 10-continued

2H-Isoquinolin-1-one Derivatives of Formula 4

| Compound | Code | Analytical Data | Mass, % Yield, State |
|---|---|---|---|
| | IQ-085 | AnalpH2_MeOH_QC: Rt 6.01 min; m/z 446 [M + 1]+ | 37 mg, 18%, white solid |
| | IQ-143 | AnalpH2_MeOH_QC: Rt 7.21 min; m/z 448 [M + 1]+ | 98 mg, 30%, white solid |
| | IQ-142 | AnalpH2_MeOH_QC: Rt 6.42 min; m/z 448 [M + 1]+ | 164 mg, 50%, white solid |

TABLE 10-continued

2H-Isoquinolin-1-one Derivatives of Formula 4

| Compound | Code | Analytical Data | Mass, % Yield, State |
|---|---|---|---|
| (structure) | IQ-047 | AnalpH2_MeOH_QC: Rt 6.82 min; m/z 460 [M + 1]+ | 38 mg, 16%, white solid |
| (structure) | IQ-044 | AnalpH2_MeOH_QC: Rt 6.91 min; m/z 454 [M + 1]+ | 138 mg, 46%, white solid |
| (structure) | IQ-040 | AnalpH2_MeOH_QC: Rt 6.41 min; m/z 434 [M + 1]+ | 395 mg, 46%, white solid |

TABLE 10-continued

2H-Isoquinolin-1-one Derivatives of Formula 4

| Compound | Code | Analytical Data | Mass, % Yield, State |
|---|---|---|---|
| 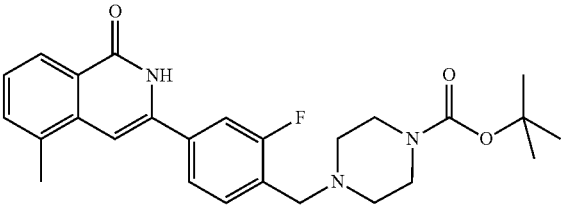 [SMILES: Cc1cccc2c(=O)[nH]c(-c3ccc(CN4CCN(C(=O)OC(C)(C)C)CC4)c(F)c3)cc12] | IQ-058 | AnalpH2_MeOH_QC(1): Rt 7.21 min; m/z 452 [M + 1]⁺ | 120 mg, 39%, pale yellow solid |
| 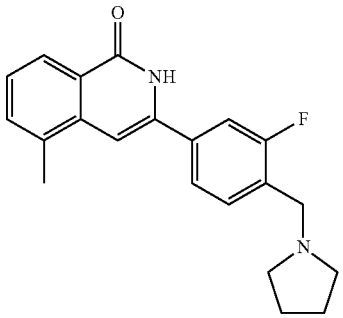 [SMILES: Cc1cccc2c(=O)[nH]c(-c3ccc(CN4CCCC4)c(F)c3)cc12] | IQ-039 | AnalpH2_MeOH_QC: Rt 5.23 min; m/z 337 [M + 1]⁺ | 29 mg, 11%, pale yellow solid |
| 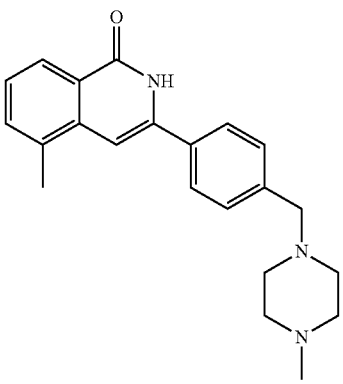 [SMILES: Cc1cccc2c(=O)[nH]c(-c3ccc(CN4CCN(C)CC4)cc3)cc12] | IQ-038 | AnalpH2_MeOH_QC: Rt 5.47 min; m/z 348 [M + 1]⁺ | 615 mg, 59%, white solid<br>$^1$H NMR (400 MHz, DMSO-$d_6$):<br>δ 11.56 (br s, 1H), 8.07 (d, J = 8.1 Hz, 1H, J = 7.78 (d, J = 8.3 Hz, 2H), 7.56 (d, J = 6.8 Hz, 1H), 7.41 (d, J = 8.3 Hz, 2H), 7.37 (t, J = 7.6 Hz, 1H), 6.85 (s, 1H), 3.51 (s, 2H), 2.56 (s, 3H), 2.33 (br s, 8H), 2.16 (s, 3H) |
| 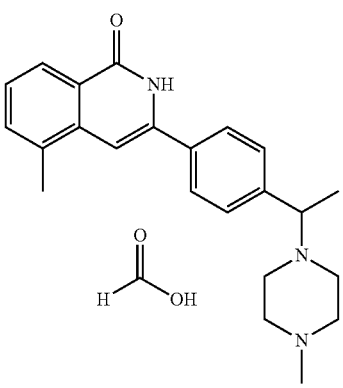 [SMILES: Cc1cccc2c(=O)[nH]c(-c3ccc(C(C)N4CCN(C)CC4)cc3)cc12 ; O=CO] | IQ-048 | AnalpH2_MeOH_QC: Rt 5.77 min; m/z 362 [M + 1]⁺ | 44 mg, 15%, cream solid |

TABLE 10-continued
2H-Isoquinolin-1-one Derivatives of Formula 4
| Compound | Code | Analytical Data | Mass, % Yield, State |
|---|---|---|---|
| 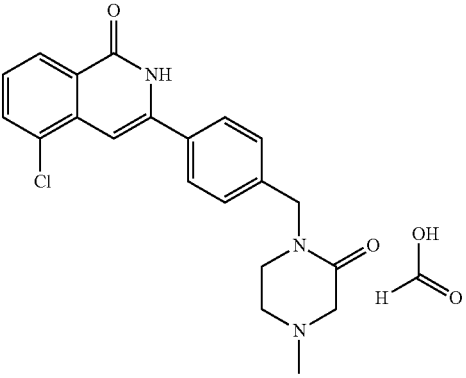 | IQ-056 | AnalpH9_MeOH_QC (Sunfire 1): Rt 7.22 min; m/z 382 [M + 1]+ | 16 mg, 4%, light beige solid |
| 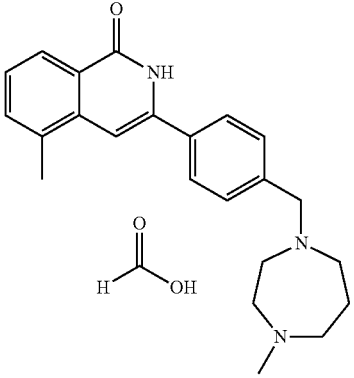 [SMILES: Cc1cccc2c(=O)[nH]c(-c3ccc(CN4CCCN(C)CC4)cc3)cc12 ; O=CO] | IQ-065 | AnalpH2_MeOH_QC(1): Rt 4.49 min; m/z 362 [M + 1]+ | 14 mg, 5%, cream solid |
| 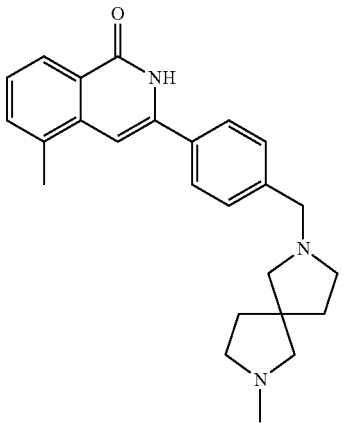 [SMILES: Cc1cccc2c(=O)[nH]c(-c3ccc(CN4CCC5(CCN(C)C5)C4)cc3)cc12] | IQ-088 | AnalpH2_MeOH_QC (Sunfire): Rt 2.93 min; m/z 388 [M + 1]+ | 12 mg, 13%, white solid |

TABLE 10-continued

2H-Isoquinolin-1-one Derivatives of Formula 4

| Compound | Code | Analytical Data | Mass, % Yield, State |
|---|---|---|---|
| | IQ-043 | AnalpH2_MeOH_QC: Rt 5.75 min; m/z 368 [M + 1]⁺ | 92 mg, 38%, white solid |
| | IQ-054 | AnalpH2_MeOH_QC (Sunfire): Rt 6.13 min; m/z 362 [M + 1]⁺ | 19 mg, 6%, pale orange solid |
| | IQ-087 | AnalpH2_MeOH_QC: Rt 4.69 min; m/z 374 [M + 1]⁺ | 17 mg, 16%, orange solid |
| | IQ-053 | AnalpH2_MeOH_QC: Rt 4.09 min; m/z 376 [M + 1]⁺ | 14 mg, 3%, white solid<br>$^1$H NMR (400 MHz, DMSO-$d_6$):<br>δ 11.53 (br s, 1H), 8.30 (s, formic acid CHO, 0.5H), 8.07 (d, J = 8.4 Hz, 1H), 7.78 (d, J = 8.4 Hz, 2H), 7.56 (d, J = 6.8 Hz, 1H), 7.41 (d, J = 8.4 Hz, 2H), 7.37 (d, J = 8.0 Hz, 1H), 6.85 (s, 1H), 3.50 (s, 2H), 2.86-2.83 (m, 2H), 2.56 (s, 3H), 2.18 (s, 6H), 2.12-2.04 (m, 1H), 1.98-1.92 (m, 2H), 1.74-1.71 (m, 2H), 1.44-1.34 (m, 2H). |

TABLE 10-continued
2H-Isoquinolin-1-one Derivatives of Formula 4
| Compound | Code | Analytical Data | Mass, % Yield, State |
|---|---|---|---|
| 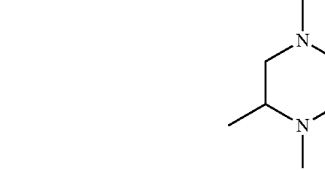 | IQ-052 | AnalpH2_MeOH_QC: Rt 5.70 min; m/z 362 [M + 1]⁺ | 37 mg, 21%, white solid |
| 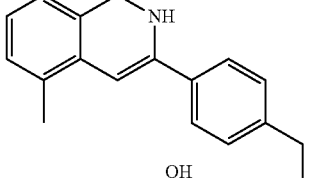 | IQ-050 | AnalpH2_MeOH_QC: Rt 5.60 min; m/z 374 [M + 1]⁺ | 9 mg, 8.5%, beige solid |
| 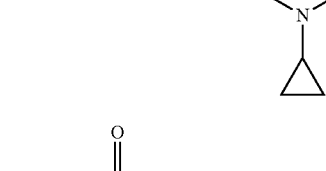 | IQ-046 | AnalpH2_MeOH_QC: Rt 5.81 min; m/z 374 [M + 1]⁺ | 154 mg, 32%, yellow yellow solid |
| 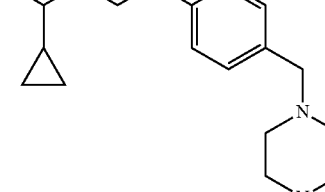 | IQ-037 | AnalpH2_MeOH_QC: Rt 5.27 min; m/z 665 [2M + 1]⁺ | 79 mg, 30%, beige solid |

TABLE 10-continued

2H-Isoquinolin-1-one Derivatives of Formula 4

| Compound | Code | Analytical Data | Mass, % Yield, State |
|---|---|---|---|
| (structure) | IQ-036 | AnalpH2_MeOH_QC: Rt 5.12 min; m/z 319 [M + 1]$^+$ | 172 mg, 68%, yellow/orange solid |
| (structure) | IQ-035 | AnalpH2_MeOH_QC: Rt 5.11 min; m/z 335 [M + 1]$^+$ | 51 mg, 19%, white solid |
| (structure) | | AnalpH2_MeOH_4 min(1): Rt 2.86 min m/z 587 [M + 1]$^+$. | 213 mg, 46%, white solid |

TABLE 10-continued

2H-Isoquinolin-1-one Derivatives of Formula 4

| Compound | Code | Analytical Data | Mass, % Yield, State |
|---|---|---|---|
| 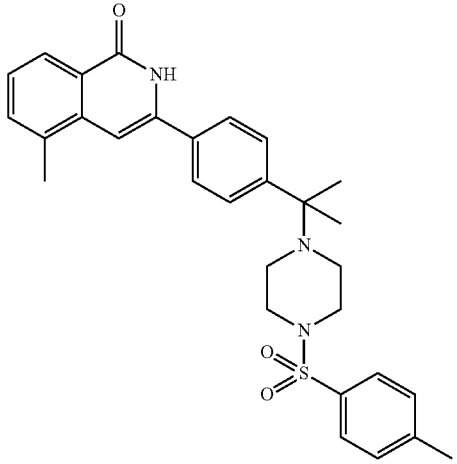 [SMILES: Cc1ccc(S(=O)(=O)N2CCN(C(C)(C)c3ccc(-c4cc5c(C)cccc5c(=O)[nH]4)cc3)CC2)cc1] | IQ-148 | AnalpH2_MeOH_QC(1): Rt 7.99 min m/z 516 [M + 1]⁺. | 34 mg (29%) White solid |
| 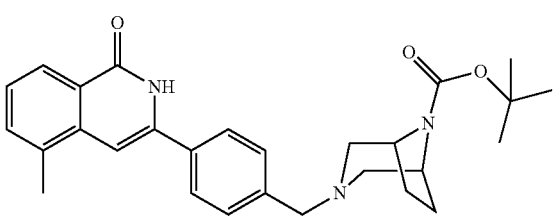 [SMILES: Cc1cccc2c(=O)[nH]c(-c3ccc(CN4CC5CCC(C4)N5C(=O)OC(C)(C)C)cc3)cc12] | IQ-155 | AnalpH2_MeOH_QC: Rt 7.77 min m/z 460 [M + 1]⁺. | 32 mg, 23%, white solid |
| 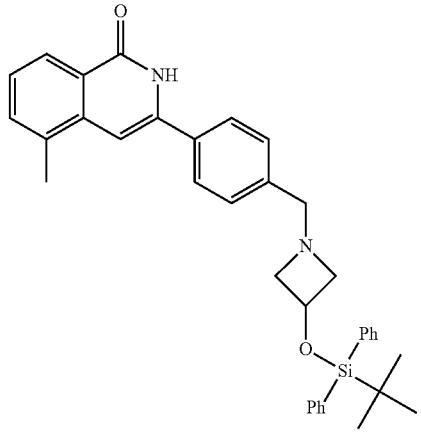 [SMILES: Cc1cccc2c(=O)[nH]c(-c3ccc(CN4CC(O[Si](c5ccccc5)(c5ccccc5)C(C)(C)C)C4)cc3)cc12] | Intermediate for IQ-167 | AnalpH2_MeOH_4 min(3): Rt 2.77 min; m/z 559 [M + 1]⁺ | 210 mg, 89%, off-white solid |
| 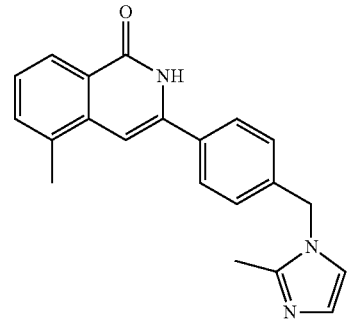 [SMILES: Cc1cccc2c(=O)[nH]c(-c3ccc(Cn4ccnc4C)cc3)cc12] | IQ-168 | AnalpH2_MeOH_QC(2): Rt 4.74 min; m/z 330 [M + 1]⁺ | 8.2 mg, 52 %, pale yellow solid ¹H NMR (400 MHz, DMSO-d₆): δ 11.59 (br s, 1H), 8.08 (d, J = 8.0 Hz, 1H), 7.85 (d, J = 8.0 Hz, 2H), 7.57 (d, J = 6.8 Hz, 1H), 7.48 (s, 1H), 7.40-7.36 (m, 3H), 7.24 (s, 1H), 6.87 (s, 1H), 5.35 (s, 2H), 2.56 (s, 3H), 2.45 (s, 3H). |

TABLE 10-continued

2H-Isoquinolin-1-one Derivatives of Formula 4

| Compound | Code | Analytical Data | Mass, % Yield, State |
|---|---|---|---|
| 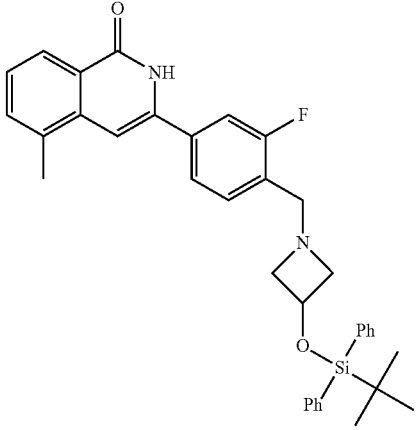 [SMILES: Cc1cccc2c(=O)[nH]c(-c3ccc(CN4CC(O[Si](c5ccccc5)(c5ccccc5)C(C)(C)C)C4)c(F)c3)cc12] | Intermediate for IQ-169 | AnalpH2_MeOH_4 min(3): Rt 2.89 min; m/z 577 [M + 1]$^+$ | 35 mg, 54%, cream solid |
| 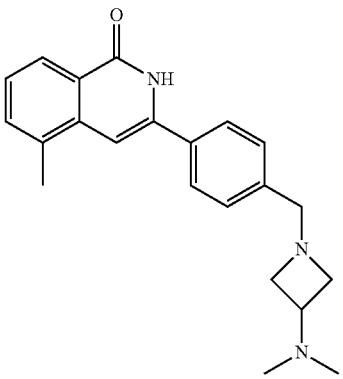 [SMILES: Cc1cccc2c(=O)[nH]c(-c3ccc(CN4CC(N(C)C)C4)cc3)cc12] | IQ-174 | AnalpH2_MeOH_QC(1): Rt 4.77 min; m/z 348 [M + 1]$^+$ | 119.5 mg, 43%, off-white solid |
| 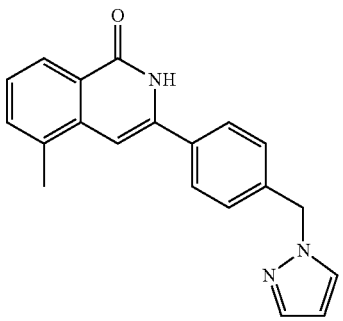 | IQ-182 | AnalpH2_MeOH_QC(2): Rt 7.52 min; m/z 316 [M + 1]+ | 61 mg, 10% off-white solid $^1$H NMR (400 MHz, DMSO-d$_6$): δ 11.57 (br s, 1H), 8.07 (d, J = 8.0 Hz, 1H), 7.89 (d, J = 2.4 Hz, 1H), 7.79 (d, J = 8.4 Hz, 2H), 7.56 (d, J = 7.2 Hz, 1H), 7.49 (d, J = 1.6 Hz, 1H), 7.37 (t, J = 7.6 Hz, 1H), 7.32 (d, J = 8.0 Hz, 2H), 6.84 (s, 1H), 6.30 (t, J = 2.0 Hz, 1H), 5.41 (s, 2H), 2.55 (s, 3H). |

Scheme A, Step B (Protocol 2): Synthesis of Boc-Protected 2H-isoquinolin-1-one Derivatives of Formula 4 Via Reverse Addition Protocol N-Methyl-4-(5-methyl-1-oxo-1,2-dihydro-isoquinolin-3-yl)-N-(1-methyl-piperidin-4-yl)-benzamide (IQ-100)

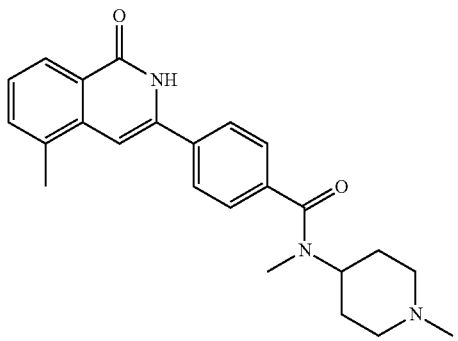 [SMILES: Cc1cccc2c(=O)[nH]c(-c3ccc(C(=O)N(C)C4CCN(C)CC4)cc3)cc12]

To a solution of N,N-diethyl-2,3-dimethyl-benzamide (578 mg, 2.82 mmol) in anhydrous THF (3 mL) under $N_2$ at −78° C. was added dropwise n-BuLi (2.5M in n-hexanes, 2.4 mL, 5.92 mmol) to give a deep red solution. The reaction mixture was stirred at −78° C. for 30 minutes. The reaction mixture was transferred dropwise, via syringe, to a reaction vessel containing 4-cyano-N-methyl-N-(1-methyl-piperidin-4-yl)-benzamide (725 mg, 2.82 mmol) in anhydrous THF (5 mL) at −78° C. and under $N_2$. The reaction mixture was stirred at −78° C. for 3.5 h. Water (10 mL) was added and the reaction mixture was extracted with EtOAc (10 mL) and $CH_2Cl_2$ (10 mL). The combined organic layers concentrated in vacuo and the resultant solid was triturated with 2:1 isohexane/EtOAc, filtered and dried in vacuo. The crude material was purified by silica gel column chromatography, eluting with $CH_2Cl_2$ and increasing the polarity to 15% MeOH/$CH_2Cl_2$ to afford N-methyl-4-(5-methyl-1-oxo-1,2-dihydro-isoquinolin-3-yl)-N-(1-methyl-piperidin-4-yl)-benzamide as a white solid (487 mg, 44%).

$^1$H NMR (400 MHz, DMSO-$d_6$): δ11.80-11.41 (brs, 1H), 8.10 (d, J=8 Hz, 1H), 7.89 (d, J=8 Hz, 2H), 7.58 (d, J=7 Hz, 1H), 7.48 (d, J=8 Hz, 2H), 7.39 (t, J=7 Hz, 1H), 6.93 (s, 1H), 3.31 (s, 3H), 2.96-2.70 (m, 5H), 2.58 (s, 3H), 2.23-1.96 (m, 3H), 1.93-1.71 (brs, 2H), 1.71-1.53 (br s, 2H).

AnalpH2_MeOH_QC(Sunfire): Rt 4.29 min; m/z 390 [M+1]$^+$.

The following 2H-isoquinolin-1-one derivatives are prepared using analogous procedures.

TABLE 11

2H-isoquinolin-1-one derivatives of Formula 4

| Compound | Code | Analytical Data | Mass, % Yield, State |
|---|---|---|---|
|  | IQ-105 | AnalpH2_MeOH_QC(1): Rt 4.97 min; m/z 388 [M + 1]$^+$ | 2.7 mg, 3%, white solid |
|  | IQ-106 | AnalpH2_MeOH_QC(1): Rt 4.98 min; m/z 390 [M + 1]$^+$ | 4 mg, 2%, white solid |

TABLE 11-continued 2H-isoquinolin-1-one derivatives of Formula 4

| Compound | Code | Analytical Data | Mass, % Yield, State |
|---|---|---|---|
| 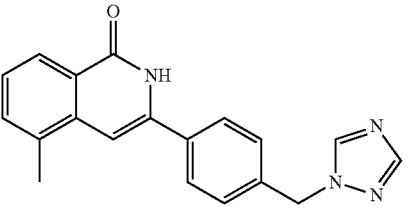 [SMILES: Cc1cccc2c(=O)[nH]c(-c3ccc(Cn4cncn4)cc3)cc12] | IQ-171 | AnalpH2_MeOH_QC(1): Rt 7.41 min; m/z 317 [M + 1]$^+$ | 8.5 mg, 4%, white solid |
| 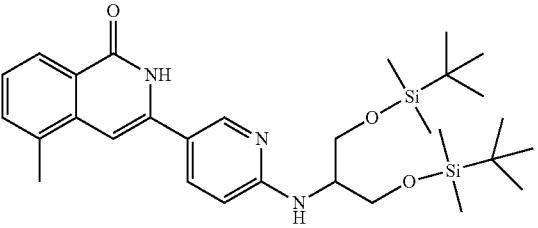 [SMILES: Cc1cccc2c(=O)[nH]c(-c3ccc(NC(CO[Si](C)(C)C(C)(C)C)CO[Si](C)(C)C(C)(C)C)nc3)cc12] | Intermediate for IQ-219 | AnalpH2_MeOH_4 min(3): Rt 2.59 min; m/z 554 [M + 1]$^+$ | Used in next step as crude material |
| 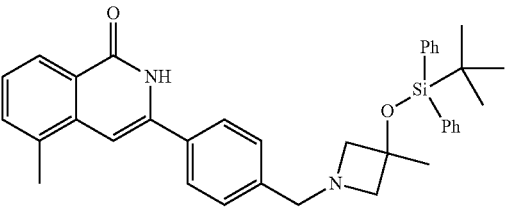 [SMILES: Cc1cccc2c(=O)[nH]c(-c3ccc(CN4CC(C)(O[Si](c5ccccc5)(c5ccccc5)C(C)(C)C)C4)cc3)cc12] | Intermediate for IQ-172 | AnalpH2_MeOH_4 min(3): Rt 2.86 min; m/z 573 [M + 1]$^+$ | 63 mg, 27%, white solid |
| 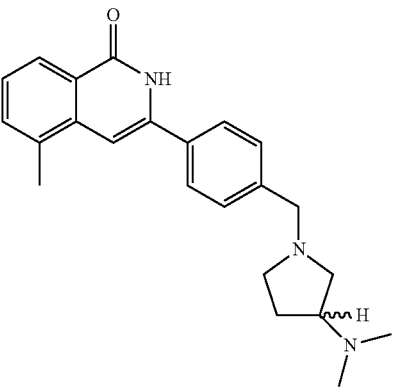 [SMILES: Cc1cccc2c(=O)[nH]c(-c3ccc(CN4CCC(N(C)C)C4)cc3)cc12] | IQ-173 | AnalpH2_MeOH_QC(1): Rt 4.46 min; m/z 363 [M + 1]$^+$ | 41 mg, 23%, white solid |

Scheme A, Step B (Protocol 3): Synthesis of Boc-Protected 2H-isoquinolin-1-one Derivatives of Formula 4 (LDA Protocol)

4-[4-(5-Bromo-1-oxo-1,2-dihydro-isoquinolin-3-yl)-benzyl]-piperazine-1-carboxylic acid tert-butyl ester (IQ-149)

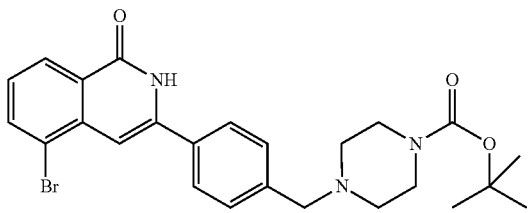 [SMILES: CC(C)(C)OC(=O)N1CCN(Cc2ccc(-c3cc4c(Br)cccc4c(=O)[nH]3)cc2)CC1]

To a stirred solution of N,N-diisopropylamine (1.56 mL, 11.10 mmol) in THF (5 mL) under $N_2$ at −78° C. was added n-BuLi (2.5M in hexanes) (4.44 mL, 11.10 mmol) and the reaction stirred at −78° C. for 20 min, after which time a solution of 3-bromo-N,N-diethyl-2-methyl-benzamide (1 g, 3.70 mmol) in THF (5 mL) was added, and the reaction stirred at −78° C. for 30 minutes. A solution of 4-(4-cyano-benzyl)-piperazine-1-carboxylic acid tert-butyl ester (1.15 g, 3.70 mmol) in THF (5 mL) was added and the reaction stirred at −78° C. for 2 h. The reaction was quenched with ice and water, EtOAc added and concentrated in vacuo. The crude material was purified by silica gel column chromatography, eluting with isohexane and increasing the polarity to 100% EtOAc to afford 4-[4-(5-bromo-1-oxo-1,2-dihydro-isoquinolin-3-yl)-benzyl]-piperazine-1-carboxylic acid tert-butyl ester as a cream solid (1.22 g, 66%).

AnalpH2_MeOH_QC: Rt 6.94 min; m/z 498 [M+1]$^+$.

The following 2H-isoquinolin-1-one derivatives are prepared using analogous procedures.

4-[4-(5-Ethyl-1-oxo-1,2-dihydro-isoquinolin-3-yl)-benzyl]-piperazine-1-carboxylic acid tert-butyl ester (IQ-151)

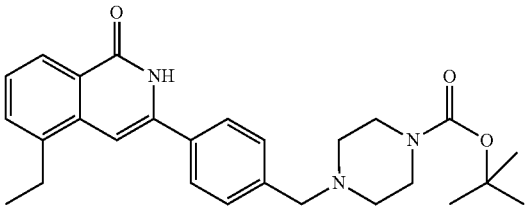 [SMILES: CCc1cccc2c(=O)[nH]c(-c3ccc(CN4CCN(C(=O)OC(C)(C)C)CC4)cc3)cc12]

To a stirred solution of 4-[4-(5-Bromo-1-oxo-1,2-dihydro-isoquinolin-3-yl)-benzyl]-piperazine-1-carboxylic acid tert-butyl ester (200 mg, 0.4 mmol) in anhydrous THF (4 mL) under $N_2$ was added dichlorobis(tri-o-tolylphosphine)palladium(II) (14 mg, 0.02 mmol), $CeCl_3$ (99 mg, 0.4 mmol) and $AlEt_3$ (1M in hexanes, 1.5 mL, 1.2 mmol) and the reaction stirred at RT for 4 h. The reaction was quenched with ice, diluted with 0.5M aqueous Rochelle's salts (30 mL) and extracted with EtOAc (3×40 mL). The combined organics were washed with Rochelle's salts (2×50 mL), brine (50 mL), dried over $MgSO_4$, filtered and concentrated in vacuo and the crude residue purified by reverse phase preparative HPLC-MS to afford 4-[4-(5-ethyl-1-oxo-1,2-dihydro-isoquinolin-3-yl)-benzyl]-piperazine-1-carboxylic acid tert-butyl ester as an orange solid (83 mg, 61%).

AnalpH2_MeOH_QC(1):Rt 5.13 min; m/z 446 [M+1]$^+$.

TABLE 12

2H-isoquinolin-1-one derivatives of Formula 4

| Compound | Code | Analytical Data | Mass, % Yield, State |
|---|---|---|---|
|  | IQ-033 | AnalpH2_MeOH_QC: Rt 5.40 min; m/z 357 [M + 1]$^+$ | 56 mg, 15% cream solid |
|  | IQ-156 | AnalpH2_MeOH_4 min: Rt 1.85 min; m/z 454 [M + 1]$^+$. | 122 mg, 71%, pale yellow solid |

5-Methyl-3-[4-(2-methylamino-ethoxy)-phenyl]-2H-isoquinolin-1-one (IQ-127)

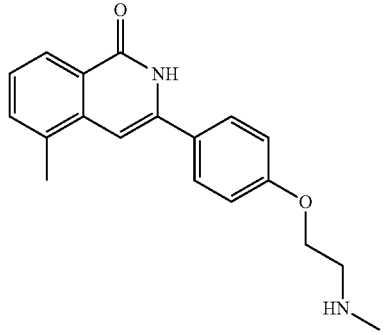 [SMILES: CNCCOc1ccc(-c2cc3c(C)cccc3c(=O)[nH]2)cc1]

1-Chloro-ethyl chloroformate (97 mg, 0.68 mmol) in 1,2-dichloroethane (0.3 mL) was added to a solution of 3-[4-(2-dimethylamino-ethoxy)-phenyl]-5-methyl-2H-isoquinolin-1-one (35 mg, 0.109 mmol) in 1,2-dichloroethane (0.6 mL) at cooled to 0° C., and stirred for 10 min. The reaction mixture was irradiated using a microwave (300 W, 180° C., 15 min) then concentrated in vacuo and EtOH (0.8 mL) added. The reaction mixture was heated at 80° C. for 15 h, allowed to cool and passed through a SCX-2 cartridge (1 g), eluting with 0.5M $NH_3$ in MeOH. The crude material was concentrated in vacuo and purified by reverse phase preparative HPLC-MS to afford 5-methyl-3-[4-(2-methylamino-ethoxy)-phenyl]-2H-isoquinolin-1-one as a white solid (4 mg, 12%).

AnalpH2_MeOH_QC: Rt 5.43 min; m/z 309 [M+1]$^+$.

Scheme A, Step C (Protocol 1): Synthesis of 2H-isoquinolin-1-one Derivatives of formula 5 (via BOC deprotection)

N-Methyl-4-(5-methyl-1-oxo-1,2-dihydro-isoquinolin-3-yl)-N-piperidin-4-ylmethyl-benzamide (IQ-093)

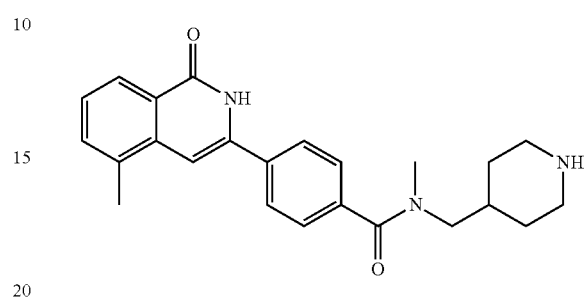

To 4-({methyl-[4-(5-methyl-1-oxo-1,2-dihydro-isoquinolin-3-yl)-benzoyl]-amino}-methyl)-piperidine-1-carboxylic acid tert-butyl ester (170 mg, 0.35 mmol) in $CH_2Cl_2$ (5 mL) was added 4M HCl/dioxane (2 mL) and the reaction mixture stirred at RT for 4 h. The solvent was removed in vacuo and the crude product purified by reverse phase preparative HPLC-MS to obtain N-methyl-4-(5-methyl-1-oxo-1,2-dihydro-isoquinolin-3-yl)-N-piperidin-4-ylmethyl-benzamide as a pale orange solid (44 mg, 33%).

$^1$H NMR (400 MHz, DMSO-d$_6$): δ 8.09 (d, J=8 Hz, 1H), 7.89 (d, J=8 Hz, 2H), 7.57 (d, J=7 Hz, 1H), 7.50 (br d, J=8 Hz, 1H), 7.45 (br d, J=8 Hz, 1H), 6.92 (s, 1H), 3.35 (d, J=7 Hz, 1H), 3.15 (d, J=7 Hz, 1H), 2.97 (s, 2H), 2.92 (s, 3H), 2.84-2.82 (m, 1H), 2.51 (s, 3H), 2.46-2.36 (m, 1H), 1.84 (s, 0.5H), 1.77 (s, 0.5H), 1.61 (d, J=10 Hz, 1H), 1.42 (d, J=10 Hz, 1H), 1.11-1.08 (m, 1H), 0.70-0.68 (m, 1H).

AnalpH2_MeOH_QC(Sunfire1): Rt 4.49 min; m/z 390 [M+1]$^+$.

The following 2H-isoquinolin-1-one derivatives are prepared using analogous procedures.

TABLE 13

2H-isoquinolin-1-one Formula 5

| Compound | Code | Analytical Data | Mass, % Yield, State |
|---|---|---|---|
|  | IQ-094 | AnalpH2_MeOH_QC (Sunfire1): Rt 4.82 min; m/z 410 [M + 1]$^+$ | 66 mg, 60%, white solid |

TABLE 13-continued 2H-isoquinolin-1-one Formula 5

| Compound | Code | Analytical Data | Mass, % Yield, State |
|---|---|---|---|
| (structure) | IQ-070 | AnalpH2_MeOH_QC(1): Rt 5.19 min; m/z 338 [M + 1]$^+$ | 63 mg, 94%, pale pink solid |
| (structure) | IQ-067 | AnalpH2_MeOH_QC(1): Rt 5.57 min; m/z 348 [M + 1]$^+$ | 14 mg, 12%, orange solid |
| (structure) | IQ-073 | AnalpH2_MeOH_QC(1): Rt 5.32 min; m/z 348 [M + 1]$^+$ | 7 mg, 28%, white solid |
| (structure) | IQ-090 | AnalpH2_MeOH_QC(1): Rt 3.96 min; m/z 360 [M + 1]$^+$ | 48 mg, 33%, pale yellow solid |

TABLE 13-continued

2H-isoquinolin-1-one Formula 5

| Compound | Code | Analytical Data | Mass, % Yield, State |
|---|---|---|---|
| 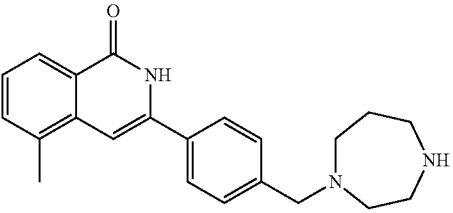 ClH | IQ-062 ClH | AnalpH2_MeOH_QC(1): Rt 4.23 min; m/z 348 [M + 1]+ | 211 mg, 100%, pale orange solid |
| 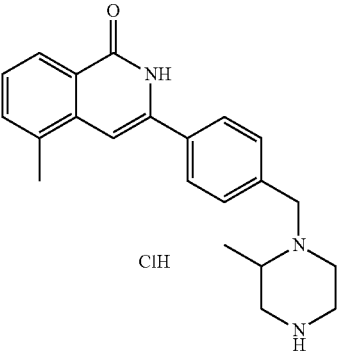 ClH | IQ-051-1 | AnalpH2_MeOH_QC: Rt 5.65 min; m/z 348 [M + 1]+ | 108 mg, 77%, cream solid |
| 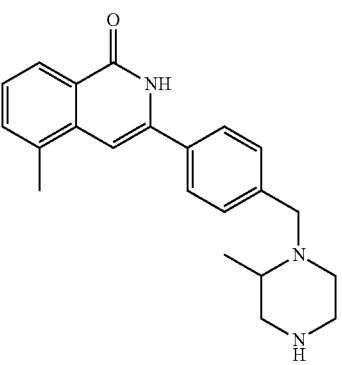 Chiral<br>Enantiomer 1 | IQ-051-2 | AnalpH2_MeOH_QC(1): Rt 5.47 min; m/z 348 [M + 1]+ | 10.2 mg, 35% recovery, off-white solid; obtained via Chiral_Method_2 |
| 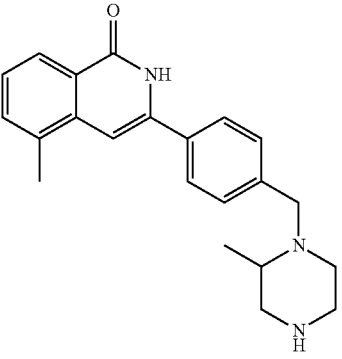 [SMILES: Cc1cccc2c(=O)[nH]c(-c3ccc(CN4CCNCC4=O)cc3)cc12] Chiral<br>Enantiomer 2 | IQ-051-3 | AnalpH2_MeOH_QC(1): Rt 5.47 min; m/z 348 [M + 1]+ | 8.3 mg, 29% recovery, off-white solid; obtained via Chiral_Method_2 |

TABLE 13-continued

2H-isoquinolin-1-one Formula 5

| Compound | | Code | Analytical Data | Mass, % Yield, State |
|---|---|---|---|---|
| 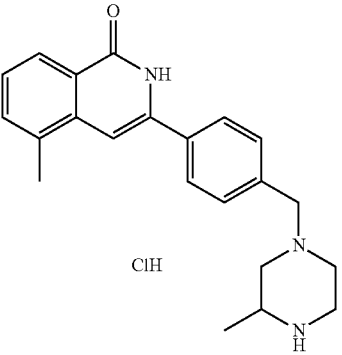 [SMILES: Cc1cccc2c(=O)[nH]c(-c3ccc(CN4CCNC(C)C4)cc3)cc12 ; Cl]<br>ClH | | IQ-084-3 | AnalpH2_MeOH_QC:<br>Rt 5.61 min; m/z<br>348 [M + 1]+ | 34 mg, 42%, cream solid |
| 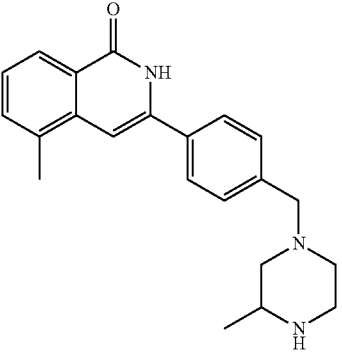<br>Enantiomer 1 | Chiral | IQ-084-1 | AnalpH2_MeOH_QC<br>(Sunfire1): Rt<br>4.67 min; m/z 348<br>[M + 1]+ | 4.5 mg, 13% recovery, white solid; obtained via Chiral_Method_1 |
| 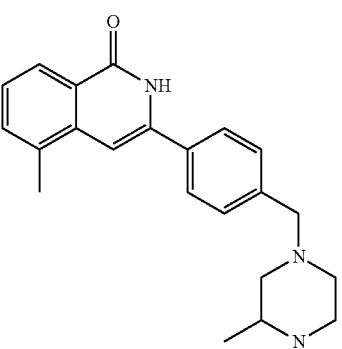<br>Enantiomer 2 | Chiral | IQ-084-2 | AnalpH2_MeOH_QC<br>(Sunfire1): Rt<br>4.66 min; m/z 348<br>[M + 1]+ | 3.5 mg, 11% recovery, white solid; obtained via Chiral_Method_1 |
| 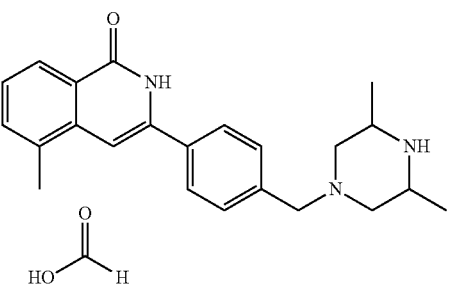 | | IQ-063 | AnalpH2_MeOH_QC(1):<br>Rt 5.56 min;<br>m/z 362 [M + 1]+ | 87 mg, 55%, cream solid |

TABLE 13-continued
2H-isoquinolin-1-one Formula 5
| Compound | Code | Analytical Data | Mass, % Yield, State |
|---|---|---|---|
| 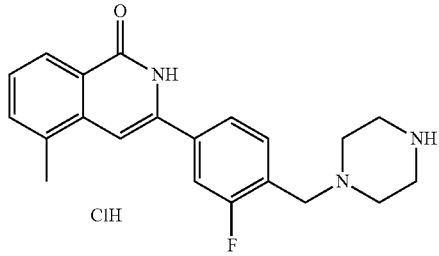 [SMILES: Cc1cccc2c(=O)[nH]c(-c3ccc(CN4CCNCC4)c(F)c3)cc12 ; Cl] | IQ-059 | AnalpH2_MeOH_QC(1): Rt 5.51 min; m/z 352 [M + 1]$^+$ | 112 mg, 100%, pale orange solid |
| 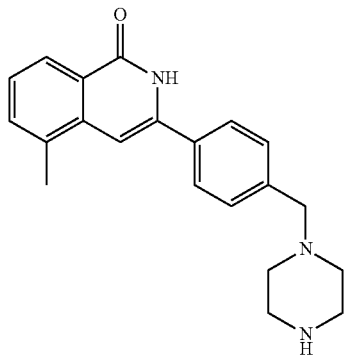 [SMILES: Cc1cccc2c(=O)[nH]c(-c3ccc(CN4CCNCC4)cc3)cc12] | IQ-082 | AnalpH2_MeOH_QC: Rt 5.36 min; m/z 334 [M + 1]$^+$ | 107 mg, 38%, white solid |
| 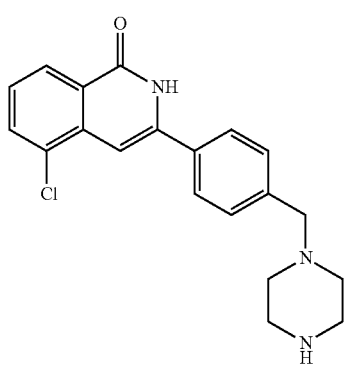 | IQ-083 | AnalpH2_MeOH_QC: Rt 5.87 min; m/z 354 [M + 1]$^+$ | 115 mg, 97%, yellow yellow solid |
| 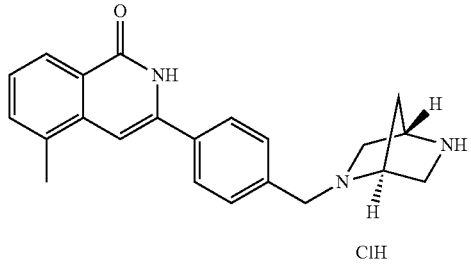 [SMILES: Cc1cccc2c(=O)[nH]c(-c3ccc(CN4C[C@@H]5C[C@H]4CN5)cc3)cc12 ; Cl] | IQ-086 | AnalpH2_MeOH_QC: Rt 4.77 min; m/z 346 [M + 1]$^+$ | 22 mg, 72%, white solid |

TABLE 13-continued
2H-isoquinolin-1-one Formula 5
| Compound | Code | Analytical Data | Mass, % Yield, State |
|---|---|---|---|
| 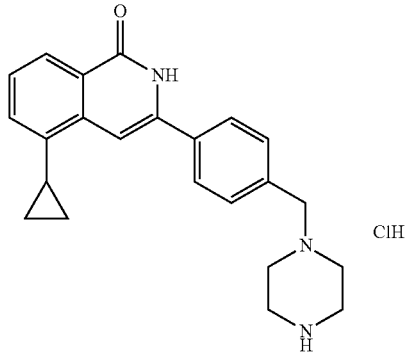 [SMILES: O=c1[nH]c(-c2ccc(CN3CCNCC3)cc2)cc2c(C3CC3)cccc12 ; Cl] | IQ-049 | AnalpH2_MeOH_QC: Rt 5.91 min; m/z 360 [M + 1]$^+$ | 25 mg, 96%, off-white solid |
| 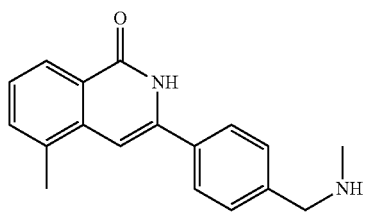 [SMILES: CNCc1ccc(-c2cc3c(C)cccc3c(=O)[nH]2)cc1] | IQ-029 | AnalpH2_MeOH_QC: Rt 5.00 min; m/z 279 [M + 1]$^+$ | 9 mg, 24%, off-white solid |
| 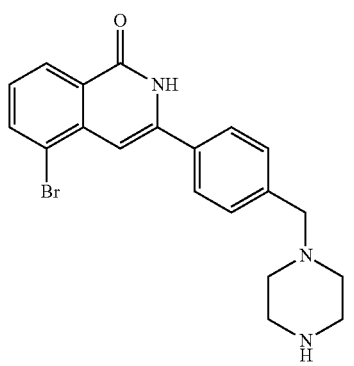 [SMILES: O=c1[nH]c(-c2ccc(CN3CCNCC3)cc2)cc2c(Br)cccc12] | IQ-150 | AnalpH2_MeOH_QC(1): Rt 5.83 min; m/z 400 [M + 1]$^+$ | 367 mg, 56%, cream solid |
| 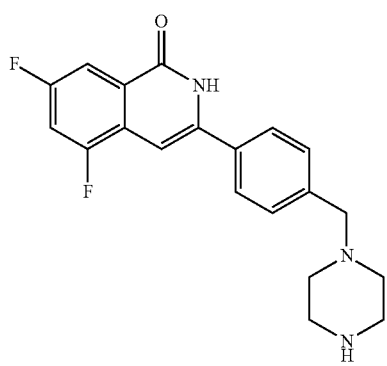 [SMILES: O=c1[nH]c(-c2ccc(CN3CCNCC3)cc2)cc2c(F)cc(F)cc12] | IQ-158 | AnalpH2_MeOH_QC: Rt 5.62 min; m/z 356 [M + 1]$^+$ | 22 mg, 65% white solid |
| 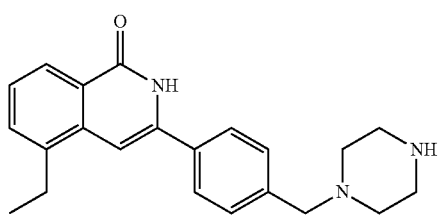 [SMILES: CCc1cccc2c(=O)[nH]c(-c3ccc(CN4CCNCC4)cc3)cc12] | IQ-081 | AnalpH2_MeOH_QC(1): Rt 5.71 min; m/z 348 [M + 1]$^+$ | 29 mg, 48%, pale peach solid |

TABLE 13-continued 2H-isoquinolin-1-one Formula 5

| Compound | Code | Analytical Data | Mass, % Yield, State |
|---|---|---|---|
| 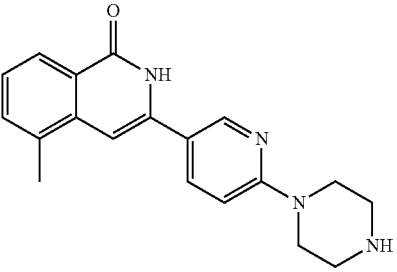 [SMILES: Cc1cccc2c(=O)[nH]c(-c3ccc(N4CCNCC4)nc3)cc12] | IQ-028-1 | AnalpH2_MeOH_QC (Sunfire1): Rt 4.29 min; m/z 321 [M + 1]⁺ | 212 mg, 45%, orange solid $^1$H NMR (400 MHz, DMSO-d$_6$): δ11.42 (br s, 1H), 8.58 (d, J = 2.3 Hz, 1H), 8.05 (d, J = 7.8 Hz, 1H), 7.97 (dd, J = 8.8, 1.0 Hz, 1H), 7.53 (d, J = 6.8 Hz, 1H), 7.32 (t, J = 7.6 Hz, 1H), 6.9 (d, J = 8.8 Hz, 1H), 6.77 (s, 1H), 3.53 (t, J = 5.1 Hz, 4H), 2.81 (t, J = 5.1 Hz, 4H), 2.54 (s, 3H). |
| 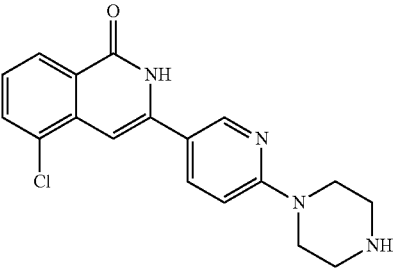 | IQ-027 | AnalpH2_MeOH_QC (Sunfire1): Rt 4.73 min; m/z 341 [M + 1]⁺ | 460 mg, 66%, pale yellow solid $^1$H NMR (400 MHz, DMSO-d$_6$): δ8.54 (d, J = 2.2 Hz, 1H), 8.16 (d, J = 7.8 Hz, 1H), 7.93 (dd, J = 9.1, 2.5 Hz, 1H), 7.85 (dd, J = 7.6 Hz, 1.0 1H), 7.43 (t, J = 7.8 Hz, 1H), 6.90 (d, J = 9.1 Hz, 1H), 6.83 (s, 1H), 3.54-3.52 (m, 4H), 2.80-2.78 (m, 4H). |
| 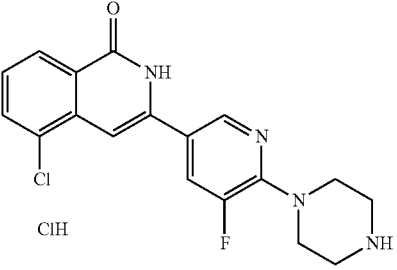 [SMILES: O=c1[nH]c(-c2cnc(N3CCNCC3)c(F)c2)cc2c(Cl)cccc12 ; Cl] | IQ-024 | AnalpH2_MeOH_QC: Rt 5.74 min; m/z 359 [M + 1]⁺ | 82 mg, 67%, pale orange solid |
| 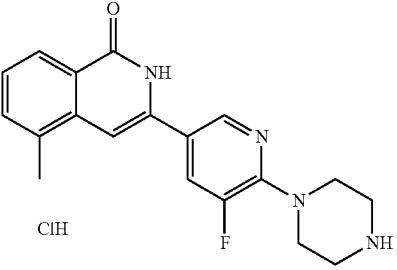 [SMILES: Cc1cccc2c(=O)[nH]c(-c3cnc(N4CCNCC4)c(F)c3)cc12 ; Cl] | IQ-023 | AnalpH2_MeOH_QC: Rt 5.41 min; m/z 339 [M + 1]⁺ | 51 mg, 97%, yellow solid |
| 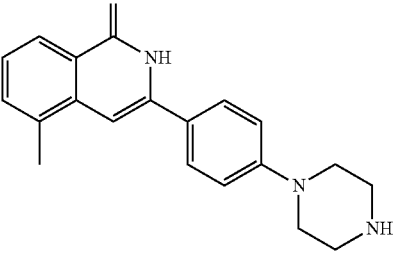 | IQ-016 | AnalpH2_MeOH_QC: Rt 5.35 min; m/z 320 [M + 1]⁺ | 59 mg, 41%, beige solid |

TABLE 13-continued

2H-isoquinolin-1-one Formula 5

| Compound | Code | Analytical Data | Mass, % Yield, State |
|---|---|---|---|
| 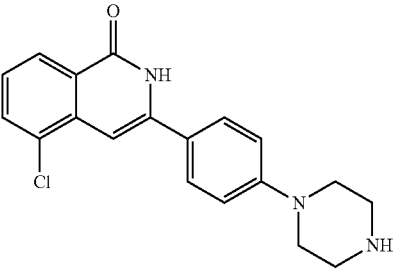 [SMILES: O=c1[nH]c(-c2ccc(N3CCNCC3)cc2)cc2c(Cl)cccc12] | IQ-014 | AnalpH2_MeOH_QC: Rt 5.65 min; m/z 340 [M + 1]$^+$ | 20 mg, 10%, yellow yellow solid |
| 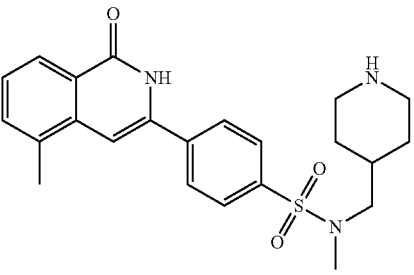 [SMILES: Cc1cccc2c(=O)[nH]c(-c3ccc(S(=O)(=O)N(C)CC4CCNCC4)cc3)cc12] | IQ-115 | AnalpH2_MeOH_QC (Sunfire1): RT 4.81 min; m/z 426 [M + 1]$^+$. | 60 mg, 32%, cream solid |
| 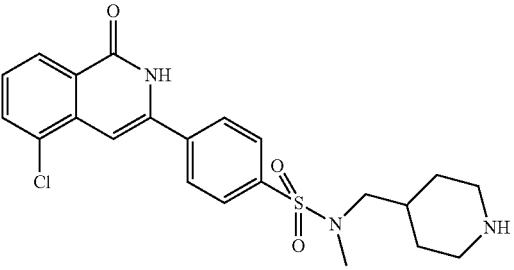 [SMILES: CN(CC1CCNCC1)S(=O)(=O)c1ccc(-c2cc3c(Cl)cccc3c(=O)[nH]2)cc1] | IQ-116 | AnalpH2_MeOH_QC (Sunfire1): RT 5.13 min; m/z 446 [M + 1]$^+$. | 36 mg, 21%, pale orange solid |
| 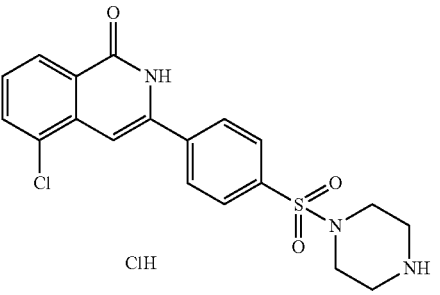 | IQ-124 | AnalpH2_MeOH_QC: RT 5.79 min; m/z 404 [M + 1]$^+$. | 146 mg, 89%, yellow yellow solid |
| 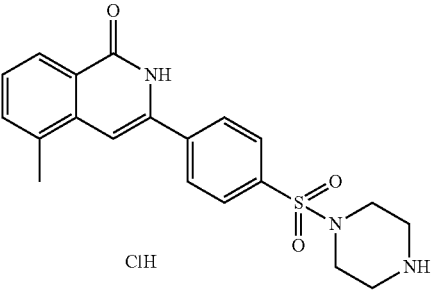 [SMILES: Cc1cccc2c(=O)[nH]c(-c3ccc(S(=O)(=O)N4CCNCC4)cc3)cc12 ; Cl] | IQ-123 | AnalpH2_MeOH_QC: RT 5.50 min; m/z 384 [M + 1]$^+$. | 54 mg, 59%, yellow yellow solid |

TABLE 13-continued

2H-isoquinolin-1-one Formula 5

| Compound | Code | Analytical Data | Mass, % Yield, State |
|---|---|---|---|
| (structure) | IQ-159 | AnalpH2_MeOH_QC: Rt 6.08 min; m/z 360 [M + 1]+ | 4.4 mg, 17% pale cream solid |

Scheme A, Step C (Protocol 2): Synthesis of 2H-isoquinolin-1-one Derivatives of formula 5 (via TBDMS Deprotection)

3-{6-[4-(2-Hydroxy-ethyl)-piperazin-1-yl]-pyridin-3-yl}-5-methyl-2H-isoquinolin-1-one (IQ-011)

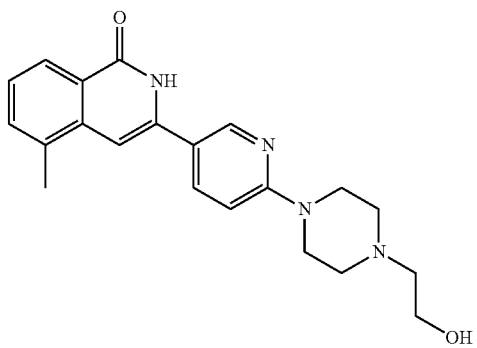 [SMILES: O=c1[nH]c(-c2ccc(N3CCN(CCO)CC3)nc2)cc2c(Cl)cccc12]

To a solution of 3-(6-{4-[2-(tert-butyl-dimethyl-silanyloxy)-ethyl]-piperazin-1-yl}-pyridin-3-yl)-5-methyl-2H-isoquinolin-1-one (214 mg, 0.45 mmol) in THF (1.5 mL) at 5° C. was added 1M TBAF/THF (0.58 mL, 0.58 mmol) dropwise. The reaction mixture was allowed to warm to RT and stirred for 1 h. The reaction mixture was diluted with EtOAc (10 mL) and washed with water and brine. The organic layer was concentrated in vacuo and purified by reverse phase preparative HPLC-MS to obtain 3-{6-[4-(2-hydroxy-ethyl)-piperazin-1-yl]-pyridin-3-yl}-5-methyl-2H-isoquinolin-1-one as a yellow solid (27 mg, 16%).

$^1$H NMR (400 MHz, DMSO-$d_6$): δ11.61-11.29 (br s, 1H), 8.59 (d, J=2.5 Hz, 1H), 8.05 (d, J=8 Hz, 1H), 7.98 (dd, J=9, 2.5 Hz, 1H), 7.53 (d, J=8 Hz, 1H), 7.32 (t, J=8 Hz, 1H), 6.92 (d, J=9 Hz, 1H), 6.77 (s, 1H), 4.43 (t, J=5 Hz, 1H), 3.59-3.54 (m, 6H), 2.54 (s, 3H), 2.54-2.52 (m, 4H), 2.44 (t, J=5 Hz, 2H). AnalpH2_MeOH_QC: Rt 5.04 min; m/z 365 [M+1]+.

The following 2H-isoquinolin-1-one of formula 5 derivatives are prepared using analogous procedures.

TABLE 14

2H-isoquinolin-1-one derivatives of Formula 5

| Compound | Code | Analytical Data | Mass, % Yield, State |
|---|---|---|---|
| (structure) | IQ-012 | AnalpH2_MeOH_QC: Rt 5.40 min; m/z 385 [M + 1]+ | 21 mg, 12%, pale yellow solid |

TABLE 14-continued 2H-isoquinolin-1-one derivatives of Formula 5

| Compound | Code | Analytical Data | Mass, % Yield, State |
|---|---|---|---|
| | IQ-219 | AnalpH2_MeOH_QC(1): Rt 5.08 min; m/z 326 [M + 1]+ | 65 mg, 13%, white solid |

Scheme A, Step C (Protocol 3): Synthesis of 2H-isoquinolin-1-one Derivatives of formula 5 (via TBDPS Deprotection)

3-[4-(4-Hydroxy-piperidin-1-ylmethyl)-phenyl]-5-methyl-2H-isoquinolin-1-one (IQ-074)

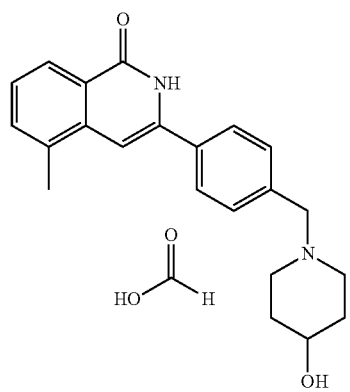

To a stirred solution of 3-{4-[4-(tert-butyl-diphenyl-silanyloxy)-piperidin-1-ylmethyl]-phenyl}-5-methyl-2H-isoquinolin-1-one (213 mg, 0.36 mmol) in $CH_2Cl_2$ (2 mL) was added 1.25M methanolic HCl (1 mL) and the reaction stirred at RT for 48 h. The reaction mixture was concentrated in vacuo and the crude residue purified by reverse phase preparative HPLC-MS to afford 3-[4-(4-hydroxy-piperidin-1-ylmethyl)-phenyl]-5-methyl-2H-isoquinolin-1-one as a pale yellow solid (80 mg, 64%).

AnalpH2_MeOH_QC(1): Rt 5.03 min; m/z 349 [M+1]+.

$^1$H NMR (400 MHz, DMSO-$d_6$): δ11.63-11.35 (br s, 1H), 8.15 (s, 0.8H) 8.07 (d, J=7 Hz, 1H), 7.78 (d, J=8 Hz, 2H), 7.56 (d with fine coupling, J=7 Hz, 1H), 7.41 (d, J=8 Hz, 2H), 7.37 (t, J=8 Hz, 1H), 6.85 (s, 1H), 4.66-4.52 (br s, 1H), 3.52 (s, 2H), 3.50-3.45 (m, 1H), 2.70-2.67 (m, 2H), 2.56 (s, 3H), 2.11-2.06 (m, 2H), 1.74-1.70 (m, 2H), 1.45-1.36 (m, 2H).

The following 2H-isoquinolin-1-one derivatives are prepared using analogous procedures.

TABLE 15

2H-isoquinolin-1-one derivatives of Formula 5

| Compound | Code | Analytical Data | Mass, % Yield, State |
|---|---|---|---|
| | IQ-120 | AnalpH2_MeOH_QC(1): Rt 7.31 min; m/z 373 [M + 1]+ | 39 mg, 60%, white solid |

TABLE 15-continued
2H-isoquinolin-1-one derivatives of Formula 5
| Compound | Code | Analytical Data | Mass, % Yield, State |
|---|---|---|---|
| 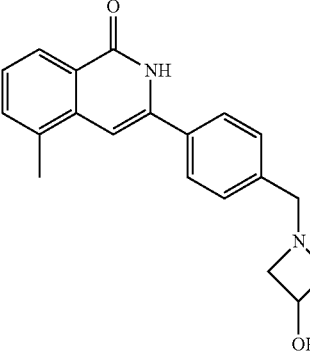 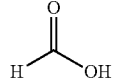 | IQ-167 | AnalpH2_MeOH_QC(1): Rt 5.04 min; m/z 321 [M + 1]$^+$ | 70 mg, 50%, off-white solid |
| 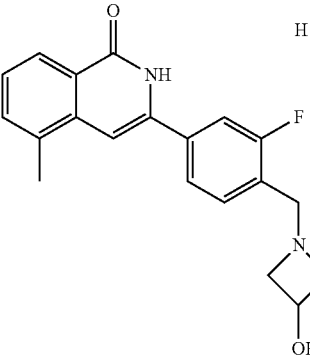  | IQ-169 | AnalpH2_MeOH_QC(1): Rt 5.11 min; m/z 339 [M + 1]$^+$ | 3.5 mg, 15%, off-white solid |
| 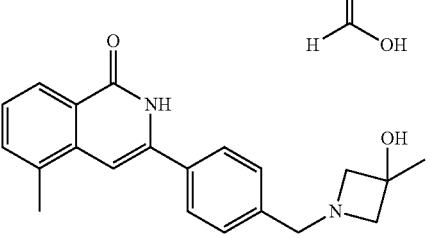 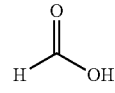 | IQ-172 | AnalpH2_MeOH_QC(1): Rt 5.09 min; m/z 335 [M + 1]$^+$ | 17 mg, 49%, off-white solid |

Scheme A, Step C (Protocol 4): Synthesis of 2H-isoquinolin-1-one Derivatives of formula 5 (via Tosyl Deprotection) (IQ-075)

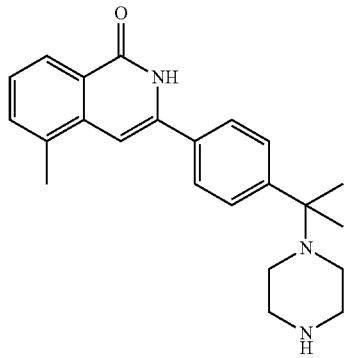 [SMILES: Cc1cccc2c(=O)[nH]c(-c3ccc(C(C)(C)N4CCNCC4)cc3)cc12]

To a solution of 5-methyl-3-(4-{1-methyl-1-[4-(toluene-4-sulfonyl)-piperazin-1-yl]-ethyl}-phenyl)-2H-isoquinolin-1-one (33 mg, 0.064 mmol) in HBr (33% w/w in acetic acid) (0.25 mL) was added 4-hydroxybenzoic acid (27 mg, 0.194 mmol) and the reaction stirred for 16 h at RT afterwhich time the reaction was concentrated in vacuo and the crude residue purified by preperative HPLC to afford 5-Methyl-3-[(4-(1-methyl-1-piperazin-1-yl]-ethyl)-phenyl]-2H-isoquinolin-1-one as a pale orange solid (1.06 mg, 4.5%).

AnalpH2_MeOH_QC(1): RT 6.01 min; m/z 362 [M+1]$^+$.

Scheme A, Step D (Protocol 1): Synthesis of 2H-isoquinolin-1-one Derivatives of formula 6 (via acylation)

3-[4-(4-Acetyl-piperazin-1-ylmethyl)-phenyl]-5-methyl-2H-isoquinolin-1-one (IQ-055)

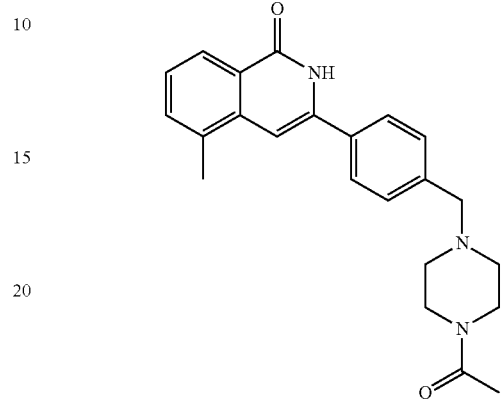

To a stirred solution of acetic acid (0.005 mL, 0.068 mmol) in CH$_2$Cl$_2$ (5 mL) was added TBTU (22 mg, 0.068 mmol) and N,N-diisopropylethylamine (0.036 mL, 0.20 mmol) and the reaction stirred for 10 min at RT. 5-Methyl-3-(4-piperazin-1-ylmethylphenyl)-2H-isoquinolin-1-one (23 mg, 0.068 mmol) was then added and the reaction stirred for 2 h at RT. The reaction mixture was concentrated in vacuo and purified by reverse phase preparative HPLC-MS to afford 3-[4-(4-acetyl-piperazine-1-ylmethyl)-phenyl]-5-methyl-2H-isoquinolin-1-one as a white solid (2 mg, 9%).

$^1$H NMR (400 MHz, DMSO-d$_6$): δ 11.70-11.38 (br s, 1H), 8.08 (d, J=8 Hz, 1H), 7.80 (d, J=8 Hz, 2H), 7.56 (d, J=8 Hz, 1H), 7.44 (d, J=8 Hz, 2H), 7.37 (t, J=8 Hz, 1H), 6.92 (s, 1H), 3.57 (s, 2H), 3.46-3.42, (m, 4H), 2.56 (s, 3H), 2.44-2.39 (m, 2H), 2.35-2.32 (m, 2H), 1.99 (3H, s).

AnalpH2_MeOH_QC(Sunfire): Rt 4.38 min; m/z 376 [M+1]$^+$.

The following 2H-isoquinolin-1-one derivatives are prepared using analogous procedures.

TABLE 16

2H-isoquinolin-1-one derivatives of Formula 6

| Compound | Code | Analytical Data | Mass, % Yield, State |
|---|---|---|---|
| (structure) | IQ-017 | AnalpH2_MeOH_QC: Rt 7.76 min; m/z 362 [M + 1]$^+$ | 18 mg, 36%, beige solid |

TABLE 16-continued 2H-isoquinolin-1-one derivatives of Formula 6

| Compound | Code | Analytical Data | Mass, % Yield, State |
|---|---|---|---|
| (structure) | IQ-015 | AnalpH2_MeOH_QC: Rt 8.16 min; m/z 382 [M + 1]+ | 11 mg, 43%, yellow solid |
| (structure) | IQ-045 | AnalpH2_MeOH_QC Rt 5.62 min m/z 396 [M + 1]+. | 17 mg, 42%, white solid |

Scheme A, Step D (Protocol 2): Synthesis of 2H-isoquinolin-1-one Derivatives of formula 6 (via acylation)

3-[2-(4-Cyclopropanecarbonyl-piperazin-1-yl)-pyrimidin-5-yl]-5-methyl-2H-isoquinolin-1-one (IQ-157)

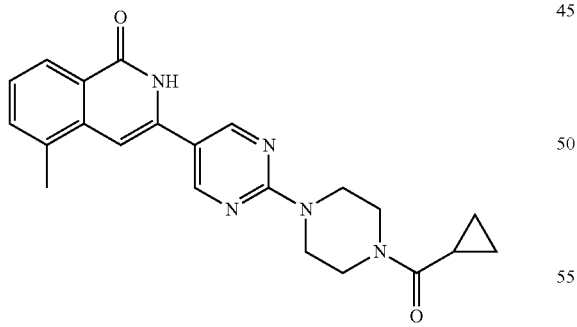

Cyclopropylcarbonyl chloride (9 μL, 2.28 mmol) was added to a stirred solution of 5-methyl-3-(2-piperazin-1-yl-pyrimidin-5-yl)-2H-isoquinolin-1-one (36 mg, 0.11 mmol) and N,N-diisopropylethylamine (23 μL, 0.132 mmol) in CH$_2$Cl$_2$ (2 mL) at −20° C. and allowed to stir for 10 min. The reaction mixture was concentrated in vacuo. The crude residue was purified by reverse phase preparative HPLC-MS to afford 3-[2-(4-cyclopropanecarbonyl-piperazin-1-yl)-pyrimidin-5-yl]-5-methyl-2H-isoquinolin-1-one as a white solid (19 mg, 45%).

$^1$H NMR (400 MHz, DMSO-d$_6$): δ11.82-11.11 (br s, 1H), 8.85 (s, 2H), 8.05 (d, J=8 Hz, 1H), 7.55 (d, J=8 Hz, 1H), 7.35 (t, J=8 Hz, 1H), 6.84 (s, 1H), 3.96-3.76 (br m, 6H), 3.64-3.54 (br s, 2H), 2.54 (s, 3H), 2.08-2.00 (m, 1H), 0.82-0.70 (m, 4H). AnalpH2_MeOH_QC(1): Rt 8.05 min; m/z 390 [M+1]+.

Scheme A, Step D (Protocol 3): Synthesis of 2H-isoquinolin-1-one Derivatives of formula 6 (urea formation) (IQ-068)

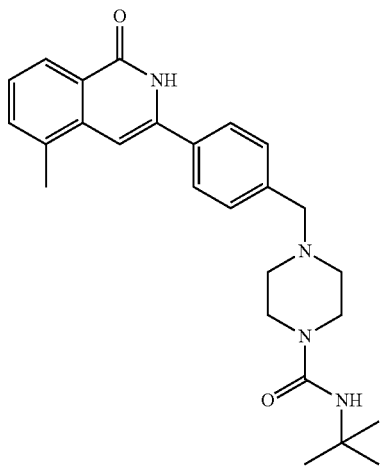 [SMILES: Cc1cccc2c(=O)[nH]c(-c3ccc(CN4CCN(C(=O)NC(C)(C)C)CC4)cc3)cc12]

To a stirred solution of 5-methyl-3-(4-piperazin-1-ylmethyl-phenyl)-2H-isoquinolin-1-one (40 mg, 0.12 mmol) in CH$_2$Cl$_2$ (0.5 mL) was added tert-butyl isocyanate (0.014 mL, 0.12 mmol) and the reaction mixture stirred at RT for 1 h after which time the solvent was removed in vacuo and the crude residue purified by reverse phase preparative HPLC-MS to afford 4-[4-(5-methyl-1-oxo-1,2-dihydro-isoquinolin-3-yl)-benzyl]-piperazine-1-carboxylic acid tert-butylamide as a white solid (28 mg, 54%).

$^1$H NMR (400 MHz, DMSO-d$_6$): δ 11.50-11.12 (brs, 1H), 7.83 (d, J=8 Hz, 1H), 7.55 (d, J=8 Hz, 2H), 7.32 (d, J=8 Hz, 1H), 7.19 (d, J=8 Hz, 2H), 7.13 (t, J=8 Hz, 1H), 6.62 (s, 1H), 5.49 (s, 1H), 3.30 (s, 2H), 3.03-3.01, (m, 4H) 2.32 (s, 3H), 2.10-2.08 (m, 4H), 1.01 (s, 9H).

AnalpH2_MeOH_QC(1): Rt 5.83 min; m/z 433 [M+1]$^+$.

Synthesis of 3-(1-Oxy-pyridin-3-yl)-2H-isoquinolin-1-one Derivatives 27

Scheme H

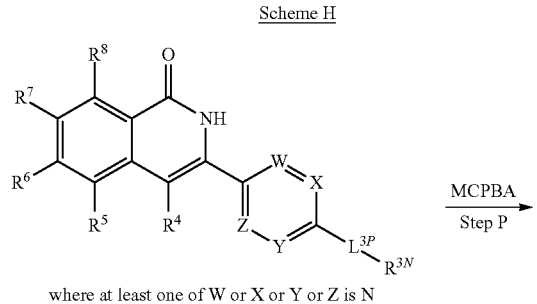

where at least one of W or X or Y or Z is N
4

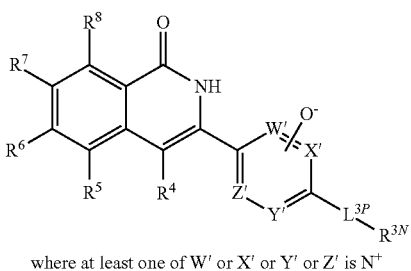

where at least one of W' or X' or Y' or Z' is N$^+$
27

Scheme H, Step P: N-Oxidation of 3-(pyridinyl)-2H-isoquinolin-1-one Derivatives 27

5-Chloro-3-[6-(4-methyl-piperazin-1-yl)-1-oxy-pyridin-3-yl]-2H-isoquinolin-1-one (IQ-002-2)

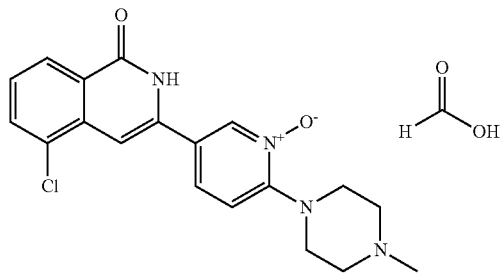 [SMILES: CN1CCN(c2ccc(-c3cc4c(Cl)cccc4c(=O)[nH]3)c[n+]2[O-])CC1 ; O=CO]

MCPBA (41 mg, 0.184 mmol) was added to a solution of 5-chloro-3-[6-(4-methyl-piperazin-1-yl)-pyridin-3-yl]-2H-isoquinolin-1-one (58 mg, 0.164 mmol) in CH$_2$Cl$_2$ (7 mL) at −78° C. and allowed to warm to RT and stirred at this temperature for a further 40 minutes. The reaction mixture was quenched with saturated, aqueous NaHCO$_3$ (2 mL) and extracted with CH$_2$Cl$_2$ followed by EtOAc. The combined organic layer was concentrated in vacuo and passed through an SCX-2 cartridge (5 g), eluting with 10% NH$_3$/MeOH. The desired fractions were concentrated in vacuo and the crude material purified by reverse phase preparative HPLC-MS to obtain 5-chloro-3-[6-(4-methyl-piperazin-1-yl)-1-oxy-pyridin-3-yl]-2H-isoquinolin-1-one as a white solid (19 mg, 33%).

$^1$H NMR (400 MHz, DMSO-d$_6$): δ12.30-12.00 (brs, 1H), 8.59 (d, J=8 Hz, 1H), 8.31 (s, 0.6H), 8.17 (d, J=9 Hz, 1H), 8.01 (dd, J=9, 3 Hz, 1H), 7.84 (d, J=8 Hz, 1H), 7.43 (t, J=8 Hz, 1H), 7.03 (d, J=9 Hz, 1H), 6.84 (s, 1H), 4.29-4.27 (m, 2H), 3.59-3.49 (m, 4H), 3.35-3.31 (m, 2H), 3.25 (s, 3H).

AnalpH9_MeOH_QC: Rt 7.20 min; m/z 371 [M+1]$^+$.

The following 2H-isoquinolin-1-one derivatives are prepared using analogous procedures.

TABLE 17

2H-isoquinolin-1-one derivatives 27

| Compound | Code | Analytical Data | Mass, % Yield, State |
|---|---|---|---|
|  | IQ-028-2 | AnalpH9_MeOH_QC (Sunfire1): Rt 5.86 min; m/z 337 [M + 1]$^+$ | 48 mg, 57%, brown solid |

General Procedure for Synthesis of 2H-isoquinolin-1-one derivatives of Formula 34

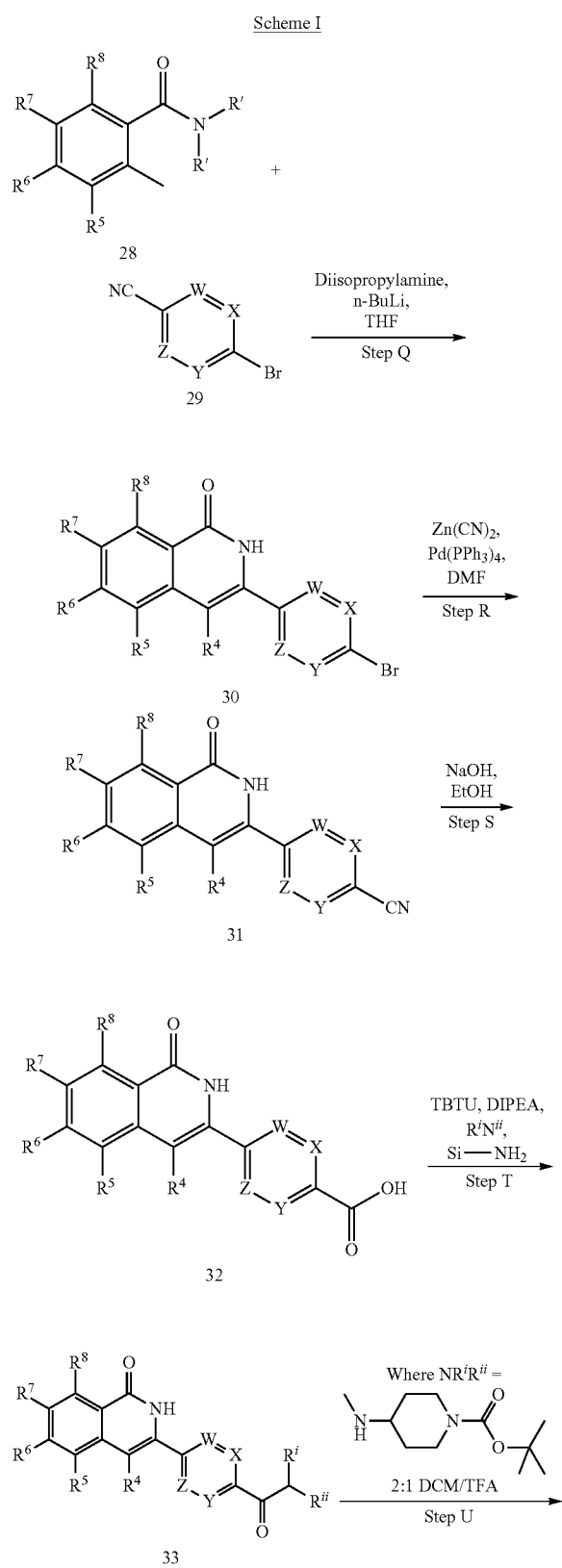

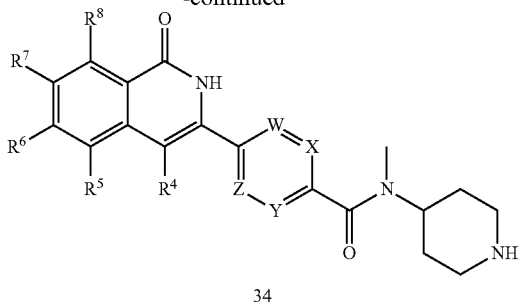

Scheme I, Step Q Synthesis of 3-(4-Bromo-phenyl)-5-methyl-2H-isoquinolin-1-one

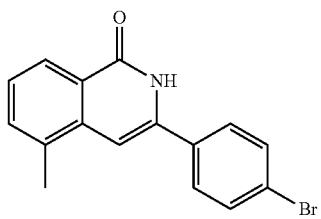 [SMILES: Cc1cccc2c(=O)[nH]c(-c3ccc(Br)cc3)cc12]

To N,N-diisopropylamine (2.54 mL, 18 mmol) in anhydrous THF (15 mL), under $N_2$ at $-78°$ C. was added n-BuLi dropwise (2.5M in n-hexanes, 7.2 mL, 18 mmol) and the reaction mixture maintained at this temperature for 30 minutes. A solution of N,N-diethyl-2,3-dimethyl-benzamide (1.23 g, 6 mmol) in anhydrous THF (15 mL) was added dropwise to give a deep red solution. After 20 minutes at $-78°$ C., 4-bromobenzonitrile (1.09 g, 6 mmol) in anhydrous THF (15 mL) was added dropwise and the reaction mixture allowed to stir at this temperature for 2.5 h. The reaction mixture was quenched by adding dropwise onto ice, upon which a pale yellow solid precipitated out. The solid was triturated with iso-hexane/EtOAc (2:1), filtered and dried in vacuo to afford 3-(4-bromo-phenyl)-5-methyl-2H-isoquinolin-1-one as a pale yellow solid (1.1 g, 58%).

AnalpH2_MeOH_4 min(1): Rt 3.25 min; m/z 314 $[M+1]^+$.

Scheme I, Step R: Synthesis of 4-(5-Methyl-1-oxo-1,2-dihydro-isoquinolin-3-yl)-benzonitrile

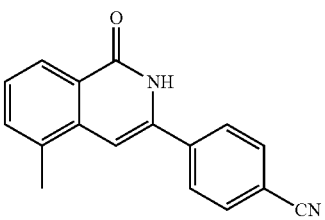 [SMILES: Cc1cccc2c(=O)[nH]c(-c3ccc(C#N)cc3)cc12]

3-(4-Bromo-phenyl)-5-methyl-2H-isoquinolin-1-one (200 mg, 0.64 mmol), zinc cyanide (90 mg, 0.76 mmol) and tetrakis(triphenylphosphine)palladium(0) (74 mg, 0.064 mmol) were stirred in DMF (2.1 mL) and degassed with $N_2$. The reaction mixtures were irradiated using a microwave (300 W, 180° C., 30 min). The reaction mixtures were combined and the resulting precipitate was filtered, washed with DMF and water and dried to give 4-(5-methyl-1-oxo-1,2-dihydro-isoquinolin-3-yl)-benzonitrile as a yellowish solid (718 mg, 79%) which was used in the next step without further purification.

AnalpH2_MeOH_4 min(1): Rt 2.83 min; m/z 261 [M+1]⁺.

Scheme I, Step S: Synthesis of 4-(5-Methyl-1-oxo-1,2-dihydro-isoquinolin-3-yl)-benzoic acid

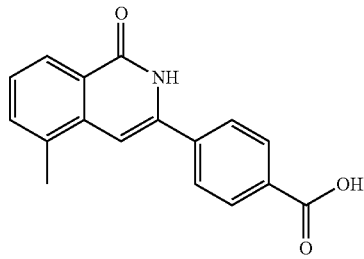 [SMILES: Cc1cccc2c(=O)[nH]c(-c3ccc(C(=O)O)cc3)cc12]

To 4-(5-methyl-1-oxo-1,2-dihydro-isoquinolin-3-yl)-benzonitrile (100 mg, 0.38 mmol) was added 2M NaOH (1.5 mL) and the reaction mixture irradiated using a microwave (300 W, 130° C., 20 min). The reaction mixtures was diluted with water and adjusted to pH2 with 2M HCl whereupon a pale yellow solid precipitated out of solution. The solid was filtered, washed with water and dried. The solid was dissolved in DMF and passed through a Si-thiol cartridge to remove any residual palladium, eluting with DMF. The eluent was removed in vacuo to give 4-(5-methyl-1-oxo-1,2-dihydro-isoquinolin-3-yl)-benzoic acid as a pale yellow solid (120 mg, 63%).

AnalpH9_MeOH_4 min(1): Rt 2.24 min; m/z 280 [M+1]⁺.

Scheme I, Step T: Synthesis of 3-Benzamide-5-Methyl-2H-isoquinolin-1-one Derivatives of formula 33

N-Methyl-4-(5-methyl-1-oxo-1,2-dihydro-isoquinolin-3-yl)-N-(tetrahydro-pyran-4-ylmethyl)-benzamide (IQ-097)

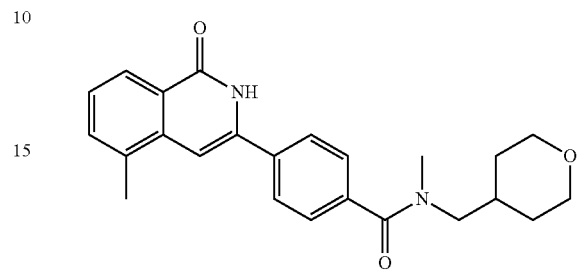

To 4-(5-methyl-1-oxo-1,2-dihydro-isoquinolin-3-yl)-benzoic acid (35 mg, 0.125 mmol), TBTU (40 mg, 0.125 mmol) was added 0.36M N,N-diisopropylethylamine/$CH_2Cl_2$ (0.35 mL, 0.125 mmol) and anhydrous DMF (0.9 mL). The reaction mixture was stirred at RT for 45 min after which time methyl-(tetrahydro-pyran-4-ylmethyl)-amine (19 mg, 0.15 mmol) in anhydrous DMF (0.45 mL) was added and the reaction mixture was stirred at RT overnight. The reaction mixture was passed through a Si—$NH_2$ cartridge (1 g), eluting with DMF (2× column volumes), MeOH (2× column volumes) and the solvent removed in vacuo and the crude product purified by reverse phase preparative HPLC-MS to obtain N-methyl-4-(5-methyl-1-oxo-1,2-dihydro-isoquinolin-3-yl)-N-(tetrahydro-pyran-4-ylmethyl)-benzamide as a yellow foam (24 mg, 48%).

¹H NMR (400 MHz, DMSO-$d_6$): δ11.69-11.54 (br s, 1H), 8.09 (d, J=7 Hz, 1H), 7.89 (d, J=8 Hz, 2H), 7.58 (d, J=7 Hz, 1H), 7.52 (br d, J=8 Hz, 1H), 7.46 (br d, J=8 Hz, 1H), 7.40 (t, J=7 Hz, 1H), 6.92 (s, 1H), 3.90 (br d, J=11 Hz, 1H), 3.75 (br d, J=11 Hz, 1H), 3.40-3.17 (m, 4H), 2.99 (br s, 1H), 2.94 (br s, 2H), 2.58 (s, 3H), 2.08-1.82 (br m, 1H), 1.63 (br d, J=12 Hz, 1H), 1.44 (br d, J=12 Hz, 1H), 1.32-1.25 (m, 1H), 0.95-0.80 (m, 1H).

AnalpH2_MeOH_QC(1): Rt 7.69 min; m/z 391 [M+1]⁺.

The following 2H-isoquinolin-1-one derivatives are prepared using analogous procedures

TABLE 18

2H-isoquinolin-1-one derivatives of Formula 33

| Compound | Code | Analytical Data | Mass, % Yield, State |
|---|---|---|---|
| (structure: 5-methyl-3-[4-(morpholine-4-carbonyl)phenyl]-2H-isoquinolin-1-one) | IQ-107 | AnalpH2_MeOH_QC(1): Rt 7.44 min; m/z 349 [M + 1]⁺ | 12 mg, 51%, white solid |

TABLE 18-continued 2H-isoquinolin-1-one derivatives of Formula 33

| Compound | Code | Analytical Data | Mass, % Yield, State |
|---|---|---|---|
| | IQ-146 | AnalpH2_MeOH_QC(1): Rt 5.27 min; m/z 376 [M + 1]+ | 16 mg, 35%, off-white solid |
| | IQ-098 | AnalpH2_MeOH_QC(1): Rt 5.51 min; m/z 416 [M + 1]+ | 15 mg, 29%, off-white solid |
| | IQ-153 | AnalpH2_MeOH_4 min: Rt 3.15 min; m/z 476 [M + 1]+ | 21 mg, 100%, beige solid |

Scheme I, Step U: Synthesis of 3-Benzamide-5-Methyl-2H-isoquinolin-1-one Derivatives of formula 34

N-Methyl-4-(5-methyl-1-oxo-1,2-dihydro-isoquinolin-3-yl)-N-piperidin-4-yl-benzamide (IQ-096)

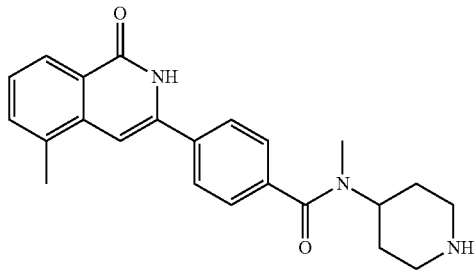 [SMILES: Cc1cccc2c(=O)[nH]c(-c3ccc(C(=O)N(C)C4CCNCC4)cc3)cc12]

To 4-{methyl-[4-(5-methyl-1-oxo-1,2-dihydro-isoquinolin-3-yl)-benzoyl]-amino}-piperidine-1-carboxylic acid tert-butyl ester (21 mg, 0.044 mmol) was added 2:1 CH₂Cl₂/TFA (1 mL) and the reaction mixture stirred at RT for 1 h. The solvent was removed in vacuo, re-dissolved in MeOH and passed through an SCX-2 cartridge (1 g). The column was washed with MeOH (4× column volumes), the desired product eluted from the cartridge with 0.5M NH₃/MeOH (4× column volumes) and concentrated in vacuo. The crude product was purified by reverse phase preparative HPLC-MS to obtain N-methyl-4-(5-methyl-1-oxo-1,2-dihydro-isoquinolin-3-yl)-N-piperidin-4-yl-benzamide as a white solid (2.4 mg, 14%).

AnalpH2_MeOH_QC(1): Rt 5.10 min; m/z 376 [M+1]+.

Synthesis of 2H-isoquinolin-1-one derivatives of
Formula 4 & 5 (via Route 2)
Scheme J
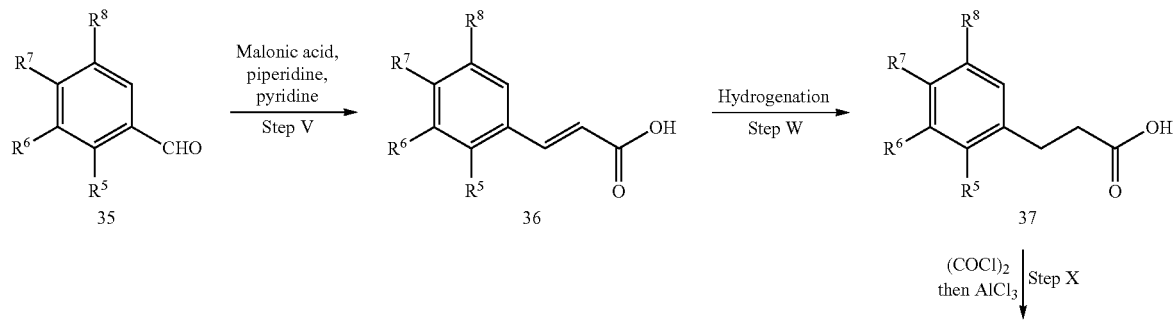
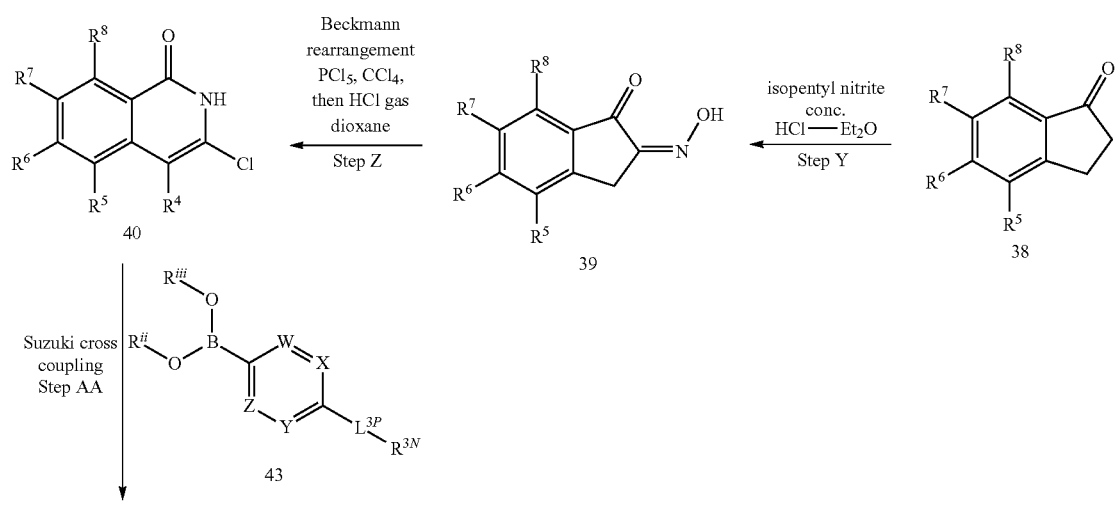
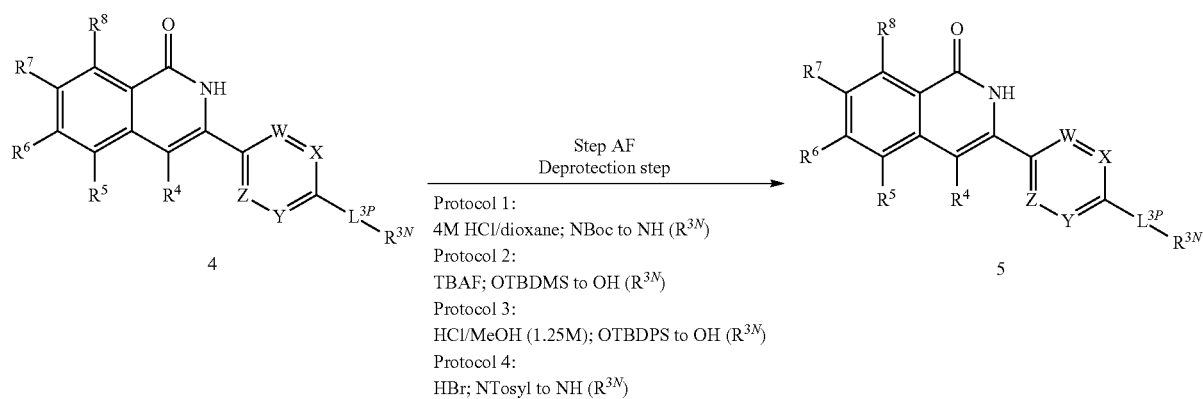
Step AF
Deprotection step
Protocol 1:
4M HCl/dioxane; NBoc to NH ($R^{3N}$)
Protocol 2:
TBAF; OTBDMS to OH ($R^{3N}$)
Protocol 3:
HCl/MeOH (1.25M); OTBDPS to OH ($R^{3N}$)
Protocol 4:
HBr; NTosyl to NH ($R^{3N}$)

Scheme J, Step V: Synthesis of Phenyl Acrylic Acid Derivatives of Formula 36

(E)-3-(4-Fluoro-2-methylphenyl)acrylic acid

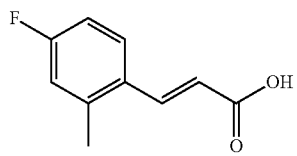 [SMILES: O=C(O)/C=C/c1ccc(F)cc1F]

A stirred solution of 4-fluoro-2-methyl-benzaldehyde (20 g, 144.9 mmol) and malonic acid (30.1 g, 289.8 mmol) in pyridine (100 mL) was heated to 50° C. Piperidine (10 mL) was added and the reaction mixture was heated at 70° C. for 18 h. The reaction mixture was cooled RT and poured into chilled aqueous 1N HCl solution (1500 mL), the resulting precipitate was filtered and washed with petroleum ether 60-80 and dried in vacuo to obtain (E)-3-(4-fluoro-2-methylphenyl)acrylic acid (18 g, 69%) as an off white solid.

$^1$H NMR (400 MHz, CDCl$_3$): δ8.00 (d, J=16 Hz, 1H), 7.60-7.55 (m, 1H), 6.96-6.90 (m, 2H), 6.32 (d, J=16 Hz, 1H), 2.44 (s, 3H).

AnalpH2_MeCN_FA_7 min(XTERRA1.m): Rt 3.34 min; m/z 181 [M+1]$^+$.

The following phenyl acrylic acid derivatives of formula 36 are prepared using analogous procedures.

TABLE 19

Phenyl acrylic acid Derivatives 36

| Compound | Reference | Analytical Data | Mass, % Yield, State |
|---|---|---|---|
| ![F-phenyl acrylic acid with 2-F] | Reported as commercially available | AnalpH2_MeCN_FA_7 min (XTERRA1.m): Rt 3.16 min; m/z 185 [M + 1]$^+$. | 25 g, 64%, off-white solid |

TABLE 19-continued

Phenyl acrylic acid Derivatives 36

| Compound | Reference | Analytical Data | Mass, % Yield, State |
|---|---|---|---|
| ![F-phenyl acrylic acid with methyl] | Reported as commercially available | AnalpH2_MeOH_4 min(3): Rt 2.63 min; m/z not observed | 6.3 g, 97%, white solid |

Scheme J, Step W: Synthesis of Phenyl Propanoic Derivatives 37

3-(4-Fluoro-2-methylphenyl)propanoic acid

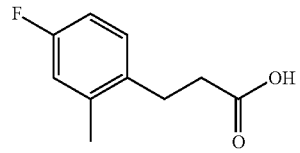 [SMILES: O=C(O)CCc1ccc(F)cc1F]

To a solution of (E)-3-(4-fluoro-2-methylphenyl)acrylic acid (13 g, 72.22 mmol) in EtOH (250 mL) was added PtO$_2$ (250 mg) and then hydrogenated at 30 psi for 3 h. The reaction mixture was filtered on a Celite® pad, washed with MeOH (100 mL), and the filtrate was concentrated, washed with diethyl ether (20 mL), n-pentane (50 mL) and dried in vacuo to give 3-(4-fluoro-2-methylphenyl)propanoic acid as an off-white solid (10 g, 77%).

$^1$H NMR (400 MHz, CDCl$_3$): δ 7.13-7.05 (m, 1H), 6.90-6.79 (m, 2H), 2.95-2.85 (2H, m), 2.65-2.55 (2H, m), 2.31 (s, 3H)

AnalpH2_MeCN_FA_7 min(XTERRA1.m): Rt 3.33 min; m/z 181 [M−1]$^−$.

The following phenyl propanoic derivatives 37 are prepared using analogous procedures.

TABLE 20

Phenyl Propanoic Derivatives 37

| Compound | Reference | Analytical Data | Mass, % Yield, State |
|---|---|---|---|
| ![F,F-phenyl propanoic acid] | Reported as commercially available | AnalpH2_MeCN_FA_7 min (XTERRA1.m): Rt 3.19 min; m/z 185 [M − 1]$^−$. | 8 g, 73%, off-white solid |
| ![F-methylphenyl propanoic acid] | Reported as commercially available | AnalpH2_MeOH_4 min(3): Rt 2.58 min; m/z not observed | 6.37 g, 100%, white solid |

Scheme J, Step X: Indanone Synthesis

6-Fluoro-4-methyl-2,3-dihydro-1H-inden-1-one

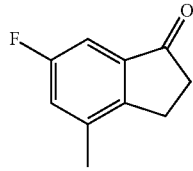

To a solution of 3-(4-fluoro-2-methylphenyl)propanoic acid (12 g, 65.93 mmol) in $CH_2Cl_2$ (200 mL) was added oxalyl chloride (11.3 mL, 131.7 mmol) and stirred at RT for 16 h. The reaction mixture was concentrated in vacuo and re-dissolved in $CH_2Cl_2$ (150 mL) and added to a suspension of $AlCl_3$ (11.4 g, 85.7 mmol) in $CH_2Cl_2$ (150 mL) at 0° C. The reaction mixture was heated at 50° C. for 3 h and allowed to stir at RT for 16 h. The reaction mixture poured into ice water (150 mL), extracted with $CH_2Cl_2$ (2×100 mL), the organic extract was washed with 1N NaOH solution (2×50 mL), brine solution (50 mL), dried over $Na_2SO_4$ and concentrated in vacuo. The crude material was purified by silica gel column chromatography, eluting with 10% EtOAc/petroleum ether 60-80 to afford 6-fluoro-4-methyl-2,3-dihydro-1H-inden-1-one as an off white solid (7 g, 70%).

$^1$H NMR (400 MHz, $CDCl_3$): δ 7.28-7.25 (m, 1H), 7.18-7.12 (m, 1H), 3.03-2.96 (m, 2H), 2.78-2.73 (m, 2H), 2.35 (s, 3H).

AnalpH2_MeCN_TFA__4 min(1): Rt 1.89 min; m/z 165 [M+1]$^+$.

The following indanone derivatives 38 are prepared using analogous procedures.

TABLE 21

Indanone Derivatives 38

| Compound | Reference | Analytical Data | Mass, % Yield, State |
|---|---|---|---|
| ![structure] | Commercially available | N/A | N/A |
| ![structure] | Reported as commercially available | AnalpH2_MeCN_TFA_4 min(1): Rt 1.80 min; m/z 169 [M + 1]$^+$. | 5.2 g, 57%, off-white solid |
| ![structure] | Commercially available | N/A | N/A |

TABLE 21-continued

Indanone Derivatives 38

| Compound | Reference | Analytical Data | Mass, % Yield, State |
|---|---|---|---|
| ![structure] | Reported as commercially available | AnalpH2_MeOH_4 min(3): Rt 2.23 min; m/z 165[M + 1]$^+$ | 5.62 g, 98%, off-white solid |

Scheme J, Step Y: Synthesis 2-(hydroxyimino-2,3-dihydro-1H-inden-1-one Derivatives 39

6-Fluoro-2-(hydroxyimino)-4-methyl-2,3-dihydro-1H-inden-1-one

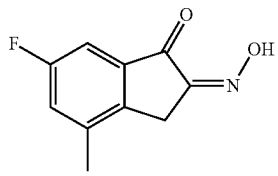

To a stirred solution of 6-fluoro-4-methyl-2,3-dihydro-1H-inden-1-one (1 g, 6.09 mmol) in a mixture of diethyl ether (10 mL) and concentrated HCl (10 mL) was added isopentyl nitrite (0.73 mL, 5.47 mmol) and stirred at RT for 3 h. The precipitated solid was collected by filtration and washed with MeOH to obtain 6-fluoro-2-(hydroxyimino)-4-methyl-2,3-dihydro-1H-inden-1-one as a brown solid (800 mg, 68%).

$^1$H NMR (400 MHz, DMSO-$d_6$): δ12.73 (s, 1H), 7.52-7.45 (m, 1H), 7.32-7.29 (m, 1H), 3.67 (s, 2H), 2.35 (s, 3H).

AnalpH2_MeCN_FA__7 min(XTERRA1.m): Rt 3.04 min; m/z 194 [M+1]$^+$.

The following 2-(hydroxyimino-2,3-dihydro-1H-inden-1-one derivatives 39 are prepared using analogous procedures.

TABLE 22

2-(hydroxyimino-2,3-dihydro-1H-inden-1-one Derivatives of formula 39

| Compound | Reference | Analytical Data | Mass, % Yield, State |
|---|---|---|---|
| ![structure] | | AnalpH9_MeCN_AB_10 min (Develosil): Rt 2.85 min; m/z 176 [M + 1]$^+$ | 5 g, 43%, pale yellow solid. |

TABLE 22-continued 2-(hydroxyimino-2,3-dihydro-1H-inden-1-one Derivatives of formula 39

| Compound | Reference | Analytical Data | Mass, % Yield, State |
|---|---|---|---|
| (6-fluoro-4-fluoro indanone oxime) | | AnalpH2_MeCN_FA_7 min (XTERRA1.m): Rt 2.93 min; m/z 198 [M + 1]+ | 1 g, 57% brown solid |
| (4,7-difluoro indanone oxime) | | AnalpH2_MeOH_4 min(1): Rt 2.08 min; m/z 198 [M + 1]+ | 4.27 g, 72%, beige solid |
| (7-fluoro-4-methyl indanone oxime) | | AnalpH2_MeOH_4 min(3): Rt 2.17 min; m/z 194 [M + 1]+ | 3.84 g, 58%, pale brown solid |

Scheme J, Step Z: Synthesis of 3-chloro-isoquinolin-1(2H)-one derivatives of formula 40

3-Chloro-7-fluoro-5-methylisoquinolin-1(2H)-one

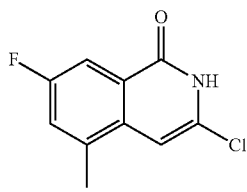

To a solution of 6-fluoro-2-(hydroxyimino)-4-methyl-2,3-dihydro-1H-inden-1-one (800 mg, 4.12 mmol) in anhydrous CCl$_4$ (100 mL) was added PCl$_5$ (1.28 g, 6.18 mmol) and stirred at RT for 16 h. The reaction mixture was concentrated in vacuo and the residue dissolved in anhydrous 1,4-dioxane (100 mL), cooled 0° C., the solution was saturated with HCl gas and allowed to stir RT for 16 h. The reaction mixture was heated at 60° C. for 2 h, cooled to RT and diluted with EtOAc (50 mL), washed with water (25 mL), saturated NaHCO$_3$ solution (25 mL), brine solution (25 mL), dried (Na$_2$SO$_4$), filtered and concentrated in vacuo. The crude material was washed with diethyl ether (10 mL), n-pentane (10 mL) and was dried in vacuo to obtain 3-chloro-7-fluoro-5-methylisoquinolin-1(2H)-one as a pale yellow solid (550 mg, 68%).

$^1$H NMR (400 MHz, DMSO-d$_6$): δ12.55-12.40 (br s, 1H), 7.70-7.63 (m, 1H), 7.55-7.49 (m, 1H), 6.84-6.70 (br s, 1H), 2.48 (s, 3H).

AnalpH2_MeOH_4 min(1): Rt 2.74 min; m/z 212 [M+1]+.

The following 3-chloro-isoquinolin-1(2H)-one derivatives 40 are prepared using analogous procedures.

TABLE 23

3-Chloro-isoquinolin-1(2H)-one Derivatives of formula 40

| Compound | Reference | Analytical Data | Mass, % Yield, State |
|---|---|---|---|
| (5-methyl-3-chloro-isoquinolinone) | Compound reported by Krämer et al., 1969 | AnalpH2_MeOH_4 min: Rt 2.67 min(1); m/z 193 [M + 1]+ | 1.1 g, 20%, white solid |
| (7-fluoro-5-fluoro-3-chloro-isoquinolinone) | Novel | AnalpH2_MeOH_4 min(1): Rt 2.78 min; m/z 216 [M + 1]+ | 650 mg, 62%, off white solid |
| (8-fluoro-5-fluoro-3-chloro-isoquinolinone) | Novel | AnalpH2_MeOH_4 min(1): Rt 2.51 min; m/z 215 [M +1]+ | 150 mg, 28%, off-white solid |
| (8-fluoro-5-methyl-3-chloro-isoquinolinone) | | AnalpH2_MeOH_4 min(3): Rt 2.46 min; m/z 212 [M + 1]+ | 2.43 g, 58%, pale yellow solid |

Synthesis of Boronic Acid/Ester Intermediates 43 (required for Step AA, Scheme J)

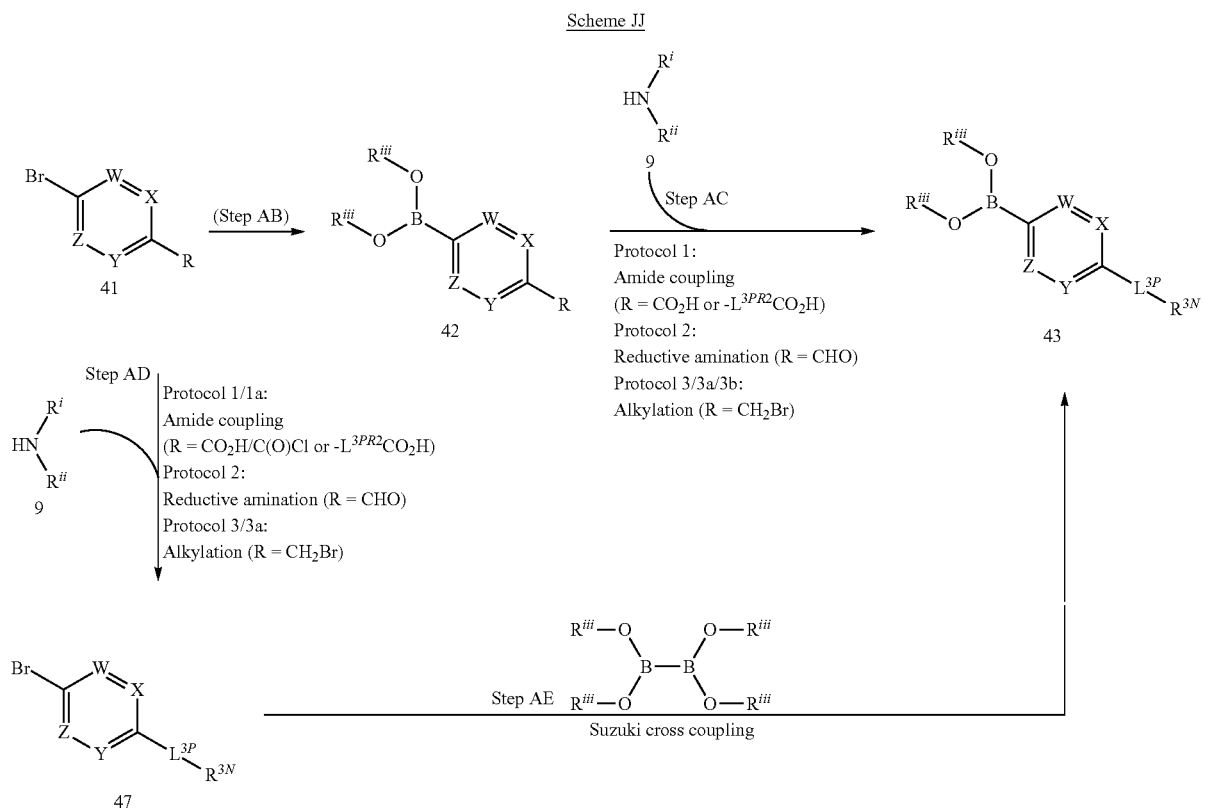

Scheme JJ: Synthesis of an Example of Amine of Formula 9

1-[2-(tert-Butyl-diphenyl-silanyloxy)-ethyl]-piperazine

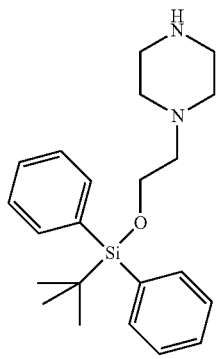 [SMILES: CC(C)(C)[Si](OCCN1CCNCC1)(c1ccccc1)c1ccccc1]

To 2-piperazin-1-yl-ethanol (2 g, 15.36 mmol) in $CH_2Cl_2$ (70 mL) and pyridine (1.85 mL, 23.04 mmol) was added DMAP (188 mg, 1.53 mmol) and TBDPS chloride (3.37 mL, 18.44 mmol) and the reaction mixture stirred at RT for 18 h. The reaction mixture was concentrated in vacuo and the crude material was purified by silica gel column chromatography, eluting with $CH_2Cl_2$ and increasing the polarity to 10% MeOH/$CH_2Cl_2$ to obtain 1-[2-(tert-butyl-diphenyl-silanyloxy)-ethyl]-piperazine as a colourless oil (1.1 g, 21%).

AnalpH2_MeOH_4 min(3): Rt 2.48 min; m/z 369 $[M+1]^+$.

Scheme JJ, Step AC (Protocol 1): Synthesis of Aryl Boronic Acid or Boronic Ester Derivatives of Formula 43 (via Amide Coupling)

2-Fluoro-4-(morpholine-4-carbonyl)-boronic acid

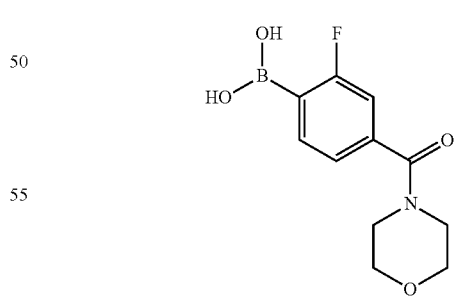

To 4-carboxy-2-fluoro-benzene boronic acid (150 mg, 0.82 mmol), TBTU (262 mg, 0.82 mmol) in anhydrous DMF (8 mL), was added 0.36M N,N-diisopropylethylamine in anhydrous $CH_2Cl_2$ (2.3 mL, 0.82 mmol) and the reaction mixture stirred at RT for 45 min. Morpholine (85 mg, 0.99 mmol) in anhydrous DMF (1 mL) was added and the reaction mixture stirred for 18 hr at RT. The reaction mixture was concentrated in vacuo and the crude material was purified by reverse phase preparative HPLC-MS to afford 2-fluoro-4-(morpholine-4-carbonyl)-boronic acid as a white solid (98 mg, 47%).

AnalpH2_MeOH_4 min: Rt 1.47 min; m/z 254 [M+1]⁺.

The following aryl boronic acid or boronic ester derivatives 43 are prepared using analogous procedures.

TABLE 24

Aryl boronic acid or boronic ester derivatives of Formula 43

| Compound | Analytical Data | Mass, % Yield, State |
|---|---|---|
|  | AnalpH2_MeOH_4 min: Rt 0.32, 0.43 min; m/z 267 [M + 1]⁺ | 240 mg, 55%, white solid |
|  | AnalpH2_MeOH_ 4 min: Rt 0.33, 0.61 min; m/z 307 [M + 1]⁺ | 245 mg, 49%, white solid |
|  | AnalpH2_MeOH_ 4 min(3): Rt 1.83 min; m/z 282 [M + 1]⁺ | 554 mg, 65%, off-white solid |
|  | AnalpH2_MeOH_ 4 min(3): Rt 3.45 min; m/z 460 [M + 1]⁺ | 1.56 g, 96%, cream solid |

TABLE 24-continued

Aryl boronic acid or boronic ester derivatives of Formula 43

| Compound | Analytical Data | Mass, % Yield, State |
|---|---|---|
| (4-boronic acid phenyl)-(4-methylpiperazin-1-yl)methanone | AnalpH2_MeOH_4 min(3): Rt 0.31 min; m/z 249 [M + 1]$^+$ | 1.54 g, 54%, colourless oil |
| (4-boronic acid phenyl)-[4-(2-(tert-butyldiphenylsilyloxy)ethyl)piperazin-1-yl]methanone | AnalpH2_MeOH_4 min(3): Rt 2.76 min; m/z 516 [M + 1]$^+$ | 978 mg, 64%, white solid |
| 2-(4-boronic acid phenyl)-1-(4-methylpiperazin-1-yl)ethanone | AnalpH9_MeOH_4 min(2): Rt 1.62 min; m/z 263 [M + 1]$^+$ | 242 mg, 83%, dark orange oil |
| 2-(4-boronic acid phenyl)-N-methyl-N-(1-methylpiperidin-4-yl)acetamide | AnalpH2_MeOH_4 min(3): Rt 0.77 min; m/z 291 [M + 1]$^+$ | 127 mg, 65%, white solid |

TABLE 24-continued
Aryl boronic acid or boronic ester derivatives of Formula 43
| Compound | Analytical Data | Mass, % Yield, State |
|---|---|---|
| 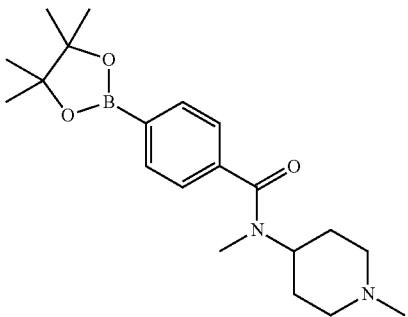 | AnalpH2_MeOH_4 min(3): Rt 1.71 min; m/z 359.5 [M + 1]$^+$ | 992 mg, 46%, pale yellow solid |
| 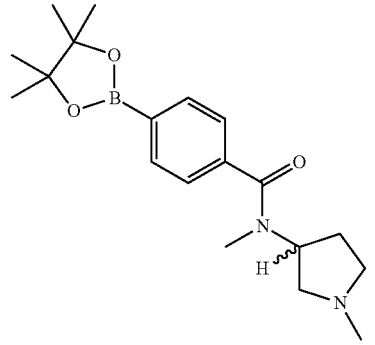 [SMILES: CN1CCC(N(C)C(=O)c2ccc(B3OC(C)(C)C(C)(C)O3)cc2)C1] | AnalpH2_MeOH_4 min(3): Rt 1.70 min; m/z 345 [M + 1]$^+$ | 294 mg, 24%, off-white solid |
| 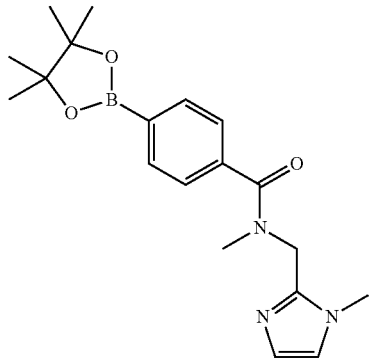 | AnalpH2_MeOH_4 min(3): Rt 1.72 min; m/z 356 [M + 1]$^+$ | 532 mg, 74%, yellow oil |
| 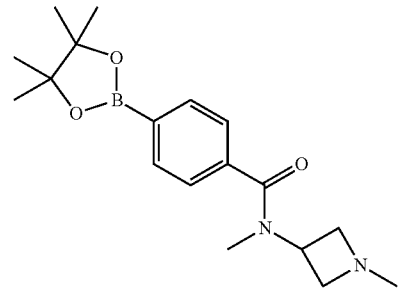 | AnalpH2_MeOH_4 min(3): Rt 1.66 min; m/z 331 [M + 1]$^+$ | 118 mg, 25%, white solid |

TABLE 24-continued

Aryl boronic acid or boronic ester derivatives of Formula 43

| Compound | Analytical Data | Mass, % Yield, State |
|---|---|---|
| (structure) | AnalpH2_MeOH_4 min(3): Rt 3.21 min; m/z 431 [M + 1]⁺ | 899 mg, 67%, cream solid |
| (structure) | AnalpH2_MeOH_4 min(3): Rt 1.68 min; m/z 331 [M + 1]⁺ | 233 mg, 49%, yellow solid |
| (structure) | AnalpH2_MeOH_4 min(3): Rt 1.73 min; m/z 359 [M + 1]⁺ | 149 mg, 19%, yellow oil |
| (structure) | AnalpH2_MeOH_4 min(3): Rt 1.74 min; m/z 387 [M + 1]⁺ | 995 mg, 91%, yellow solid |

TABLE 24-continued

Aryl boronic acid or boronic ester derivatives of Formula 43

| Compound | Analytical Data | Mass, % Yield, State |
|---|---|---|
| | AnalpH2_MeOH_ 4 min(3): Rt 1.77 min; m/z 373 [M + 1]+ | 589 mg, 81%, yellow solid |
| | AnalpH2_MeOH_ 4 min(3): Rt 1.80 min; m/z 373 [M + 1]+ | 593 mg, 82%, dark yellow solid |
| | AnalpH2_MeOH_ 4 min(3): Rt 3.25 min; m/z 445 [M + 1]+ | 889 mg, quant., white solid |
| | AnalpH2_MeOH_ 4 min(3): Rt 1.75 min; m/z 359 [M + 1]+ | 784 mg, 73%, yellow/orange foam |

Scheme JJ, Step AC (Protocol 2): Synthesis of Aryl Boronic Acid Derivatives of Formula 43 (via Reductive Amination)

Pyridin-2-ylmethyl-[1-(4-cyclopropylmethyl-piperazine)]-5-boronic acid

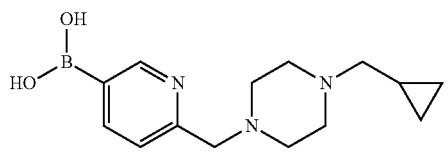 [SMILES: OB(O)c1ccc(CN2CCN(CC3CC3)CC2)nc1]

To a stirred solution of 2-formylpyridine-5-boronic acid pinacolate (200 mg, 1.33 mmol) in DCE (10 mL) was added 1-(cyclopropylmethyl)piperazine (0.217 mL, 1.46 mmol) and stirred at RT for 30 min. Sodium triacetoxyborohydride (424 mg, 2.00 mmol) was added and the reaction mixture stirred for 18 h at RT. The reaction mixture concentrated in vacuo and the residue was diluted with water (20 mL) and the aqueous layer washed with EtOAc. The combined aqueous layer was concentrated in vacuo and the crude material was purified by reverse phase preparative HPLC-MS to obtain pyridin-2-ylmethyl-[1-(4-cyclopropylmethyl-piperazine)]-5-boronic acid as a pale yellow oil (140 mg, 38%). AnalpH2_MeOH_4 min: Rt 0.33 min; m/z 275 [M+1]$^+$.

The following aryl boronic acid derivatives 43 are prepared using analogous procedures.

TABLE 25

Aryl boronic acid derivatives of Formula 43

| Compound | Analytical Data | Mass, % Yield, State |
|---|---|---|
| (structure) | AnalpH9_MeOH_4 min: Rt 1.85 min; m/z 290 [M + 1]$^+$ | 122 mg, 32%, brown oil |
| (structure) | AnalpH2_MeOH_4 min: Rt 1.72 min; m/z 362 [M + 1]$^+$ | 68 mg, 47%, pale yellow solid |
| (structure) | AnalpH2_MeOH_4 min: Rt 0.73 min; m/z 253 [M + 1]$^+$ | 164 mg, 55%, off-white solid |

Scheme JJ, Step AC (Protocol 3): Synthesis of Aryl Boronic Ester Derivatives of Formula 43 (via Alkylation)

2-Methyl-1-[4-(4,4,5,5-tetramethyl-[1,3,2]diox-aborolan-2-yl)-benzyl]-1H-benzoimidazole

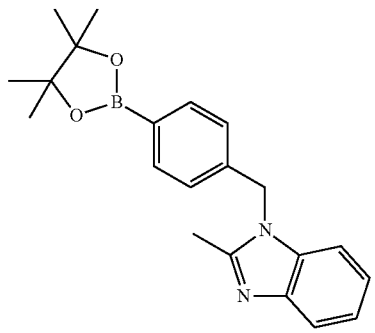 [SMILES: Cc1nc2ccccc2n1Cc1ccc(B2OC(C)(C)C(C)(C)O2)cc1]

To a solution of 4-bromomethylphenylboronic acid pinacol ester (564 mg, 1.90 mmol) in acetone (19 mL) was added 2-methylbenzimidazole (377 mg, 2.85 mmol), potassium iodide (16 mg, 0.095 mmol) and $K_2CO_3$ (394 mg, 2.85 mmol) and the reaction mixture heated at 60° C. for 3.25 h. The reaction mixture was diluted with $H_2O$ and extracted with EtOAc (×2). The organic layers were combined, dried (phase separation cartridge) and concentrated in vacuo. The crude material was purified by reverse phase preparative HPLC-MS to afford 2-Methyl-1-[4-(4,4,5,5-tetramethyl-[1,3,2]diox-aborolan-2-yl)-benzyl]1H-benzoimidazole as an off-white solid (234 mg, 35%).

AnalpH2_MeOH_4 min(3): Rt 2.26 min; m/z 349 [M+1]$^+$.

The following aryl boronic ester derivatives 43 are prepared using analogous procedures.

TABLE 26

Aryl boronic ester derivatives of Formula 43

| Compound | Analytical Data | Mass, % Yield, State |
|---|---|---|
| 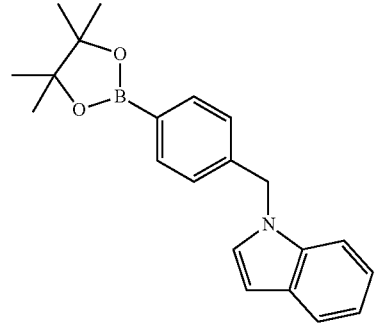 [SMILES: CC1(C)OB(c2ccc(Cn3ccc4ccccc43)cc2)OC1(C)C] | AnalpH2_MeOH_4 min(3): Rt 2.49 min; m/z 335 [M + 1]$^+$. | 385 mg, 53%, white solid |

TABLE 26-continued

Aryl boronic ester derivatives of Formula 43

| Compound | Analytical Data | Mass, % Yield, State |
|---|---|---|
| (imidazole structure) | Commercially available | N/A |

Scheme JJ, Step AC (Protocol 3a): Synthesis of Aryl Boronic Ester Derivatives of Formula 43 (via Alkylation)

1-[4-(4,4,5,5-Tetramethyl-[1,3,2]dioxaborolan-2-yl)-benzyl]-1H-indole

To NaH (78 mg, 1.94 mmol) in anhydrous DMF (4 mL) under $N_2$, at 0° C. was added indole (227 mg, 1.94 mmol) in anhydrous DMF (5 mL). The reaxtion mixture was maintained at this temperature for 10 min. 4-bromomethylphenylboronic acid pinacol ester (523 mg, 1.76 mmol) in anhydrous DMF (8 mL) was added and the reaction stirred at RT for 18 h. The reaction mixture was diluted with $H_2O$ and extracted with $CH_2Cl_2$ (×2). The organic phases were combined, washed with brine, dried (phase separation cartridge) and the solvent removed in vacuo. The crude material was purified by silica gel column chromatography eluting with isohexane and increasing the polarity to 5% EtOAc/isohexane. The compound was further purified by reverse phase preparative HPLC-MS to afford 1-[4-(4,4,5,5-Tetramethyl-[1,3,2]dioxaborolan-2-yl)-benzyl]-1H-indole as an off-white solid (120 mg, 10%).

AnalpH2_MeOH_4 min(3): Rt 3.50 min; m/z 334 [M+1]$^+$.

The following aryl boronic ester derivatives 43 are prepared using analogous procedures.

TABLE 27

Aryl boronic ester derivatives of Formula 43

| Compound | Analytical Data | Mass, % Yield, State |
|---|---|---|
| (structure) | AnalpH2_MeOH_ 4 min(3): Rt 3.34 min; m/z 284 [M + 1]⁺ | 130 mg, 23%, white solid |

Scheme JJ, Step AC (Protocol 3b): Synthesis of Aryl Boronic Ester Derivatives of Formula 43 (via Alkylation)

Methyl-{1-[4-(4,4,5,5-tetramethyl-[1,3,2]dioxaborolan-2-yl)-benzyl]-azetidin-3-yl}-carbamic acid tert-butyl ester

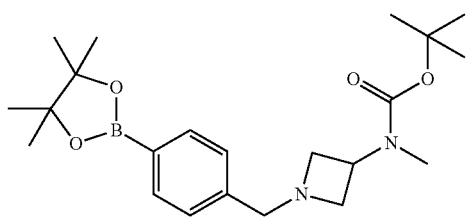 [SMILES: CN(C(=O)OC(C)(C)C)C1CN(Cc2ccc(B3OC(C)(C)C(C)(C)O3)cc2)C1]

To 4-bromomethylboronic acid pinacol ester (500 mg, 168 mmol) and azetidin-3-yl-methyl-carbamic acid tert-butyl ester hydrochloride (561 mg, 2.52 mmol) in anhydrous THF (12 mL) was added NEt₃ (704 µl, 5.05 mmol). The reaction mixture was stirred at RT, under N₂ balloon, for 18 h. The reaction mixture was concentrated in vacuo, suspended in CH₂Cl₂ and washed with H₂O. The aqueous layer was separated and washed with CH₂Cl₂. The organic layers were combined, dried (phase separation cartridge) and the solvent removed in vacuo. The crude material was purified by silica gel column chromatography eluting with CH₂Cl₂ and increasing the polarity to 20% MeOH/CH₂Cl₂ to afford methyl-{1-[4-(4,4,5,5-tetramethyl-[1,3,2]dioxaborolan-2-yl)-benzyl]-azetidin-3-yl}-carbamic acid tert-butyl ester as a colourless oil (441 mg, 65%).

AnalpH2_MeOH_4 min(3): Rt 2.21 min; m/z 403 [M+1]⁺.

Scheme JJ, Step AD (Protocol 1): Synthesis of Aryl Bromide Derivatives of Formula 47 (via Amide Coupling)

(5-Bromo-pyrimidin-2-yl)-(4-cyclopropylmethyl-piperazin-1-yl)-methanone

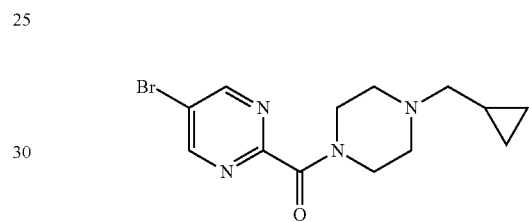

To 5-bromopyrimidine-2-carboxylic acid (100 mg, 0.49 mmol) and TBTU (158 mg, 0.49 mmol) in anhydrous DMF 94.4. mL) was added DIPEA (0.36M in CH₂Cl₂, 1.4 mL, 0.49 mmol) and the reaction mixture stirred at RT for 40 min. N-cyclopropylmethylpiperazine (83 mg, 0.59 mmol) in anhydrous DMF (1 mL) was added and the reaction stirred at RT for 18 h. The reaction mixture was passed through a Si—NH₂ cartridge (5 g), eluting with DMF and MeOH. The eluents were combined, concentrated in vacuo and purified by reverse phase preparative HPLC-MS to obtain (5-bromo-pyrimidin-2-yl)-(4-cyclopropylmethyl-piperazin-1-yl)-methanone as a pale yellow solid (46 mg, 29%).

AnalpH2_MeOH_4 min(3): Rt 0.35, 0.81 min; m/z 325 [M+1]⁺.

The following bromo aryl derivatives 47 are prepared using analogous procedures.

TABLE 28

Aryl bromide derivatives of Formula 47

| Compound | Analytical Data | Mass, % Yield, State |
|---|---|---|
| (structure) | AnalpH2_MeOH_ 4 min(3): Rt 0.84 min; m/z 325 [M + 1]⁺ | 390 mg, 53%, colorless oil, solidifies on standing |

TABLE 28-continued

Aryl bromide derivatives of Formula 47

| Compound | Analytical Data | Mass, % Yield, State |
|---|---|---|
| ![structure] 5-bromo-pyrimidine-2-carbonyl-4-methylpiperazine | AnalpH9_MeOH_4 min(2): Rt 1.64 min; m/z 285 [M + 1]$^+$ | 314 mg, 50%, tan solid |
| ![structure] 5-bromo-pyridine-2-carbonyl-4-methylpiperazine | AnalpH9_MeOH_4 min(2): Rt 2.06 min; m/z 284 [M + 1]$^+$ | 1.17 g, 83%, dark orange oil |
| ![structure] 4-bromo-2,6-difluorobenzoyl-3-(TBDPS-oxy)-azetidine | AnalpH2_MeOH_4 min(3): Rt 3.65 min; m/z 530 [M + 1]$^+$ | 971 mg, 82%, orange oil |
| ![structure] 2-(4-bromophenyl)-2-methyl-1-(3-hydroxyazetidin-1-yl)-propan-1-one | AnalpH2_MeOH_4 min(3): Rt 2.64 min; m/z 298 [M + 1]$^+$ | 500 mg, 81%, white solid |
| ![structure] 2-(4-bromophenyl)-1-(3-hydroxyazetidin-1-yl)-propan-1-one | AnalpH2_MeOH_4 min(3): Rt 2.47 min; m/z 284 [M + 1]$^+$ | 457 mg, 67%, pale yellow solid |

Scheme JJ, Step AD (Protocol 1a): Synthesis of Aryl Bromide Derivatives of Formula 47 (via Amide Coupling-via Acid Chloride)

2-(4-Bromo-phenyl)-1-[3-(tert-butyl-diphenyl-silanyloxy)-azetidin-1-yl]-ethanone

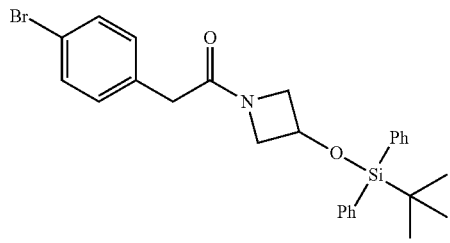 [SMILES: CC(C)(C)[Si](OC1CN(C(=O)Cc2ccc(Br)cc2)C1)(c1ccccc1)c1ccccc1]

To 4-bromophenyl acetylchloride (300 mg, 1.28 mmol) in CH$_2$Cl$_2$ (5 mL) was added 3-(tert-Butyl-diphenyl-silanyloxy)-azetidine (399 mg, 1.28 mmol), DIPEA (670 µL, 3.85 mmol) and the reaction stirred at RT for 2 h. The crude material was purified by silica gel column chromatography, eluting with isohexane and increasing the polarity to 80% EtOAc/isohexane to obtain 2-(4-bromo-phenyl)-1-[3-(tert-butyl-diphenyl-silanyloxy)-azetidin-1-yl]-ethanone as a colourless glass (632 mg, 97%).

AnalpH2_MeOH_4 min(3): Rt 3.71 min; m/z 510 [M+1]$^+$.

Scheme JJ, Step AD (Protocol 3): Synthesis of Aryl Bromide Derivatives of Formula 47 (via Alkylation)

1-(4-Bromo-benzyl)-3-(tert-butyl-diphenyl-silanyloxy)-azetidine

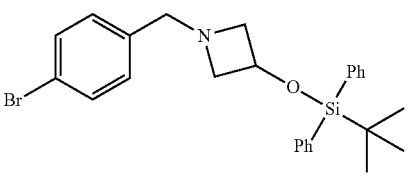 [SMILES: CC(C)(C)[Si](OC1CN(Cc2ccc(Br)cc2)C1)(c1ccccc1)c1ccccc1]

To 4-bromomethylbenzyl bromide (300 mg, 1.2 mmol) in THF (5 mL) was added NEt$_3$ (418 µL, 3 mmol) and the reaction mixture stirred at RT for 10 min. 3-(tert-Butyl-diphenyl-silanyloxy)-azetidine hydrochloride (628 mg, 1.8 mmol) was added and the reaction stirred at RT for 18 h. The reaction mixture was concentrated in vacuo and the residue partitioned between $CH_2Cl_2$ and 5% $NaHCO_3$ (aq). The organic phase was separated, dried ($MgSO_4$) and concentrated in vacuo. The crude material was purified by silica gel column chromatography, eluting with isohexane and increasing the polarity to 50% EtOAc/isohexane to obtain 1-(4-Bromo-benzyl)-3-(tert-butyl-diphenyl-silanyloxy)-azetidine as a colourless oil (328 mg, 57%).

AnalpH2_MeOH_4 min(3): Rt 2.77 min; m/z 480 [M+1]$^+$.

Scheme JJ, Step AD (Protocol 3a): Synthesis of Aryl Bromide Derivatives of Formula 47 (via Alkylation)

1-[1-(4-Bromo-phenyl)-1-methyl-ethyl]-azetidin-3-ol

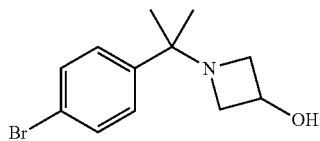

1-(4-Bromophenyl)-1-methyl-ethylamine (1 g, 4.67 mmol) and epichlorohydrin (439 µl, 5.6 mmol) in EtOH (15 mL) were heated at 70° C. for 18 h. The reaction mixture was concentrated in vacuo and purified by reverse phase preparative HPLC-MS to obtain 1-[1-(4-bromo-phenyl)-1-methyl-ethyl]-azetidin-3-ol as a white solid (489 mg, 38%).

AnalpH2_MeOH_4 min(3): Rt 2.77 min; m/z 480 [M+1]$^+$.

Scheme JJ, Step AE: Synthesis of Aryl Boronic Acid or Boronic Ester Derivatives of Formula 43

2-(4-Cyclopropylmethyl-piperazine-1-carbonyl)-pyrimidine-5-boronic acid

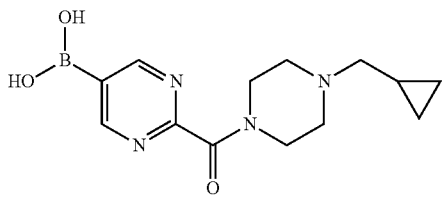 [SMILES: O=C(c1ncc(B(O)O)cn1)N1CCN(CC2CC2)CC1]

(5-Bromo-pyrimidin-2-yl)-(4-cyclopropylmethyl-piperazin-1-yl)-methanone (46 mg, 0.14 mmol), bis(pinacolato)diboron (43 mg, 0.17 mmol), Pd(dppf)Cl$_2$ (12 mg, 0.014 mmol) and potassium acetate (42 mg, 0.42 mmol) in 1,4-dioxane (0.7 mL) were added to a microwave vial and the reaction mixture purged with N$_2$ for 10 min. The reaction mixture was irradiated using a microwave reactor (300 W, 120° C., 20 min). The reaction mixture was passed through a Si-thiol cartridge (2 g) and the column washed with MeOH (4× column volumes). The solvent was removed in vacuo and purified by reverse phase preparative HPLC-MS. The sample was passed through a SCX-2 cartridge (500 mg) and the column washed with MeOH (4× column volumes). The compound was eluted from the column with 0.5M NH$_3$/MeOH to afford 2-(4-cyclopropylmethyl-piperazine-1-carbonyl)-pyrimidine-5-boronic acid as a white solid (29 mg, 70%).

AnalpH9_MeOH_4 min(2): Rt 1.15 min; m/z 291 [M+1]$^+$.

The following aryl boronic acid or boronic ester derivatives 43 are prepared using analogous procedures.

TABLE 29

Aryl boronic acid or boronic ester derivatives of Formula 43

| Compound | Analytical Data | Mass, % Yield, State |
|---|---|---|
| ![structure] | AnalpH2_MeOH_ 4 min(3): Rt 0.3 min; m/z 251 [M + 1]$^+$ | 163 mg, 68%, white solid |
| ![structure] | AnalpH2_MeOH_ 4 min(3): Rt 3.72 min; m/z 556 [M + 1]$^+$ | 141 mg, 47%, brown oil |

Scheme J, Step AA: Synthesis of 2H-isoquinolin-1-one derivatives of formula 4 (via Suzuki cross-coupling)

5-Methyl-3-[2-(4-methyl-piperazin-1-yl)-pyrimidin-5-yl]-2H-isoquinolin-1-one (IQ-025)

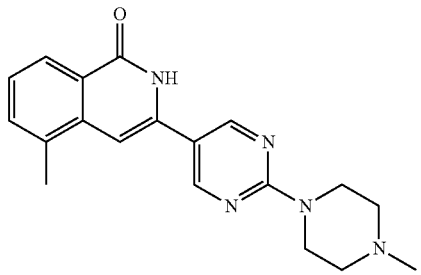 [SMILES: Cc1cccc2c(=O)[nH]c(-c3cnc(N4CCN(C)CC4)nc3)cc12]

3-Chloro-5-methyl-2H-isoquinolin-1-one (50 mg, 0.26 mmol), 2-(4-methylpiperazin-1-yl)pyrimidine-5-boronic acid pinacol ester (118 mg, 0.39 mmol), $K_2CO_3$ (73 mg, 0.52 mmol) and Pd(dppf)$Cl_2$ (10 mg, 0.013 mmol) in DME/EtOH/$H_2O$ 4:0.5:1 (2.75 mL) were added to a microwave vial and the reaction mixture purged with $N_2$ for 10 min. The reaction mixture was irradiated using a microwave reactor (300 W, 100° C., 60 min). The reaction mixture was filtered through celite and concentrated in vacuo. The crude material was purified by silica gel column chromatography, eluting with $CH_2Cl_2$ and increasing the polarity to 50% MeOH/$CH_2Cl_2$. The crude material was trituared with MeOH and washed with isohexane to afford 5-methyl-3-[2-(4-methyl-piperazin-1-yl)-pyrimidin-5-yl]-2H-isoquinolin-1-one as an off-white solid (28 mg, 32%).

AnalpH2_MeOH_QC(1): Rt 4.97 min; m/z 336 [M+1]$^+$.

The following 2H-isoquinolin-1-one derivatives are prepared using analogous procedures.

TABLE 30

| 2H-isoquinolin-1-one derivatives of Formula 4 | | | |
|---|---|---|---|
| Compound | Code | Analytical Data | Mass, % Yield, State |
| | IQ-099 | AnalpH2_MeOH_QC(1): Rt 4.74 min; m/z 391 [M + 1]$^+$ | 13 mg, 10%, cream solid |
| | IQ-071 | AnalpH2_MeOH_QC(1): Rt 6.35 min; m/z 435 [M + 1]$^+$ | 31 mg, 27%, cream solid |

TABLE 30-continued
2H-isoquinolin-1-one derivatives of Formula 4
| Compound | Code | Analytical Data | Mass, % Yield, State |
|---|---|---|---|
| 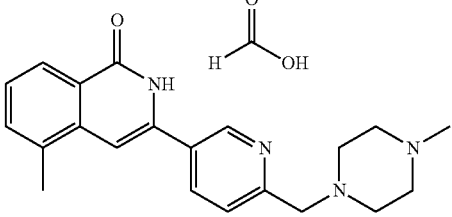 | IQ-057 | AnalpH2_MeOH_QC(1): Rt 4.84 min; m/z 349 [M + 1]+ | 17 mg, 20%, pale orange solid |
| 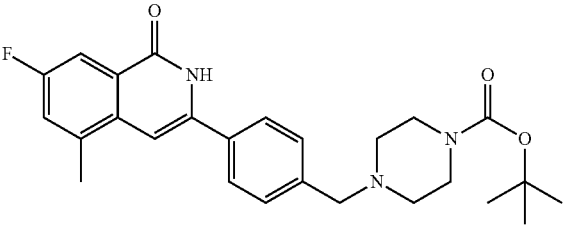 [SMILES: Cc1cc(F)cc2c(=O)[nH]c(-c3ccc(CN4CCN(C(=O)OC(C)(C)C)CC4)cc3)cc12] | IQ-076 | AnalpH2_MeOH_QC(1): Rt 6.56 min; m/z 452 [M + 1]+ | 72 mg, 66%, pale orange solid |
| 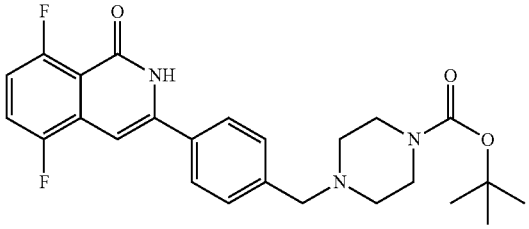 [SMILES: CC(C)(C)OC(=O)N1CCN(Cc2ccc(-c3cc4c(F)ccc(F)c4c(=O)[nH]3)cc2)CC1] | IQ-077 | AnalpH2_MeOH_QC(1): Rt 6.69 min; m/z 456 [M + 1]+ | 46 mg, 29%, pale brown solid |
| 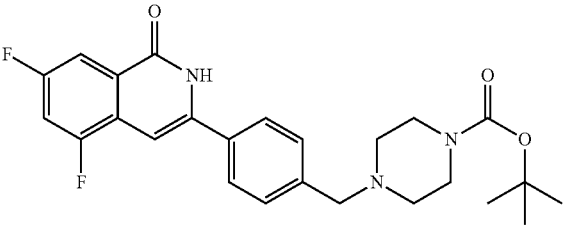 [SMILES: CC(C)(C)OC(=O)N1CCN(Cc2ccc(-c3cc4c(F)cc(F)cc4c(=O)[nH]3)cc2)CC1] | IQ-154 | AnalpH2_MeOH_QC(1):: Rt 6.69 min; m/z 456 [M + 1]+ | 46 mg, 29%, pale brown solid |
| 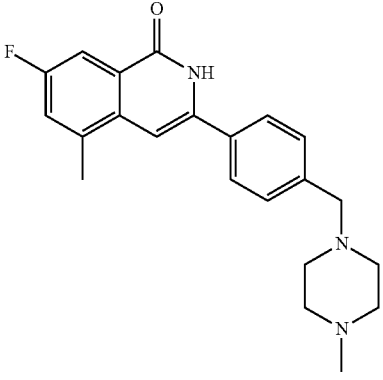 [SMILES: Cc1cc(F)cc2c(=O)[nH]c(-c3ccc(CN4CCN(C)CC4)cc3)cc12] | IQ-080 | AnalpH2_MeOH_QC(1): Rt 5.57 min; m/z 366 [M + 1]+ | 39 mg, 45%, brown solid |

TABLE 30-continued 2H-isoquinolin-1-one derivatives of Formula 4

| Compound | Code | Analytical Data | Mass, % Yield, State |
|---|---|---|---|
| (structure) | IQ-138 | AnalpH2_MeOH_QC(1): Rt 5.63 min; m/z 370 [M + 1]+ | 25 mg, 29%, white solid |
| (structure) | IQ-161 | AnalpH2_MeOH_QC: Rt 5.19 min; m/z 389 [M + 1]+ | 44 mg, 40%, pale brown solid |
| (structure) | IQ-162 | AnalpH2_MeOH_QC: Rt 5.41 min; m/z 404 [M + 1]+ | 48 mg, 43%, pale brown solid |
| (structure) | IQ-163 | AnalpH2_MeOH_QC: Rt 7.44 min; m/z 367 [M + 1]+ | 19 mg, 11%, off-white solid |
| (structure) | IQ-164 | AnalpH2_MeOH_QC: Rt 5.19 min; m/z 380 [M + 1]+ | 40 mg, 23%, beige solid |

TABLE 30-continued
2H-isoquinolin-1-one derivatives of Formula 4
| Compound | Code | Analytical Data | Mass, % Yield, State |
|---|---|---|---|
| 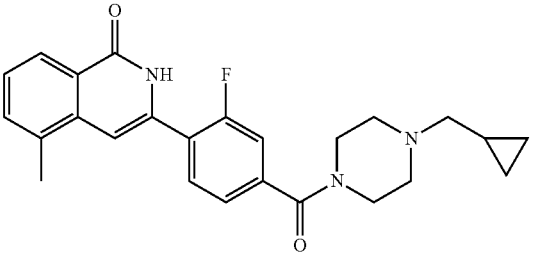 [SMILES: Cc1cccc2c(=O)[nH]c(-c3ccc(C(=O)N4CCN(CC5CC5)CC4)cc3F)cc12] | IQ-165 | AnalpH2_MeOH_QC: Rt 5.38 min; m/z 420 [M + 1]$^+$ | 50 mg, 26%, light brown solid |
| 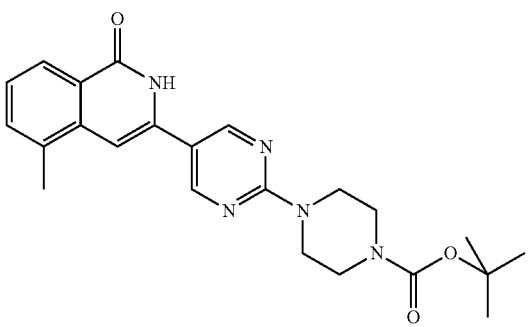 [SMILES: Cc1cccc2c(=O)[nH]c(-c3cnc(N4CCN(C(=O)OC(C)(C)C)CC4)nc3)cc12] | | AnalpH2_MeOH_4 min(1): Rt 3.31 min; m/z 422 [M + 1]$^+$ | Used in next step as crude material |
| 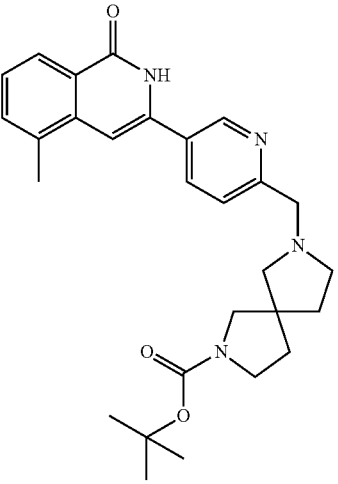 [SMILES: Cc1cccc2c(=O)[nH]c(-c3ccc(CN4CCC5(CCN(C(=O)OC(C)(C)C)C5)C4)nc3)cc12] | | AnalpH2_MeOH_4 min: Rt 2.31 min; m/z 476 [M + 1]$^+$ | Used in next step as crude material |
| 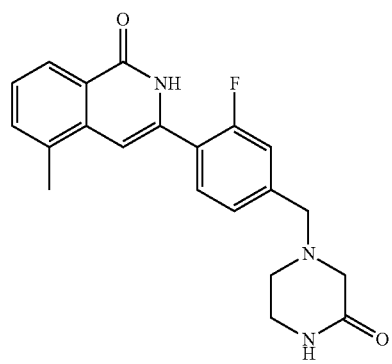 [SMILES: Cc1cccc2c(=O)[nH]c(-c3ccc(CN4CCNC(=O)C4)cc3F)cc12] | IQ-166 | AnalpH2_MeOH_QC: Rt 7.23 min; m/z 366 [M + 1]$^+$ | 23 mg, 20%, white solid |

TABLE 30-continued 2H-isoquinolin-1-one derivatives of Formula 4

| Compound | Code | Analytical Data | Mass, % Yield, State |
|---|---|---|---|
| | IQ-229 | AnalpH2_MeOH_QC(1): Rt 4.36 min; m/z 426 [M + 1]⁺ | 4.8 mg, 15%, off-white solid |
| | IQ-187 | AnalpH2_MeOH_QC(1): Rt 8.05 min; m/z 395 [M + 1]⁺ | 79 mg, 42%, off-white solid |
| | IQ-188 | AnalpH2_MeOH_QC(1): Rt 7.10 min; m/z 335 [M + 1]⁺ | 92 mg, 27%, white solid |

TABLE 30-continued 2H-isoquinolin-1-one derivatives of Formula 4

| Compound | Code | Analytical Data | Mass, % Yield, State |
|---|---|---|---|
| (structure) | IQ-225 | AnalpH2_MeOH_QC(1): Rt 4.27 min; m/z 382 [M + 1]+ | 7 mg, 8%, pale yellow solid |
| (structure) | IQ-226 | AnalpH2_MeOH_QC(1): Rt 4.74 min; m/z 384 [M + 1]+ | 3.6 mg, 4%, beige solid |
| (structure) | IQ-227 | AnalpH2_MeOH_QC(1): Rt 5.19 min; m/z 384 [M + 1]+ | 3.4 mg, 3%, white solid |
| (structure) | IQ-189 | AnalpH2_MeOH_QC(1): Rt 4.89 min; m/z 380 [M + 1]+ | 4.7 mg, 5%, white solid |
| (structure) | IQ-190 | AnalpH2_MeOH_QC(1): Rt 5.25 min; m/z 380 [M + 1]+ | 5 mg, 5%, white solid |

TABLE 30-continued 2H-isoquinolin-1-one derivatives of Formula 4

| Compound | Code | Analytical Data | Mass, % Yield, State |
|---|---|---|---|
| [structure] | Intermediate for IQ-228 | AnalpH2_MeOH_ 4 min(3): Rt 3.22 min; m/z 652 [M + 1]⁺ | 83 mg, 54%, beige solid |
| [structure] | Intermediate for IQ-192 | AnalpH2_MeOH_ 4 min(3): Rt 3.19 min; m/z 649 [M + 1]⁺ | 63 mg, 36%, beige solid |
| [structure] | Intermediate for IQ-193 | AnalpH2_MeOH_ 4 min(3): Rt 3.10 min; m/z 649 [M + 1]⁺ | 79 mg, 44%, beige solid |
| [structure] | IQ-214 | AnalpH2_MeOH_ QC(1): Rt 7.24 min; m/z 349 [M + 1]⁺ | 20 mg, 17%, off-white solid |
| [structure] | IQ-215 | AnalpH2_MeOH_ QC(1): Rt 7.45 min; m/z 367 [M + 1]⁺ | 44 mg, 37%, off-white solid |

TABLE 30-continued 2H-isoquinolin-1-one derivatives of Formula 4

| Compound | Code | Analytical Data | Mass, % Yield, State |
|---|---|---|---|
| 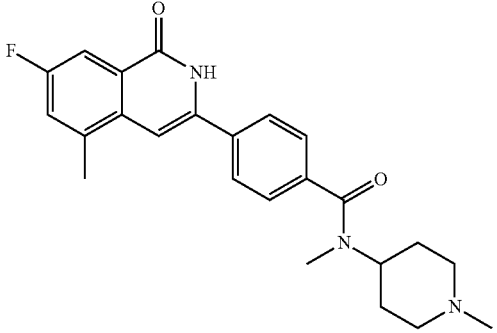 [SMILES: Cc1cc(F)cc2c(=O)[nH]c(-c3ccc(C(=O)N(C)C4CCN(C)CC4)cc3)cc12] | IQ-195 | AnalpH2_MeOH_QC(1): Rt 5.35 min; m/z 408 [M + 1]⁺ | 72 mg, 38% white solid ¹H NMR (400 MHz, DMSO-d₆): δ11.77 (br s, 1H), 7.89 (d, J = 8.8 Hz, 2H), 7.74 (dd, J = 9.6, 2.8 Hz, 1H), 7.52, (dd, J = 9.6, 2.8 Hz, 1H), 7.48 (d, J = 7.6 Hz, 2H), 6.94 (s, 1H), 4.33-4.24 (br s, 0.5H), 2.92-2.73 (m, 5H), 2.61 (s, 3H), 2.22-1.93 (m, 4H), 1.92-1.55 (m, 5.5H). |
| 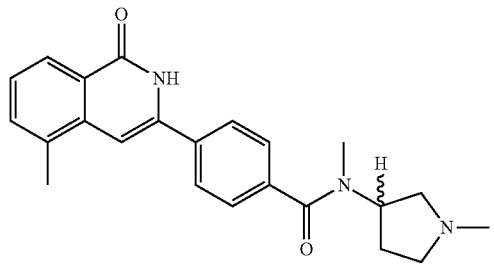 [SMILES: Cc1cccc2c(=O)[nH]c(-c3ccc(C(=O)N(C)C4CCN(C)C4)cc3)cc12] | IQ-196 | AnalpH2_MeOH_QC(1): Rt 5.17 min; m/z 377 [M + 1]⁺ | 99 mg, 81%, brown solid |
| 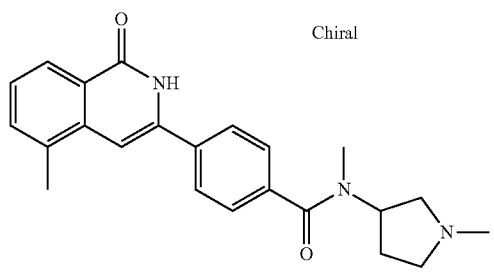 [SMILES: Cc1cccc2c(=O)[nH]c(-c3ccc(C(=O)N(C)C4CCN(C)C4)cc3)cc12 ; "Chiral"]  Chiral  Enantiomer 1 | IQ-205-1 | AnalpH2_MeOH_QC(2): Rt 4.69 min; m/z 376.5 [M + 1]⁺ | 13.4 mg, 37.5%, off-white solid; obtained via Chiral_Method_3 |
| 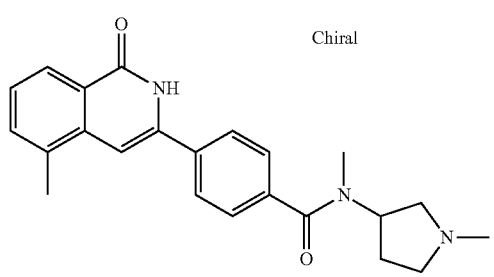 [SMILES: Cc1cccc2c(=O)[nH]c(-c3ccc(C(=O)N(C)C4CCN(C)C4)cc3)cc12 ; "Chiral"]  Chiral  Enantiomer 2 | IQ-205-2 | AnalpH2_MeOH_QC(2): Rt 4.67 min; m/z 376.5 [M + 1]⁺ | 12.4 mg, 34.7 %, off-white solid; obtained via Chiral_Method_3 |

TABLE 30-continued 2H-isoquinolin-1-one derivatives of Formula 4

| Compound | Code | Analytical Data | Mass, % Yield, State |
|---|---|---|---|
| (structure) | IQ-197 | AnalpH2_MeOH_QC(1): Rt 5.35 min; m/z 394 [M + 1]⁺ | 60 mg, 48%, off-white solid |
| (structure) Chiral, Enantiomer 1 | IQ-207-1 | AnalpH2_MeOH_QC(2): Rt 4.84 min; m/z 394 [M + 1]⁺ | 5.5 mg, 37%, white solid; obtained via Chiral_Method_3 |
| (structure) Chiral, Enantiomer 2 | IQ-207-2 | AnalpH2_MeOH_QC(2): Rt 4.83 min; m/z 394.5 [M + 1]⁺ | 4.9 mg, 33%, white solid; obtained via Chiral_Method_3 |
| (structure) | IQ-198 | AnalpH2_MeOH_QC(1): Rt 5.22 min; m/z 388 [M + 1]⁺ | 80 mg, 40%, off-white solid |
| (structure) | IQ-199 | AnalpH2_MeOH_QC(1): Rt 5.11 min; m/z 362 [M + 1]⁺ | 70 mg, 72%, off-white solid |

TABLE 30-continued 2H-isoquinolin-1-one derivatives of Formula 4

| Compound | Code | Analytical Data | Mass, % Yield, State |
|---|---|---|---|
| (structure) | Intermediate for IQ-200 | AnalpH2_MeOH_ 4 min(3): Rt 3.08 min; m/z 462.5 [M + 1]+ | Used in next step as crude material |
| (structure) | Intermediate for IQ-186 | AnalpH2_MeOH_ 4 min(3): Rt 3.12 min; m/z 480.5 [M +1]+ | Used in next step as crude material |
| (structure) | IQ-201 | AnalpH2_MeOH_ QC(1): Rt 5.31 min; m/z 380.4 [M + 1]+ | 37 mg, 34%, off-white solid |
| (structure) | IQ-202 | AnalpH2_MeOH_ QC(1): Rt 5.11 min; m/z 362 [M + 1]+ | 16 mg, 16%, white solid |

TABLE 30-continued 2H-isoquinolin-1-one derivatives of Formula 4

| Compound | Code | Analytical Data | Mass, % Yield, State |
|---|---|---|---|
| | IQ-203 | AnalpH2_MeOH_QC(1): Rt 5.35 min; m/z 381 [M + 1]$^+$ | 16 mg, 15%, white solid |
| | IQ-204 | AnalpH2_MeOH_QC(1): Rt 5.29 min; m/z 390.5 [M + 1]$^+$ | 57 mg, 42%, off-white solid |
| | IQ-175 | AnalpH2_MeOH_QC(1): Rt 5.30 min; m/z 376.5 [M + 1]$^+$ | 131 mg, 49%, off-white solid |
| | IQ-176 | AnalpH2_MeOH_QC(1): Rt 5.48 min; m/z 404.5 [M + 1]$^+$ | 43 mg, 31%, off-white solid |

TABLE 30-continued
2H-isoquinolin-1-one derivatives of Formula 4
| Compound | Code | Analytical Data | Mass, % Yield, State |
|---|---|---|---|
| 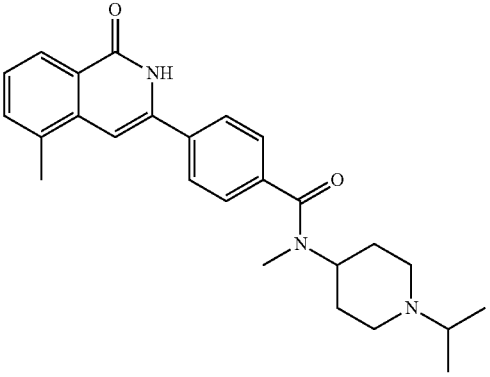 [SMILES: Cc1cccc2c(=O)[nH]c(-c3ccc(C(=O)N(C)C4CCN(C(C)C)CC4)cc3)cc12] | IQ-20 | AnalpH2_MeOH_QC(2): Rt 4.91, min; m/z 418.5 [M + 1]⁺ | 28 mg, 13% white solid |
| 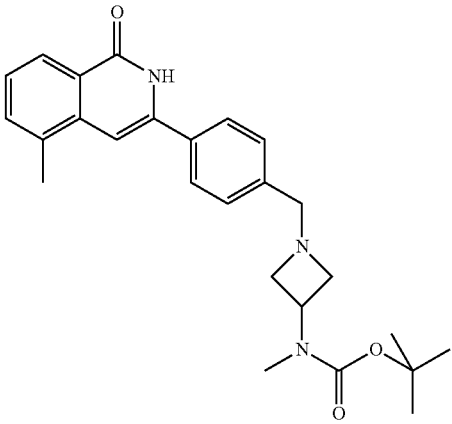 [SMILES: Cc1cccc2c(=O)[nH]c(-c3ccc(CN4CC(N(C)C(=O)OC(C)(C)C)C4)cc3)cc12] | Intermediate for IQ-177 | AnalpH2_MeOH_4 min(3): Rt 2.16 min; m/z 434.5 [M + 1]⁺ | 154 mg, 83%, brown, sticky solid |
| 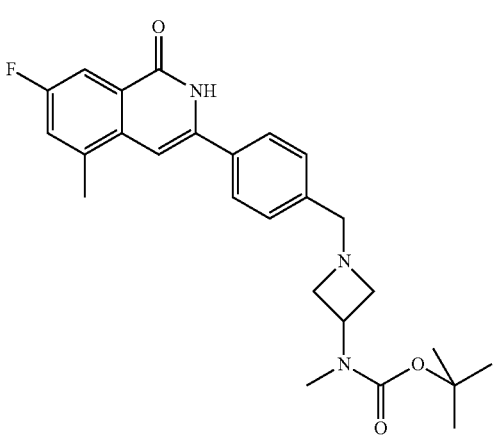 [SMILES: Cc1cc(F)cc2c(=O)[nH]c(-c3ccc(CN4CC(N(C)C(=O)OC(C)(C)C)C4)cc3)cc12] | Intermediate for IQ-178 | AnalpH2_MeOH_4 min(3): Rt 2.21 min; m/z 452.5 [M + 1]⁺ | 159 mg, 83%, brown, sticky solid |

TABLE 30-continued 2H-isoquinolin-1-one derivatives of Formula 4

| Compound | Code | Analytical Data | Mass, % Yield, State |
|---|---|---|---|
| 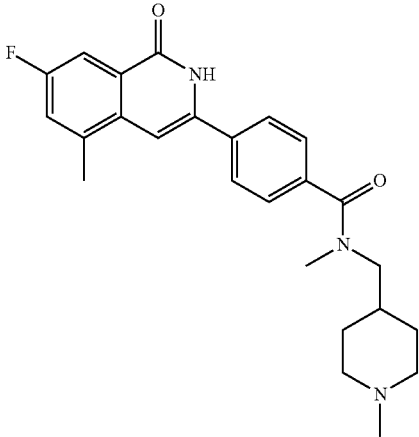 [SMILES: Cc1cc(F)cc2c(=O)[nH]c(-c3ccc(C(=O)N(C)CC4CCN(C)CC4)cc3)cc12] | IQ-208 | AnalpH2_MeOH_QC(2): Rt 4.96 min; AnalpH2_MeOH_4 min(2): m/z 422 [M + 1]$^+$ | 42 mg, 19%, white solid |
| 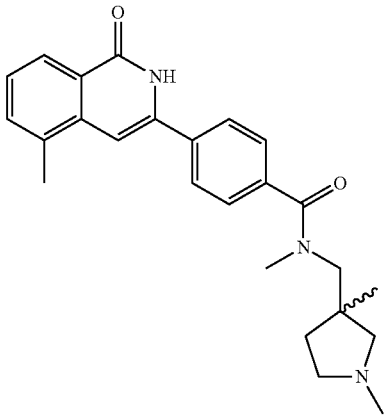 [SMILES: Cc1cccc2c(=O)[nH]c(-c3ccc(C(=O)N(C)CC4(C)CCN(C)C4)cc3)cc12] | IQ-209 | AnalpH2_MeOH_QC(2): Rt 4.89 min; AnalpH2_MeOH_4 min(2): m/z 404 [M + 1]$^+$ | 86 mg, 38%, beige solid |
| 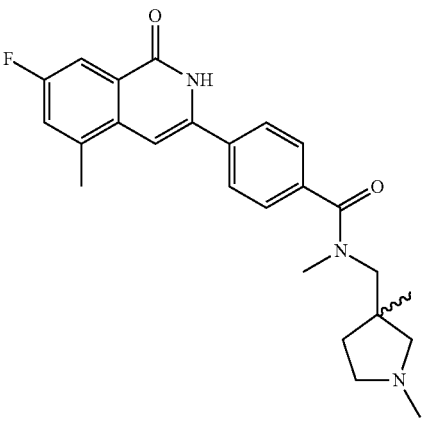 [SMILES: Cc1cc(F)cc2c(=O)[nH]c(-c3ccc(C(=O)N(C)CC4(C)CCN(C)C4)cc3)cc12] | IQ-210 | AnalpH2_MeOH_QC(2): Rt 5.02 min; AnalpH2_MeOH_4 min(2): m/z 422.5 [M + 1]$^+$ | 92 mg, 29%, off-white solid $^1$H NMR (400 MHz, DMSO-d$_6$): δ11.72 (br s, 1H), 7.88 (d, J = 8.3 Hz, 2H), 7.74 (br dd, J = 9.3, 2.7 Hz, 1H), 7.55-7.44 (m, 3H), 6.93 (s, 1H), 3.63 (br d, J = 13.2 Hz, 1H), 3.44 (br d, J = 13.2 Hz, 1H), 3.00 (br s, 3H), 2.60 (s, 3H), 2.48-2.44 (m, 1H), 2.29 (d, J = 9.1 Hz, 1H), 2.24 (s, 3H), 2.13 (br s, 1H), 1.86-1.79 (m, 1H), 1.56-1.50 (m, 1H), 1.13 (s, 3H), 0.89 (br s, 1H). |

TABLE 30-continued 2H-isoquinolin-1-one derivatives of Formula 4

| Compound | Code | Analytical Data | Mass, % Yield, State |
|---|---|---|---|
| (structure) | IQ-211 | AnalpH2_MeOH_QC(2): Rt 4.76 min; m/z 390.5 [M + 1]⁺ | 22 mg, 10%, off-white solid |
| (structure) | IQ-212 | AnalpH2_MeOH_QC(2): Rt 4.89 min; AnalpH2_MeOH_4 min(2): m/z 408 [M + 1]⁺ | 84 mg, 37%, off-white solid |
| (structure) | Intermediate for IQ-213 | AnalpH2_MeOH_4 min(3): Rt 3.16 min; m/z 494 [M + 1]⁺ | Used in next step as crude material |
| (structure) | IQ-180 | AnalpH2_MeOH_QC(2): Rt 4.75 min; m/z 316 [M + 1]⁺ | 140 mg, 79%, beige solid |

TABLE 30-continued
2H-isoquinolin-1-one derivatives of Formula 4
| Compound | Code | Analytical Data | Mass, % Yield, State |
|---|---|---|---|
| 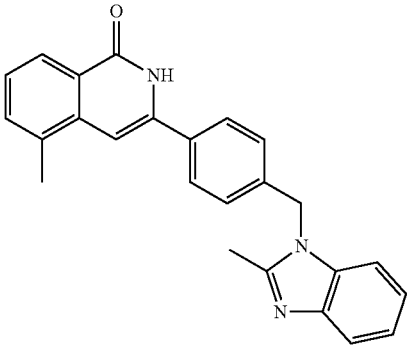 [SMILES: Cc1cccc2c(=O)[nH]c(-c3ccc(Cn4c(C)nc5ccccc54)cc3)cc12] | IQ-179 | AnalpH2_MeOH_QC(2): Rt 5.81 min; m/z 380.5 [M + 1]$^+$ | 66 mg, 31%, beige solid |
| 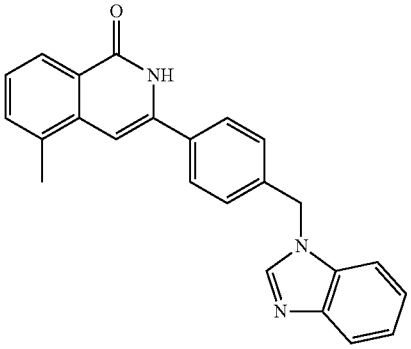 [SMILES: Cc1cccc2c(=O)[nH]c(-c3ccc(Cn4cnc5ccccc54)cc3)cc12] | IQ-181 | AnalpH2_MeOH_QC(2): Rt 6.56 min; m/z 366.5 [M + 1]$^+$ | 101 mg, 49%, beige solid |
| 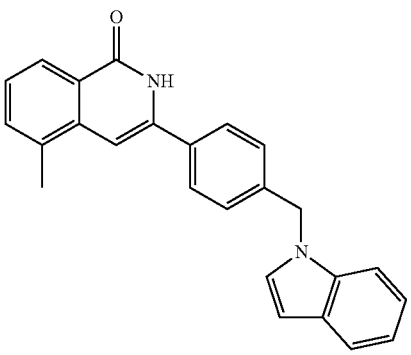 [SMILES: Cc1cccc2c(=O)[nH]c(-c3ccc(Cn4ccc5ccccc54)cc3)cc12] | IQ-183 | AnalpH2_MeOH_QC(2): Rt 8.54 min; m/z 365.5 [M + 1]$^+$ | 17 mg, 16%, beige solid |
| 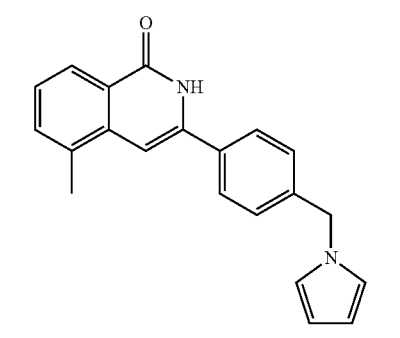 [SMILES: Cc1cccc2c(=O)[nH]c(-c3ccc(Cn4cccc4)cc3)cc12] | IQ-184 | AnalpH2_MeOH_QC(2): Rt 8.16 min; m/z 315 [M + 1]$^+$ | 10.6 mg, 5%, brown solid |

Scheme J, Step AF (Protocol 1): Synthesis of 2H-isoquinolin-1-one Derivatives of formula 5 (via BOC deprotection)

7-Fluoro-5-methyl-3-(4-piperazin-1-ylmethyl-phenyl)-2H-isoquinolin-1-one (IQ-078)

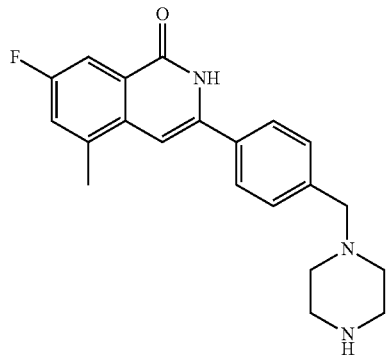 [SMILES: O=c1[nH]c(-c2ccc(CN3CCNCC3)cc2)cc2c(F)cc(F)cc12]

The synthesis is analogous to the Boc deprotection procedure used in Scheme A, Step C (Protocol 1) above to give 7-Fluoro-5-methyl-3-(4-piperazin-1-ylmethyl-phenyl)-2H-isoquinolin-1-one as an off-white solid (18.4 mg, 37%).

$^1$H NMR (400 MHz, DMSO-$d_6$): δ7.86 (d, J=8 Hz, 2H), 7.81 (dd, J=9, 3 Hz, 1H), 7.60 (dd, J=9, 3 Hz, 1H), 7.50 (d, J=8 Hz, 2H), 6.94 (s, 1H), 3.57 (s, 2H), 2.79-2.77 (m, 4H), 2.68 (s, 3H), 2.39 (br s, 4H).

AnalpH2_MeOH_QC(1): Rt 5.49 min; m/z 352 [M+1]$^+$

The following 2H-isoquinolin-1-one derivatives are prepared using analogous procedures.

TABLE 31

| 2H-isoquinolin-1-one Formula 5 | | | |
|---|---|---|---|
| Compound | Reference | Analytical Data | Mass, % Yield, State |
| 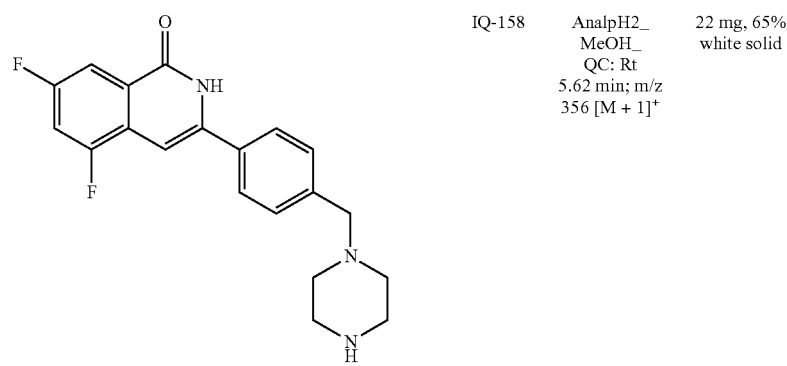 | IQ-079 | AnalpH2_MeOH_QC(1): Rt 5.05 min; m/z 356 [M + 1]$^+$ | 8 mg, 14%, off-white solid |
| | IQ-158 | AnalpH2_MeOH_QC: Rt 5.62 min; m/z 356 [M + 1]$^+$ | 22 mg, 65% white solid |

TABLE 31-continued
2H-isoquinolin-1-one Formula 5
| Compound | Reference | Analytical Data | Mass, % Yield, State |
|---|---|---|---|
| 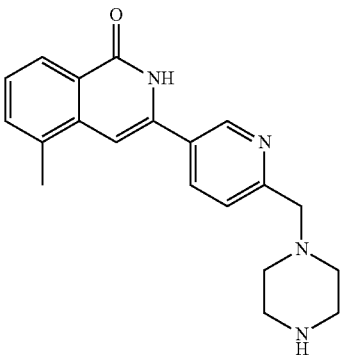 [SMILES: Cc1cccc2c(=O)[nH]c(-c3ccc(CN4CCNCC4)nc3)cc12] | IQ-072 | AnalpH2_MeOH_QC(1): Rt 4.87 min; m/z 335 [M + 1]⁺ | 11 mg, 50%, white solid |
| 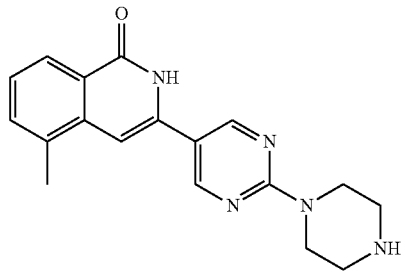 [SMILES: Cc1cccc2c(=O)[nH]c(-c3cnc(N4CCNCC4)nc3)cc12] | IQ-026 | AnalpH2_MeOH_QC(1): Rt 5.05 min; m/z 322 [M + 1]⁺ | 28 mg, 17%, white solid |
| 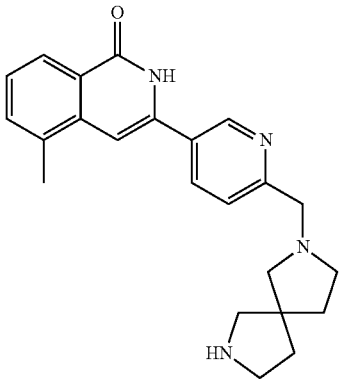 [SMILES: Cc1cccc2c(=O)[nH]c(-c3ccc(CN4CCC5(CCNC5)C4)nc3)cc12] | IQ-160 | AnalpH2_MeOH_QC: Rt 4.31 mins; m/z 375 [M + 1]⁺ | 16 mg, 29% light brown solid |
| 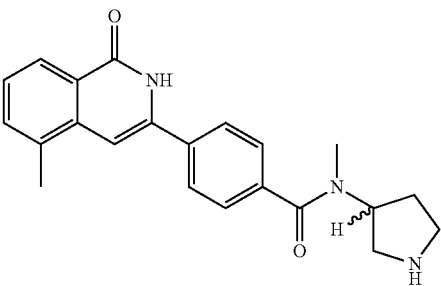 [SMILES: Cc1cccc2c(=O)[nH]c(-c3ccc(C(=O)N(C)C4CCNC4)cc3)cc12] | IQ-200 | AnalpH2_MeOH_QC(1): Rt 5.21 min; m/z 362.5 [M + 1]⁺ | 210 mg, 76%, off-white solid |

TABLE 31-continued 2H-isoquinolin-1-one Formula 5

| Compound | Reference | Analytical Data | Mass, % Yield, State |
|---|---|---|---|
| | IQ-186 | AnalpH2_MeOH_QC(1): Rt 5.39 min; m/z 380.5 [M + 1]+ | 135 mg, 61%, off-white solid |
| | IQ-177 | AnalpH2_MeOH_QC(2): Rt 3.68 min; m/z 334.5 [M + 1]+ | 35 mg, 29%, white solid |
| | IQ-178 | AnalpH2_MeOH_QC(2): Rt 3.84 min; m/z 352.5 [M + 1]+ | 42 mg, 34%, white solid |
| | IQ-213 | AnalpH2_MeOH_QC(2): Rt 4.81 min; AnalpH2_MeOH_4min(2): m/z 394 [M + 1]+ | 80 mg, 36%, off-white solid |

Scheme J, Step AF (Protocol 3): Synthesis of 2H-isoquinolin-1-one Derivatives of formula 5 (via TBDPS deprotection)

5,7-Difluoro-3-{4-[4-(2-hydroxy-ethyl)-piperazine-1-carbonyl]-phenyl}-2H-isoquinolin-1-one (IQ-228)      5

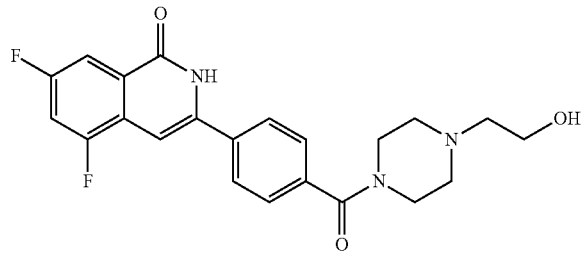 [SMILES: Cc1cc(F)cc2c(=O)[nH]c(-c3ccc(C(=O)N4CCN(CCO)CC4)cc3)cc12]

The synthesis is analogous to the TBDPS deprotection procedure used in Scheme A, Step C (Protocol 3) above to give 5,7-difluoro-3-{4-[4-(2-hydroxy-ethyl)-piperazine-1-carbonyl]-phenyl}-2H-isoquinolin-1-one as a white solid (20 mg, 48%).

$^1$H NMR (400 MHz, DMSO-$d_6$): δ11.96 (br s, 1H), 7.87 (d, J=8 Hz, 2H), 7.80-7.75 (m, 2H), 7.50 (d, J=8 Hz, 2H), 6.91 (s, 1H), 4.46-4.44 (m, 1H), 3.63 (br s, 2H), 3.50 (q, J=7 Hz, 2H), 3.35 (br s, 6H), 2.42 (t, J=6 Hz, 2H).

AnalpH2_MeOH_QC(1): Rt 5.19 min; m/z 414 [M+1]$^+$.

The following 2H-isoquinolin-1-one derivatives are prepared using analogous procedures.

N,N-Bis-(2-hydroxy-ethyl)-4-(5-methyl-1-oxo-1,2-dihydro-isoquinolin-3-yl)-benzamide (IQ-191)

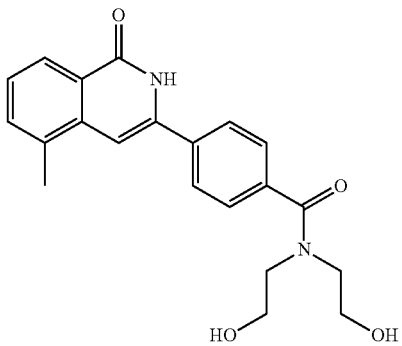 [SMILES: Cc1cccc2c(=O)[nH]c(-c3ccc(C(=O)N(CCO)CCO)cc3)cc12]

To a stirred solution of N,N-Bis-(2-methoxy-ethyl)-4-(5-methyl-1-oxo-1,2-dihydro-isoquinolin-3-yl)-benzamide (40 mg, 0.10 mmol) in CH$_2$Cl$_2$ (2.5 mL) under N$_2$ at −78° C. was added boron tribromide (1M in CH$_2$Cl$_2$, 2.54 mL, 2.54 mmol). The reaction was allowed to warm to RT and stirred for 16 h. The reaction mixture was quenched with H$_2$O and extracted with EtOAc (5 mL) upon which a pale yellow solid precipitated and was filtered off. The aqueous phase was further extracted with CH$_2$Cl$_2$ (5 mL). The combined organics were evaporated to dryness. Product was found to be also present in the aqueous phase and was passed through an Isolute-103 cartridge (500 mg), washing with H$_2$O (4× col-

TABLE 32

| 2H-isoquinolin-1-one Formula 5 | | | |
|---|---|---|---|
| Compound | Reference | Analytical Data | Mass, % Yield, State |
| ![IQ-192 structure] | IQ-192 | AnalpH2_MeOH_QC(3): Rt 9.23 min; m/z 410 [M + 1]$^+$ | 26 mg, 64%, white solid |
| ![IQ-193 structure] | IQ-193 | AnalpH2_MeOH_QC(1): Rt 4.90 min; m/z 410 [M + 1]$^+$ | 37 mg, 75%, white solid | umn volumes). The product was eluted from the column with MeOH (4× column volumes) and evaporated to dryness. The combined crude product was purified by reverse phase preparative HPLC-MS to obtain N,N-bis-(2-hydroxy-ethyl)-4-(5-methyl-1-oxo-1,2-dihydro-isoquinolin-3-yl)-benzamide as a white solid (23 mg, 63%).

$^1$H NMR (400 MHz, DMSO-$d_6$): δ11.64 (br s, 1H), 8.09 (d, J=8 Hz, 1H), 7.88 (d, J=8 Hz, 2H), 7.58 (d, J=7 Hz, 1H), 7.52 (d, J=8.6 Hz, 2H), 7.39 (t, J=7.6 Hz, 1H), 6.92 (s, 1H), 4.88-4.82 (m, 2H), 3.66-3.62 (m, 2H), 3.56-3.53 (m, 2H), 3.49-3.48 (m, 2H), 2.58 (s, 3H).

AnalpH2_MeOH_QC(1): Rt 6.76 min; m/z 367 [M+1]$^+$.

General Procedure for Synthesis of 2H-isoquinolin-1-ones Amide Derivatives of Formula 4

Scheme K

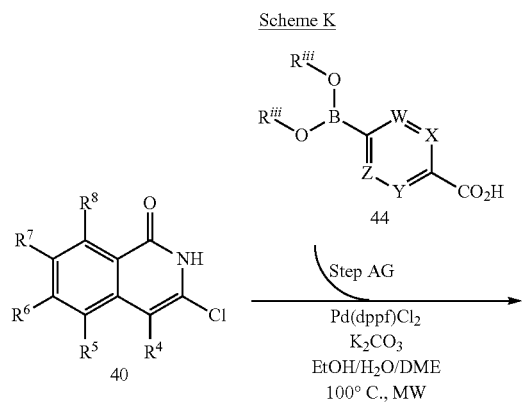

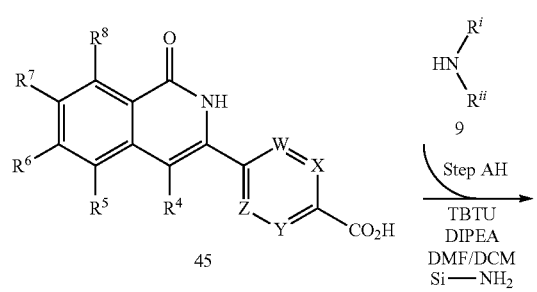

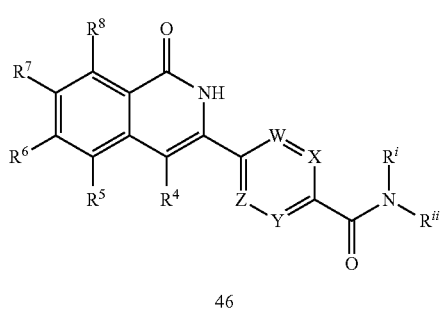

Scheme K, Step AG: Synthesis of 4-(5-Methyl-1-oxo-1,2-dihydro-isoquinolin-3-yl)-benzoic acid

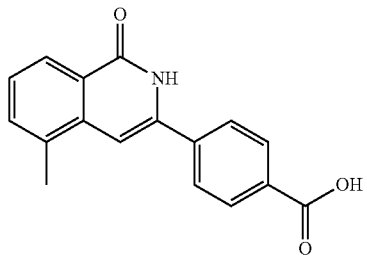 [SMILES: Cc1cccc2c(=O)[nH]c(-c3ccc(C(=O)O)cc3)cc12]

3-Chloro-5-methyl-2H-isoquinolin-1-one (50 mg, 0.26 mmol), 4-carboxybenezeneboronic acid (64 mg, 0.39 mmol), $K_2CO_3$ (73 mg, 0.52 mmol) and Pd(dppf)Cl$_2$ (11 mg, 0.013 mmol) in DME/EtOH/H2O 4:0.5:1 (2.75 mL) were added to a microwave vial and the reaction mixture purged with $N_2$ for 10 min. The reaction mixture was irradiated using a microwave (300 W, 120° C., 2 h). The reaction mixture was concentrated in vacuo, water added and the mixture acidified to pH2 with 0.2M HCl aq. A brown solid precipitated from the solution which was filtered and dried in vacuo, dissolved in DMF and passed through a Si-thiol cartridge, eluting with DMF (4× column volumes) and the solvent removed in vacuo. The resulting solid was triturated with MeOH, filtered and dried to give 4-(5-methyl-1-oxo-1,2-dihydro-isoquinolin-3-yl)-benzoic acid as a beige solid (29 mg, 40%).

AnalpH2_MeOH_QC(1): Rt 7.93 min; m/z 280 [M+1]$^+$.

Scheme K, Step AE: Synthesis of N-Methyl-4-(5-methyl-1-oxo-1,2-dihydro-isoquinolin-3-yl)-N-(1-methyl-piperidin-4-ylmethyl)-benzamide (IQ-095)

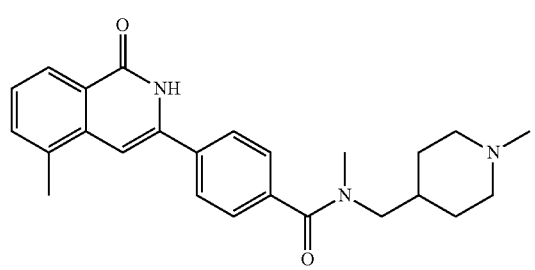 [SMILES: Cc1cccc2c(=O)[nH]c(-c3ccc(C(=O)N(C)CC4CCN(C)CC4)cc3)cc12]

The synthesis is analogous to the acid coupling procedure used in Step E above to give N-methyl-4-(5-methyl-1-oxo-1,2-dihydro-isoquinolin-3-yl)-N-(1-methyl-piperidin-4-ylmethyl)-benzamide as a pale yellow foam (27 mg, 93%).

$^1$H NMR (400 MHz, DMSO-$d_6$): δ11.65-11.59 (br s, 1H), 8.09 (d, J=8 Hz, 1H), 7.89 (d, J=8 Hz, 2H), 7.57 (d, J=7 Hz, 1H) 7.51 (br d, J=7 Hz, 1H), 7.45 (br d, J=7 Hz, 1H) 7.39 (t, J=7 Hz, 1H), 6.92 (s, 1H), 3.39-3.37 (m, 1H), 3.18-3.14 (m, 1H), 2.98 (s, 1H), 2.93 (s, 2H), 2.78 (d, J=10 Hz, 1H), 2.66 (d, J=10 Hz, 1H), 2.58 (s, 3H), 2.16 (s, 2H), 2.08 (s, 1H), 1.88-1.63 (m, 4H), 1.48-1.44 (d, J=10 Hz, 1H), 1.28-1.21 (m, 1H), 0.89-0.80 (m, 1H).

AnalpH2_MeOH_QC(1): Rt 5.18 min; m/z 404 [M+1]$^+$.

General Procedure for Synthesis of 2H-isoquinolin-1-ones Amide Derivatives of Formula 4 & 5 (Via Route 2a)

Scheme L

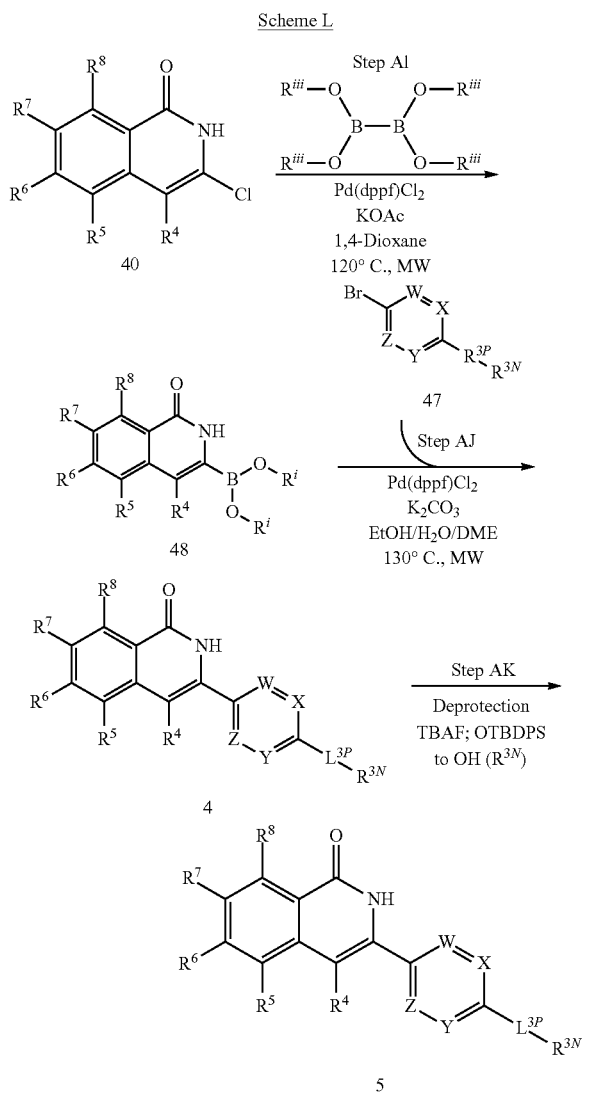

Scheme L, Step AI: Synthesis of Aryl Boronic Acid Derivatives of Formula 48

5-Methyl-1-oxo-1,2-dihydro-isoquinoline-3-boronic acid

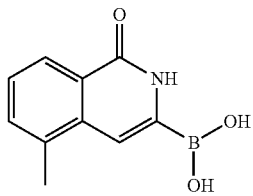

3-Chloro-5-methyl-2H-isoquinolin-1-one (100 mg, 0.52 mmol), bis(pinacolato)diboron (157 mg, 0.62 mmol), Pd(dppf)Cl$_2$ (42 mg, 0.054 mmol) and KOAc (153 mg, 1.56 mmol) in 1,4-dioxane (2 mL) were added to a microwave vial and the reaction mixture purged with N$_2$ for 10 min. The reaction mixture was irradiated using a microwave reactor (300 W, 120° C., 20 min). The reaction mixture was passed through a Si-thiol cartridge and concentrated in vacuo. The crude product was purified by reverse phase preparative HPLC-MS to afford 5-methyl-1-oxo-1,2-dihydro-isoquinoline-3-boronic acid as a white solid (51 mg, 49%).

AnalpH2_MeOH_4 min(3): Rt 2.18 min; m/z 204 [M+1]$^+$.

The following boronic acid derivatives 48 are prepared using analogous procedures.

TABLE 33

Boronic acid derivatives of Formula 48

| Compound | Analytical Data | Mass, % Yield, State |
|---|---|---|
| ![F-substituted compound] | AnalpH2_MeOH_ 4 min(3): Rt 2.18 min; m/z 222 [M + 1]$^+$ | 59 mg, 38%, pale yellow solid |
| ![F-substituted compound] | AnalpH2_MeOH_ 4 min(3): Rt 2.41 min; m/z 222 [M + 1]$^+$ | 84 mg, 40%, off-white solid |

Scheme L, Step AJ: Synthesis of 2H-isoquinolin-1-one Derivatives of Formula 4 (via Suzuki Cross-Coupling)

3-[5-(4-Cyclopropylmethyl-piperazine-1-carbonyl)-pyridin-2-yl]-5-methyl-2H-isoquinolin-1-one (IQ-223)

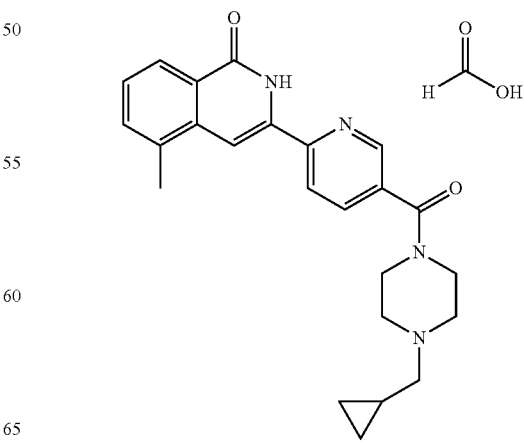

5-Methyl-1-oxo-1,2-dihydro-isoquinoline-3-boronic acid (40 mg, 0.20 mmol), (6-bromo-pyridin-3-yl)-(4-cyclopropylmethyl-piperazin-1-yl)-methanone (95 mg, 0.30 mmol), $K_2CO_3$ (56 mg, 0.4 mmol) and Pd(dppf)Cl$_2$ (16 mg, 0.02 mmol) in DME/EtOH/H$_2$O 4:0.5:1 (3.5 mL) were added to a microwave vial and the reaction mixture purged with N$_2$ for 10 min. The reaction mixture was irradiated using a microwave reactor (300 W, 130° C., 60 min). The reaction mixture was filtered through a Si-thiol and concentrated in vacuo. The crude material was purified by reverse phase preparative HPLC-MS to obtain 3-[5-(4-cyclopropylmethyl-piperazine-1-carbonyl)-pyridin-2-yl]-5-methyl-2H-isoquinolin-1-one as a brown solid (18 mg, 22%).

AnalpH2_MeOH_QC(1): Rt 4.97 min; m/z 403 [M+1]$^+$.

The following 2H-isoquinolin-1-one derivatives are prepared using analogous procedures.

TABLE 34

2H-isoquinolin-1-one derivatives of Formula 4

| Compound | Code | Analytical Data | Mass, % Yield, State |
|---|---|---|---|
| | IQ-224 | AnalpH2_MeOH_QC(1): Rt 4.41 min; m/z 364 [M + 1]$^+$ | 3.2 mg, 16%, off-white solid |
| | IQ-220 | AnalpH2_MeOH_QC(3): Rt 8.03 min; m/z 363 [M + 1]$^+$ | 34 mg, 34%, white solid |
| | IQ-221 | AnalpH2_MeOH_QC(3): Rt 7.66 min; m/z 381 [M + 1]$^+$ | 78 mg, 76%, beige solid |

TABLE 34-continued 2H-isoquinolin-1-one derivatives of Formula 4

| Compound | Code | Analytical Data | Mass, % Yield, State |
|---|---|---|---|
| (structure) | IQ-222 | AnalpH2_MeOH_QC(1): Rt 4.96 min; m/z 381 [M + 1]+ | 35 mg, 24%, beige solid |
| (structure) | IQ-194 | AnalpH2_MeOH_QC(1): Rt 7.15 min; m/z 371 [M + 1]+ | 32 mg, 16%, white solid |
| (structure) | Intermediate for IQ-170 | AnalpH2_MeOH_4 min(3): Rt 2.80 min; m/z 577 [M + 1]+ | 300 mg, quant., black oil |
| (structure) | IQ-217 | AnalpH2_MeOH_QC(1): Rt 7.87 min; m/z 378 [M + 1]+ | 41 mg, 32%, pale brown solid |

TABLE 34-continued
2H-isoquinolin-1-one derivatives of Formula 4
| Compound | Code | Analytical Data | Mass, % Yield, State |
|---|---|---|---|
| 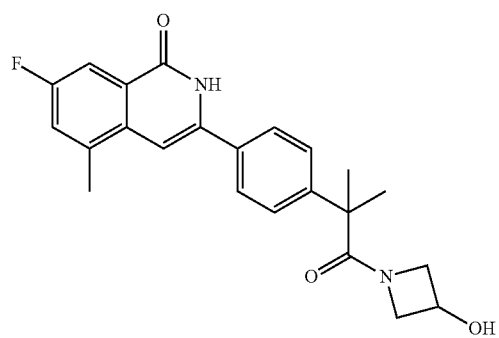 [SMILES: Cc1cc(F)cc2c(=O)[nH]c(-c3ccc(C(C)(C)C(=O)N4CC(O)C4)cc3)cc12] | IQ-218 | AnalpH2_MeOH_QC(1): Rt 8.00 min; m/z 396 [M + 1]$^+$ | 37 mg, 27%, off-white solid |
| 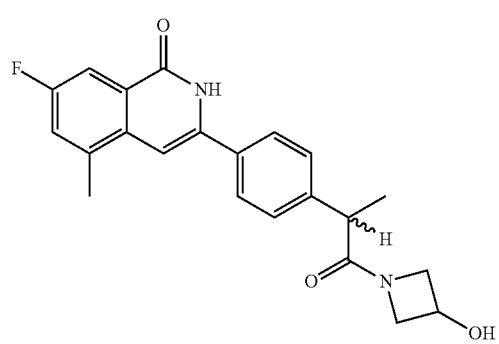 [SMILES: Cc1cc(F)cc2c(=O)[nH]c(-c3ccc(C(C)C(=O)N4CC(O)C4)cc3)cc12] | IQ-216 | AnalpH2_MeOH_QC(1): Rt 7.74 min; m/z 381 [M + 1]$^+$ | 140 mg, 69%, off-white solid |
| 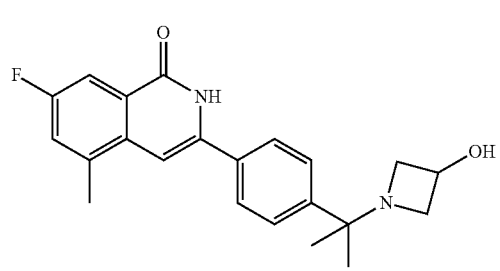 [SMILES: Cc1cc(F)cc2c(=O)[nH]c(-c3ccc(C(C)(C)N4CC(O)C4)cc3)cc12] | IQ-185 | AnalpH2_MeOH_QC(1): Rt 5.54 min; m/z 367 [M + 1]$^+$ | 14.4 mg, 5.5%, white solid $^1$H NMR (400 MHz, DMSO-d$_6$): δ11.68 (br s, 1H), 7.76 (d, J = 8.8 Hz, 2H), 7.58 (dd, J = 9.2, 2.8 Hz, 1H), 7.58 (d, J = 8.8 Hz, 2H), 7.51 (dd, J = 9.6, 2.8 Hz, 1H), 6.85 (s, 1H), 5.22 (d, J = 6.4 Hz, 1H), 4.22-4.15 (m, 1H), 3.25 (dd, J = 7.2, 6.0 Hz, 2H), 2.87 (dd, J = 7.2, 6.0 Hz, 2H), 2.59 (s, 3H), 1.28 (s, 6H). |

Scheme L, Step AK: Synthesis of 2H-isoquinolin-1-one Derivatives of Formula 5 (via TBDPS Deprotection)

7-Fluoro-3-[4-(3-hydroxy-azetidin-1-ylmethyl)-phenyl]-5-methyl-2H-isoquinolin-1-one (IQ-170)

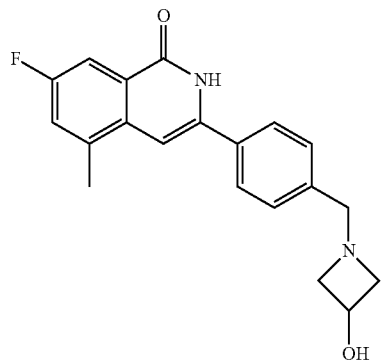 [SMILES: Cc1cc(F)cc2c(=O)[nH]c(-c3ccc(CN4CC(O)C4)cc3)cc12]

The synthesis is analogous to the TBDPS deprotection procedure used in Scheme A, Step C (Protocol 3) above to give 7-Fluoro-3-[4-(3-hydroxy-azetidin-1-ylmethyl)-phenyl]-5-methyl-2H-isoquinolin-1-one as a white solid (3 mg, 11%).

AnalpH2_MeOH_QC(1): Rt 5.25 min; m/z 339 [M+1]$^+$.

General Procedure for Synthesis of 2H-isoquinolin-1-one Acetylene Derivatives of Formula 51 & 52

Scheme M, Step AL: Synthesis of 2H-isoquinolin-1-one Derivatives of Formula 50

5-Bromo-3-[4-(2-dimethylaminoethoxy)phenyl]-2H-isoquinolin-1-one (IQ-237)

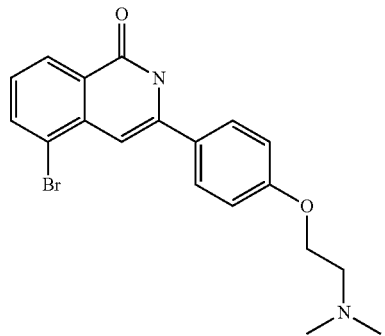 [SMILES: CN(C)CCOc1ccc(-c2cc3c(Br)cccc3c(=O)[nH]2)cc1]

The synthesis is analogous to the cyclisation procedure used in Scheme A Step B (protocol 3) above to give 5-bromo-3-[4-(2-dimethylaminoethoxy)phenyl]-2H-isoquinolin-1-one as a yellow solid (1.23 g, 86%).

$^1$H NMR (400 MHz, DMSO-d$_6$): δ 11.78 (br s, 1H), 8.21 (d, J=8 Hz, 1H), 8.02 (d, J=8 Hz, 1H), 7.72 (d, J=8.8 Hz, 2H), 7.37 (t, J=7.8 Hz, 1H), 7.07 (d, J=8.8 Hz, 2H), 6.80 (s, 1H), 4.11 (t, J=5.8 Hz, 2H), 2.64 (t, J=5.8 Hz, 2H), 2.22 (s, 6H).

AnalpH2_MeOH_QC: Rt 5.69 min; m/z 387 [M+1]$^+$.

The following 2H-isoquinolin-1-one derivatives are prepared using analogous procedures.

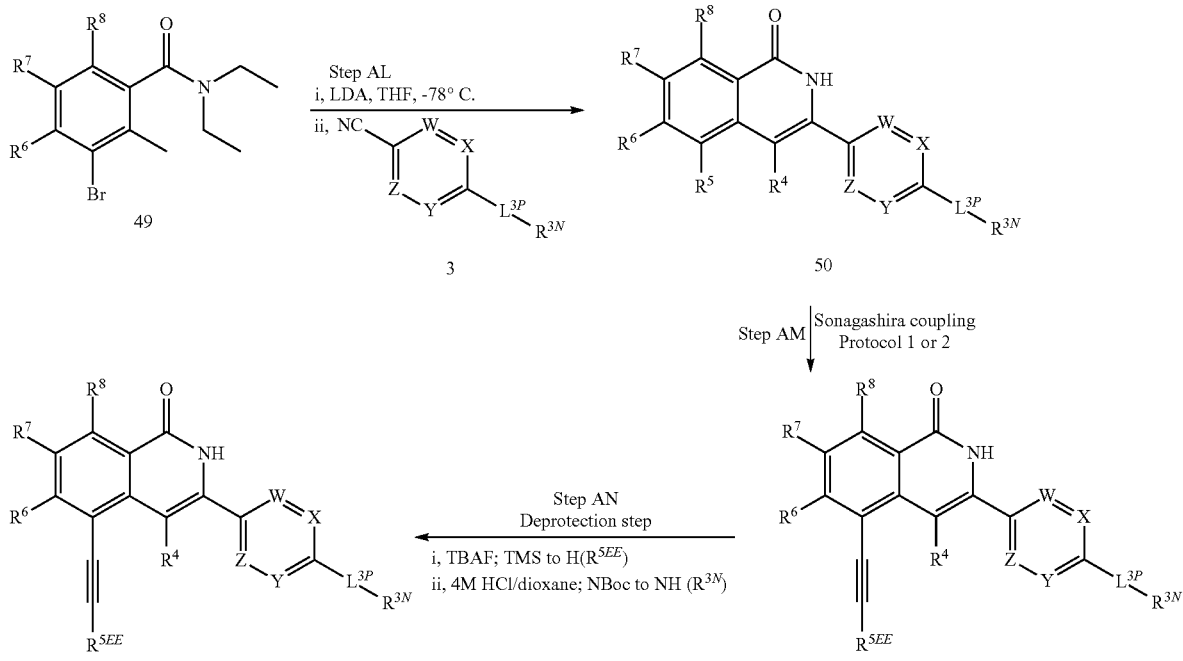

Scheme M

TABLE 35

2H-isoquinolin-1-one derivatives of Formula 4

| Compound | Code | Analytical Data | Mass, % Yield, State |
|---|---|---|---|
| ![structure] | IQ-238 | AnalpH2_MeOH_4 min: Rt 1.97 min; m/z 412 [M + 1]+ | 845 mg, 79%, pale orange/pink solid |

Scheme M, Step AM (Protocol 1): Synthesis of 2H-isoquinolin-1-one Derivatives of Formula 51

3-[4-(2-Dimethylaminoethoxy)phenyl]-5-(4-hydroxybut-1-ynyl)-2H-isoquinolin-1-one (IQ-236)

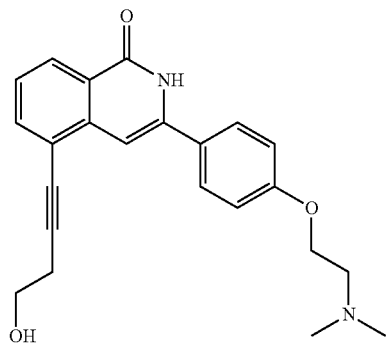 [SMILES: CN(C)CCOc1ccc(-c2cc3c(C#CCCO)cccc3c(=O)[nH]2)cc1]

5-Bromo-3-[4-(2-dimethylaminoethoxy)phenyl]-2H-isoquinolin-1-one (50.0 mg, 0.130 mmol), triethylamine (1.1 mL, 8.36 mmol), dichlorobis(triphenylphosphine)palladium (II) (5.0 mg, 0.0065 mmol), copper (I) iodide (3.0 mg, 0.009 mmol), 3-butyn-1-ol (20 μL, 0.260 mmol) in DMF (1.1 mL) were added to a microwave vial and the reaction mixture purged with $N_2$ for 5 min. The reaction mixture was irradiated using a microwave reactor (300 W, 100° C., 90 min). The reaction mixture was filtered through Celite® 545, diluted with DMSO and was purified by reverse phase preparative HPLC-MS to obtain 3-[4-(2-dimethylaminoethoxy)phenyl]-5-(4-hydroxybut-1-ynyl)-2H-isoquinolin-1-one as a brown solid (19.0 mg, 39%).

$^1$H NMR (400 MHz, CDCl$_3$): δ9.77 (br s, 1H), 8.31 (d, J=8.4 Hz, 1H), 7.75 (dd, J=7.6, 1.0 Hz, 1H), 7.64 (d, J=8.8 Hz, 2H), 7.37 (t, J=7.8 Hz, 1H), 7.17 (s, 1H), 7.03 (d, J=8.8 Hz, 2H), 4.29 (t, J=5.2 Hz, 2H), 3.91 (t, J=6.2 Hz, 2H), 3.12 (t, J=4.4 Hz, 2H), 2.83 (t, J=6.2 Hz, 2H), 2.60 (s, 6H).

AnalpH2_MeOH_QC: Rt 5.17 min; m/z 377 [M+1]+.

The following 2H-isoquinolin-1-one derivatives are prepared using analogous procedures.

TABLE 36

2H-isoquinolin-1-one Formula 51

| Compound | Code | Analytical Data | Mass, % Yield, State |
|---|---|---|---|
| ![structure] | IQ-232 | AnalpH2_MeOH_QC: Rt 4.93 min; m/z 363 [M + 1]+ | 19 mg, 20%, brown oil |

TABLE 36-continued
2H-isoquinolin-1-one Formula 51
| Compound | Code | Analytical Data | Mass, % Yield, State |
|---|---|---|---|
| 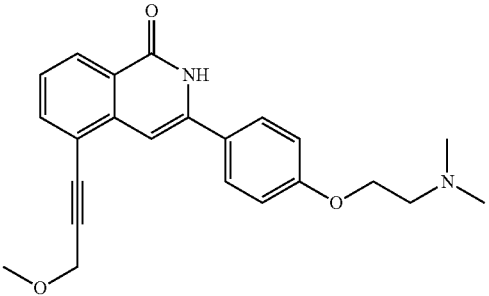 | IQ-234 | AnalpH2_MeOH_QC: Rt 5.53 min; m/z 377 [M + 1]$^+$ | 36 mg 34% beige solid |
| 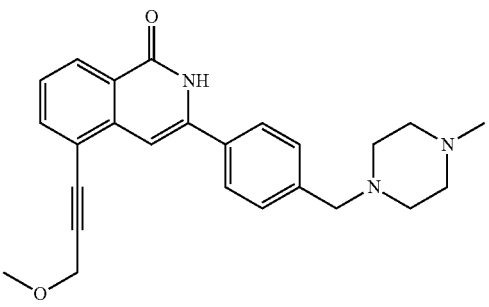 | IQ-233 | AnalpH2_MeOH_QC(1): Rt 5.70 min; m/z 402 [M + 1]$^+$ | 23 mg, 44%, beige solid |
| 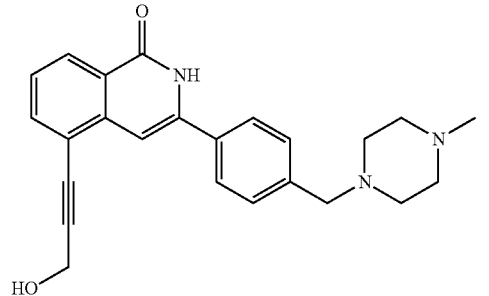 [SMILES: CN1CCN(Cc2ccc(-c3cc4c(C#CCO)cccc4c(=O)[nH]3)cc2)CC1] | IQ-231 | AnalpH2_MeOH_QC(1): Rt 5.06 min; m/z 388 [M + 1]$^+$ | 25 mg, 41%, beige solid |
| 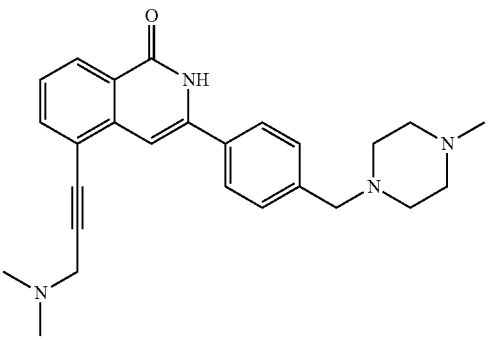 | IQ-235 | AnalpH2_MeOH_4 min: Rt 0.94 min m/z 415 [M + 1]$^+$ | 36 mg, 54%, off-white solid |

Scheme M, Step AM (Protocol 2): Synthesis of 2H-isoquinolin-1-one Derivatives of Formula 51

4-[4-(1-Oxo-5-trimethylsilanylethynyl-1,2-dihydroisoquinolin-3-yl)benzyl]piperazine-1-carboxylic acid tert-butyl ester

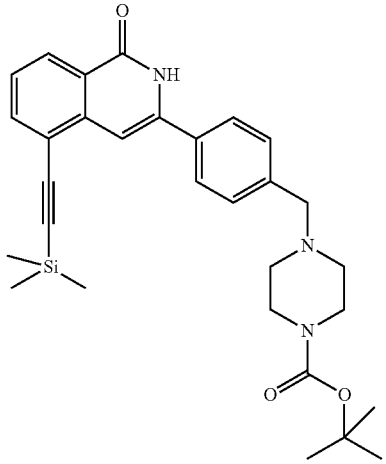 [SMILES: CC(C)(C)OC(=O)N1CCN(Cc2ccc(-c3cc4c(C#C[Si](C)(C)C)cccc4c(=O)[nH]3)cc2)CC1]

4-[4-(5-Bromo-1-oxo-1,2-dihydro-isoquinolin-3-yl)benzyl]piperazine-1-carboxylic acid (140.0 mg, 0.281 mmol), ethynyltrimethylsilane (119 µL, 0.843 mmol), triethylamine (391 µL, 2.81 mmol), dichlorobis(triphenylphosphine)palladium(II) (19.6 mg, 0.028 mmol), and triphenylphosphine (3.67 mg, 0.014 mmol) in anhydrous DMF (3 mL) were added to a microwave vial and the reaction mixture purged with $N_2$ for 5 min. Copper (I) iodide (5.33 mg, 0.028 mmol) was added and the mixture was degassed for a further minute. The reaction mixture was irradiated using a microwave reactor (300 W, 110° C., 1 h). The reaction mixture was then concentrated in vacuo, diluted with water (50 mL) and extracted with EtOAc (2×50 mL). The combined organic layer was washed with brine (50 mL), dried over $Na_2SO_4$, filtered and concentrated in vacuo. The crude material was purified by silica gel column chromatography, eluting with iso-hexane and increasing the polarity to 100% EtOAc/iso-hexane to afford 4-[4-(1-oxo-5-trimethylsilanylethynyl-1,2-dihydroisoquinolin-3-yl)benzyl]piperazine-1-carboxylic acid tert-butyl ester as a yellow solid (70.3 mg, 49%).

AnalpH2_MeOH_4 min (3): Rt 3.05 min; m/z 515.5 [M+1]$^+$.

Scheme M, Step AN (Step 1): Synthesis of 2H-isoquinolin-1-one Derivatives of Formula 52

4-[4-(5-Ethynyl-1-oxo-1,2-dihydroisoquinolin-3-yl)benzyl]piperazine-1-carboxylic acid tert-butyl ester

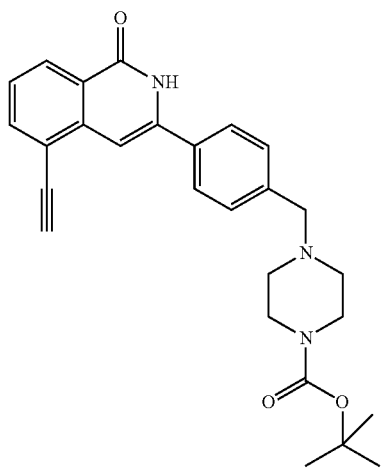 [SMILES: C#Cc1cccc2c(=O)[nH]c(-c3ccc(CN4CCN(C(=O)OC(C)(C)C)CC4)cc3)cc12]

To a stirred solution of 4-[4-(1-oxo-5-trimethylsilanylethynyl-1,2-dihydroisoquinolin-3-yl)benzyl]piperazine-1-carboxylic acid tert-butyl ester compound (70.0 mg, 0.136 mmol) in THF (5 mL) was added TBAF (1M in THF, 272 µL, 0.272 mmol). The resulting reaction mixture was stirred at RT for 2 h and then quenched by the addition of water (20 mL). The mixture was extracted with EtOAc (3×20 mL) and the combined organic layer was washed with brine (50 mL), dried over $Na_2SO_4$, filtered and concentrated in vacuo to obtain 4-[4-(5-ethynyl-1-oxo-1,2-dihydroisoquinolin-3-yl)benzyl]piperazine-1-carboxylic acid tert-butyl ester (60.3 mg, 100%) as an orange solid. The crude compound was used for the next step without further purification.

AnalpH2_MeOH_4 min (3): Rt 2.35 min; m/z 444.5 [M+1]$^+$.

Scheme M, Step AN (Step 2): Synthesis of 2H-isoquinolin-1-one Derivatives of Formula 52

5-Ethynyl-3-(4-piperazin-1-ylmethylphenyl)-2H-isoquinolin-1-one (IQ-230)

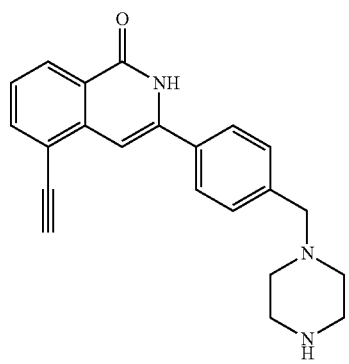 [SMILES: C#Cc1cccc2c(=O)[nH]c(-c3ccc(CN4CCNCC4)cc3)cc12]

4-[4-(5-Ethynyl-1-oxo-1,2-dihydroisoquinolin-3-yl)benzyl]piperazine-1-carboxylic acid tert-butyl ester (60.3 mg, 0.136 mmol) and 4M HCl/dioxane (3 mL) in $CH_2Cl_2$ (3 mL) were stirred at RT for 2 h. The reaction mixture was concentrated in vacuo and the crude material was purified by reverse phase preparative HPLC-MS to obtain 5-ethynyl-3-(4-piperazin-1-ylmethylphenyl)-2H-isoquinolin-1-one as an off-white solid (16.0 mg, 34%).

$^1$H NMR (400 MHz, DMSO-d$_6$): δ8.23 (d, J=8 Hz, 1H), 7.89 (dd, J=7.6 Hz, 1H), 7.72 (d, J=8.4 Hz, 1H), 7.47 (t, J=7.6 Hz, 1H), 7.43 (d, J=8.0 Hz, 2H), 6.97 (s, 1H), 4.67 (s, 1H), 3.48 (s, 2H), 2.69-2.67 (m, 4H), 2.30 (br s, 4H).

AnalpH2_MeOH_QC (1): Rt 5.46 min; m/z 344.5 [M+1]$^+$.

Biological Methods

Biochemical Assay 1:
TNKS1/PARP Biochemical Assay

Tankyrase activity was assayed using a 96-well format HT Universal Chemiluminescent PARP Assay Kit (Trevigen, Inc, cat. no. 4676-096-K) according to the manufacturer's instructions. In short, tankyrase/PARP activity is quantified by the incorporation of biotinylated nicotinamide adenine dinucleotide (biotin-NAD$^+$) onto the immobilised pseudo substrate, Histone. The extent of poly(Biotin-ADP)ribosylation (PARylation) in the presence of increasing dose of inhibitor is then quantified by binding of streptavidin conjugated horse radish peroxidase (strep-HRP) followed by chemiluminescent detection.

Prior to assay initiation, inhibitor stocks were prepared in aqueous DMSO (10% (v/v)) from 5 millimolar (mM) stock in 100% DMSO (Sigma Aldrich, cat. no. 265855) as 10× concentrations. For the primary assay (i.e., single dose at 1 micromolar (μM) final concentration) this corresponded to 10 μM in 10% DMSO. For $IC_{50}$ determination, this corresponded to 100 μM, 30 μM, 10 μM, 3.0 μM, 1.0 μM, 0.30 μM, 0.10 μM and 0 μM in 10% DMSO for final concentrations of 10 μM, 3.0 μM, 1.0 μM, 0.30 μM, 0.10 μM, 0.030 μM, 0.010 μM and 0 μM with 1% (v/v) final DMSO. The assay was initiated by the addition of 10× inhibitor (5 microliters (μL)) or 10% aqueous DMSO (5 μL) to triplicate wells. Twenty microliters of diluted TNKS1 protein (200 nanomolar (nM) final conc.) in PARP buffer (Trevigen, Inc, cat. no. 4671-096-02) was added to each histone coated well, which was previously hydrated with PARP buffer. Triplicate wells with 1% DMSO/buffer alone (no enzyme) were also added as a measure of assay 'noise'. Positive control for PARP inhibition included the addition of 4-amino-1,8-naphthalimide (Sigma Aldrich, cat. no A0966) in corresponding doses.

The mixture was incubated for 10 minutes at room temperature and the PARylation reaction initiated by the addition of PARP cocktail (25 μL, Trevigen, Inc) containing biotin-$NAD^+$ (Trevigen, Inc, cat. no. 4670-500-01), activated DNA (Trevigen, Inc, cat. no. 4671-096-06) and PARP buffer. The reaction was incubated for 1.5 hours (for TNKS1) or 1 hour (for PARP1) at room temperature. The reaction mixture was then removed by aspiration and the wells washed (3×200 μL) with phosphate buffered saline containing Triton X-100 (0.1% (v/v), Sigma Aldrich cat. no. T8787). The wells were then washed (3×200 μL) with phosphate buffered saline and then incubated with strep-HRP (50 μL, Trevigen, Inc, cat. no. 4800-30-06) in strep-diluent (1:500 dilution, Trevigen Inc, cat. no. 4671-096-04) for 1 hour at room temperature. The Strep-HRP mixture was then aspirated and the wells washed (3×200 μL) with phosphate buffered saline containing Triton X-100 (0.1% (v/v)) followed by phosphate buffered saline (3×200 μL) and then incubated with PeroxyGlow™ reagent (100 μL, Trevigen, Inc, cat. nos. 4675-096-01, 4675-096-02, room temperature, mixed 1:1).

The amount of light emitted as a result of the peroxidase-chemiluminescent reagent reaction was in proportion to the extent of poly(Biotin-ADP)ribosylation and was immediately measured with a $Victor^2$ plate reader (Perkin Elmer, luminescence detection assay, luminescent units described as 'Counts Per Second' (CPS)). The data were normalised to the DMSO control after subtraction of 'noise' and was expressed as % PARP activity as a function of inhibitor dose. Inhibition was expressed as 100%-(% PARP activity). Dose response curves used to determine $IC_{50}$ values were Log transformed and analysed by non-linear regression analysis (variable slope) using Prism (GraphPad Software, Inc) and were presented as $IC_{50}$ with 95% confidence interval to determine relative potency.

Preparation of Recombinant Proteins:

Tankyrase1 (pNIC-Bsa-4-TNKS1$^{PARP}$) expression construct was obtained from the Structural Genomics Consortium (SGC) and expresses the active PARP domain of TNKS1 as a polyhistidine tagged protein. The expression and purification of TNKS1 protein was carried out according to the SGC protocol provided at http://www.thesgc.org/structures/materials_methods/2RF5/, which is summarised in the following table.

| | |
|---|---|
| Structure | TNKS1 |
| PDB Code | 2RF5 |
| Entry clone accession | BC098394 |
| Entry clone source | Mammalian Gene Collection |
| Tag | N-terminal hexahistidine tag with integrated TEV protease cleavage site: mhhhhhhssgvdlgtenlyfq*s(m) |
| Construct sequence | mhhhhhhssgvdlgtenlyfq*sMQGTNPYLTFHCVNQGTILLDLAPEDKEYQS VEEEMQSTIREHRDGGNAGGIFNRYNVIRIQKVVNKKLRERFCHRQKE VSEENHNHHNERMLFHGSPFINAIIHKGFDERHAYIGGMFGAGIYFAEN SSKSNQYVYGIGGGTGCPTHKDRSCYICHRQMLFCRVTLGKSFLQFSTI KMAHAPPGHHSVIGRPSVNGLAYAEYVIYRGEQAYPEYLITYQIMKPEA PSQTATAAEQ |
| Vector | pNIC-Bsa4 |
| Expression host | E.coli Rosetta2(DE3) (Novagen) |
| Growth method | Cells from a glycerol stock were streaked onto LB-agar plates. 5-10 colonies were used to inoculate 20 mL TB supplemented with 8 g/l glycerol, 100 μg/mL kanamycin and 34 μg/mL chloramphenicol. The cells were grown at 30° C. overnight. The overnight culture (20 mL) was used to inoculate 1.5 l TB supplemented with 8 g/l glycerol, 50 μg/mL kanamycin and approximately 200 μl PPG P2,000 81380 anti-foam solution (Fluka). The culture was grown in a LEX bioreactor system (Harbinger Biotechnology) at 37° C. until $OD_{600}$ reached ~2. The culture was down-tempered to 18° C. over a period of 1 hour before target expression was induced by addition of 0.5 mM IPTG. Expression was allowed to continue overnight and cells were harvested the following morning by centrifugation (5,500 × g, 10 min, 4° C.). The resulting cell pellet (38.2 g wet cell weight) was resuspended in lysis buffer (2 mL/g cell pellet), supplemented with one tablet of Complete EDTA-free |

```
                    -continued
       protease inhibitor (Roche Applied Science). The cell suspension was
       stored at -80° C.

Extraction         Lysis buffer: 50 mM HEPES, 300 mM NaCl, 10% glycerol, 10 mM
buffers            imidazole, 0.5 mM TCEP, pH 7.8

Extraction         The cell suspension was quickly thawed in water and 2500 U Benzonase
procedure          (Merck) was added. Cells were disrupted by sonication (Vibra-Cell,
                   Sonics) at 80% amplitude for 3 min effective time (pulsed 4s on, 4s off)
                   and cell debris was removed by centrifugation (49,100 x g, 20 min, 4° C.).
                   The supernatant was decanted and filtered through a 0.45 µm flask filter.

Purification       IMAC wash1 buffer: 30 mM HEPES, 500 mM NaCl, 10% glycerol, 10 mM
buffers            imidazole, 0.5 mM TCEP, pH 7.5.
                   IMAC wash2 buffer: 30 mM HEPES, 500 mM NaCl, 10% glycerol, 25 mM
                   imidazole, 0.5 mM TCEP, pH 7.5.
                   IMAC elution buffer: 30 mM HEPES, 500 mM NaCl, 10% glycerol, 500
                   mM imidazole, 0.5 mM TCEP, pH 7.5.
                   Gel filtration (GF) buffer: 30 mM HEPES, 300 mM NaCl, 10% glycerol,
                   0.5 mM TCEP, pH 7.5

Purification       Columns:
procedure          IMAC: Ni-charged 1 mL HiTrap Chelating HP (GE Healthcare). Gel
                   filtration column: HiLoad 16/60 Superdex 75 Prep Grade (GE
                   Healthcare).
                   Procedure:
                   Purification of the protein was performed as a two step process on an
                   ÄKTAxpress system (GE Healthcare). Prior to purification, columns were
                   equilibrated with IMAC wash1 buffer and gel filtration buffer,
                   respectively. The filtered lysate was loaded onto the Ni-charged
                   HiTrap Chelating
                   column and washed with IMAC wash1 buffer followed by IMAC wash2
                   buffer. Bound protein was eluted from the IMAC column with IMAC
                   elution buffer and automatically loaded onto the gel filtration column.
                   Fractions containing the target protein were pooled and fresh TCEP was
                   added to a final concentration of 2 mM. The protein was subsequently
                   concentrated using a Amicon Ultra-15 centrifugal filter device, 10,000
                   NMWL (Millipore) to 22.8 mg/mL in a volume of 0.28 mL. The identity of
                   the protein was confirmed by mass spectrometry.
```

Tankyrase2 (pNIC-Bsa-4-TNKS2$^{PARP}$) expression construct was also obtained from the Structural Genomics Consortium (SGC) and prepared in an analogous method to TNKS1.

PARP1 protein was commercially available and was obtained from Trevigen, Inc (PARP-HSA 'High Specific Activity', cat. no. 4668-50-010).

Cell-Based Assay 1:

Wnt-Luciferase Reporter Assay

Generation of Reporter Cell Lines:

A Wnt dependent cell line (i.e., DLD1 colorectal adenocarcinoma cell line) was transduced with replication incompetent VSV-g pseudotyped lentiviral particles expressing the firefly luciferase gene under the control of minimal cytomegalovirus (mCMV) promoter and tandem repeats of the TCF/LEF transcriptional response element. Post-transduction selection using puromycin (Sigma Aldrich, cat. no. P8833, 1.5 micrograms per milliliter (ug/mL)) for one week resulted in an enriched polyclonal cell population (DLD1-Wnt-Luc cells) that was expanded and collected for minimal passage and stored in liquid nitrogen.

Wnt-Reporter Assay:

DLD1-Wnt-Luc cells were seeded (5000 cells/well) in a 96-well plate (Greiner Bio-One, cat. no. 655098) in Dubelco's Modified Eagle Medium (DMEM, GIBCO/Invitrogen, cat no. 41965-039) supplemented with Fetal Bovine Serum (FBS, 10%, GIBCO/Invitrogen, cat no. 10108-165). After overnight incubation, the media was replaced with OptiMEM (GIBCO/Invitrogen, cat no. 11058-021) supplemented with FBS (0.5%) and non-essential amino acids (1%, GIBCO/Invitrogen, cat no. 11140-035) and the appropriate putative TNKS inhibitor at a final concentration of 10 µM, 3 µM, 1 µM, 0.30 µM, 0.10 µM, 0.030 µM, 0.010 µM and 0 µM with 1% (v/v) final DMSO in double-triplicate wells. Positive control includes the use of XAV-939 (Maybridge, FisherScientific, 3,5,7,8-tetrahydro-2-[4-(trifluoromethyl)phenyl]-4H-thiopyrano[4,3-c]pyrimidin-4-one, cat. no. RF03920, see: Huang et al., Nature, 2009, Vol. 461, pp. 614-620). Cells were incubated for 20-22 hours before assaying for luciferase (first set of triplicates: Wnt activation) and viability (second set of triplicates: cell survival for data normalisation vs Wnt-activation) using ONE-Glo (Promega, cat. no. E6110) and Cell-Titer-Glo (Promega, cat. no. G7570) reagents consecutively. The assay was measured using a Victor$^2$ plate reader. The data were normalised to the DMSO control and were expressed as % Wnt activity as a function of inhibitor dose. Dose response curves used to determine $IC_{50}$ values were Log transformed and analysed by non-linear regression analysis (variable slope) using Prism (GraphPad Software, Inc).

Cell-Based Assay 2:

Western Blotting for Direct and Downstream Targets of TNKS Inhibitors: Axin 1

DLD1 cells were assayed for the effect of putative Tankyrase1/2 inhibitors on TNKS1/2, Axin1/2 and β-catenin protein levels. Effective TNKS inhibitors will (1) increase TNKS protein levels by inhibition of auto-PARylation and subsequent proteasomal degradation, (2) increase Axin1/2 protein levels by inhibition of TNKS induced PARylation and subsequent proteasomal degradation and, consequently, stabilisation of the Axin/APC/GSK/CK destruction complex leading to (3) decrease of β-catenin protein levels. Reduction of nuclear accumulation of β-catenin and ultimately, reduction of β-catenin/TCF/LEF transcriptional activation of Wnt target genes should correlate with loss of Wnt-luc reporter signal in the Wnt reporter assay.

DLD1 cells were seeded in a 6-well dish at 10000 cells/well in DMEM supplemented with 10% FBS. After overnight incubation, cells were dosed with an appropriate amount of putative Tankyrase1/2 inhibitor (2 uM, 0.75 uM, 0.25 uM, 0 uM) in DMEM (0.5% FBS, 1% DMSO). After 20-22 hours incubation, the cells were washed in cold PBS and lysed in lysis buffer (50 mM Tris pH 8.0, 500 mM NaCl, 0.5% NP-40, complete protease inhibitor cocktail (Roche, cat. no. 11836153001)), centrifuged at 15000 rpm for 10 minutes and the protein concentration of the supernatant quantified using Bradford reagent (BioRad protein assay reagent, cat. no. 500-0006). Protein samples (25-50 ug) in protein sample loading buffer ('Laemmli buffer', Laemmli, U. K., Nature, 1970, 227, 680-685) were denatured by boiling and loaded onto a sodium dodecyl sulfate-polyacrylamide gel (SDS-PAGE with 10% acrylamide) and separated by electrophroresis followed by electroblotting onto nitrocellulose membrane. The membrane was blocked in skimmed milk (5% in Tris-base saline with 0.01% Tween[20] (TBS-T)) and subsequently probed overnight with the required antibody: Tankyrase1/2 (1:1000, Santa Cruz, cat. no. sc-8337); Axin1 (1:1000, Cell Signalling Technology, cat. no. 2087); Axin2 (1:1000, Cell Signalling Technology, cat. no. 2151); β-catenin (1:1000, Cell Signalling Technology, cat. no. 9581). After washing in TBS-T, the membrane was probed with a species specific secondary antibody conjugated to HRP (1:5000, Pierce/ThermoFisher), washed again in TBS-T and reacted with chemiluminescent detection reagents (ECL, GE Healthcare, cat. no. RPN2109) followed by exposure to X-ray film (FujiFilm XR).

Cell-Based Assay 3:
Western Blotting for Direct and Downstream Targets of TNKS Inhibitors Unrelated to the Wnt Pathway: TNKS Appropriate cell lines (HeLa, HT1080, HTC75) were also assayed for the effect of TNKS inhibition on TNKS stabilisation (see, e.g., Smith et al., Science, 1998, Vol. 282, pp. 1484-1487). Cells were seeded, dosed and whole cell lysates were isolated and western blotted as described above. Primary antibodies included TNKS (1:1000, Santa Cruz Biotech, cat. no. SC8377).

Cell-Based Assay 4:
Clonogenic Inhibition in DLD1 or HT55 Cells

In order to determine the efficacy of chronic dosing of putative TNKS inhibitors, long term clonogenic or 'colony formation' assays were carried out. This included the sparse seeding of cells in a 6-well dish followed by continuous dosing of cells over 12-14 days (depending on relative cell growth). Appropriate cell lines (DLD1 or HT55) were seeded at 500 cells/well in a 6-well dish in DMEM supplemented with FBS. After overnight incubation, cells were treated with the appropriate putative TN KS inhibitor at 10 μM, 3 μM, 1 μM, 0.30 μM, 0.1 μM and 0 μM at 0.2-1% final DMSO concentration (cell line dependent) in DMEM supplemented with 10% FBS (DLD1 cells were dosed in DMEM supplemented with 0.5% FBS). Dosages were carried out in triplicate. Cell media containing compound or DMSO only was replenished every 48 hours. Termination of the assay included the fixation of cells with trichlororacetic acid (1 mL, 10% (v/v), Sigma Aldrich, cat. no. T6399) and incubation for 16 hours at 4° C. Fixed cells were then washed with water, allowed to dry and stained with sulforhodamine B solution (sulforhodamine B 0.05% (w/v), Sigma Aldrich cat. no. S1402, acetic acid 1% (v/v), Fisher Scientific, cat. no. A/0400/PB17)) for 12 hours at room temperature. The stain was then removed and the cells washed copiously with aqueous acetic acid (1% v/v) and allowed to dry.

Quantification of colony formation was then carried out by dissolution of incorporated sulforhodamine B in Tris-base (1 mL, 10 mM, pH 10) and measurement of absorbance at 560 nM. The data was normalised to the DMSO control and was expressed as surviving fraction as a function of inhibitor dose. Dose response curves used to determine $GI_{50}$ values were Log transformed and analysed by non-linear regression analysis (variable slope) using Prism (GraphPad Software, Inc).

Biological Data

The following compounds were tested in the TNKS1/PARP Biochemical Assay described above:
IQ-001, IQ-002-1, IQ-002-2, IQ-003, IQ-004, IQ-005, IQ-006, IQ-007, IQ-008, IQ-009, IQ-010, IQ-011, IQ-012, IQ-013, IQ-014, IQ-015, IQ-016, IQ-017, IQ-018, IQ-019, IQ-020, IQ-021, IQ-023, IQ-024, IQ-025, IQ-026, IQ-027, IQ-028-1, IQ-028-2, IQ-029, IQ-030, IQ-031, IQ-032, IQ-033, IQ-034, IQ-035, IQ-036, IQ-037, IQ-038, IQ-039, IQ-040, IQ-041, IQ-042, IQ-043, IQ-044, IQ-045, IQ-046, IQ-047, IQ-048, IQ-049, IQ-050, IQ-051-1, IQ-051-2, IQ-051-3, IQ-052, IQ-053, IQ-054, IQ-055, IQ-056, IQ-057, IQ-059, IQ-060, IQ-062, IQ-063, IQ-065, IQ-067, IQ-068, IQ-070, IQ-071, IQ-072, IQ-073, IQ-074, IQ-075, IQ-076, IQ-077, IQ-078, IQ-079, IQ-080, IQ-081, IQ-082, IQ-083, IQ-084-1, IQ-084-2, IQ-084-3, IQ-085, IQ-086, IQ-087, IQ-088, IQ-089, IQ-090, IQ-091, IQ-092, IQ-093, IQ-094, IQ-095, IQ-096, IQ-097, IQ-098, IQ-099, IQ-100, IQ-101, IQ-102, IQ-103, IQ-104, IQ-105, IQ-106, IQ-107, IQ-108, IQ-109, IQ-110, IQ-111, IQ-112, IQ-113, IQ-114, IQ-115, IQ-116, IQ-117, IQ-118, IQ-119, IQ-120, IQ-121, IQ-122, IQ-123, IQ-124, IQ-125, IQ-126, IQ-127, IQ-128, IQ-129, IQ-130, IQ-131, IQ-132, IQ-133, IQ-134, IQ-135, IQ-136, IQ-138, IQ-139, IQ-140, IQ-141, IQ-142, IQ-143, IQ-144, IQ-145, IQ-148, IQ-149, IQ-150, IQ-151, IQ-154, IQ-157, IQ-158, IQ-160, IQ-161, IQ-162, IQ-163, IQ-164, IQ-165, IQ-166, IQ-167, IQ-168, IQ-169, IQ-170, IQ-171, IQ-172, IQ-173, IQ-174, IQ-175, IQ-176, IQ-177, IQ-178, IQ-179, IQ-180, IQ-181, IQ-182, IQ-183, IQ-184, IQ-185, IQ-186, IQ-187, IQ-188, IQ-189, IQ-190, IQ-191, IQ-192, IQ-193, IQ-194, IQ-195, IQ-196, IQ-197, IQ-198, IQ-199, IQ-200, IQ-201, IQ-202, IQ-203, IQ-204, IQ-205-1, IQ-205-2, IQ-206, IQ-207-1, IQ-207-2, IQ-208, IQ-209, IQ-210, IQ-211, IQ-212, IQ-213, IQ-214, IQ-215, IQ-216, IQ-217, IQ-218, IQ-219, IQ-220, IQ-221, IQ-222, IQ-223, IQ-224, IQ-225, IQ-226, IQ-227, IQ-228, IQ-229, IQ-230, IQ-231, IQ-232, IQ-233, IQ-234, IQ-236.

All of the compounds have a TNKS1 $IC_{50}$ of less than 5 μM.

The following compounds have a TNKS1 $IC_{50}$ of less than 0.5 μM:
IQ-001, IQ-002-1, IQ-002-2, IQ-003, IQ-004, IQ-005, IQ-006, IQ-007, IQ-008, IQ-009, IQ-010, IQ-011, IQ-012, IQ-013, IQ-014, IQ-015, IQ-016, IQ-017, IQ-018, IQ-019, IQ-020, IQ-021, IQ-023, IQ-024, IQ-025, IQ-026, IQ-027, IQ-028-1, IQ-028-2, IQ-029, IQ-031, IQ-032, IQ-033, IQ-034, IQ-035, IQ-036, IQ-037, IQ-038, IQ-039, IQ-040, IQ-041, IQ-042, IQ-043, IQ-044, IQ-045, IQ-046, IQ-047, IQ-048, IQ-049, IQ-050, IQ-051-1, IQ-051-2, IQ-051-3, IQ-052, IQ-053, IQ-054, IQ-055, IQ-056, IQ-057, IQ-059, IQ-060, IQ-062, IQ-063, IQ-065, IQ-067, IQ-068, IQ-070, IQ-071, IQ-072, IQ-073, IQ-074, IQ-075, IQ-076, IQ-077, IQ-078, IQ-079, IQ-080, IQ-081, IQ-082, IQ-083, IQ-084-1, IQ-084-2, IQ-084-3, IQ-085, IQ-086, IQ-087, IQ-088, IQ-089, IQ-090, IQ-091, IQ-092, IQ-093, IQ-094, IQ-095, IQ-096, IQ-097, IQ-098, IQ-099, IQ-100, IQ-101, IQ-102, IQ-103, IQ-104, IQ-105, IQ-106, IQ-107, IQ-108, IQ-109, IQ-110, IQ-111, IQ-112, IQ-113, IQ-114, IQ-115, IQ-116, IQ-117, IQ-118, IQ-119, IQ-120, IQ-121, IQ-122, IQ-123, IQ-124, IQ-125, IQ-126, IQ-127, IQ-128, IQ-129, IQ-130, IQ-132, IQ-133, IQ-134, IQ-135, IQ-136, IQ-138, IQ-140, IQ-142, IQ-143, IQ-145, IQ-148, IQ-149, IQ-150, IQ-154, IQ-157, IQ-158, IQ-160, IQ-161, IQ-162, IQ-163, IQ-164, IQ-165, IQ-166, IQ-167, IQ-168, IQ-169, IQ-170, IQ-171, IQ-172, IQ-173, IQ-174, IQ-175, IQ-176, IQ-177, IQ-178, IQ-179, IQ-180, IQ-181, IQ-182, IQ-184, IQ-185, IQ-186, IQ-187, IQ-188, IQ-189, IQ-190, IQ-191, IQ-192, IQ-193, IQ-194, IQ-195, IQ-196, IQ-197, IQ-198, IQ-199, IQ-200, IQ-201, IQ-202, IQ-203, IQ-204, IQ-205-1, IQ-205-2, IQ-206, IQ-207-1, IQ-207-2, IQ-208, IQ-209, IQ-210, IQ-211, IQ-212, IQ-213, IQ-214, IQ-215, IQ-216, IQ-217, IQ-218, IQ-219, IQ-220, IQ-221, IQ-222, IQ-223, IQ-224, IQ-225, IQ-226, IQ-227, IQ-228, IQ-229, IQ-230, IQ-231, IQ-232, IQ-234, IQ-236.

The following compounds have a TNKS1 $IC_{50}$ of less than 0.05 µM:
IQ-001, IQ-002-1, IQ-003, IQ-004, IQ-005, IQ-006, IQ-007, IQ-008, IQ-011, IQ-012, IQ-013, IQ-014, IQ-015, IQ-016, IQ-017, IQ-018, IQ-019, IQ-021, IQ-023, IQ-025, IQ-026, IQ-027, IQ-028-1, IQ-028-2, IQ-029, IQ-032, IQ-033, IQ-034, IQ-035, IQ-036, IQ-037, IQ-038, IQ-042, IQ-045, IQ-048, IQ-050, IQ-051-1, IQ-051-2, IQ-051-3, IQ-052, IQ-053, IQ-054, IQ-055, IQ-056, IQ-057, IQ-059, IQ-062, IQ-065, IQ-067, IQ-068, IQ-070, IQ-073, IQ-074, IQ-078, IQ-080, IQ-081, IQ-082, IQ-083, IQ-084-1, IQ-084-2, IQ-084-3, IQ-085, IQ-086, IQ-087, IQ-088, IQ-090, IQ-093, IQ-094, IQ-095, IQ-096, IQ-097, IQ-098, IQ-099, IQ-100, IQ-101, IQ-102, IQ-104, IQ-105, IQ-106, IQ-107, IQ-108, IQ-109, IQ-111, IQ-112, IQ-115, IQ-116, IQ-117, IQ-118, IQ-120, IQ-121, IQ-123, IQ-124, IQ-125, IQ-127, IQ-129, IQ-130, IQ-134, IQ-138, IQ-149, IQ-158, IQ-160, IQ-162, IQ-167, IQ-168, IQ-169, IQ-170, IQ-171, IQ-172, IQ-173, IQ-174, IQ-175, IQ-176, IQ-177, IQ-178, IQ-180, IQ-182, IQ-185, IQ-187, IQ-188, IQ-189, IQ-190, IQ-191, IQ-192, IQ-193, IQ-194, IQ-195, IQ-196, IQ-197, IQ-198, IQ-199, IQ-200, IQ-201, IQ-203, IQ-204, IQ-205-1, IQ-205-2, IQ-206, IQ-207-1, IQ-207-2, IQ-208, IQ-209, IQ-210, IQ-211, IQ-212, IQ-213, IQ-214, IQ-215, IQ-216, IQ-217, IQ-218, IQ-219, IQ-220, IQ-222, IQ-224, IQ-226, IQ-227, IQ-228, IQ-231.

The following compounds have a TNKS1 $IC_{50}$ of less than 0.02 µM:
IQ-001, IQ-004, IQ-005, IQ-006, IQ-008, IQ-011, IQ-014, IQ-016, IQ-017, IQ-018, IQ-025, IQ-028-1, IQ-029, IQ-032, IQ-034, IQ-038, IQ-048, IQ-051-1, IQ-054, IQ-055, IQ-062, IQ-082, IQ-086, IQ-088, IQ-093, IQ-097, IQ-099, IQ-100, IQ-102, IQ-104, IQ-107, IQ-109, IQ-115, IQ-117, IQ-118, IQ-120, IQ-123, IQ-125, IQ-130, IQ-162, IQ-167, IQ-168, IQ-170, IQ-172, IQ-175, IQ-176, IQ-177, IQ-178, IQ-180, IQ-182, IQ-188, IQ-189, IQ-190, IQ-191, IQ-192, IQ-193, IQ-194, IQ-195, IQ-196, IQ-197, IQ-198, IQ-199, IQ-200, IQ-204, IQ-205-2, IQ-208, IQ-209, IQ-210, IQ-211, IQ-213, IQ-214, IQ-215, IQ-219, IQ-222, IQ-227.

For example, IQ-016 has a TNKS1 $IC_{50}$ of 0.012 µM.

The following compounds were tested in the Wnt-Luciferase Reporter Assay described above:
IQ-001, IQ-002-1, IQ-003, IQ-004, IQ-005, IQ-006, IQ-007, IQ-008, IQ-009, IQ-010, IQ-011, IQ-012, IQ-013, IQ-014, IQ-015, IQ-016, IQ-017, IQ-018, IQ-019, IQ-020, IQ-021, IQ-023, IQ-024, IQ-025, IQ-026, IQ-027, IQ-028-1, IQ-029, IQ-031, IQ-032, IQ-033, IQ-034, IQ-035, IQ-036, IQ-037, IQ-038, IQ-040, IQ-041, IQ-042, IQ-043, IQ-045, IQ-046, IQ-048, IQ-050, IQ-051-1, IQ-051-2, IQ-051-3, IQ-052, IQ-053, IQ-054, IQ-055, IQ-056, IQ-057, IQ-059, IQ-060, IQ-062, IQ-063, IQ-065, IQ-067, IQ-068, IQ-070, IQ-071, IQ-072, IQ-073, IQ-074, IQ-075, IQ-076, IQ-077, IQ-078, IQ-079, IQ-080, IQ-081, IQ-082, IQ-083, IQ-084-1, IQ-084-2, IQ-084-3, IQ-085, IQ-086, IQ-087, IQ-088, IQ-089, IQ-090, IQ-091, IQ-093, IQ-094, IQ-095, IQ-096, IQ-097, IQ-098, IQ-099, IQ-100, IQ-101, IQ-102, IQ-103, IQ-104, IQ-105, IQ-106, IQ-107, IQ-108, IQ-109, IQ-110, IQ-111, IQ-112, IQ-115, IQ-116, IQ-117, IQ-118, IQ-119, IQ-120, IQ-121, IQ-122, IQ-123, IQ-124, IQ-125, IQ-127, IQ-128, IQ-129, IQ-130, IQ-132, IQ-133, IQ-134, IQ-135, IQ-138, IQ-142, IQ-143, IQ-148, IQ-149, IQ-150, IQ-151, IQ-154, IQ-157, IQ-158, IQ-160, IQ-161, IQ-162, IQ-163, IQ-164, IQ-165, IQ-166, IQ-167, IQ-168, IQ-169, IQ-170, IQ-171, IQ-172, IQ-173, IQ-174, IQ-175, IQ-176, IQ-177, IQ-178, IQ-179, IQ-180, IQ-181, IQ-182, IQ-183, IQ-184, IQ-185, IQ-186, IQ-187, IQ-188, IQ-189, IQ-190, IQ-191, IQ-192, IQ-193, IQ-194, IQ-195, IQ-196, IQ-197, IQ-198, IQ-199, IQ-200, IQ-201, IQ-202, IQ-203, IQ-204, IQ-205-1, IQ-205-2, IQ-206, IQ-207-1, IQ-207-2, IQ-208, IQ-209, IQ-210, IQ-211, IQ-212, IQ-213, IQ-214, IQ-215, IQ-216, IQ-217, IQ-218, IQ-219, IQ-220, IQ-221, IQ-222, IQ-223, IQ-224, IQ-225, IQ-226, IQ-227, IQ-228, IQ-229, IQ-230, IQ-231, IQ-232, IQ-234, IQ-236.

All of the compounds have a Wnt $IC_{50}$ of less than 10 µM.
The following compounds have a Wnt $IC_{50}$ of less than 5 µM:
IQ-001, IQ-002-1, IQ-003, IQ-004, IQ-005, IQ-006, IQ-007, IQ-008, IQ-009, IQ-010, IQ-011, IQ-012, IQ-013, IQ-014, IQ-015, IQ-016, IQ-017, IQ-018, IQ-019, IQ-020, IQ-021, IQ-023, IQ-024, IQ-025, IQ-026, IQ-027, IQ-028-1, IQ-029, IQ-031, IQ-032, IQ-033, IQ-034, IQ-035, IQ-036, IQ-037, IQ-038, IQ-040, IQ-041, IQ-042, IQ-043, IQ-045, IQ-046, IQ-048, IQ-050, IQ-051-1, IQ-051-2, IQ-051-3, IQ-052, IQ-053, IQ-054, IQ-055, IQ-056, IQ-057, IQ-059, IQ-060, IQ-062, IQ-063, IQ-065, IQ-067, IQ-068, IQ-070, IQ-071, IQ-072, IQ-073, IQ-074, IQ-075, IQ-076, IQ-077, IQ-078, IQ-079, IQ-080, IQ-081, IQ-082, IQ-083, IQ-084-1, IQ-084-2, IQ-084-3, IQ-085, IQ-086, IQ-087, IQ-088, IQ-089, IQ-090, IQ-091, IQ-093, IQ-094, IQ-095, IQ-096, IQ-097, IQ-098, IQ-099, IQ-100, IQ-101, IQ-102, IQ-103, IQ-104, IQ-105, IQ-106, IQ-107, IQ-108, IQ-109, IQ-110, IQ-111, IQ-112, IQ-115, IQ-116, IQ-117, IQ-118, IQ-119, IQ-120, IQ-121, IQ-122, IQ-123, IQ-124, IQ-125, IQ-127, IQ-128, IQ-129, IQ-130, IQ-132, IQ-133, IQ-134, IQ-135, IQ-138, IQ-142, IQ-143, IQ-148, IQ-149, IQ-150, IQ-151, IQ-154, IQ-157, IQ-158, IQ-160, IQ-161, IQ-162, IQ-163, IQ-164, IQ-165, IQ-166, IQ-167, IQ-168, IQ-169, IQ-170, IQ-171, IQ-172, IQ-173, IQ-174, IQ-175, IQ-176, IQ-177, IQ-178, IQ-179, IQ-180, IQ-181, IQ-182, IQ-183, IQ-184, IQ-185, IQ-186, IQ-187, IQ-188, IQ-189, IQ-190, IQ-191, IQ-192, IQ-193, IQ-194, IQ-195, IQ-196, IQ-197, IQ-198, IQ-199, IQ-200, IQ-201, IQ-202, IQ-203, IQ-204, IQ-205-1, IQ-205-2, IQ-206, IQ-207-1, IQ-207-2, IQ-208, IQ-209, IQ-210, IQ-211, IQ-212, IQ-213, IQ-214, IQ-215, IQ-216, IQ-217, IQ-218, IQ-219, IQ-220, IQ-221, IQ-222, IQ-223, IQ-224, IQ-225, IQ-226, IQ-227, IQ-228, IQ-230, IQ-231, IQ-232, IQ-234.

The following compounds have a Wnt $IC_{50}$ of less than 0.5 µM:
IQ-001, IQ-002-1, IQ-003, IQ-004, IQ-005, IQ-006, IQ-007, IQ-008, IQ-009, IQ-010, IQ-011, IQ-012, IQ-013, IQ-014, IQ-015, IQ-016, IQ-017, IQ-018, IQ-019, IQ-020, IQ-021, IQ-023, IQ-025, IQ-026, IQ-027, IQ-028-1, IQ-029, IQ-031, IQ-034, IQ-035, IQ-036, IQ-037, IQ-038, IQ-040, IQ-041, IQ-042, IQ-043, IQ-045, IQ-048, IQ-050, IQ-051-1, IQ-051-2, IQ-051-3, IQ-052, IQ-053, IQ-054, IQ-055, IQ-056, IQ-057, IQ-059, IQ-060, IQ-062, IQ-063, IQ-065, IQ-067, IQ-068, IQ-071, IQ-072, IQ-073, IQ-074, IQ-075, IQ-076, IQ-077, IQ-078, IQ-079, IQ-080, IQ-082, IQ-083, IQ-084-1, IQ-084-2, IQ-084-3, IQ-085, IQ-086, IQ-087, IQ-088, IQ-089, IQ-090, IQ-091, IQ-095, IQ-096, IQ-097, IQ-098, IQ-099, IQ-100, IQ-101, IQ-102, IQ-104, IQ-105, IQ-106, IQ-107, IQ-108, IQ-109, IQ-110, IQ-111, IQ-112, IQ-115, IQ-116, IQ-117, IQ-118, IQ-119, IQ-120, IQ-121, IQ-122, IQ-123, IQ-125, IQ-127, IQ-130, IQ-133, IQ-134, IQ-138, IQ-142, IQ-143, IQ-148, IQ-154, IQ-157, IQ-158, IQ-161, IQ-162, IQ-166, IQ-167, IQ-168, IQ-169, IQ-170, IQ-171, IQ-172, IQ-173, IQ-174, IQ-175, IQ-176, IQ-177, IQ-178, IQ-179, IQ-180, IQ-181, IQ-182, IQ-183, IQ-184, IQ-185, IQ-186, IQ-187, IQ-188, IQ-189, IQ-190, IQ-192, IQ-193, IQ-194, IQ-195, IQ-196, IQ-197, IQ-198, IQ-199, IQ-200, IQ-201, IQ-202, IQ-203, IQ-204, IQ-205-1, IQ-205-2, IQ-206, IQ-207-1, IQ-207-2, IQ-208, IQ-209, IQ-210, IQ-211, IQ-212, IQ-213, IQ-214, IQ-215, IQ-218, IQ-219, IQ-220, IQ-222, IQ-226, IQ-227, IQ-228, IQ-231, IQ-234.

The following compounds have a Wnt $IC_{50}$ of less than 0.05 µM:
IQ-001, IQ-003, IQ-004, IQ-005, IQ-006, IQ-008, IQ-011, IQ-015, IQ-016, IQ-017, IQ-018, IQ-028-1, IQ-035, IQ-038, IQ-040, IQ-042, IQ-048, IQ-051-2, IQ-051-3, IQ-054, IQ-055, IQ-062, IQ-065, IQ-067, IQ-068, IQ-073, IQ-078, IQ-080, IQ-097, IQ-098, IQ-100, IQ-102, IQ-104, IQ-105, IQ-106, IQ-107, IQ-108, IQ-109, IQ-111, IQ-117, IQ-118, IQ-120, IQ-121, IQ-123, IQ-125, IQ-133, IQ-148, IQ-157, IQ-167, IQ-168, IQ-170, IQ-171, IQ-173, IQ-174, IQ-175, IQ-176, IQ-177, IQ-178, IQ-179, IQ-180, IQ-181, IQ-182, IQ-184, IQ-185, IQ-190, IQ-192, IQ-195, IQ-198, IQ-201, IQ-206, IQ-209, IQ-210, IQ-211, IQ-212, IQ-215, IQ-234.

For example, IQ-016 has a Wnt $IC_{50}$ of 0.014 µM.

The following compounds were studied using the Western Blotting Assays described above, and were found to stabilize Axin1 and to stabilize TNKS: IQ-002-1, IQ-003, IQ-027, IQ-034, IQ-036, IQ-037, IQ-038, IQ-053, IQ-100, IQ-102, IQ-127, IQ-130, IQ-133.

The following compounds were tested in the Long-Term Clonogenic Assay described above (DLD1 cells):
IQ-001, IQ-002-1, IQ-003, IQ-004, IQ-005, IQ-006, IQ-007, IQ-008, IQ-009, IQ-011, IQ-016, IQ-017, IQ-018, IQ-019, IQ-021, IQ-023, IQ-026, IQ-027, IQ-028-1, IQ-032, IQ-034, IQ-038, IQ-040, IQ-042, IQ-043, IQ-048, IQ-051-2, IQ-051-3, IQ-053, IQ-054, IQ-057, IQ-065, IQ-067, IQ-068, IQ-072, IQ-073, IQ-074, IQ-075, IQ-081, IQ-082, IQ-083, IQ-084-1, IQ-084-2, IQ-086, IQ-088, IQ-090, IQ-091, IQ-095, IQ-096, IQ-097, IQ-099, IQ-100, IQ-101, IQ-102, IQ-103, IQ-104, IQ-105, IQ-106, IQ-107, IQ-108, IQ-109, IQ-111, IQ-118, IQ-121, IQ-123, IQ-125, IQ-127, IQ-128, IQ-129, IQ-130, IQ-149, IQ-161, IQ-162, IQ-166, IQ-167, IQ-168, IQ-169, IQ-188, IQ-189, IQ-190, IQ-231, IQ-234.

All of the compounds have a Clonogenic $SF_{50}$ (DLD1) of less than 10 µM.

The following compounds have a Clonogenic $SF_{50}$ (DLD1) of less than 2 µM:
IQ-001, IQ-002-1, IQ-003, IQ-005, IQ-006, IQ-007, IQ-008, IQ-009, IQ-011, IQ-016, IQ-017, IQ-018, IQ-019, IQ-021, IQ-023, IQ-027, IQ-028-1, IQ-034, IQ-038, IQ-040, IQ-042, IQ-043, IQ-048, IQ-051-2, IQ-051-3, IQ-053, IQ-054, IQ-057, IQ-065, IQ-067, IQ-068, IQ-073, IQ-074, IQ-075, IQ-081, IQ-082, IQ-083, IQ-084-1, IQ-084-2, IQ-086, IQ-088, IQ-090, IQ-091, IQ-102, IQ-104, IQ-105, IQ-106, IQ-107, IQ-108, IQ-109, IQ-111, IQ-118, IQ-121, IQ-123, IQ-125, IQ-127, IQ-129, IQ-149, IQ-161, IQ-162, IQ-166, IQ-168, IQ-190.

The following compounds have a Clonogenic $SF_{50}$ (DLD1) of less than 0.5 µM:
IQ-006, IQ-007, IQ-008, IQ-011, IQ-016, IQ-018, IQ-027, IQ-028-1, IQ-040, IQ-042, IQ-051-2, IQ-053, IQ-065, IQ-067, IQ-073, IQ-075, IQ-081, IQ-082, IQ-083, IQ-088, IQ-090, IQ-091, IQ-104, IQ-105, IQ-107, IQ-108, IQ-109, IQ-111, IQ-118, IQ-123, IQ-125, IQ-161, IQ-162, IQ-166, IQ-168.

For example, IQ-016 has a Clonogenic $SF_{50}$ (DLD1) of 0.291 µM.

The following compounds were tested in the Long-Term Clonogenic Assay described above (HT55 cells):
IQ-168, IQ-185, IQ-007, IQ-018, IQ-027, IQ-053, IQ-173, IQ-006, IQ-195, IQ-075, IQ-080, IQ-170, IQ-016, IQ-011, IQ-182, IQ-174, IQ-177, IQ-178, IQ-197, IQ-201, IQ-158, IQ-204, IQ-048, IQ-196, IQ-117, IQ-210, IQ-199, IQ-176, IQ-059, IQ-179, IQ-198, IQ-054, IQ-209, IQ-005, IQ-042, IQ-213, IQ-218, IQ-100, IQ-127, IQ-171, IQ-208, IQ-206, IQ-205-1, IQ-205-2, IQ-207-1, IQ-207-2, IQ-028-1.

All of the compounds have a Clonogenic $SF_{50}$ (HT55) of less than 10 µM.

The following compounds have a Clonogenic $SF_{50}$ (HT55) of less than 3 µM:
IQ-006, IQ-007, IQ-011, IQ-016, IQ-018, IQ-027, IQ-028-1, IQ-048, IQ-053, IQ-059, IQ-075, IQ-080, IQ-117, IQ-158, IQ-168, IQ-170, IQ-173, IQ-174, IQ-176, IQ-177, IQ-178, IQ-179, IQ-182, IQ-185, IQ-195, IQ-196, IQ-197, IQ-199, IQ-201, IQ-204, IQ-205-1, IQ-205-2, IQ-207-1, IQ-207-2, IQ-210.

The following compounds have a Clonogenic $SF_{50}$ (HT55) of less than 1.5 µM:
IQ-006, IQ-007, IQ-011, IQ-016, IQ-018, IQ-027, IQ-028-1, IQ-053, IQ-075, IQ-080, IQ-168, IQ-170, IQ-173, IQ-185, IQ-195, IQ-205-1, IQ-207-1.

For example, IQ-016 has a Clonogenic $SF_{50}$ (HT55) of 1.235 µM.

—$R^5$ Comparison No. 1:

As demonstrated by this comparison, the presence of $R^5$ as —Me (as compared to —H) decreased Wnt $IC_{50}$ by a factor of about 13.

| Code | Structure | TNKS1 $IC_{50}$ (µM) | Wnt $IC_{50}$ (µM) |
|---|---|---|---|
| IQ-025 | 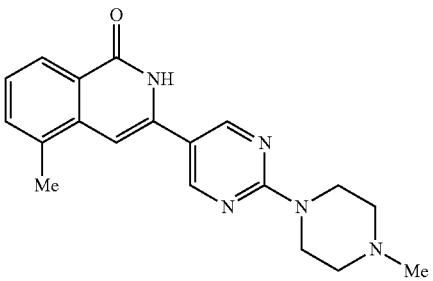 | 0.017 | 0.062 |

| Code | Structure | TNKS1 IC$_{50}$ (μM) | Wnt IC$_{50}$ (μM) |
|---|---|---|---|
| REF-1 | (isoquinolin-1(2H)-one linked to pyrimidine-piperazine-Me) | 0.033 | 0.825 |

—R$^5$Comparison No. 2:

As demonstrated by this comparison, the presence of R$^5$ as -Me (as compared to —H) decreased Wnt IC$_{50}$ (by a factor of about 24).

| Code | Structure | TNKS1 IC$_{50}$ (μM) | Wnt IC$_{50}$ (μM) |
|---|---|---|---|
| IQ-080 | (7-F, 5-Me isoquinolinone linked to phenyl-CH$_2$-piperazine-Me) | 0.029 | 0.042 |
| REF-2 | (7-F isoquinolinone linked to phenyl-CH$_2$-piperazine-Me) | 0.048 | 1.003 |

—R$^5$Comparison No. 3:

As demonstrated by this comparison, the presence of R$^5$ as -Me (as compared to —H) decreased Wnt IC$_{50}$ (by a factor of about 62).

Also as demonstrated by this comparison, the presence of R$^5$ as —Cl (as compared to —H) decreased Wnt IC$_{50}$ (by a factor of about 4).

| Code | Structure | TNKS1 IC$_{50}$ (μM) | Wnt IC$_{50}$ (μM) |
|---|---|---|---|
| IQ-003 | (5-Me isoquinolinone linked to pyridine-piperazine-Me) | 0.021 | 0.012 |

| Code | Structure | TNKS1 IC$_{50}$ (μM) | Wnt IC$_{50}$ (μM) |
|---|---|---|---|
| IQ-002 | 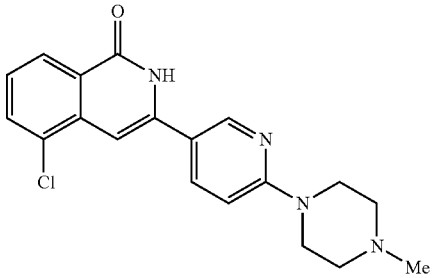 [SMILES: CN1CCN(c2ccc(-c3cc4c(Cl)cccc4c(=O)[nH]3)cn2)CC1] | 0.039 | 0.179 |
| REF-3 | 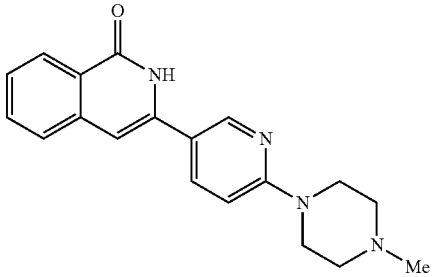 [SMILES: CN1CCN(c2ccc(-c3cc4ccccc4c(=O)[nH]3)cn2)CC1] | 0.024 | 0.742 |

—R$^5$Comparison No. 4:

As demonstrated by this comparison, the presence of R$^5$ as -Me (as compared to —H) decreased Wnt IC$_{50}$ (by a factor of at least 9).

| Code | Structure | TNKS1 IC$_{50}$ (μM) | Wnt IC$_{50}$ (μM) |
|---|---|---|---|
| IQ-034 | 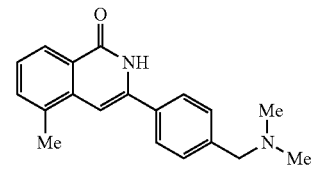 [SMILES: Cc1cccc2c(=O)[nH]c(-c3ccc(CN(C)C)cc3)cc12] | 0.012 | 1.07 |
| REF-4 | 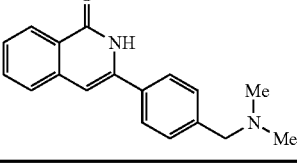 | 0.018 | >10 |

—R$^5$Comparison No. 5:

As demonstrated by this comparison, the presence of R$^5$ as -Me (as compared to —H) decreased Wnt IC$_{50}$ (by a factor of at least 60).

| Code | Structure | TNKS1 IC$_{50}$ (μM) | Wnt IC$_{50}$ (μM) |
|---|---|---|---|
| IQ-130 | 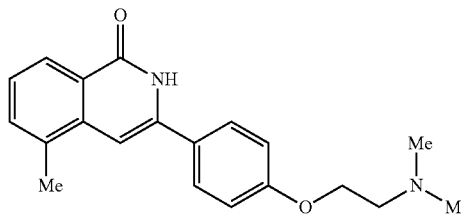 | 0.016 | 0.165 |

| Code | Structure | TNKS1 IC$_{50}$ (μM) | Wnt IC$_{50}$ (μM) |
|---|---|---|---|
| REF-5 | *(isoquinolin-1(2H)-one with 3-(4-(2-(dimethylamino)ethoxy)phenyl) substituent)* | 0.017 | >10 |

—R$^5$Comparison No. 6:

As demonstrated by this comparison, the presence of R$^5$ as -Me (as compared to —OH) decreased Wnt IC$_{50}$ (by a factor of at least 14).

| Code | Structure | TNKS1 IC$_{50}$ (μM) | Wnt IC$_{50}$ (μM) |
|---|---|---|---|
| IQ-157 | *(5-methyl-3-(2-(4-(cyclopropanecarbonyl)piperazin-1-yl)pyrimidin-5-yl)isoquinolin-1(2H)-one)* | 0.051 | 0.041 |
| REF-6 | *(5-hydroxy-3-(2-(4-(cyclopropanecarbonyl)piperazin-1-yl)pyrimidin-5-yl)isoquinolin-1(2H)-one)* | 0.024 | 0.611 |

—R$^5$Comparison No. 7:

As demonstrated by this comparison, the presence of R$^5$ as -Me (as compared to —OH) decreased Wnt IC$_{50}$ (by a factor of at least 36).

Also as demonstrated by this comparison, the additional change of R$^7$ as —F (as compared to —H) further decreased Wnt IC$_{50}$ (now by a factor of at least 60).

| Code | Structure | TNKS1 IC$_{50}$ (μM) | Wnt IC$_{50}$ (μM) |
|---|---|---|---|
| IQ-220 | (5-Me-isoquinolin-1(2H)-one-3-yl)-pyridine-2-yl-C(O)-(4-methylpiperazine) | 0.026 | 0.274 |
| IQ-222 | (7-F-5-Me-isoquinolin-1(2H)-one-3-yl)-pyridine-2-yl-C(O)-(4-methylpiperazine) | 0.016 | 0.174 |
| REF-7 | (5-OH-isoquinolin-1(2H)-one-3-yl)-pyridine-2-yl-C(O)-(4-methylpiperazine) | 0.042 | >10 |

-L$^{3P}$-R$^{3N}$ Comparison No. 1:

As demonstrated by this comparison, the presence of -L$^{3P}$-R$^{3N}$ as N-(cyclopropylmethyl)-piperazino-carbonyl (as compared to —OMe) decreased Wnt IC$_{50}$ (by a factor of at least about 3).

| Code | Structure | TNKS1 IC$_{50}$ (μM) | Wnt IC$_{50}$ (μM) |
|---|---|---|---|
| IQ-223 | (5-Me-isoquinolin-1(2H)-one-3-yl)-pyridine-2-yl-C(O)-(4-cyclopropylmethyl-piperazine) | 0.076 | 1.34 |
| REF-8 | (5-Me-isoquinolin-1(2H)-one-3-yl)-(5-OMe-pyridine-2-yl) | 0.039 | 4.32 |

The foregoing has described the principles, preferred embodiments, and modes of operation of the present invention. However, the invention should not be construed as limited to the particular embodiments discussed. Instead, the above-described embodiments should be regarded as illustrative rather than restrictive. It should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Abbot et al., 2010, "Heterocyclic antiviral compounds", US patent publication number US 2010/0226879 A1 published 9 Sep. 2010.

Adaimy et al., 2007 "Mutation in WNT10A is associated with an autosomal recessive ectodermal dysplasia: the odonto-onycho-dermal dysplasia", Am. J. Hum. Genet., Vol. 81, pp. 821-828.

Balemans et al., 2001, "Increased bone density in sclerosteosis is due to the deficiency of a novel secreted protein (SOST)", Hum. Mol. Genet., Vol. 10, pp. 537-543.

Balemans et al., 2002, "Identification of a 52 kb deletion downstream of the SOST gene in patients with van Buchem disease", J. Med. Genet., Vol. 39, pp. 91-97.

Bao et al., 2012, "Inhibition of tankyrases induces Axin stabilization and blocks Wnt signalling in breast cancer cells", PLoS One, Vol. 7, No. 11, e48670.

Bergmann et al., 2006, "Mutations in the gene encoding the Wnt-signaling component R-spondin 4 (RSPO4) cause autosomal recessive anonychia", Am. J. Hum. Genet., Vol. 79, pp. 1105-1109.

Beugelmans et al., 1992, "A common and general access to berberine and benzo[c]phenanthridine alkaloids", Tetrahedron, Vol. 48, No. 38, pp. 8285-8294.

Blaydon et al., 2006, "The gene encoding R-spondin 4 (RSPO4), a secreted protein implicated in Wnt signaling, is mutated in inherited anonychia", Nat. Genet., Vol. 38, pp. 1245-1247.

Bregman et al., 2013, "Discovery of a class of novel tankyrase inhibitors that bind to both the nicotinamide pocket and the induced pocket", J. Med. Chem., DOI: 10.1021/jm301607v, published 14 Jan. 2013.

Caricasole et al., 2003, "The Wnt pathway, cell-cycle activation and beta-amyloid: novel therapeutic strategies in Alzheimer's disease?", Trends Pharmacol. Sci., Vol. 24, pp. 233-238.

Casás-Selves et al., 2012, "Tankyrase and the canonical Wnt pathway protect lung cancer cells from EGFR inhibition", Cancer Research, Vol. 72, No. 16, pp. 4154-4164.

Chang et al., 2005, "Tankyrase-1 polymerization of poly (ADP-ribose) is required for spindle structure and function", Nat. Cell Biol., Vol. 7, No. 11, pp. 1133-1139.

Chen et al., 2013, "4-Piperidinyl compounds for use as tankyrase inhibitors", international patent publication number WO 2013/008217 A1 published 17 Jan. 2013.

Cheon et al., 1997, "Synthesis and structure-activity relationship studies of 2,3-dihydroimidazo[2,1-a]isoquinoline analogs as antitumour agents", Arch. Pharm. Res., Vol., 20, No. 2, pp. 138-143.

Cheon et al., 2001, "Structure-activity relationship studies of isoquinolineone type anticancer agent", Arch. Pharm. Res., Vol. 24, No. 4, pp. 276-280.

Cheung et al., 2009, "Methods and compositions for measuring WNT activation and for treating WNT-related cancers", international patent publication number WO 2009/059994 A2 published 14 May 2009.

Cheung et al., 2013, "4-Oxo-3,5,7,8-tetrahydro-4H-pyrano{4,3-d}pyrimidinyl compounds for use as tankyrase inhibitors", international patent publication number WO 2013/010092 A1 published 17 Jan. 2013.

Cheung et al., 2013, "Novel 2-piperidin-1-yl-acetamide compounds for use as tankyrase inhibitors", international patent publication number WO 2013/012723 A1 published 23 Jan. 2013.

Cho et al., 1998, "Synthesis and comparative molecular field analysis (CoMFA) of antitumor 3-arylisoquinoline derivatives", Bioorganic & Medicinal Chemistry, Vol. 6, No. 12, pp. 2449-2458.

Cho et al., 1998, "Synthesis and biological evaluation of 3-arylisoquinolines as antitumor agents", Bioorganic & Medicinal Chemistry Letters, Vol. 8, No. 1, pp. 41-46.

Cho et al., 2002, "Molecular modeling of 3-arylisoquinoline antitumor agents active against A-549. A comparative molecular field analysis study", Bioorganic & Medicinal Chemistry, Vol. 10, No. 9, pp. 2953-2961.

Christodoulides et al., "WNT10B mutations in human obesity", Diabetologia, Vol. 49, pp. 678-684.

Couture et al., 1992, "Intramolecular Peterson olefination of ortho-trimethylsilylmethyl-N-acyl-N-alkylbenzamides. A new route to 2-alkyl-1(2H)isoquinolones", J. Organometallic Chem., Vol. 440, Nos. 1-2, pp. 7-13.

Couture et al., 2000, "A convenient synthesis of 3-aryl-2-methyl-3,4-dihydro-1(2H)-isoquinolones and -1,2,3,4-tetrahydroisoquinolines", Synthetic Comm., Vol. 30, No. 15, pp. 2775-2784.

Daniels, 2004, "Abnormal cytokinesis in cells deficient in the breast cancer susceptibility protein BRCA2", Science, Vol. 306, No 5697, pp. 876-879.

Deng et al., 2002, "Telomeric proteins regulate episomal maintenance of Epstein-Barr virus origin of plasmid replication", Mol. Cell, Vol. 9, pp. 493-503.

Distler et al., 2012, "Inactivation of tankyrases reduces experimental fibrosis by inhibiting canonical Wnt signalling", Ann. Rheum. Dis., 12 Nov. 2012, e-publication ahead of print.

Fancy et al., 2011, "Axin2 as regulatory and therapeutic target in newborn brain injury and remyelination", Nat. Neurosci., Vol. 14, pp. 1009-1016.

Fujio et al., 2009, "Isoquinoline compound and pharmaceutical use thereof", United States Patent Publication number US 2009/0076276.

Gong et al., 2001, "LDL receptor-related protein 5 (LRP5) affects bone accrual and eye development", Cell, Vol. 107, pp. 513-523.

Grzeschik et al., 2007, "Deficiency of PORCN, a regulator of Wnt signaling, is associated with focal dermal hypoplasia", Nat. Genet., Vol. 39, pp. 833-835.

Guimond et al., 2010, "Rhodium(III)-catalyzed isoquinolone synthesis: The N-0 bond as a handle for C—N bond formation and catalyst turnover", J. Am. Chem. Soc., Vol. 132, pp. 6908-6909.

Hansen et al., 2008, "Compounds for the Prevention and Treatment of Cardiovascular Dieases", international patent publication number WO 2008/092231 A1 published 7 Aug. 2008.

Hansen et al., 2010, "Novel anti-inflammatory agents", international patent publication number WO 2010/106436 A2 published 23 Sep. 2010.

Hansen et al., 2010, "Novel anti-inflammatory agents", international patent publication number WO 2010/123975 A1 published 28 Oct. 2010.

Harley, 2008, "Telomerase and cancer therapeutics", Nat. Rev. Cancer, Vol. 8, No. 3, pp. 167-169.

Hattori et al., 2005, "1-(2H)-isoquinolone derivatives and use thereof as anticancer agents", international patent publication number WO 2005/075432 A1 published 18 Aug. 2005.

Hattori et al., 2006, "1-(2H)-isoquinolone derivative", European patent publication number EP 1 724 262 A1, published 22 Nov. 2006.

Hsiao et al., 2008, "Tankyrase function at telomeres, spindle poles, and beyond", Biochimie, Vol. 90, No. 1, pp. 83-92.

Hsiao et al., 2009, "Sister telomeres rendered dysfunctional by persistent cohesion are fused by NHEJ", J. Cell. Biol., Vol. 184, No. 4, pp. 515-526.

Huang et al., 2009, "Tankyrase inhibition stabilizes axin and antagonizes Wnt signalling", Nature, Vol. 461, No. 7264, pp. 614-620.

Hughes et al., 2007, "Novel Intramolecular Reactivity of Oximes: Synthesis of Cyclic and Spiro-fused Imines", Organic Letters, Vol. 9, pp. 981-983.

James et al., 2012, "WIKI4, a novel inhibitor of tankyrase and Wnt/β-catenin signaling", PLoS One, Vol. 7, No. 12, e50457.

Johansson et al., 2007, "Pharmaceutical compositions for the prevention and treatment of complex diseases and their delivery by insertable medical devices", international patent publication number WO 2007/016525 A2 published 8 Feb. 2007.

Johnson et al., 2004, "Isoquinolinone derivatives and their use as therapeutic agents", international patent publication number WO 2004/058717 A1 published 15 Jul. 2004.

Kaelin, 2009, "Synthetic lethality: a framework for the development of wiser cancer therapeutics", Genome Med., Vol. 1, No. 10, p. 99.

Khadka et al., 2012, "Synthesis of 12-oxobenzo[c]phenanthridines and 4-substituted 3-arylisoquinolones via Vilsmeier-Haack reaction", Tetrahedron, Vol. 68, No. 1, p. 250-261.

Kim et al., 2002, "Hypothetical drug binding receptor site analysis using CoMFA method for 3-arylisoquinolines active against SK-OV-3 tumor cell line", Yakhak Hoechi, Vol. 46, No. 4, pp. 219-225

Kozlovsky et al., 2002, "GSK-3 and the neurodevelopmental hypothesis of schizophrenia", Eur. Neuropsychopharmacol., Vol. 12, pp. 13-25.

Krämer et al., 1969, "Reaktionen mit Halogenwasserstoffaddukten der Nitrile, I. Eine neue Isochinolinsynthese", Chemische Berichte., Vol. 102, pp. 3656-3665.

Krishnakumar et al., 2010, "The PARP side of the nucleus: molecular actions, physiological outcomes, and clinical targets", Mol. Cell., Vol. 39, No. 1, pp. 8-24.

Lammi et al., 2004, "Mutations in AXIN2 cause familial tooth agenesis and predispose to colorectal cancer", Am. J. Hum. Genet., Vol. 74, pp. 1043-1050.

Le et al., 2004, "A versatile total synthesis of benzo[c] phenanthridine and protoberberine alkaloids using lithiated toluamide-benzonitrile cycloaddition", J. Org. Chem., Vol. 69, pp. 2768-2772.

Li et al., 2010, "Platinum(II)-catalyzed intramolecular cyclization of alkynylbenzonitriles: synthesis of 1-alkoxy-isoquinolines and isoquinolones", Tetrahedron Letters, Vol. 51, pp. 6422-6425.

Li et al., 2011, "Herpes Simplex Virus Requires PARP Activity for Efficient Replication and Induces ERK-dependent Phosphorylation and ICP0-dependent Nuclear Localization of Tankyrase 1", J. Virol., Vol. 86, pp. 492-503.

Lord et al., 2008, "Targeted therapy for cancer using PARP inhibitors", Curr. Opin. Pharmacol., Vol. 8, No. 4, pp. 363-369.

Loughlin et al., 2004, "Functional variants within the secreted frizzled-related protein 3 gene are associated with hip osteoarthritis in females," Proc. Natl. Acad. Sci. USA, Vol. 101, pp. 9757-9762.

Marsili et al., 1968, "Conversion of indones to quinoline and isoquinoline derivatives. III. Schmidt reaction with 2,3-diphenylindone and similar compounds", Tetrahedron, Vol. 24, No. 14, pp. 4981-4991.

McCabe et al., 2009a, "Materials and methods for exploiting synthetic lethality in BRCA-associated cancers", international patent publication number WO 2009/027650 A1 published 5 Mar. 2009.

McCabe, 2009b, "Targeting Tankyrase 1 as a therapeutic strategy for BRCA-associated cancer", Oncogene, Vol. 28, No. 11, pp. 1465-1470.

McPhee et al., 2004, "Macrocyclic isoquinoline peptide inhibitors of hepatitis C virus", international patent publication number WO 2004/094452 A2 published 4 Nov. 2004.

Merchant et al., 1984, "Synthesis of Heterocyclic Compounds involving Reactions of Indan-1-ones", Indian Journal of Chemistry, Section B: Organic Chemistry including Medicinal Chemistry, Vol. 23, pp. 863-865.

Miyaoka et al., 1999, "Increased expression of Wnt-1 in schizophrenic brains", Schizophr. Res., Vol. 38, pp. 1-6.

Molander et al., 2003, "Lanthanide assisted cross-coupling of aryl bromides with triethylaluminum", Tetrahedron Letters, Vol. 44, pp. 8593-8595.

Moon et al., 2004, "WNT and beta-catenin signalling: diseases and therapies", Nat. Rev. Genet., Vol. 5, pp. 691-701.

Mudher et al., 2002, "Alzheimer's disease-do tauists and baptists finally shake hands?", Trends Neurosci., Vol. 25, pp. 22-26.

Musso et al., 2003, "Indanylidenes. 1. Design and synthesis of (E)-2-(4,6-difluoro-1-indanylidene)acetamide, a potent, centrally acting muscle relaxant with anti-inflammatory and analgesic activity, Vol. 46, pp. 399-408.

Naoto et al., 2009, "Imidazole derivative", European patent publication number EP 2090570 A1.

Nettekoven et al., 2006, "piperazinyl pyridine derivatives as anti-obesity agents", international patent publication number WO 2006/063718 A1 published 22 Jun. 2006.

Oda et al., 2002, "2-Pyridone ring formation through the photo-reaction of arenecarbothioamides with unsaturated carboxylic acids", Heterocycles, Vol. 56, pp. 69-72.

Olbrich et al., 1985, "CNDO/S-Cl calculations of some carbonyl-containing organic luminophores with a stilbene subchromophore", Z. Naturforsch, Vol. 40a, pp. 859-863.

Papeo et al., 2010, "Isoquinolin-1(2H)-one derivatives as PARP-1 inhibitors", international patent publication number WO 2010/133647 A1 published 25 Nov. 2010.

Parma et al., 2006, "R-spondin1 is essential in sex determination, skin differentiation and malignancy", Nat. Genet., Vol. 38, pp. 1304-1309.

Pinto et al., 2003, "Lactam-containing compounds and derivatives thereof as factor XA inhibitors", international patent publication number WO 03/026652 A1 published 3 Apr. 2003.

Ratcliffe et al., 2011, "Condensed azine-derivatives for the treatment of diseases related to the acetylcholine receptor", international patent publication number WO 2011/045258 A1 published 21 Apr. 2011.

Ren et al., 2011, "Chemical compounds, compositions and methods for kinase modulation", international patent publication number WO 2011/146882 A1 published 24 Nov. 2011.

Riffell et al., 2012, "Tankyrase-targeted therapeutics: expanding opportunities in the PARP family", *Nat. Rev. Drug Discovery*, Vol. 11, No. 12, pp. 923-936.

Robitaille et al., 2002, "Mutant frizzled-4 disrupts retinal angiogenesis in familial exudative vitreoretinopathy", *Nat. Genet.*, Vol. 32, pp. 326-330.

Roy et al., 2009, "Solution-phase synthesis of a diverse isocoumarin library", *J. Combinatorial Chemistry*, Vol. 11, No. 6, pp. 1128-1135.

Sarkhel et al., 1978, "Synthesis fo some 3-aryl-5-methoxy-7-methylisocoumarins", Indian J. Chem., Vol. 16B, No. 11, pp. 1034-1036.

Shkreli et al., 2011, "Reversible cell-cycle entry in adult kidney podocytes through regulated control of telomerase and Wnt signaling", *Nat. Med.*, submitted for publication.

Shuler et al., 2012, "Preparation and X-Ray Crystal Structure of 3-(4-(Dimethylamino)phenyl)-2-(phenylamino)isoquinolin-1(2H)-one, 3-(4-Methoxyphenyl)-2-(phenylamino)isoquinolin-1(2H)-one, and 2-Methyl-N'-(4-methylbenzoyl)-N'-phenylbenzohydrazide from Polylithiated 2-methylbenzoic Acid Phenylhydrazide and Methyl 4-dimethylaminobenzoate, Methyl 4-methoxybenzoate, or Methyl 4-methylbenzoate", *J. Chem. Crystallography*, Vol. 42, No. 9, pp. 952-959.

Sin et al., 2008, "Hepatitis C Virus Inhibitors", international patent publication number WO 2008/060927 A2 published 22 May 2008.

Snieckus et al., 1989, "Directed ortho metalation of N,N-diethylbenzamides. Silicon protection of ortho sites and the o-methyl group", *J. Org. Chem.*, Vol. 54, pp. 4372-4385.

Sunderland et al., 2010, "Synthesis of 4-alkyl, 4-aryl and 4-arylamino-5-aminoisoquinolin-1-ones and identification of a new PARP-2 selected inhibitor", *Organic & Biomolecular Chemistry*, DOI: 10.1039/c0ob00665c.

Suto et al., 1993, "Substituted dihydroisoquinolinones and related compounds as potentiators of the lethal effects of radiation and certain chemotherapeutics agents; selected compounds, analoges and process", U.S. Pat. No. 5,177,075 granted 5 Jan. 1993.

Treus et al., 2010, "(Z)-Ethyl 2-phenyl-1-(2-vinylphenyl)vinylcarbamates. Part 1: Synthesis and preliminary studies on their divergent transformation into benzo[c]phenanthridines and 2-phenyl-1,4-naphthoquinones", *Tetrahedron*, Vol. 66, No. 52, pp. 9986-9995.

Tropsha et al., 2011, "Development of kNN QSAR models for 3-arylisoquinoline antitumor agents", *Bulletin of the Korean Chemical Society*, Vol. 32, No. 7, pp. 2397-2404.

Turner et al., 2004, "Hallmarks of 'BRCAness' in sporadic cancers", Nat. Rev. Cancer, Vol. 4, No. 10, pp. 814-819.

Ueno et al., 1999, "Fused pyridine derivatives", international patent publication number WO 99/18077 A1 published 15 Apr. 1999.

Varallo et al., 2003, "Beta-catenin expression in Dupuytren's disease: potential role for cell-matrix interactions in modulating beta-catenin levels in vivo and in vitro", *Oncogene*, Vol. 22, pp. 3680-3684.

Waaler et al., 2012, "A novel tankyrase inhibitor decreases canonical Wnt signaling in colon carcinoma cells and reduces tumor growth in conditional APC mutant mice", *Cancer Research*, Vol. 72, No. 11, pp. 2822-2832.

Wang et al., 2003, "Hepatitis C virus inhibitors", international patent publication number WO 03/099274 A1 published 4 Dec. 2003.

Wang et al., 2011, "Cardiac induction of embryonic stem cells by a small molecule inhibitor of Wnt/beta-catenin signaling", *ACS Chem. Biol.*, Vol. 6, pp. 192-197.

Wong et al., 2006, "Flavenoids and isoflavenoids for the prevention and treatment of cardiovascular diseases", international patent publication number WO 2006/045096 A2 published 27 Apr. 2006.

Wong et al., 2008, "Compounds for the prevention and treatment of cardiovascular diseases", US patent publication number US 2008/0188467 A1 published 7 Aug. 2008.

Woods et al., 2006, "Mutations in WNT7A cause a range of limb malformations, including Fuhrmann syndrome and Al-Awadi/Raas-Rothschild/Schinzel phocomelia syndrome", *Am. J. Hum. Genet.*, Vol. 79, pp. 402-408.

Xu et al., 2004, "Vascular development in the retina and inner ear: control by Norrin and Frizzled-4, a high-affinity ligand-receptor pair", *Cell*, Vol. 116, pp. 883-895.

Yeh et al., 2007, "Insulin-stimulated exocytosis of GLUT4 is enhanced by IRAP and its partner tankyrase", *Biochem. J.*, Vol. 402, pp. 279-290.

The invention claimed is:

1. A compound of the following formula, or a pharmaceutically acceptable salt or N oxide thereof:

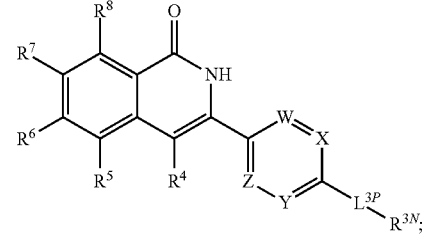

wherein:
W is $CR^W$, X is $CR^X$, Y is $CR^Y$, and Z is $CR^Z$; or
W is N, X is $CR^X$, Y is $CR^Y$, and Z is $CR^Z$; or
W is $CR^W$, X is N, Y is $CR^Y$, and Z is $CR^Z$; or
W is N, X is $CR^X$, Y is $CR^Y$, and Z is N; or
W is $CR^W$, X is N, Y is N, and Z is $CR^Z$; or
W is N, X is $CR^X$, Y is N, and Z is $CR^Z$; or
W is N, X is N, Y is $CR^Y$, and Z is $CR^Z$;
wherein:
—$R^W$ is independently —H or —$R^{WW}$;
—$R^X$ is independently —H or —$R^{XX}$;
—$R^Y$ is independently —H or —$R^{YY}$; and
—$R^Z$ is independently —H or —$R^{ZZ}$;
wherein:
—$R^{WW}$ is independently —$X^1$, —$R^1$, —OH, —$CF_3$, or —$OCF_3$;
—$R^{XX}$ is independently —$X^1$, —$R^1$, —OH, —$CF_3$, or —$OCF_3$;
—$R^{YY}$ is independently —$X^1$, —$R^1$, —OH, —$CF_3$, or —$OCF_3$; and —$R^{ZZ}$ is independently —$X^1$, —$R^1$, —OH, —$CF_3$, or —$OCF_3$;

wherein:
   each —$X^1$ is independently —F, —Cl, —Br, or —I; and
   each —$R^1$ is independently linear or branched saturated $C_{1-4}$alkyl;

and wherein:
   -$L^{3P}$- is independently a single covalent bond or -$L^{3PL}$-;

wherein:
   -$L^{3PL}$- is independently -$L^{3PR1}$-, —C(=O)—, -$L^{3PR2}$-C(=O)—, —S(=O)$_2$—, -$L^{3PR3}$-S(=O)$_2$—, or —O-$L^{3PR4}$-;

wherein:
   each -$L^{3PR1}$- is linear or branched saturated $C_{1-4}$alkylene;
   each -$L^{3PR2}$- is linear or branched saturated $C_{1-4}$alkylene;
   each -$L^{3PR3}$- is linear or branched saturated $C_{1-4}$alkylene;
   each -$L^{3PR4}$- is linear or branched saturated $C_{1-4}$alkylene;

and wherein:
   —$R^{3N}$ is independently —$NH_2$, $NHR^A$, $NR^A R^B$, or —$NR^C R^D$;

wherein:
each —$R^A$ is independently:
   —$R^{A1}$, —$R^{A2}$, —$R^{A3}$, —$R^{A4}$, —$R^{A5}$, -$L^A$-$R^{A2}$, -$L^A$—$R^{A3}$, -$L^A$—$R^{A4}$, or -$L^A$—$R^{A5}$;
each —$R^{A1}$ is linear or branched saturated $C_{1-6}$alkyl,
   and is optionally substituted with one or more groups —$R^{S1}$;
each —$R^{A2}$ is saturated $C_{3-6}$cycloalkyl,
   and is optionally substituted with one or more groups —$R^{S2C}$;
each —$R^{A3}$ is non-aromatic $C_{3-7}$heterocyclyl,
   and is optionally substituted on carbon with one or more groups —$R^{S2C}$,
   and is optionally substituted on secondary nitrogen, if present, with a group —$R^{SN}$;
each —$R^{A4}$ is independently phenyl or naphthyl,
   and is optionally substituted with one or more groups —$R^{S3C}$;
each —$R^{A5}$ is $C_{5-10}$heteroaryl,
   and is optionally substituted on carbon with one or more groups —$R^{S3C}$,
   and is optionally substituted on secondary nitrogen, if present, with a group —$R^{SN}$;
each -$L^A$- is linear or branched saturated $C_{1-4}$alkylene;

and wherein:
each —$R^{S1}$ is independently:
   —F, —Cl, —Br, —I,
   —OH, —$OR^{TT}$,
   —$OCF_3$,
   —$NH_2$, —$NHR^{TT}$, —$NR^{TT}{}_2$, —$R^{TM}$,
   —C(=O)OH, —C(=O)$OR^{TT}$, —OC(=O)$R^{TT}$,
   —C(=O)$NH_2$, —C(=O)$NHR^{TT}$, —C(=O)$NR^{TT}{}_2$, —C(=O)$R^{TM}$,
   —NHC(=O)$R^{TT}$, —$NR^{TN}$C(=O)$R^{TT}$,
   —NHC(=O)$NH_2$, —NHC(=O)$NHR^{TT}$, —NHC(=O)$NR^{TT}{}_2$, —NHC(=O)$R^{TM}$,
   —$NR^{TN}$C(=O)$NH_2$, —$NR^{TN}$C(=O)$NHR^{TT}$, —$NR^{TN}$C(=O)$NR^{TT}{}_2$, —$NR^{TN}$C(=O)$R^{TM}$,
   —NHC(=O)$OR^{TT}$, —$NR^{TN}$C(=O)$OR^{TT}$,
   —OC(=O)$NH_2$, —OC(=O)$NHR^{TT}$, —OC(=O)$NR^{TT}{}_2$, —OC(=O)$R^{TM}$,
   —C(=O)$R^{TT}$,
   —S(=O)$_2$$NH_2$, —S(=O)$_2$$NHR^{TT}$, —S(=O)$_2$$NR^{TT}{}_2$, —S(=O)$_2$$R^{TM}$,
   —NHS(=O)$_2$$R^{TT}$, —$NR^{TN}$S(=O)$_2$$R^{TT}$,
   —S(=O)$_2$$R^{TT}$,
   —CN, —$NO_2$, —$SR^{TT}$, or =O;

each —$R^{S2C}$ is independently:
   —$R^{TT}$,
   —F, —Cl, —Br, —I,
   —OH, —$OR^{TT}$,
   -$L^T$-OH, -$L^T$-$OR^{TT}$,
   —$CF_3$, —$OCF_3$,
   —$NH_2$, —$NHR^{TT}$, —$NR^{TT}{}_2$, —$R^{TM}$,
   -$L^T$-$NH_2$, -$L^T$-$NHR^{TT}$, -$L^T$-$NR^{TT}{}_2$, -$L^T$-$R^{TM}$,
   —C(=O)OH, —C(=O)$OR^{TT}$, —OC(=O)$R^{TT}$,
   —C(=O)$NH_2$, —C(=O)$NHR^{TT}$, —C(=O)$NR^{TT}{}_2$, —C(=O)$R^{TM}$,
   —NHC(=O)$R^{TT}$, —$NR^{TN}$C(=O)$R^{TT}$,
   —NHC(=O)$NH_2$, —NHC(=O)$NHR^{TT}$, —NHC(=O)$NR^{TT}{}_2$, —NHC(=O)$R^{TM}$,
   —$NR^{TN}$C(=O)$NH_2$, —$NR^{TN}$C(=O)$NHR^{TT}$, —$NR^{TN}$C(=O)$NR^{TT}{}_2$, —$NR^{TN}$C(=O)$R^{TM}$,
   —NHC(=O)$OR^{TT}$, —$NR^{TN}$C(=O)$OR^{TT}$,
   —OC(=O)$NH_2$, —OC(=O)$NHR^{TT}$, —OC(=O)$NR^{TT}{}_2$, —OC(=O)$R^{TM}$,
   —C(=O)$R^{TT}$,
   —S(=O)$_2$$NH_2$, —S(=O)$_2$$NHR^{TT}$, —S(=O)$_2$$NR^{TT}{}_2$, —S(=O)$_2$$R^{TM}$,
   —NHS(=O)$_2$$R^{TT}$, —$NR^{TN}$S(=O)$_2$$R^{TT}$,
   —S(=O)$_2$$R^{TT}$,
   —CN, —$NO_2$, —$SR^{TT}$, or =O;

each —$R^{S3C}$ is independently:
   —$R^{TT}$,
   —F, —Cl, —Br, —I,
   —OH, —$OR^{TT}$,
   -$L^T$-OH, -$L^T$-$OR^{TT}$,
   —$CF_3$, —$OCF_3$,
   —$NH_2$, —$NHR^{TT}$, —$NR^{TT}{}_2$, —$R^{TM}$,
   -$L^T$-$NH_2$, -$L^T$-$NHR^{TT}$, -$L^T$-$NR^{TT}{}_2$, -$L^T$-$R^{TM}$,
   —C(=O)OH, —C(=O)$OR^{TT}$, —OC(=O)$R^{TT}$,
   —C(=O)$NH_2$, —C(=O)$NHR^{TT}$, —C(=O)$NR^{TT}{}_2$, —C(=O)$R^{TM}$,
   —NHC(=O)$R^{TT}$, —$NR^{TN}$C(=O)$R^{TT}$,
   —NHC(=O)$NH_2$, —NHC(=O)$NHR^{TT}$, —NHC(=O)$NR^{TT}{}_2$, —NHC(=O)$R^{TM}$,
   —$NR^{TN}$C(=O)$NH_2$, —$NR^{TN}$C(=O)$NHR^{TT}$, —$NR^{TN}$C(=O)$NR^{TT}{}_2$, —$NR^{TN}$C(=O)$R^{TM}$,
   —NHC(=O)$OR^{TT}$, —$NR^{TN}$C(=O)$OR^{TT}$,
   —OC(=O)$NH_2$, —OC(=O)$NHR^{TT}$, —OC(=O)$NR^{TT}{}_2$, —OC(=O)$R^{TM}$,
   —C(=O)$R^{TT}$,
   —S(=O)$_2$$NH_2$, —S(=O)$_2$$NHR^{TT}$, —S(=O)$_2$$NR^{TT}{}_2$, —S(=O)$_2$$R^{TM}$,
   —NHS(=O)$_2$$R^{TT}$, —$NR^{TN}$S(=O)$_2$$R^{TT}$,
   —S(=O)$_2$$R^{TT}$,
   —CN, —$NO_2$, or —$SR^{TT}$;
and additionally, two adjacent groups —$R^{S3C}$, if present, may together form:
   —O—$CH_2$—O— or —O—$CH_2CH_2$—O—;

each —$R^{SN}$ is independently:
   —$R^{TT}$,
   -$L^T$-OH, -$L^T$-$OR^{TT}$,
   -$L^T$-$NH_2$, -$L^T$-$NHR^{TT}$, -$L^T$-$NR^{TT}{}_2$, -$L^T$-$R^{TM}$,
   —C(=O)$R^{TT}$,
   —C(=O)$OR^{TT}$,
   —C(=O)$NH_2$, —C(=O)$NHR^{TT}$, —C(=O)$NR^{TT}{}_2$,
   —C(=O)$R^{TM}$, or
   —S(=O)$_2$$R^{TT}$;

wherein:
    each -$L^T$- is linear or branched saturated $C_{1-4}$alkylene;
    each —$R^{TT}$ is independently linear or branched saturated $C_{1-4}$alkyl, saturated $C_{3-6}$cycloalkyl, saturated $C_{3-6}$cycloalkyl-methyl, phenyl, or benzyl; wherein said linear or branched saturated $C_{1-4}$alkyl is optionally substituted with —OH or —$OR^{TTT}$, wherein —$R^{TTT}$ is linear or branched saturated $C_{1-4}$alkyl;
    each —$R^{TN}$ is linear or branched saturated $C_{1-4}$alkyl;
    each —$R^{TM}$ is independently azetidino, pyrrolidino, piperidino, piperazino, morpholino, azepano, or diazepano, and is:
        optionally substituted on carbon with one or more groups selected from: —$R^{TMM}$, —C(=O)$R^{TMM}$, —S(=O)$_2R^{TMM}$, —F, —NH$_2$, —NHR$^{TMM}$, —NR$^{TMM}_2$, —OH, and —OR$^{TMM}$; and
        optionally substituted on secondary nitrogen, if present, with a group selected from: —$R^{TMM}$, —C(=O)$R^{TMM}$, —C(=O)OR$^{TMM}$, and —S(=O)$_2R^{TMM}$;
        wherein each —$R^{TMM}$ is independently linear or branched saturated $C_{1-4}$alkyl, saturated $C_{3-6}$cycloalkyl, saturated $C_{3-6}$cycloalkyl-methyl, phenyl, or benzyl;
and wherein:
    —$R^B$ is independently —$R^{B1}$, —$R^{B2}$, or -$L^B$-$R^{B2}$;
    —$R^{B1}$ is linear or branched saturated $C_{1-6}$alkyl, and is optionally substituted with —OH or —OR$^{BB}$,
wherein —$R^{BB}$ is linear or branched saturated $C_{1-4}$alkyl;
    —$R^{B2}$ is saturated $C_{3-6}$cycloalkyl; and
    -$L^B$- is linear or branched saturated $C_{1-4}$alkylene;
and wherein:
    —NR$^C$R$^D$ is independently —NR$^{C1}$R$^{D1}$, —NR$^{C2}$R$^{D2}$, —NR$^{C3}$R$^{D3}$, —NR$^{C4}$R$^{D4}$, or —NR$^{C5}$R$^{D5}$;
wherein:
    —NR$^{C1}$R$^{D1}$ is a monocyclic non-aromatic heterocyclyl group having from 4 to 8 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, wherein said S is optionally in the form of S(=O) or S(=O)$_2$;
    and wherein said monocyclic non-aromatic heterocyclyl group is:
optionally substituted on carbon with one or more groups —$R^{NC}$, and
optionally substituted on secondary nitrogen, if present, with a group —$R^{NN}$;
    —NR$^{C2}$R$^{D2}$ is a fused bicyclic non-aromatic heterocyclyl group having from 7 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, wherein said S is optionally in the form of S(=O) or S(=O)$_2$, or exactly 3 of said ring atoms are ring heteroatoms, one of which is N, and each of the other two is independently N, O, or S, wherein said S is optionally in the form of S(=O) or S(=O)$_2$;
    and wherein said fused bicyclic non-aromatic heterocyclyl group is:
optionally substituted on carbon with one or more groups —$R^{NC}$, and
optionally substituted on secondary nitrogen, if present, with a group —$R^{NN}$;
    —NR$^{C3}$R$^{D3}$ is a bridged non-aromatic heterocyclyl group having from 7 to 11 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, wherein said S is optionally in the form of S(=O) or S(=O)$_2$, or exactly 3 of said ring atoms are ring heteroatoms, one of which is N, and each of the other two is independently N, O, or S, wherein said S is optionally in the form of S(=O) or S(=O)$_2$;
    and wherein said bridged non-aromatic heterocyclyl group is:
optionally substituted on carbon with one or more groups —$R^{NC}$, and
optionally substituted on secondary nitrogen, if present, with a group —$R^{NN}$;
    —NR$^{C4}$R$^{D4}$ is a spiro non-aromatic heterocyclyl group having from 6 to 12 ring atoms, wherein exactly 1 of said ring atoms is a ring heteroatom, and is N, or exactly 2 of said ring atoms are ring heteroatoms, and are both N, or exactly 2 of said ring atoms are ring heteroatoms, and are N and O, or exactly 2 of said ring atoms are ring heteroatoms, and are N and S, or exactly 3 of said ring atoms are ring heteroatoms, one of which is N, and each of the other two is independently N, O, or S, wherein said S is optionally in the form of S(=O) or S(=O)$_2$;
    and wherein said spiro non-aromatic heterocyclyl group is:
optionally substituted on carbon with one or more groups —$R^{NC}$, and
optionally substituted on secondary nitrogen, if present, with a group —$R^{NN}$;
wherein:
each —$R^{NC}$ is independently:
    —$R^{QQ}$,
    —F, —Cl, —Br, —I,
    —OH, —OR$^{QQ}$,
    -$L^Q$-OH, -$L^Q$-OR$^{QQ}$,
    —CF$_3$, —OCF$_3$,
    —NH$_2$, —NHR$^{QQ}$, —NR$^{QQ}_2$, —R$^{QM}$,
    -$L^Q$-NH$_2$, -$L^Q$-NHR$^{QQ}$, -$L^Q$-NR$^{QQ}_2$, -$L^Q$-R$^{QM}$,
    —C(=O)OH, —C(=O)OR$^{QQ}$, —OC(=O)R$^{QQ}$,
    —C(=O)NH$_2$, —C(=O)NHR$^{QQ}$, —C(=O)NR$^{QQ}_2$, —C(=O)R$^{QM}$,
    —NHC(=O)R$^{QQ}$, —NR$^{QN}$C(=O)R$^{QQ}$,
    —NHC(=O)NH$_2$, —NHC(=O)NHR$^{QQ}$, —NHC(=O)NR$^{QQ}_2$, —NHC(=O)R$^{QM}$,
    —NR$^{QN}$C(=O)NH$_2$, —NR$^{QN}$C(=O)NHR$^{QQ}$,
    —NR$^{QN}$C(=O)NR$^{QQ}_2$, —NR$^{QN}$C(=O)R$^{QM}$,
    —NHC(=O)OR$^{QQ}$, —NR$^{QN}$C(=O)OR$^{QQ}$,
    —OC(=O)NH$_2$, —OC(=O)NHR$^{QQ}$, —OC(=O)NR$^{QQ}_2$, —OC(=O)R$^{QM}$,
    —C(=O)R$^{QQ}$,
    —S(=O)$_2$NH$_2$, —S(=O)$_2$NHR$^{QQ}$, —S(=O)$_2$NR$^{QQ}_2$, —S(=O)$_2$R$^{QM}$,
    —NHS(=O)$_2$R$^{QQ}$, —NR$^{QN}$S(=O)$_2$R$^{QQ}$,
    —S(=O)$_2$R$^{QQ}$,
    —CN, —NO$_2$, —SR$^{QQ}$, or =O;
each —$R^{NN}$ is independently:
    —$R^{QQ}$,
    -$L^Q$-OH, -$L^Q$-OR$^{QQ}$,
    -$L^Q$-NH$_2$, -$L^Q$-NHR$^{QQ}$, -$L^Q$-NR$^{QQ}_2$, -$L^Q$-R$^{QM}$,
    —C(=O)R$^{QQ}$,
    —C(=O)OR$^{QQ}$, —C(=O)NH$_2$, —C(=O)NHR$^{QQ}$, —C(=O)NR$^{QQ}_2$, —C(=O)R$^{QM}$, or
—S(=O)$_2$R$^{QQ}$;
wherein:
each -L$^Q$- is linear or branched saturated C$_{1-4}$alkylene;
each —R$^{QQ}$ is independently linear or branched saturated C$_{1-4}$alkyl, saturated C$_{3-6}$cycloalkyl, saturated C$_{3-6}$cycloalkyl-methyl, phenyl or benzyl; wherein said linear or branched saturated C$_{1-4}$alkyl is optionally substituted with —OH or —OR$^{QQQ}$, and said phenyl and benzyl are optionally substituted with —R$^{QQQ}$, wherein each —R$^{QQQ}$ is linear or branched saturated C$_{1-4}$alkyl;
each —R$^{QN}$ is linear or branched saturated C$_{1-4}$alkyl;
each —R$^{QM}$ is independently azetidino, pyrrolidino, piperidino, piperazino, morpholino, azepano, or diazepano, and is:
optionally substituted on carbon with one or more groups selected from: —R$^{QMM}$, —C(=O)R$^{QMM}$, —S(=O)$_2$R$^{QMM}$, —F, —NH$_2$, —NHR$^{QMM}$, —NR$^{QMM}_2$, —OH, and —OR$^{QMM}$; and
optionally substituted on secondary nitrogen, if present, with a group selected from: —R$^{QMM}$, —C(=O)R$^{QMM}$, —C(=O)OR$^{QMM}$, and —S(=O)$_2$R$^{QMM}$;
wherein each —R$^{QMM}$ is independently linear or branched saturated C$_{1-4}$alkyl, saturated C$_{3-6}$cycloalkyl, saturated C$_{3-6}$cycloalkyl-methyl, phenyl, or benzyl;
and wherein:
—NR$^{C5}$R$^{D5}$ is independently: 1H-pyrrol-1-yl; 2H-isoindol-2-yl; 1H-indol-1-yl; 1H-pyrazol-1-yl; 1H-benzoimidazol-1-yl; 1H-imidazol-1-yl; 2H-indazol-2-yl; 1H-indazol-1-yl; 4H-[1,2,4]triazol-4-yl; 1H-[1,2,3]triazol-1-yl; 1H-[1,2,4]triazol-1-yl; 1H-benzotriazol-1-yl; or 1H-tetrazol-1-yl; and is optionally substituted with one or more groups —R$^H$;
wherein each —R$^H$ is independently:
—R$^{HH}$,
—F, —Cl, —Br, —I,
—OH, —OR$^{HH}$,
-L$^H$-OH, -L$^H$-OR$^{HH}$,
—CF$_3$, —OCF$_3$,
—NH$_2$, —NHR$^{HH}$, —NR$^{HH}_2$, —R$^{HM}$,
-L$^H$-NH$_2$, -L$^H$-NHR$^{HH}$, -L$^H$-NR$^{HH}_2$, -L$^H$-R$^{HM}$,
—C(=O)OH, —C(=O)OR$^{HH}$, —OC(=O)R$^{HH}$,
—C(=O)NH$_2$, —C(=O)NHR$^{HH}$, —C(=O)NR$^{HH}_2$,
—C(=O)R$^{HM}$,
—NHC(=O)R$^{HH}$, —NR$^{HH}$C(=O)R$^{HH}$,
—NHC(=O)NH$_2$, —NHC(=O)NHR$^{HH}$, —NHC(=O)NR$^{HH}_2$, —NHC(=O)R$^{HM}$,
—NR$^{HN}$C(=O)NH$_2$, —NR$^{HN}$C(=O)NHR$^{HH}$, —NR$^{HN}$C(=O)NR$^{HH}_2$, —NR$^{HN}$C(=O)R$^{HM}$,
—NHC(=O)OR$^{HH}$, —NR$^{HN}$C(=O)OR$^{HH}$,
—OC(=O)NH$_2$, —OC(=O)NHR$^{HH}$, —OC(=O)NR$^{HH}_2$, —OC(=O)R$^{HM}$,
—C(=O)R$^{HH}$,
—S(=O)$_2$NH$_2$, —S(=O)$_2$NHR$^{HH}$, —S(=O)$_2$NR$^{HH}_2$, —S(=O)$_2$R$^{HM}$,
—NHS(=O)$_2$R$^{HH}$, —NR$^{HN}$S(=O)$_2$R$^{HH}$,
—S(=O)$_2$R$^{HH}$,
—CN, —NO$_2$, or —SR$^{HH}$;
wherein:
each -L$^H$- is linear or branched saturated C$_{1-4}$alkylene;
each —R$^{HH}$ is independently linear or branched saturated C$_{1-4}$alkyl, saturated C$_{3-6}$cycloalkyl, saturated C$_{3-6}$cycloalkyl-methyl, phenyl, or benzyl; wherein said linear or branched saturated C$_{1-4}$alkyl is optionally substituted with —OH or —OR$^{HHH}$, wherein —R$^{HHH}$ is linear or branched saturated C$_{1-4}$alkyl;
each —R$^{HN}$ is linear or branched saturated C$_{1-4}$alkyl;
each —R$^{HM}$ is independently azetidino, pyrrolidino, piperidino, piperazino, morpholino, azepano, or diazepano, and is:
optionally substituted on carbon with one or more groups selected from: —R$^{HMM}$, —C(=O)R$^{HMM}$, —S(=O)$_2$R$^{HMM}$, —F, —NH$_2$, —NHR$^{HMM}$, —NR$^{HMM}_2$, —OH, and —OR$^{HMM}$; and
optionally substituted on secondary nitrogen, if present, with a group selected from: —R$^{HMM}$, —C(=O)R$^{HMM}$, —C(=O)OR$^{HMM}$, and —S(=O)$_2$R$^{HMM}$;
wherein each —R$^{HMM}$ is independently linear or branched saturated C$_{1-4}$alkyl, saturated C$_{3-6}$cycloalkyl, saturated C$_{3-6}$cycloalkyl-methyl, phenyl, or benzyl;
and wherein:
—R$^5$ is independently —R$^{5A}$, —R$^{5B}$, —R$^{5C}$, —R$^{5D}$, or —R$^{5E}$;
—R$^{5A}$ is linear or branched saturated C$_{1-4}$alkyl;
—R$^{5B}$ is saturated C$_{3-6}$cycloalkyl;
—R$^{5C}$ is independently —F, —Cl, —Br, or —I;
—R$^{5D}$ is —CF$_3$; and
—R$^{5E}$ is independently —C≡CH or C$_{3-6}$alkynyl optionally substituted with one or more groups —R$^{EE}$; wherein each —R$^{EE}$ is independently selected from —OH, —OR$^{EEE}$, —NH$_2$, —NHR$^{EEE}$, and —NR$^{EEE}_2$;
wherein each —R$^{EEE}$ is linear or branched saturated C$_{1-4}$alkyl;
and wherein:
—R$^4$ is —H;
—R$^6$ is independently —H or —F; and
—R$^7$ is independently —H or —F; and
—R$^8$ is independently —H or —F.

2. A compound according to claim 1, wherein:
W is CR$^W$, X is CR$^X$, Y is CR$^Y$, and Z is CR$^Z$.

3. A compound according to claim 1, wherein:
W is CR$^W$, X is N, Y is CR$^Y$, and Z is CR$^Z$.

4. A compound according to claim 1, wherein:
—R$^W$, if present, is —H;
—R$^X$, if present, is —H;
—R$^Y$, if present, is —H; and
—R$^Z$, if present, is —H.

5. A compound according to claim 1, wherein -L$^{3P}$- is a single covalent bond.

6. A compound according to claim 1, wherein -L$^{3P}$- is -L$^{3PL}$-.

7. A compound according to claim 1, wherein -L$^{3PL}$-, if present, is -L$^{3PR1}$-.

8. A compound according to claim 1, wherein -L$^{3PL}$-, if present, is —C(=O)—.

9. A compound according to claim 1, wherein -L$^{3PL}$-, if present, is -L$^{3PR2}$-C(=O)—.

10. A compound according to claim 1, wherein:
each -L$^{3PR1}$-, if present, is independently —CH$_2$—, —CH(Me)-, or —C(Me)$_2$-; and
each -L$^{3PR2}$-, if present, is independently —CH$_2$—, —CH(Me)-, or —C(Me)$_2$-.

11. A compound according to claim 1, wherein —R$^{3N}$ is —NR$^A$R$^B$.

12. A compound according to claim 1, wherein —R$^{3N}$ is —NR$^C$R$^D$.

13. A compound according to claim 1, wherein each —R$^A$, if present, is independently: —R$^{A1}$, —R$^{A3}$, or -L$^A$-R$^{A3}$.

14. A compound according to claim 1, wherein:
each —$R^{A1}$, if present, is independently linear or branched saturated $C_{1-4}$alkyl, and is optionally substituted with one or more groups —$R^{S1}$; and
each —$R^{A3}$, if present, is piperidinyl,
and is optionally substituted on carbon with one or more groups —$R^{S2C}$,
and is optionally substituted on secondary nitrogen with a group —$R^{SN}$.

15. A compound according to claim 1, wherein each —$R^{SN}$, if present, is independently:
—$R^{TT}$,
—C(=O)$R^{TT}$, or
—C(=O)O$R^{TT}$.

16. A compound according to claim 1, wherein each —$R^{TT}$, if present, is -Me.

17. A compound according to claim 1, wherein —$NR^C R^D$, if present, is —$NR^{C1}R^{D1}$, wherein, —$NR^{C1}R^{D1}$ is independently selected from the following groups, and is:
optionally substituted on carbon with one or more groups —$R^{NC}$, and
optionally substituted on secondary nitrogen, if present, with a group —$R^{NN}$:

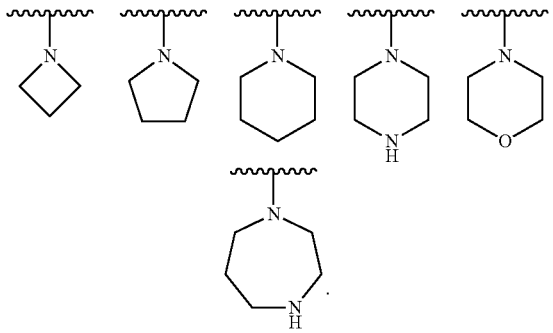

18. A compound according to claim 1, wherein:
each —$R^{NC}$, if present, is independently:
—$R^{QQ}$,
—OH, —O$R^{QQ}$,
—$NH_2$, —$NHR^{QQ}$, —$NR^{QQ}_2$, —$R^{QM}$, or
=O;

each —$R^{NN}$, if present, is independently:
—$R^{QQ}$,
-$L^Q$-OH, -$L^Q$-O$R^{QQ}$,
-$L^Q NH_2$, -$L^Q$-NH$R^{QQ}$, -$L^Q$-N$R^{QQ}_2$, -$L^Q$-$R^{QM}$,
—C(=O)$R^{QQ}$, or
—C(=O)O$R^{QQ}$; and
each —$R^{QQ}$ is independently linear or branched saturated $C_{1-4}$alkyl, saturated $C_{3-6}$cycloalkyl, or saturated $C_{3-6}$cycloalkyl-methyl.

19. A compound according to claim 1, wherein each —$R^{QQ}$, if present, is -Me.

20. A compound according to claim 1, wherein —$NR^C R^D$, if present, is —$NR^{C5}R^{D5}$, wherein —$NR^{C5}R^{D5}$ is: 1H-pyrazol-1-yl; and is optionally substituted with one or more groups —$R^H$.

21. A compound according to claim 1, wherein —$NR^C R^D$, if present, is —$NR^{C5}R^{D5}$, wherein —$NR^{C5}R^{D5}$ is: 1H-imidazol-1-yl; and is optionally substituted with one or more groups —$R^H$.

22. A compound according to claim 1, wherein each —$R^H$, if present, is independently —$R^{HH}$.

23. A compound according to claim 1, wherein —$R^5$ is —$R^{5A}$, wherein —$R^{5A}$ is -Me.

24. A compound according to claim 1, wherein —$R^5$ is —$R^{5C}$, wherein —$R^{5C}$ is —Cl.

25. A compound according to claim 1, wherein —$R^6$ is —H.

26. A compound according to claim 1, selected from IQ-001 through IQ-238 or a pharmaceutically acceptable salt or a N-oxide thereof.

27. A pharmaceutical composition comprising a compound according to claim 1, and a pharmaceutically acceptable carrier or diluent.

28. A method of preparing a pharmaceutical composition comprising the step of mixing a compound according to claim 1, and a pharmaceutically acceptable carrier or diluent.

29. A method of inhibiting PARP function, TNKS1 and/or TNKS2 function, or Wnt signalling in a cell, in vitro or in vivo, comprising contacting the cell with an effective amount of a compound according to claim 1.

30. A method of treatment of colorectal cancer, comprising administering to a subject in need of treatment a therapeutically-effective amount of a compound according to claim 1.

* * * * *